United States Patent
Vacca et al.

(10) Patent No.: US 10,934,275 B2
(45) Date of Patent: Mar. 2, 2021

(54) IRE1 SMALL MOLECULE INHIBITORS

(71) Applicant: Cornell University, Ithaca, NY (US)

(72) Inventors: Joseph P. Vacca, New York, NY (US); Dansu Li, New York, NY (US); Sarah Bettigole, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/463,056

(22) PCT Filed: Dec. 1, 2017

(86) PCT No.: PCT/US2017/064314
§ 371 (c)(1),
(2) Date: May 22, 2019

(87) PCT Pub. No.: WO2018/102751
PCT Pub. Date: Jun. 7, 2018

(65) Prior Publication Data
US 2019/0276434 A1  Sep. 12, 2019

Related U.S. Application Data

(60) Provisional application No. 62/429,498, filed on Dec. 2, 2016.

(51) Int. Cl.
| | |
|---|---|
| *A61P 35/00* | (2006.01) |
| *A61K 31/4725* | (2006.01) |
| *A61K 31/517* | (2006.01) |
| *C07D 401/14* | (2006.01) |
| *C07D 403/04* | (2006.01) |
| *C07D 403/14* | (2006.01) |
| *C07D 471/08* | (2006.01) |
| *C07D 401/04* | (2006.01) |
| *C07D 487/08* | (2006.01) |

(52) U.S. Cl.
CPC ......... *C07D 401/14* (2013.01); *C07D 401/04* (2013.01); *C07D 403/04* (2013.01); *C07D 403/14* (2013.01); *C07D 471/08* (2013.01); *C07D 487/08* (2013.01)

(58) Field of Classification Search
CPC ... A61P 35/00; A61K 31/4725; A61K 31/517; C07D 401/14; C07D 403/04; C07D 403/14; C07D 471/08
See application file for complete search history.

(56) References Cited

U.S. PATENT DOCUMENTS

| | | |
|---|---|---|
| 8,017,331 B2 | 9/2011 | Patterson et al. |
| 2015/0190466 A1 | 7/2015 | Leibel et al. |
| 2016/0237429 A1 | 8/2016 | Cubillos-Ruiz et al. |
| 2017/0252350 A1 | 9/2017 | Glimcher et al. |
| 2017/0253590 A1 | 9/2017 | Glimcher et al. |
| 2018/0346446 A1 | 12/2018 | Vacca et al. |
| 2018/0346447 A1 | 12/2018 | Vacca et al. |
| 2019/0169160 A1 | 6/2019 | Vacca et al. |

FOREIGN PATENT DOCUMENTS

| | | |
|---|---|---|
| CA | 3044259 A1 | 6/2018 |
| EP | 3548476 A1 | 10/2019 |
| WO | WO 2011/047384 | 4/2011 |
| WO | WO 2014/052669 | 4/2014 |
| WO | WO-2016/022839 A1 | 2/2016 |
| WO | WO 2017/152117 | 9/2017 |
| WO | WO-2018102751 A1 | 6/2018 |

OTHER PUBLICATIONS

Feldman et al., Structural and Functional Analysis of the Allosteric Inhibition of IRE1 α with ATP-Competitive Ligands, ACS Chem. Biol., 2016, 11(8):2195-2205.
Wang et al., "Divergent Allosteric Control of the IRE1 α Endoribonuclease using Kinase Inhibitors," Nat. Chem. Biol., 2012, 8(12):982-989.
International Search Report for PCT/US2017/064314, dated Mar. 30, 2018, 20 pages.
"European Application Seriai No. 17876623.4, Response to Communication pursuant to Rules 161(2) and 162 EPC filed Feb. 3, 2020", 53 pgs.
"International Application Serial No. PCT/US2017/064314, International Preliminary Report on Patentability dated Jun. 13, 2019", 15 pgs.
"International Application Serial No. PCT/US2017/064314, Written Opinion dated Mar. 30, 2018", 13 pgs.
"European Application Serial No. 17876623.4, Extended European Search Report dated Apr. 21, 2020", 7 pgs.

*Primary Examiner* — Brenda L Coleman
(74) *Attorney, Agent, or Firm* — Schwegman Lundberg & Woessner, P.A.

(57) ABSTRACT

Provided herein are small molecule inhibitors for the targeting or IRE1 protein family members. Binding may be direct or indirect. Further provided herein are methods of using IRE1 small molecule inhibitors for use in treating or ameliorating cancer in a subject. Moreover, IRE1 small molecule inhibitors described herein are for the treatment of cancer, where the cancer is a solid or hematologic cancer.

25 Claims, 6 Drawing Sheets
Specification includes a Sequence Listing.

IRE1 SMALL MOLECULE INHIBITORS

CROSS-REFERENCE

This application is a national stage application of International Application No. PCT/US2017/064314, filed Dec. 1, 2017, which claims benefit of U.S. Provisional Patent Application No. 62/429,498 filed on Dec. 2, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 28, 2017, is named 51089-707_601_SL.txt and is 23,840 bytes in size.

BACKGROUND

Aggressive tumors have evolved strategies that enable them to thrive under constant adverse conditions. For example, cancer cells respond to hypoxia, nutrient starvation, oxidative stress, and high metabolic demand by adjusting their protein folding capacity via the endoplasmic reticulum (ER) stress response pathway. There exists a need for improved methods and compositions to target cancer cells and counter their mechanisms of survival.

BRIEF SUMMARY

Provided in one aspect is a compound of Formula (I), or a pharmaceutically acceptable salt, or solvate thereof:

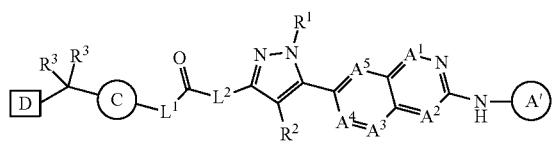

Formula (I)

wherein,

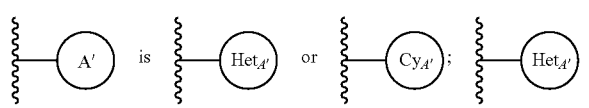 is 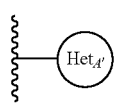 or 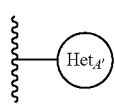; 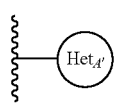

is an optionally substituted $C_3$-$C_{10}$ heterocyclyl containing at least one N, O, S, S(=O), or S(=O)$_2$; wherein if

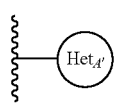

is substituted, then

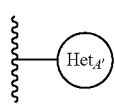

is substituted with 0-3 $R^5$;

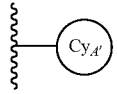

is a substituted $C_3$-$C_{10}$ cycloalkyl that is substituted with 1-3$R^4$ and 0-3$R^5$;

each $R^4$ is independently —OR$^6$, —SR$^6$, —S(=O)R$^7$, —S(=O)$_2$R$^7$, or —N(R$^6$)$_2$;
each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$ fluoroalkyl, optionally substituted $C_1$-$C_6$heteroalkyl, optionally substituted $C_3$-$C_6$cycloalkyl, optionally substituted aryl, or optionally substituted heteroaryl;
$A^1$ is N or CR$^A$; $A^2$ is N or CR$^A$; $A^3$ is N or CR$^A$; $A^4$ is N or CR$^A$; $A^5$ is N or CR$^A$;
each $R^A$ is independently H or optionally substituted $C_1$-$C_6$alkyl;
$R^1$ and $R^2$ are each independently H or optionally substituted $C_1$-$C_6$alkyl;
$L^1$ and $L^2$ are each independently —CHY—, —CH$_2$— or —NH—;
Y is optionally substituted $C_1$-$C_6$alkyl;

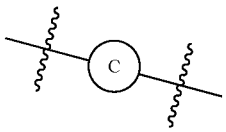

is optionally substituted aryl or optionally substituted heteroaryl, wherein if

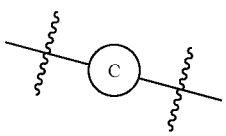

is substituted, then

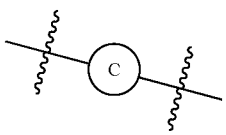

is substituted with 0-4 $R^c$;
each $R^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^1$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{11}$C(=O)R$^{11}$, —NR$^{10}$C(=O)OR$^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^3$ is independently H or optionally substituted $C_1$-$C_6$alkyl;

or $L^D$;

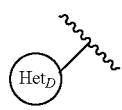

is optionally substituted heterocyclyl containing at least one N atom; wherein if

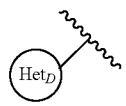

is substituted, then

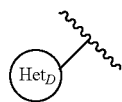

is substituted with 0-4 $R^D$;

$L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; wherein if $L^D$ is substituted, then $L^D$ is substituted with 0-4 $R^D$;

each $R^D$ is independently halogen, —CN, —OR$^{15}$, —SR$^{15}$, —S(=O)R$^{16}$, —S(=O)$_2$R$^{16}$, —S(=O)$_2$N(R$^{15}$)$_2$, —NR$^{15}$S(=O)$_2$R$^{16}$, —C(=O)R$^{16}$, —OC(=O)R$^{16}$, —CO$_2$R$^{15}$, —OCO$_2$R$^{16}$, —N(R$^{15}$)$_2$, —OC(=O)N(R$^1$)$_2$, —NR$^{15}$C(=O)R$^{16}$, —NR$^{15}$C(=O)OR$^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{12}$ and $R^{13}$ is independently H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

Also provided herein in another aspect is a compound of Formula (II), or a pharmaceutically acceptable salt, or solvate thereof:

Formula (II)

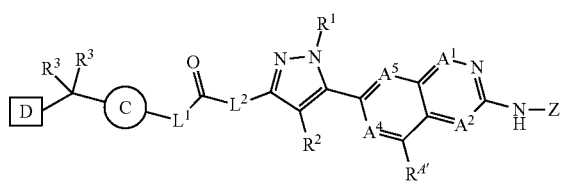

wherein,
Z is H,

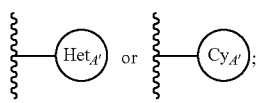

is optionally substituted $C_3$-$C_{10}$ heterocyclyl containing at least one N, O, S, S(=O), or S(=O)$_2$; wherein if

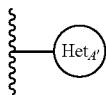

is substituted, then

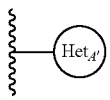

is substituted with 0-3 $R^5$;

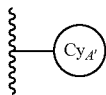

is a substituted $C_3$-$C_{10}$ cycloalkyl that is substituted with 1-3$R^4$ and 0-3$R^5$;
  each $R^4$ is independently —OR$^6$, —SR$^6$, —S(=O)R$^7$, —S(=O)$_2$R$^7$, or —N(R$^6$)$_2$;
  each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
A$^1$ is N or CR$^A$; A$^2$ is N or CR$^A$; A$^4$ is N or CR$^A$; A$^5$ is N or CR$^A$;
each R$^A$ is independently H or optionally substituted $C_1$-$C_6$alkyl;
R$^{A'}$ is optionally substituted $C_1$-$C_6$alkyl;
R$^1$ and R$^2$ are each independently H or optionally substituted $C_1$-$C_6$alkyl;
L$^1$ and L$^2$ are each independently —CHY—, —CH$_2$— or —NH—;
Y is optionally substituted $C_1$-$C_6$alkyl;

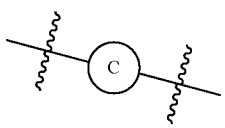

is optionally substituted aryl or optionally substituted heteroaryl, wherein if

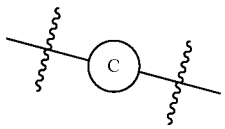

is substituted, then

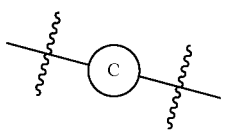

is substituted with 0-4 R$^c$;
  each R$^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{10}$C(=O)R$^{11}$, —NR$^{11}$C(=O)OR$^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
  each R$^3$ is independently H or optionally substituted $C_1$-$C_6$alkyl;

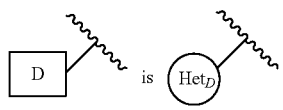

or L$^D$;

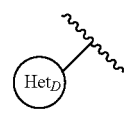

is optionally substituted heterocyclyl containing at least one N atom; wherein if

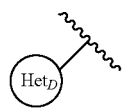

is substituted, then

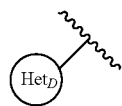

is substituted with 0-4 $R^D$;

$L^D$ is $-N(R^{12})$-(optionally substituted $C_1$-$C_6$ alkyl), $-N(R^{13})$-(optionally substituted $C_1$-$C_6$ alkylene)-$N(R^{14})_2$ or -(optionally substituted $C_1$-$C_6$ alkylene)-$N(R^{14})_2$; wherein if $L^D$ is substituted, then $L^D$ is substituted with 0-4 $R^D$;

each $R^D$ is independently halogen, $-CN$, $-OR^{15}$, $-SR^{15}$, $-S(=O)R^{16}$, $-S(=O)_2R^{16}$, $-S(=O)_2N(R^{15})_2$, $-NR^{15}S(=O)_2R^{16}$, $-C(=O)R^{16}$, $-OC(=O)R^{16}$, $-CO_2R^{15}$, $-OCO_2R^{16}$, $-N(R^{15})_2$, $-OC(=O)N(R^1)_2$, $-NR^{15}C(=O)R^{16}$, $-NR^{15}C(=O)OR^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{12}$ and $R^{13}$ is independently H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

Also provided herein in another aspect is a compound of Formula (III), or a pharmaceutically acceptable salt, or solvate thereof:

Formula (III)

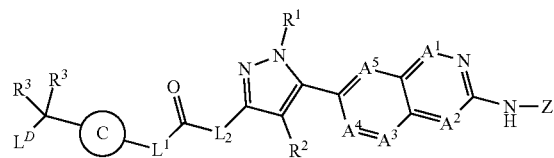

wherein,

Z is H,

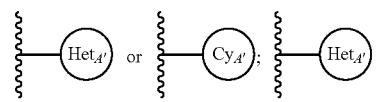

is an optionally substituted $C_3$-$C_{10}$ heterocyclyl containing at least one N, O, S, S(=O), or S(=O)$_2$; wherein if

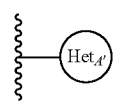

is substituted, then

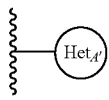

is substituted with 0-3 $R^5$;

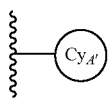

is a substituted $C_3$-$C_{10}$ cycloalkyl that is substituted with 1-3$R^4$ and 0-3$R^5$;

each $R^4$ is independently —$OR^6$, —$SR^6$, —$S(=O)R^7$, —$S(=O)_2R^7$, or —$N(R^6)_2$;

each $R^5$ is independently halogen, —CN, —$OR^8$, —$SR^8$, —$S(=O)R^9$, —$S(=O)_2R^9$, —$S(=O)_2N(R^8)_2$, —$NR^8S(=O)_2R^9$, —$C(=O)R^9$, —$OC(=O)R^9$, —$CO_2R^8$, —$OCO_2R^9$, —$N(R^8)_2$, —$OC(=O)N(R^8)_2$, —$NR^8C(=O)R^9$, —$NR^8C(=O)OR^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

$A^1$ is N or $CR^A$; $A^2$ is N or $CR^A$; $A^3$ is N or $CR^A$; $A^4$ is N or $CR^A$; $A^5$ is N or $CR^A$;

each $R^A$ is independently H or optionally substituted $C_1$-$C_6$alkyl;

$R^1$ and $R^2$ are each independently H or optionally substituted $C_1$-$C_6$alkyl;

$L^1$ and $L^2$ are each independently —CHY—, —$CH_2$— or —NH—;

Y is optionally substituted $C_1$-$C_6$alkyl;

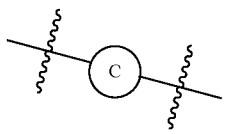

is optionally substituted aryl or optionally substituted heteroaryl, wherein if

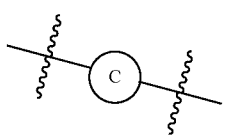

is substituted, then

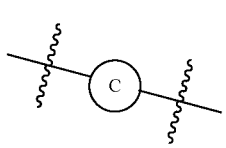

is substituted with 0-4 $R^c$;

each $R^c$ is independently H, halogen, —CN, —$OR^{10}$, —$SR^{10}$, —$S(=O)R^{11}$, —$S(=O)_2R^{11}$, —$S(=O)_2N(R^{10})_2$, —$NR^{10}S(=O)_2R^{11}$, —$C(=O)R^{11}$, —$OC(=O)R^{11}$, —$CO_2R^{10}$, —$OCO_2R^{11}$, —$N(R^{10})_2$, —$OC(=O)N(R^{10})_2$, —$NR^{10}C(=O)R^{11}$, —$NR^{10}C(=O)OR^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^3$ is independently H or optionally substituted $C_1$-$C_6$alkyl;

$L^D$ is —$N(R^{12})$-(optionally substituted $C_1$-$C_6$ alkyl), —$N(R^{13})$-(optionally substituted $C_1$-$C_6$ alkylene)-$N(R^{14})_2$ or -(optionally substituted $C_1$-$C_6$ alkylene)-$N(R^{14})_2$; wherein if $L^D$ is substituted, then $L^D$ is substituted with 0-4 $R^D$;

each $R^D$ is independently halogen, —CN, —$OR^{15}$, —$SR^{15}$, —$S(=O)R^{16}$, —$S(=O)_2R^{16}$, —$S(=O)_2N(R^{15})_2$, —$NR^{15}S(=O)_2R^{16}$, —$C(=O)R^{16}$, —$OC(=O)R^{16}$, —$CO_2R^{15}$, —$OCO_2R^{16}$, —$N(R^{15})_2$, —$OC(=O)N(R^1)_2$, —$NR^{15}C(=O)R^{16}$, —$NR^{15}C(=O)OR^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

$R^{12}$ is independently H or optionally substituted $C_3$-$C_6$alkyl;

$R^{13}$ is H or optionally substituted $C_1$-$C_6$alkyl; Each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

In some embodiments, the compound or pharmaceutically acceptable salt, or solvate thereof, selectively binds to IRE1α at one or more binding sites. In some embodiments, the IRE1α comprises an RNase domain, a kinase domain, or any combination thereof. In some embodiments, the kinase domain is an auto-transphosphorylation kinase domain. In some embodiments, the kinase domain comprises an ATP-binding pocket. In some embodiments, the kinase domain comprises an activation loop. In some embodiments, at least one binding site is within the RNase domain. In some embodiments, at least one binding site is within the kinase domain. In some embodiments, the at least one binding site is within the ATP-binding pocket of the kinase domain. In some embodiments. In some embodiments, the at least one binding site is within the activation loop of the kinase domain. In some embodiments, binding occurs at a first binding site. In some embodiments, the first binding site is located within the RNase domain, kinase domain, ATP-binding pocket, or activation loop. In some embodiments, the first binding site comprises at least one amino acid residue of within amino acid residues 465-977 of SEQ ID NO: 1. In some embodiments, the first binding site comprises at least one amino acid residue within amino acid residues 568-833 of SEQ ID NO: 1. In some embodiments, the first binding site comprises at least one amino acid residue within amino acid residues 577-586, 597, 599, 626, 642-643, 645, 648, 688, 692-693, 695, or 711 of SEQ ID NO: 1. In some embodiments, the first binding site comprises at least one amino acid residue within amino acid residues 710-725 or 729-736 of SEQ ID NO: 1. In some embodiments, the first binding site comprises at least one amino acid residue within amino acid residues 835-963 of SEQ ID NO: 1. In some embodiments, binding further occurs at a second binding site. In some embodiments, the second binding site is located within the RNase domain, the kinase domain, the ATP-binding pocket, or the activation loop. In some embodiments, the second binding site comprises at least one amino acid residue of within amino acid residues 465-977 of SEQ ID NO: 1. In some embodiments, the second binding site comprises at least one amino acid residue within amino acid residues 568-833 of SEQ ID NO: 1. In some embodiments, the second binding site comprises at least one amino acid residue within amino acid residues 577-586, 597, 599, 626, 642-643, 645, 648, 688, 692-693, 695, or 711 of SEQ ID NO: 1. In some embodiments, the second binding site comprises at least one amino acid residue within amino acid residues 710-725 or 729-736 of SEQ ID NO: 1. In some embodiments, the second binding site comprises at least one amino acid residue within amino acid residues 835-963 of SEQ ID NO: 1. In some embodiments, binding occurs when the IRE1α is in a homo-dimerized conformation. In some embodiments, binding occurs when the IRE1α is in an oligomerized conformation. In some embodiments, binding occurs when the IRE1α is in a non-oligomerized or non-dimerized conformation. In some embodiments, binding occurs when the IRE1α is in an ATP-bound state. In some embodiments, binding occurs when the IRE1α is in a non-ATP-bound state. In some embodiments, the compound selectively binds to a first IRE1a. In some embodiments, selectively binding to the first IRE1α blocks dimerization of the first IRE1α to a second IRE a. In some embodiments, selectively binding to the first IRE1α blocks auto-transphosphorylation of the first IRE1a. In some embodiments, selectively binding to the first IRE1α blocks auto-transphosphorylation of a second IRE1α to which the first IRE1α is dimerized. In some embodiments, selectively binding to the first IRE1α blocks activation of the first IRE1a. In some embodiments, selectively binding to the first IRE1α blocks activation a second IRE1α to which the first IRE1α is dimerized. In some embodiments, selectively binding to the first IRE1α blocks kinase activity of the first IRE1a. In some embodiments, selectively binding to the first IRE1α blocks kinase activity of a second IRE1α to which the first IRE1α is dimerized. In some embodiments, selectively binding to the first IRE1α blocks RNase activity of the first IRE1a. In some embodiments, selectively binding to the first IRE1α blocks RNase activity of a second IRE1α to which the first IRE1α is dimerized.

In another aspect, provided herein is a compound that selectively binds a first IRE1α at two or more sites, wherein when the compound is bound to the first IRE1α protein, the compound binds to an ATP-binding pocket of the first IRE1α and blocks the binding of ATP to the first IRE1α. In some embodiments, the ATP binding pocket is comprised within a kinase domain. In some embodiments, the ATP binding pocket is comprised within amino acid residues 465-977 of SEQ ID NO: 1 In some embodiments, the ATP binding pocket is comprised within amino acid residues 568-833 of SEQ ID NO: 1. In some embodiments, the ATP binding pocket comprises one or more of amino acid resides 577-586, 597, 599, 626, 642-643, 645, 648, 688, 692-693, 695, or 711 of SEQ ID NO: 1.

In another aspect, provided herein is a pharmaceutical composition comprising any one of the compounds described herein, or a pharmaceutically acceptable salt or solvate thereof. In some embodiments, the pharmaceutical composition further comprises one or more pharmaceutically acceptable excipients.

In another aspect, provided herein is a method for treating or ameliorating the effects of a disease associated with altered IRE1 signaling, the method comprising administering to a subject in need thereof a pharmaceutical composition, wherein the pharmaceutical composition comprises the compound of any one of the compounds described herein. In some embodiments, the disease is cancer. In some embodiments, the cancer is a solid cancer or a hematologic cancer.

In some embodiments, the cancer is ovarian cancer, breast cancer, or triple negative breast cancer (TNBC).

In another aspect, provided herein is a method for treating or ameliorating a cell proliferative disorder, the method comprising administering a pharmaceutical composition comprising a compound, or a pharmaceutically acceptable salt, or solvate thereof, that selectively binds to at least one amino acid residue of a IRE1 family protein comprising an RNase domain and kinase domain. In some embodiments, the IRE1 family protein is IRE1α. In some embodiments, the compound binds to an ATP-binding site of IRE1α. In some embodiments, the cell proliferative disorder is cancer. In some embodiments, the cancer is a solid cancer or a hematologic cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Certain Terminology

Figure 1:
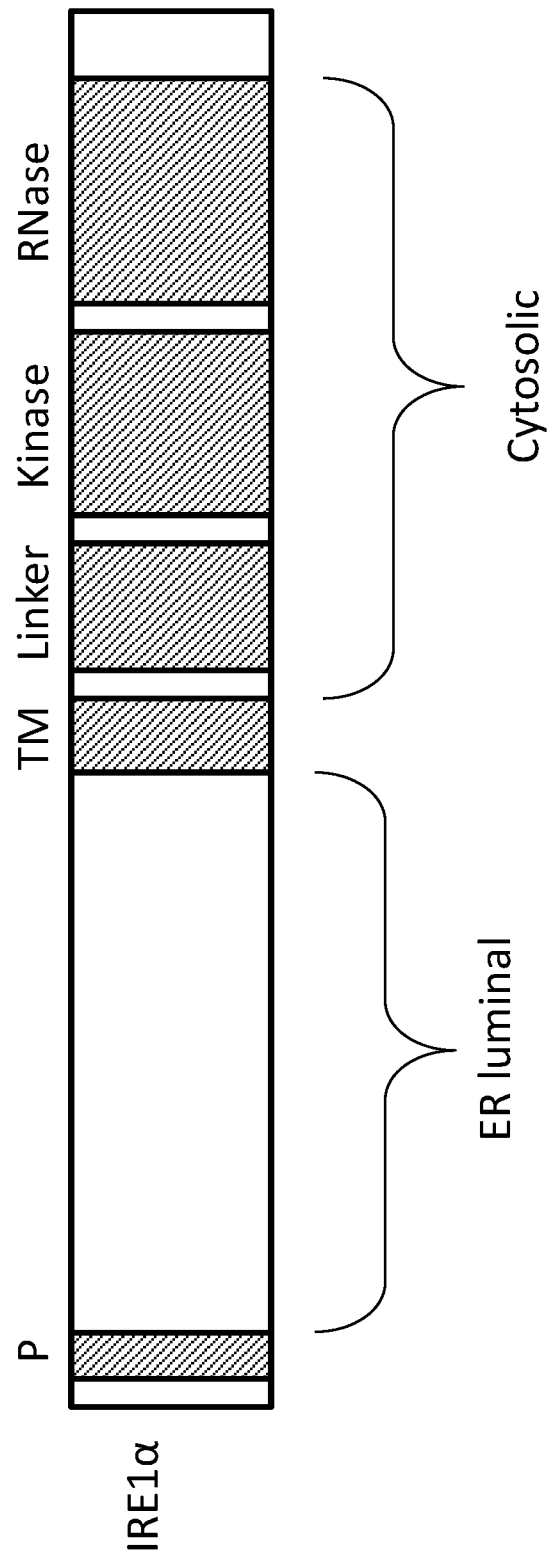
FIG. 1 shows an example diagram of the domain structure of IRE1α. A signal peptide (P) and transmembrane (TM) region are indicated.
Figure 2A:
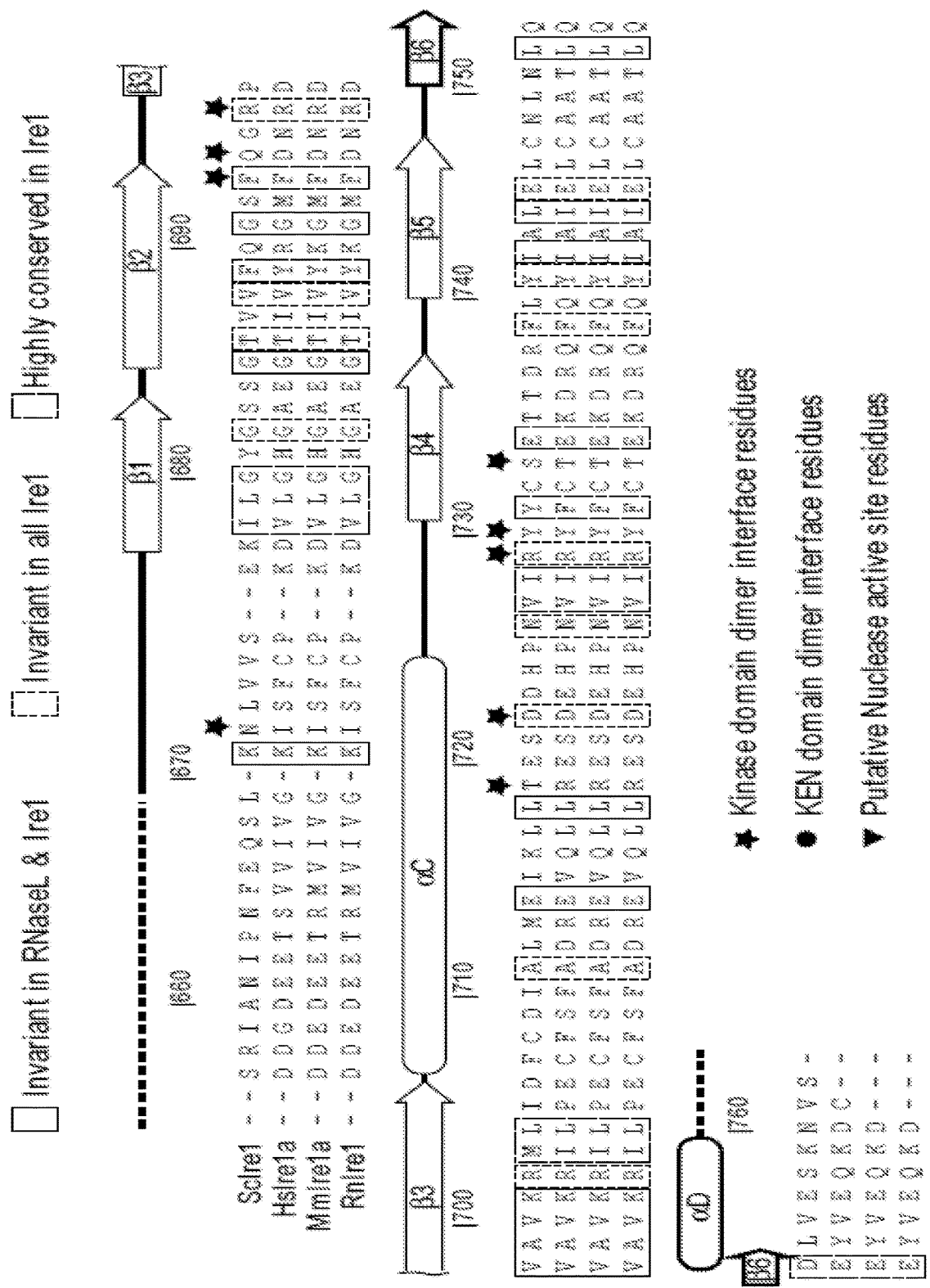
FIGS. 2A-2E shows an example alignment of the C-terminal half IRE1 orthologues from yeast (ScIre1) (SEQ ID NO: 4), human (HsIre1) (SEQ ID NO: 5), mouse (MmIre1) (SEQ ID NO: 6), and rat (RnIRE1) (SEQ ID NO: 7). Stars indicate kinase domain dimer interface residues. Circles indicate Kinase extension nuclease (KEN) domain dimer interface residues. Triangles indicate putative nuclease active site residues. Yellow highlighted residues are highly conserved in Ire1 orthologues. Green highlighted residues are invariant in all analyzed Ire1 orthologues. Blue highlighted residues are invariant in analyzed RNaseL and Ire1 orthologues.
Figure 2B:
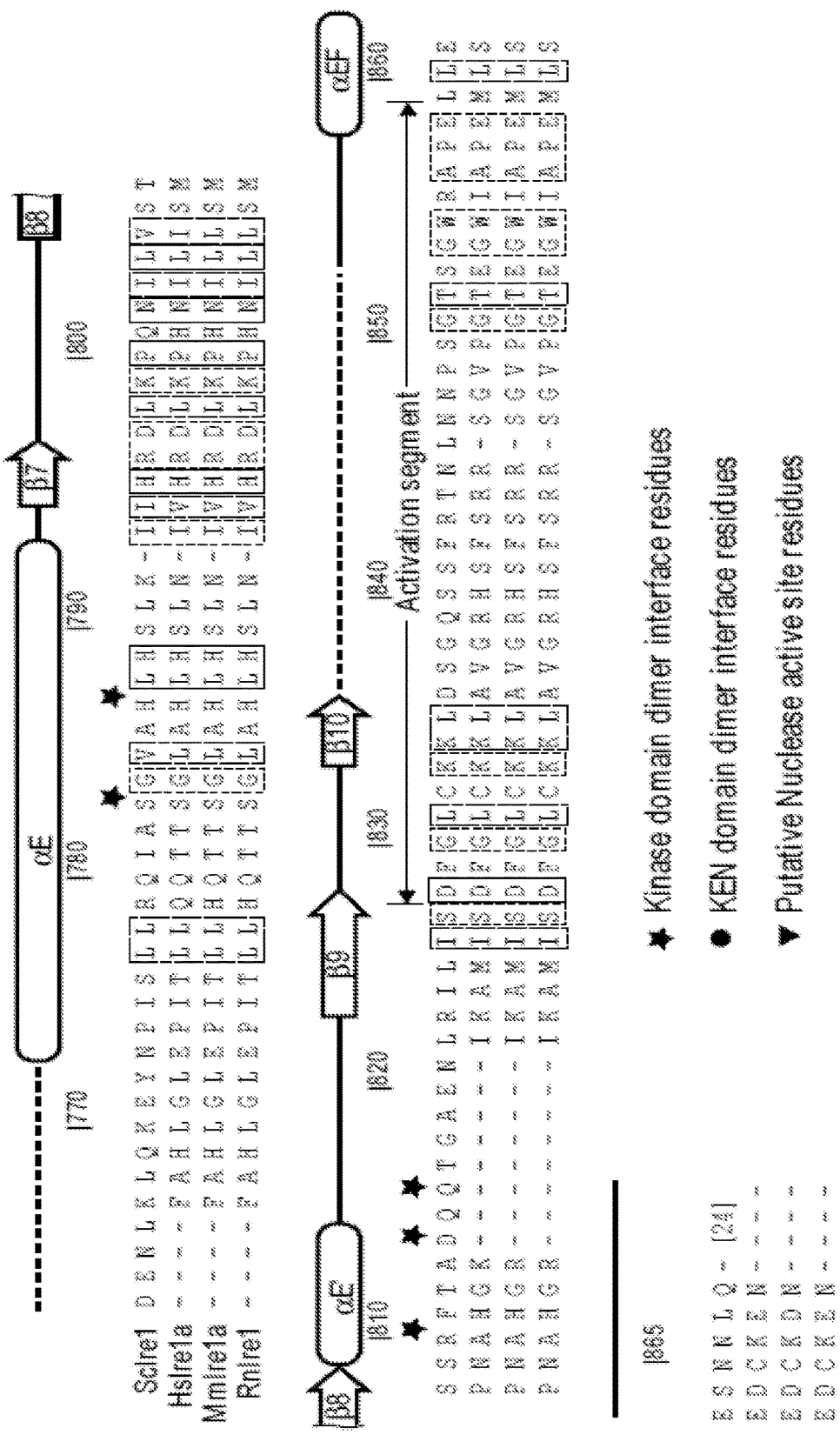
Figure 2C:
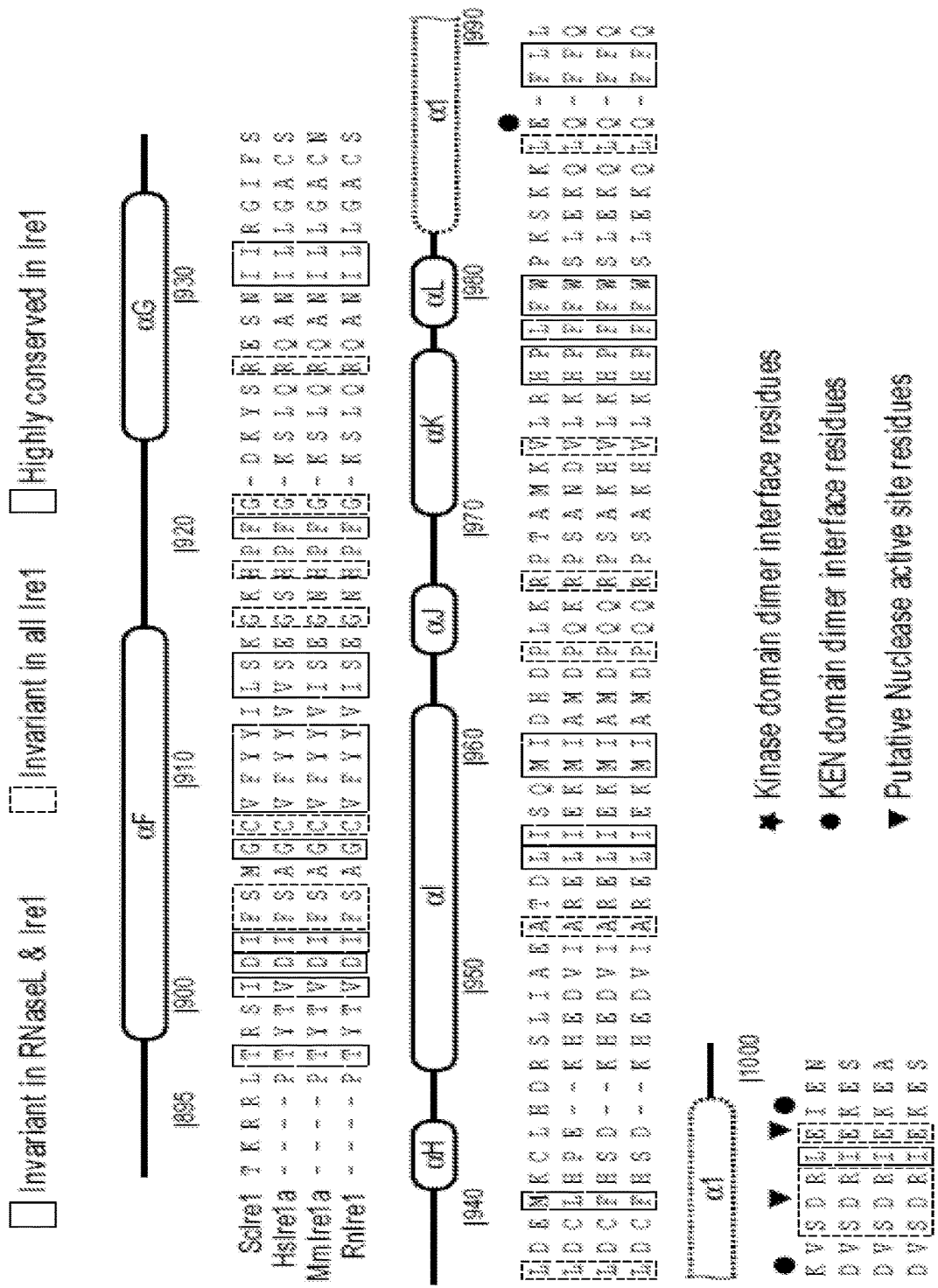
Figure 2D:
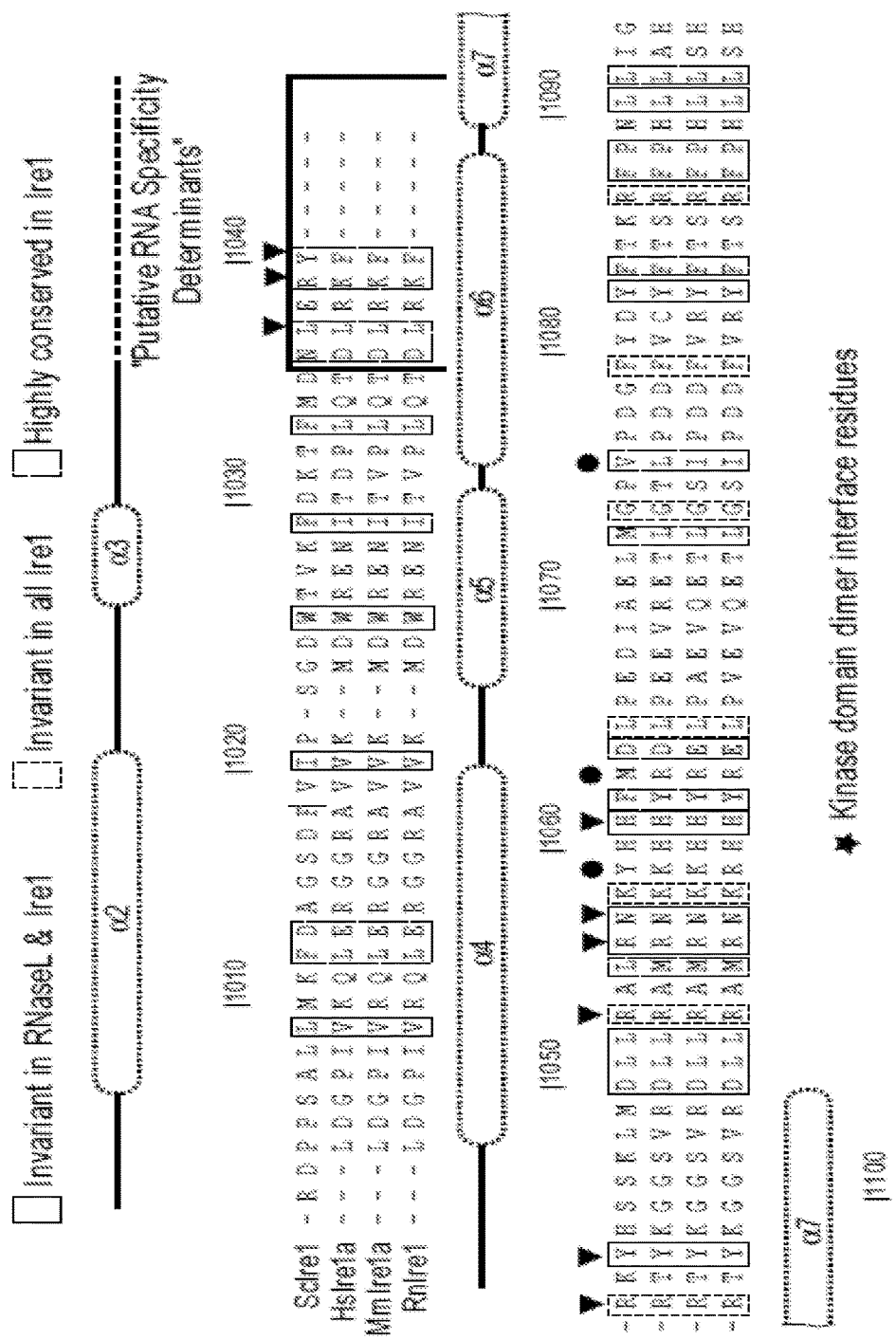
Figure 2E:
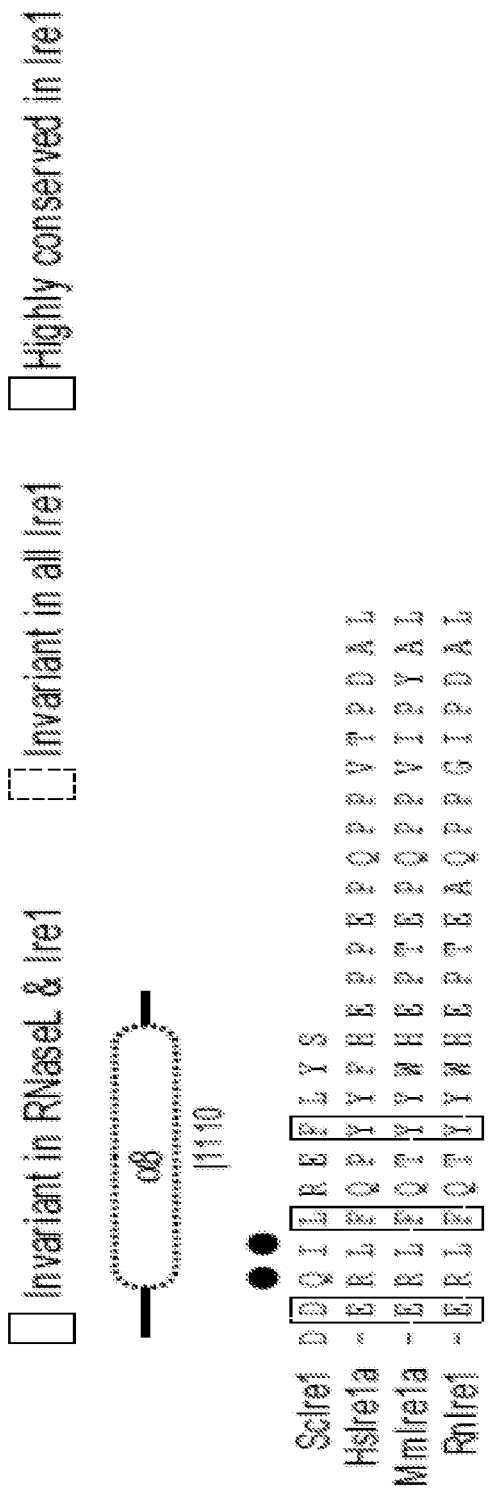

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl.

In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a C$_6$-C$_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. In some embodiments, cycloalkyl groups include groups having from 3 to 10 ring atoms. In some embodiments, cycloalkyl groups include groups having from 3 to 6 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a C$_3$-C$_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "cycloalkylene" refers to a monocyclic or polycyclic aliphatic, non-aromatic divalent radical, wherein each of the atoms forming the ring (i.e. skeletal atoms) is a carbon atom. In some embodiments, cycloalkylene are spirocyclic or bridged compounds. In some embodiments, cycloalkylenes are optionally fused with an aromatic ring, and the point of attachment is at a carbon that is not an aromatic ring carbon atom. In some embodiments, cycloalkylene groups include groups having from 3 to 10 ring atoms. In some embodiments, cycloalkylene groups include groups having from 3 to 6 ring atoms.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoralkyl is a C$_1$-C$_6$fluoroalkyl.

The term "fluoroalkyl" refers to an alkyl in which one or more hydrogen atoms are replaced by a fluorine atom. In one aspect, a fluoralkyl is a C$_1$-C$_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a C$_1$-C$_6$heteroalkyl.

The term "heteroalkylene" refers to an alkylene group in which one or more skeletal atoms of the alkylene are selected from an atom other than carbon, e.g., oxygen, nitrogen (e.g. —NH—, —N(alkyl)-, sulfur, or combinations thereof. In some embodiments, a heteroalkylene is attached to the rest of the molecule at a carbon atom of the heteroalkylene. In one aspect, a heteroalkylene is a C$_1$-C$_6$heteroalkylene.

As used herein, the term "heteroatom" refers to an atom of any element other than carbon or hydrogen. In some embodiments, the heteroatom is nitrogen, oxygen, or sulfur. In some embodiments, the heteroatom is nitrogen or oxygen. In some embodiments, the heteroatom is nitrogen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is a spirocyclic or bridged compound. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —CH$_2$N(alkyl)$_2$, —N(alkyl)$_2$, —OH, —CO$_2$H, —CO$_2$alkyl, —CH$_2$NH$_2$, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —CH$_2$NH$_2$, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O) C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CH$_2$NH$_2$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

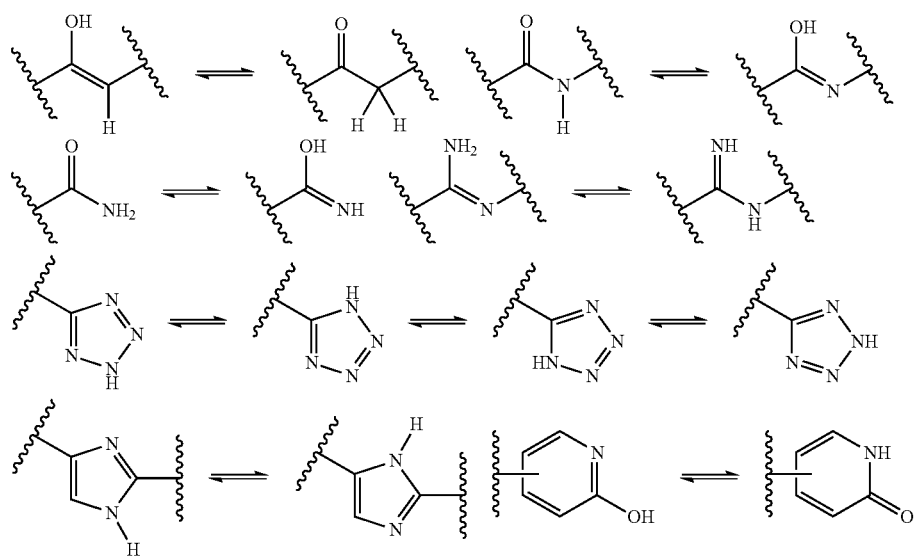

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Compounds

Compounds described herein, including pharmaceutically acceptable salts, and pharmaceutically acceptable solvates thereof, that modulate IRE1 mediated signaling, directly or indirectly.

Provided herein is a compound of Formula (I), or a pharmaceutically acceptable salt, or solvate thereof:

Formula (I)

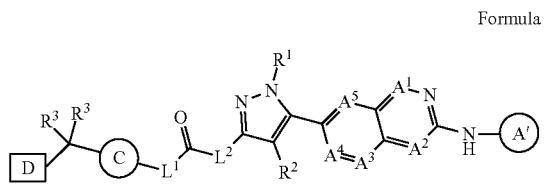

wherein,

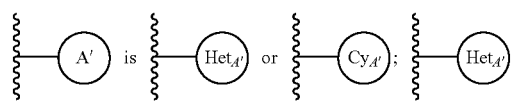

is an optionally substituted $C_3$-$C_{10}$ heterocyclyl containing at least one N, O, S, S(=O), or S(=O)$_2$; wherein if

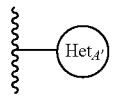

is substituted, then

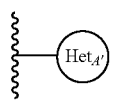

is substituted with 0-3 $R^5$;

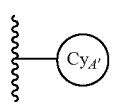

is a substituted $C_3$-$C_{10}$ cycloalkyl that is substituted with 1-3$R^4$ and 0-3$R^5$;
  each $R^4$ is independently —OR$^6$, —SR$^6$, —S(=O)R$^7$, —S(=O)$_2$R$^7$, or —N(R$^6$)$_2$;
  each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
$A^1$ is N or CR$^A$; $A^2$ is N or CR$^A$; $A^3$ is N or CR$^A$; $A^4$ is N or CR$^A$; $A^5$ is N or CR$^A$;
each R$^A$ is independently H or optionally substituted $C_1$-$C_6$alkyl;
R$^1$ and R$^2$ are each independently H or optionally substituted $C_1$-$C_6$alkyl;
L$^1$ and L$^2$ are each independently —CHY—, —CH$_2$— or —NH—;
Y is optionally substituted $C_1$-$C_6$alkyl;

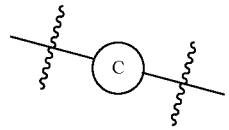

is optionally substituted aryl or optionally substituted heteroaryl, wherein if

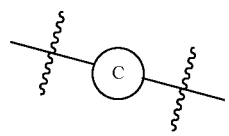

is substituted, then

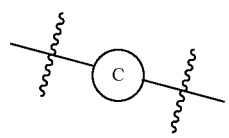

is substituted with 0-4 $R^c$;
  each $R^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{10}$C(=O)R$^{11}$, —NR$^{10}$C(=O)OR$^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
  each $R^3$ is independently H or optionally substituted $C_1$-$C_6$alkyl;

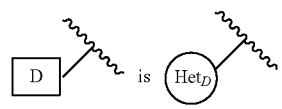

or L$^D$;

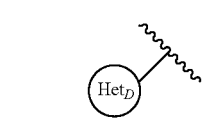

is optionally substituted heterocyclyl containing at least one N atom; wherein if

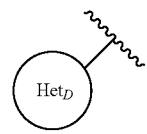

is substituted, then

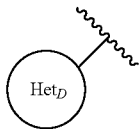

is substituted with 0-4 $R^D$;

$L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; wherein if $L^D$ is substituted, then $L^D$ is substituted with 0-4 $R^D$;

each $R^D$ is independently halogen, —CN, —O$R^{15}$, —S$R^{15}$, —S(=O)$R^{16}$, —S(=O)$_2$$R^{16}$, —S(=O)$_2$N($R^{15}$)$_2$, —N$R^{15}$S(=O)$_2$$R^{16}$, —C(=O)$R^{16}$, —OC(=O)$R^{16}$, —CO$_2$$R^{15}$, —OCO$_2$$R^{16}$, —N($R^{15}$)$_2$, —OC(=O)N($R^{15}$)$_2$, —N$R^{15}$C(=O)$R^{16}$, —N$R^{15}$C(=O)O$R^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{12}$ and $R^{13}$ is independently H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

In some embodiments,

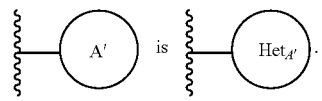

In some embodiments,

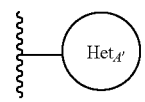

is optionally substituted $C_4$-$C_7$ heterocyclyl containing at least one N, O, S, S(=O), or S(=O)$_2$; wherein if

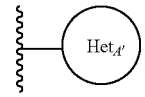

is substituted, then

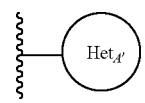

is substituted with 0-3 $R^5$.

In some embodiments, is

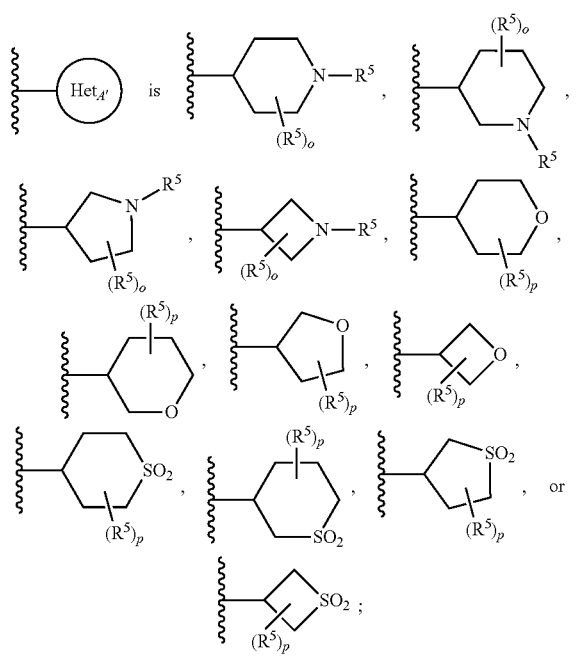

o is 0, 1, or 2; and p is 0, 1, 2, or 3.

In some embodiments,

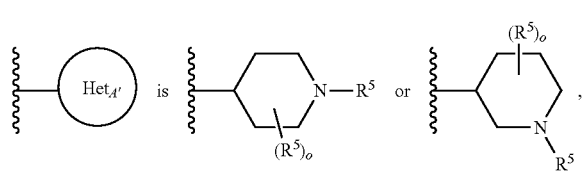

and o is 0, 1, or 2.

In some embodiments,

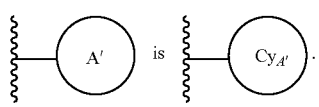

In some embodiments,

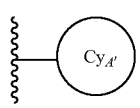

is substituted $C_4$-$C_7$ cycloalkyl that is substituted with 1-3$R^4$ and 0-3$R^5$.

In some embodiments,

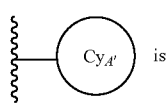

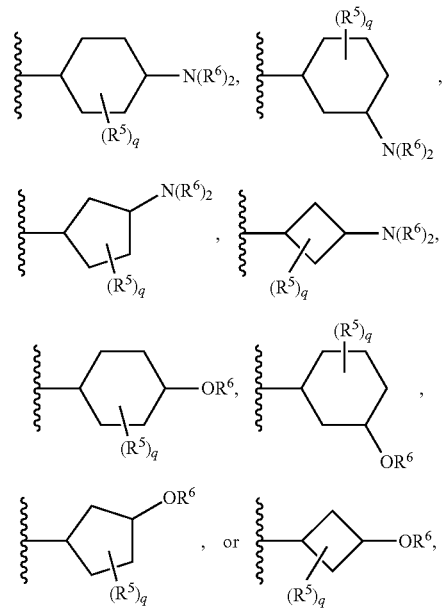

and
q is 0, 1, 2, or 3.

In some embodiments,

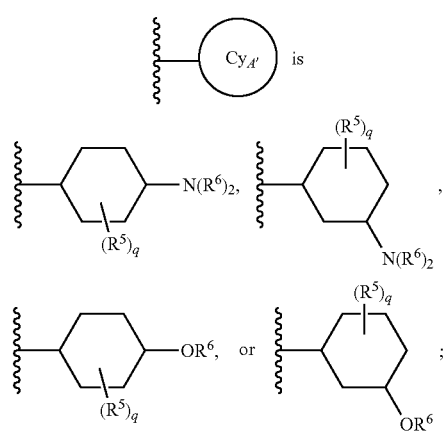

and
q is 0, 1, 2, or 3.

In some embodiments, $A^1$ is CH; $A^2$ is N or $CR^A$; $A^3$ is N or $CR^A$; $A^4$ is CH; and $A^5$ is CH. In some embodiments, $A^2$ is N. In some embodiments, $A^2$ is $CR^A$. In some embodiments, $A^3$ is $CR^A$. In some embodiments, $R^A$ is optionally substituted $C_1$-$C_6$alkyl. In some embodiments, $R^A$ is methyl, ethyl, propyl or butyl. In some embodiment, $R^A$ is ethyl, propyl or butyl. In some embodiments, $R^1$ is optionally substituted $C_1$-$C_6$alkyl. In some embodiments, $R^1$ is methyl. In some embodiments, $R^2$ is H. In some embodiments, $L^1$ and $L^2$ are each —NH—. In some embodiments, $L^1$ is —CH$_2$— and $L^2$ is —NH—. In some embodiments, $L^1$ is —NH— and $L^2$ is —CH$_2$—. In some embodiments, $L^1$ is —CHY—. In some embodiments, $L^2$ is —CHY—. In some embodiments, Y is optionally substituted $C_1$-$C_3$alkyl.

In some embodiments,

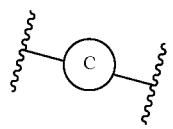

is optionally substituted aryl, wherein if

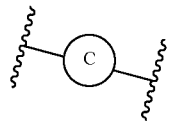

is substituted, then

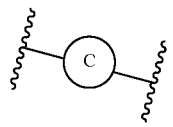

is substituted with 0-4 $R^c$.

In some embodiments,

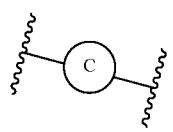

is optionally substituted heteroaryl wherein if

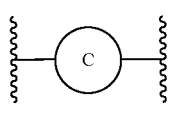

is substituted, then

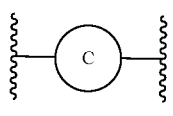

is substituted with 0-4 $R^c$.

In some embodiments,

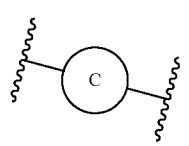 is 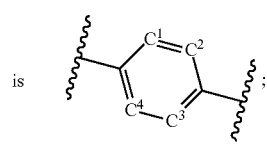 ;

$C^1$ is N or $CR^C$; $C^2$ is N or $CR^C$; $C^3$ is N or $CR^C$; and $C^4$ is N or $CR^C$.

In some embodiments, $C^1$ is $CR^C$; $C^2$ is $CR^C$; $C^3$ is $CR^C$; and $C^4$ is $CR^C$. In some embodiments, $C^1$ is $CR^C$; $C^2$ is CH; $C^3$ is CH; and $C^4$ is CH. In some embodiments, $R^c$ is optionally substituted $C_1$-$C_6$fluoroalkyl. In some embodiments, $R^c$ is —$CF_3$. In some embodiments, each $R^3$ is independently H.

In some embodiments,

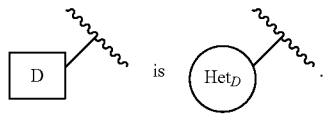

In some embodiments,

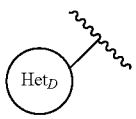

is optionally substituted heterocyclyl containing at least one N atom; and if

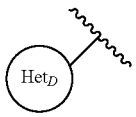

is substituted, then

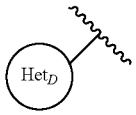

is substituted with 0-4 $R^D$.

In some embodiments,

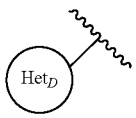

is optionally substituted heterocyclyl containing one N atom; and if

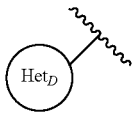

is substituted, then

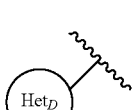

is substituted with 0-4 $R^D$.

In some embodiments,
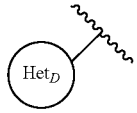
is optionally substituted heterocyclyl containing two N atoms; and if
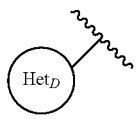
is substituted, then
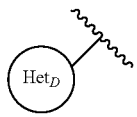
is substituted with 0-4 $R^D$.
In some embodiments, is
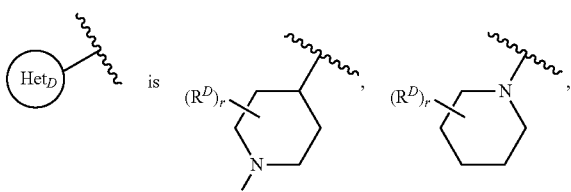
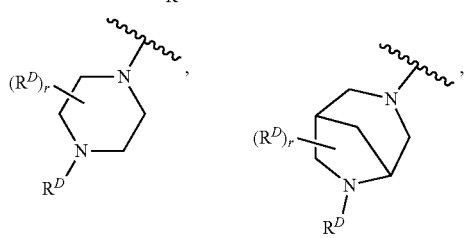
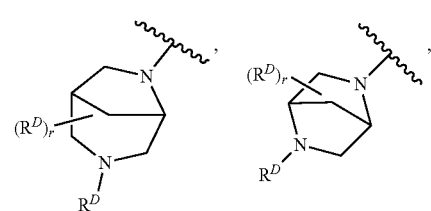
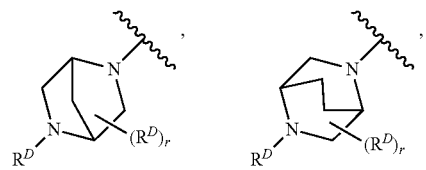
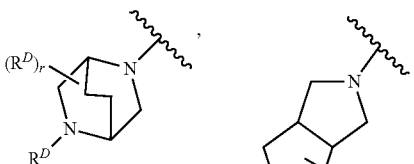
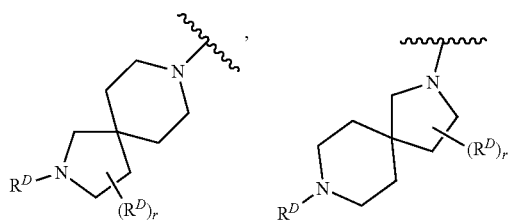
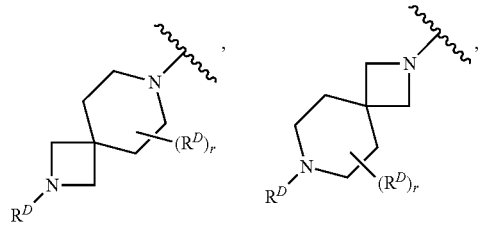
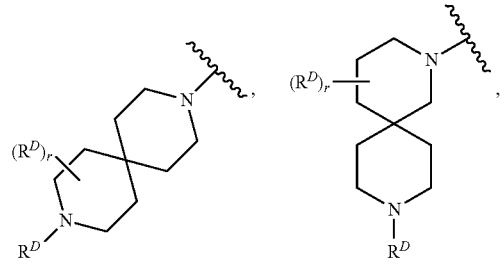
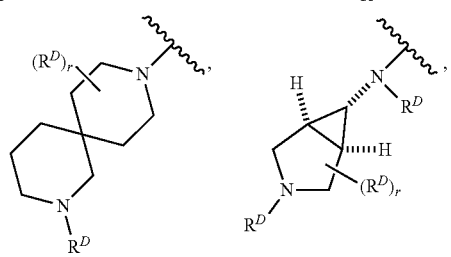
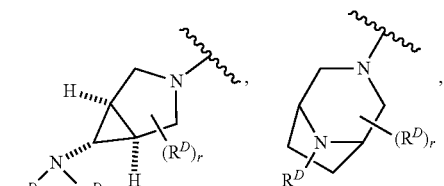
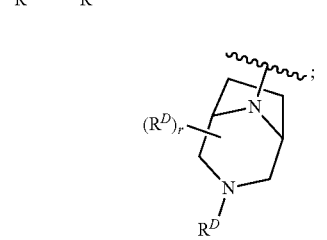
and
r is 0, 1, or 2.

In some embodiments,

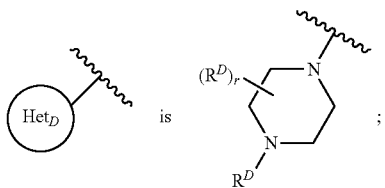 is 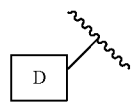

and r is 0, 1, or 2.

In some embodiments,

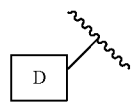

is $L^D$

In some embodiments, $L^D$ is —N(R$^{12}$)-(optionally substituted C$_1$-C$_6$ alkyl), —N(R$^{13}$)-(optionally substituted C$_1$-C$_6$ alkylene)-N(R$^{14}$)$_2$ or -(optionally substituted C$_1$-C$_6$ alkylene)-N(R$^{14}$)$_2$; and if $L^D$ is substituted, then $L^D$ is substituted with 0-4 R$^D$. In some embodiments, $L^D$ is —N(R$^{12}$)-(optionally substituted C$_1$-C$_6$ alkyl), and if $L^D$ is substituted, then $L^D$ is substituted with 0-4 R$^D$. In some embodiments, $L^D$ is —N(R$^{12}$)—CH$_2$—CH$_2$—CH$_2$—CH$_3$, —N(R$^{12}$)—CH$_2$—CH$_2$—CH$_3$, —N(R$^{12}$)—CH$_2$—CH$_3$, or —N(R$^{12}$)—CH$_3$. In some embodiments, R$^{12}$ is H or C$_1$-C$_4$alkyl. In some embodiments, R$^{12}$ is H or C$_3$-C$_4$alkyl. In some embodiments, $L^D$ is —N(R$^{13}$)-(optionally substituted C$_1$-C$_6$ alkylene)-N(R$^{14}$)$_2$, and if $L^D$ is substituted, then $L^D$ is substituted with 0-4 R$^D$. In some embodiments, $L^D$ is —N(R$^{13}$)—CH$_2$—CH$_2$—CH$_2$—CH$_2$—N(R$^{14}$)$_2$, —N(R$^{13}$)—CH$_2$—CH$_2$—CH$_2$—N(R$^{14}$)$_2$, —N(R$^{13}$)—CH$_2$—CH$_2$—N(R$^{14}$)$_2$, or —N(R$^{13}$)—CH$_2$—N(R$^{14}$)$_2$. In some embodiments, each R$^{13}$ and R$^{14}$ is independently H or C$_1$-C$_4$alkyl. In some embodiments, $L^D$ is or -(optionally substituted C$_1$-C$_6$ alkylene)-N(R$^{14}$)$_2$; and if $L^D$ is substituted, then $L^D$ is substituted with 0-4 R$^D$. In some embodiments, $L^D$ is —CH$_2$—CH$_2$—CH$_2$—CH$_2$—N(R$^{14}$)$_2$, —CH$_2$—CH$_2$—CH$_2$—N(R$^{14}$)$_2$, —CH$_2$—CH$_2$—N(R$^{14}$)$_2$, or —CH$_2$—N(R$^{14}$)$_2$. In some embodiments, each R$^{14}$ is independently H or C$_1$-C$_4$alkyl.

In some embodiments, the compound has the structure of formula (Ia)

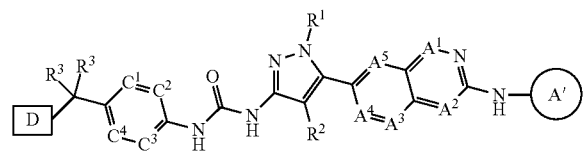

(Ia)

wherein,

C$^1$ is N or CR$^C$; C$^2$ is N or CR$^C$; C$^3$ is N or CR$^C$; and C$^4$ is N or CR$^C$.

In some embodiments, the compound has the structure of formula (Ib)

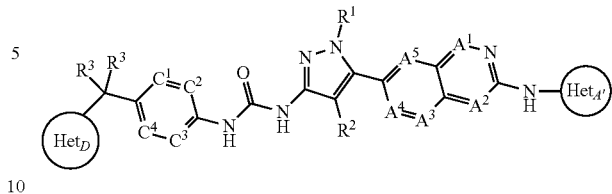

(Ib)

wherein,

C$^1$ is N or CR$^C$; C$^2$ is N or CR$^C$; C$^3$ is N or CR$^C$; and C$^4$ is N or CR$^C$.

In some embodiments, the compound has the structure of formula (Ic)

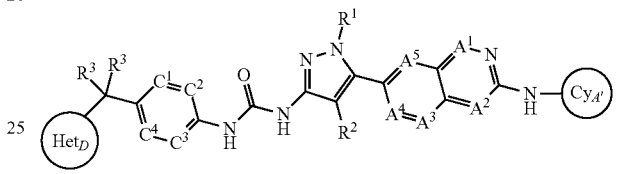

(Ic)

wherein,

C$^1$ is N or CR$^C$; C$^2$ is N or CR$^C$; C$^3$ is N or CR$^C$; and C$^4$ is N or CR$^C$.

In some embodiments, the compound has the structure of formula (Id)

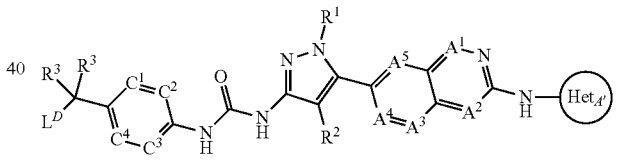

(Id)

wherein,

C$^1$ is N or CR$^C$; C$^2$ is N or CR$_C$; C$^3$ is N or CR$_C$; and C$^4$ is N or CR$_C$.

In some embodiments, the compound has the structure of formula (Ie)

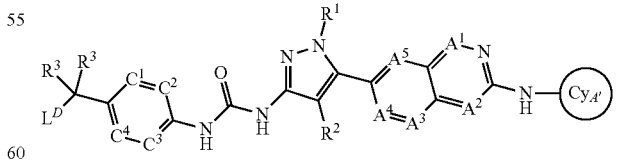

(Ie)

wherein,

C$^1$ is N or CR$^C$; C$^2$ is N or CR$^C$; C$^3$ is N or CR$^C$; and C$^4$ is N or CR$_C$.

In some embodiments, the compound has the structure of formula (If)

(If)

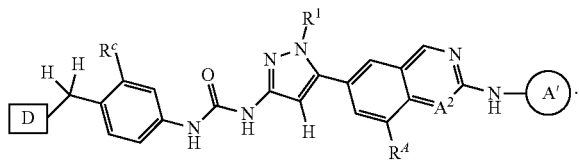

In some embodiments, the compound has the structure of formula (Ig)

(Ig)

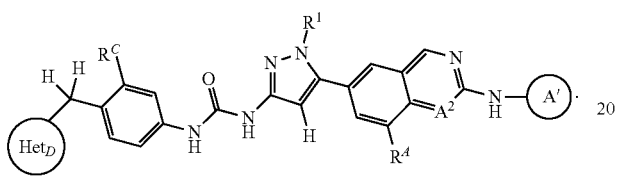

In some embodiments, the compound has the structure of formula (Ih)

(Ih)

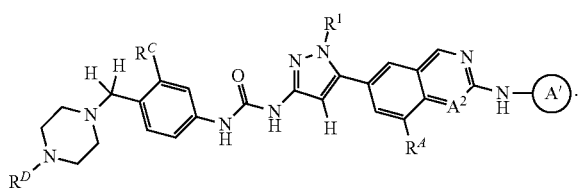

In some embodiments, the compound has the structure of formula (Ii)

(Ii)

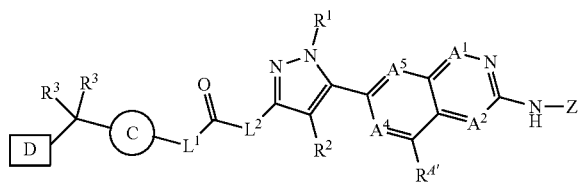

In another aspect, provided herein is a compound of Formula (II), or a pharmaceutically acceptable salt, or solvate thereof:

Formula (II)

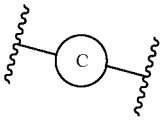

wherein
Z is H,

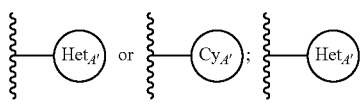

is an optionally substituted $C_3$-$C_{10}$ heterocyclyl containing at least one N, O, S, S(=O), or S(=O)$_2$; wherein if

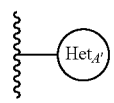

is substituted, then

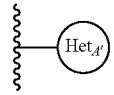

is substituted with 0-3 $R^5$;

is a substituted $C_3$-$C_{10}$ cycloalkyl that is substituted with 1-3$R^4$ and 0-3$R^5$;
each $R^4$ is independently —OR$^6$, —SR$^6$, —S(=O)R$^7$, —S(=O)$_2$R$^7$, or —N(R$^6$)$_2$;
each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
$A^1$ is N or CR$^A$; $A^2$ is N or CR$^A$; $A^4$ is N or CR$^A$; $A^5$ is N or CR$^A$;
each $R^A$ is independently H or optionally substituted $C_1$-$C_6$alkyl;
$R^{A'}$ is optionally substituted $C_1$-$C_6$alkyl;
$R^1$ and $R^2$ are each independently H or optionally substituted $C_1$-$C_6$alkyl;
$L^1$ and $L^2$ are each independently —CHY—, —CH$_2$— or —NH—;
Y is optionally substituted $C_1$-$C_6$alkyl;

is optionally substituted aryl or optionally substituted heteroaryl, wherein if is substituted, then

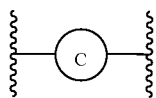

is substituted with 0-4 $R^c$;

each $R^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{10}$C(=O)R$^{11}$, —NR$^{10}$C(=O)OR$^{11}$, optionally substituted C$_1$-C$_6$alkyl, optionally substituted C$_1$-C$_6$fluoroalkyl, optionally substituted C$_1$-C$_6$heteroalkyl, optionally substituted C$_3$-C$_6$cycloalkyl, optionally substituted aryl, or optionally substituted heteroaryl;

each $R^3$ is independently H or optionally substituted C$_1$-C$_6$alkyl;

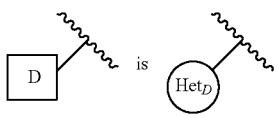

or $L^D$;

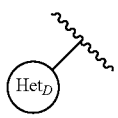

is optionally substituted heterocyclyl containing at least one N atom; wherein if

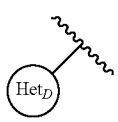

is substituted, then

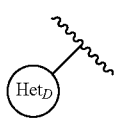

is substituted with 0-4 $R^D$;

$L^D$ is —N(R$^{12}$)-(optionally substituted C$_1$-C$_6$ alkyl), —N(R$^{13}$)-(optionally substituted C$_1$-C$_6$ alkylene)-N(R$^{14}$)$_2$ or -(optionally substituted C$_1$-C$_6$ alkylene)-N(R$^{14}$)$_2$; wherein if $L^D$ is substituted, then $L^D$ is substituted with 0-4 $R^D$;

each $R^D$ is independently halogen, —CN, —OR$^{15}$, —SR$^{15}$, —S(=O)R$^{16}$, —S(=O)$_2$R$^{16}$, —S(=O)$_2$N(R$^{15}$)$_2$, —NR$^{15}$S(=O)$_2$R$^{16}$, —C(=O)R$^{16}$, —OC(=O)R$^{16}$, —CO$_2$R$^{15}$, —OCO$_2$R$^{16}$, —N(R$^{15}$)$_2$, —OC(=O)N(R$^1$)$_2$, —NR$^{15}$C(=O)R$^{16}$, —NR$^{15}$C(=O)OR$^{16}$, optionally substituted C$_1$-C$_6$alkyl, optionally substituted C$_1$-C$_6$fluoroalkyl, optionally substituted C$_1$-C$_6$heteroalkyl, optionally substituted C$_3$-C$_6$cycloalkyl, optionally substituted aryl, or optionally substituted heteroaryl;

each $R^6$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;

each $R^8$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;

each $R^{10}$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;

each $R^{12}$ and $R^{13}$ is independently H or optionally substituted C$_1$-C$_6$alkyl;

each $R^{14}$ is independently H or optionally substituted C$_1$-C$_6$alkyl; or two $R^{14}$ are taken together with the N atom to which they are attached to form an optionally substituted heterocycle;

each $R^{15}$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle, and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

In some embodiments, Z is H. In some embodiments, Z is

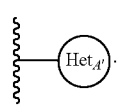

In some embodiments,

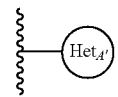

is optionally substituted $C_4$-$C_7$ heterocyclyl containing at least one N, O, S, S(=O), or S(=O)$_2$; wherein if

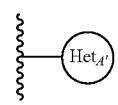

is substituted, then

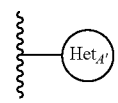

is substituted with 0-3 $R^5$.

In some embodiments, is

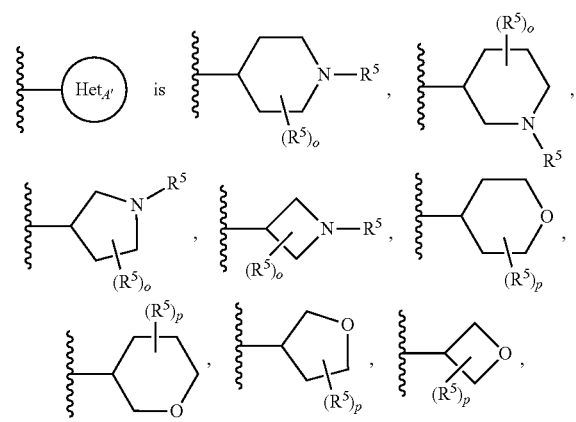

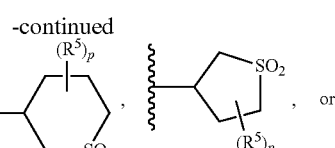

o is 0, 1, or 2; and p is 0, 1, 2, or 3.

In some embodiments,

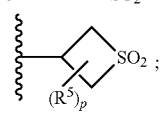

and o is 0, 1, or 2.

In some embodiments, Z is

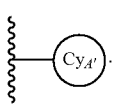

In some embodiments,

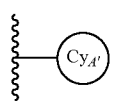

is substituted $C_4$-$C_7$ cycloalkyl that is substituted with 1-3$R^4$ and 0-3$R^5$.

In some embodiments, is

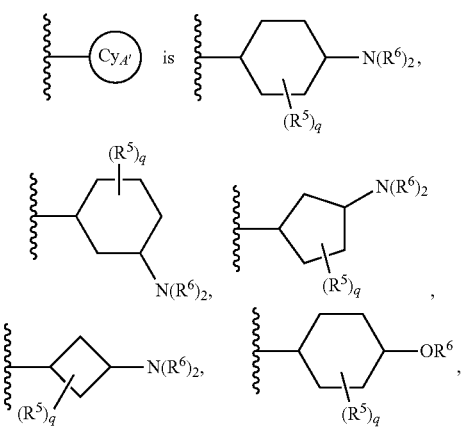

-continued

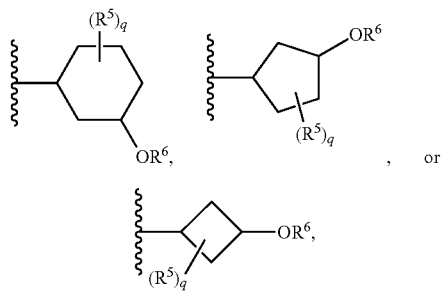

and q is 0, 1, 2, or 3.

In some embodiments,

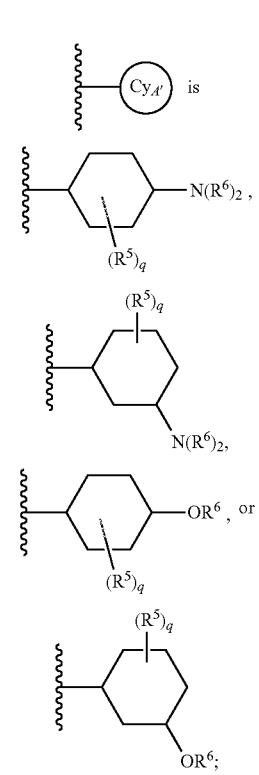

and q is 0, 1, 2, or 3.

In some embodiments, $A^1$ is CH; $A^2$ is N or $CR^A$; $A^4$ is CH; and $A^5$ is CH. In some embodiments, $A^2$ is N. In some embodiments, $A^2$ is $CR^A$. In some embodiments, $R^{A'}$ is optionally substituted $C_1$-$C_4$alkyl. In some embodiments, $R^{A'}$ is methyl, ethyl, propyl, and butyl. In some embodiments, $R^{A'}$ ethyl, propyl, and butyl. In some embodiments, $R^1$ is optionally substituted $C_1$-$C_6$alkyl. In some embodiments, $R^1$ is methyl. In some embodiments, $R^2$ is H. In some embodiments, $L^1$ and $L^2$ are each —NH—. In some embodiments, $L^1$ is —$CH_2$— and $L^2$ is —NH—. In some embodiments, $L^1$ is —NH— and $L^2$ is —$CH_2$—. In some embodiments, $L^1$ is —CHY—. In some embodiments, $L^2$ is —CHY—. In some embodiments, Y is optionally substituted $C_1$-$C_3$alkyl.

In some embodiments,

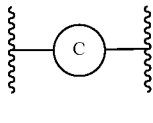

is optionally substituted aryl, wherein if

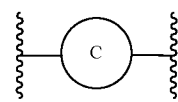

is substituted, then

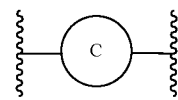

is substituted with 0-4 $R^c$.

In some embodiments,

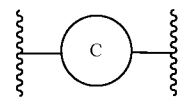

is optionally substituted heteroaryl wherein if

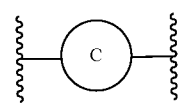

is substituted, then

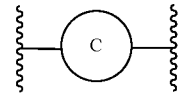

is substituted with 0-4 $R^c$.

In some embodiments,

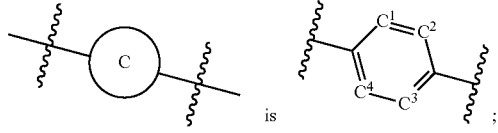

$C^1$ is N or $CR^C$; $C^2$ is N or $CR^C$; $C^3$ is N or $CR^C$; and $C^4$ is N or $CR^C$ In some embodiments, $C^1$ is $CR^C$; $C^2$ is $CR^C$; $C^3$ is $CR^C$; and $C^4$ is $CR^C$. In some embodiments, $C^1$ is $CR^C$; $C^2$ is CH; $C^3$ is CH; and $C^4$ is CH. In some embodiments, $R^c$ is optionally substituted $C_1$-$C_6$fluoroalkyl. In some embodiments, $R^c$ is —$CF_3$. In some embodiments, each $R^3$ is independently H.

In some embodiments, Z is

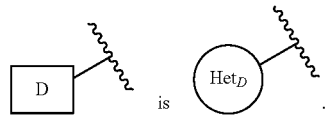

In some embodiments,

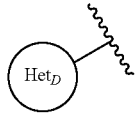

is optionally substituted heterocyclyl containing at least one N atom; and if

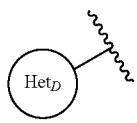

is substituted, then

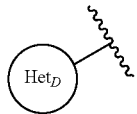

is substituted with 0-4 $R^D$.

In some embodiments,

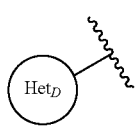

is optionally substituted heterocyclyl containing one N atom; and if

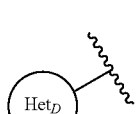

is substituted, then

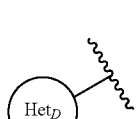

is substituted with 0-4 $R^D$.

In some embodiments,

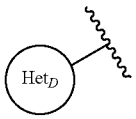

is optionally substituted heterocyclyl containing two N atoms; and if

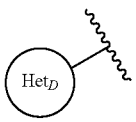

is substituted, then

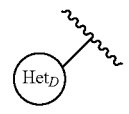

is substituted with 0-4 $R^D$.

In some embodiments,

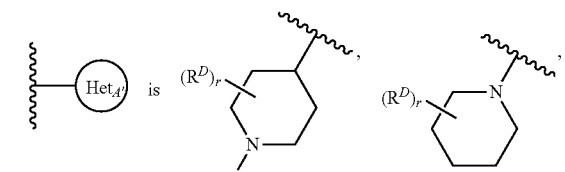

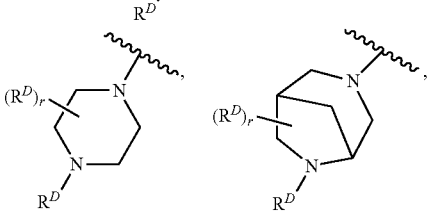

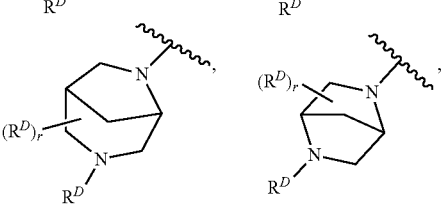

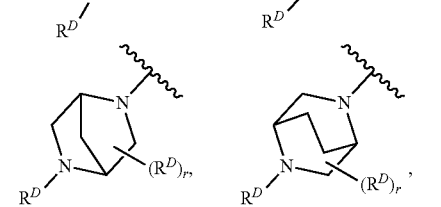

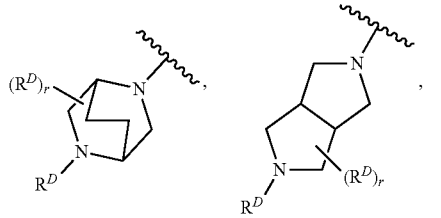

-continued

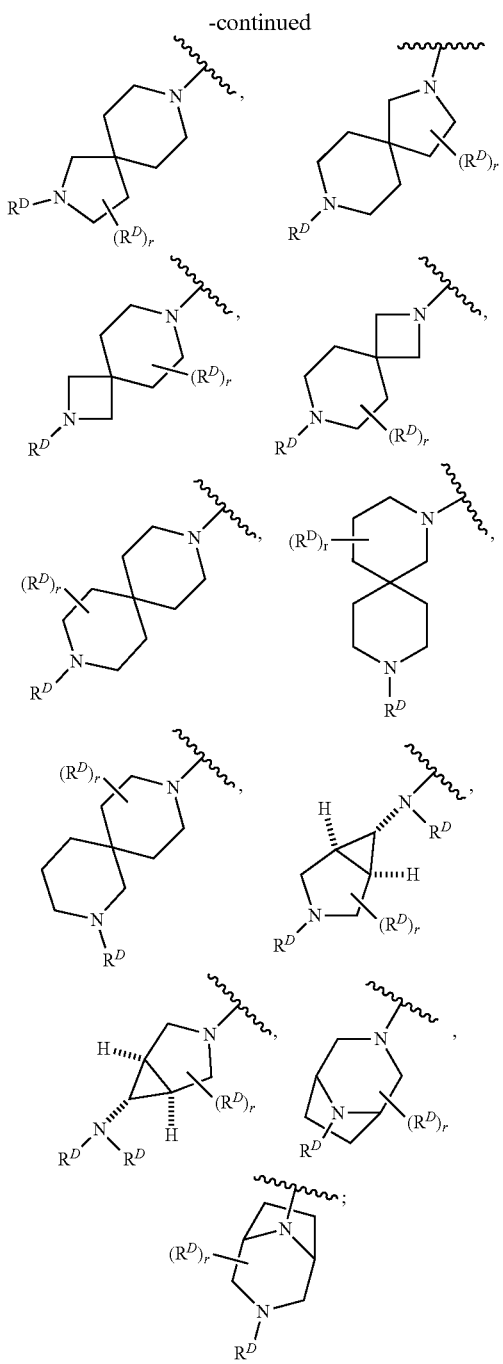

and
r is 0, 1, or 2.
In some embodiments,

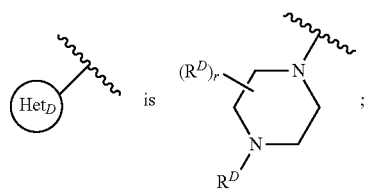

and r is 0, 1, or 2.

In some embodiments,

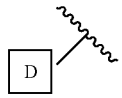

is $L^D$.

In some embodiments, $L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; and if $L^D$ is substituted, then $L^D$ is substituted with 0-4 $R^D$. In some embodiments, $L^D$ is —N($R^{12}$)-(optionally substituted $C_1$-$C_6$ alkyl), and if $L^D$ is substituted, then $L^D$ is substituted with 0-4 $R^D$. In some embodiments, $L^D$ is —N($R^{12}$)—CH$_2$—CH$_2$—CH$_2$—CH$_3$, —N($R^{12}$)—CH$_2$—CH$_2$—CH$_3$, —N($R^{12}$)—CH$_2$—CH$_3$, or —N($R^{12}$)—CH$_3$. In some embodiments, $R^{12}$ is H or $C_1$-$C_4$alkyl. In some embodiments, $R^{12}$ is H or $C_3$-$C_4$alkyl. In some embodiments, $L^D$ is —N($R^{13}$)-(optionally substituted $C_1$-$C_6$ alkylene)-N($R^{14}$)$_2$, and if $L^D$ is substituted, then $L^D$ is substituted with 0-4 $R^D$. In some embodiments, $L^D$ is —N($R^{13}$)—CH$_2$—CH$_2$—CH$_2$—CH$_2$—N($R^{14}$)$_2$, —N($R^{13}$)—CH$_2$—CH$_2$—CH$_2$—N($R^{14}$)$_2$, —N($R^{13}$)—CH$_2$—CH$_2$—N($R^{14}$)$_2$, or —N($R^{13}$)—CH$_2$—N($R^{14}$)$_2$. In some embodiments, each $R^{13}$ and $R^{14}$ is independently H or $C_1$-$C_4$alkyl. In some embodiments, $L^D$ is or -(optionally substituted $C_1$-$C_6$ alkylene)-N($R^{14}$)$_2$; and if $L^D$ is substituted, then $L^D$ is substituted with 0-4 $R^D$. In some embodiments, $L^D$ is —CH$_2$—CH$_2$—CH$_2$—CH$_2$—N($R^{14}$)$_2$, —CH$_2$—CH$_2$—CH$_2$—N($R^{14}$)$_2$, —CH$_2$—CH$_2$—N($R^{14}$)$_2$, or —CH$_2$—N($R^{14}$)$_2$. In some embodiments, each $R^{14}$ is independently H or $C_1$-$C_4$alkyl.

In some embodiments, the compound has the structure of formula (IIa)

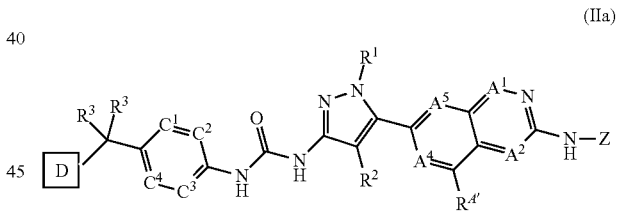

(IIa)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIb)

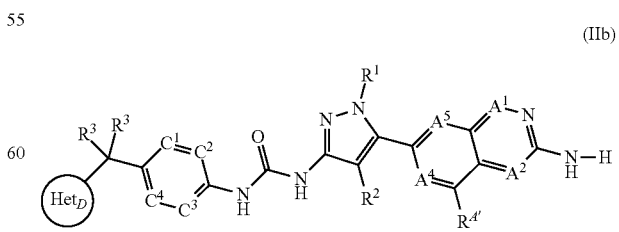

(IIb)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIc)

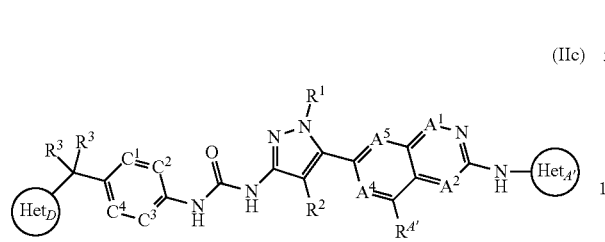
(IIc)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IId)

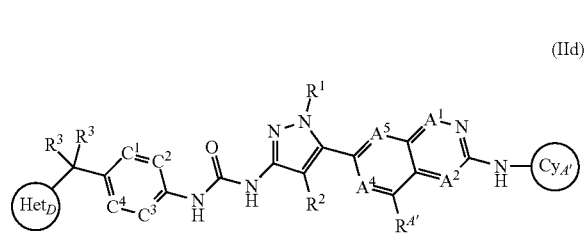
(IId)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIe)

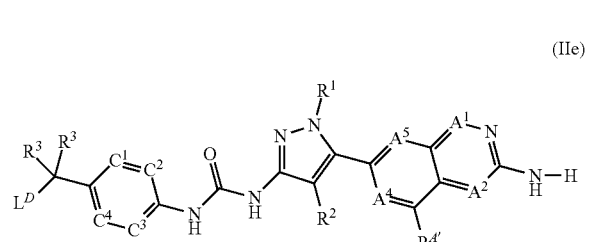
(IIe)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIf)

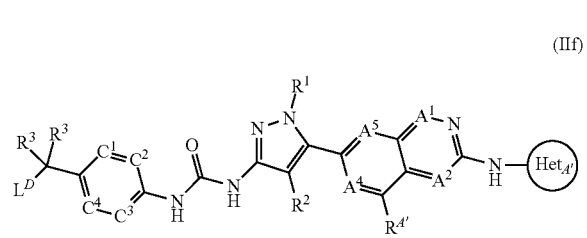
(IIf)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIg)

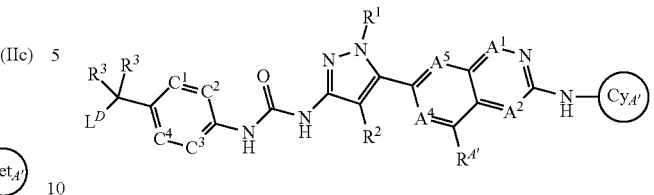
(IIg)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIh)

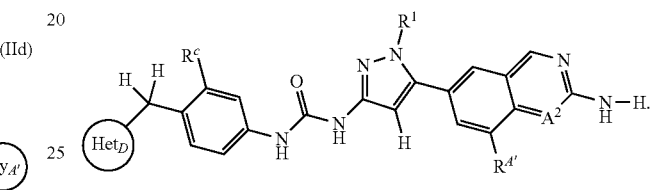
(IIh)

In some embodiments, the compound has the structure of formula (IIi)

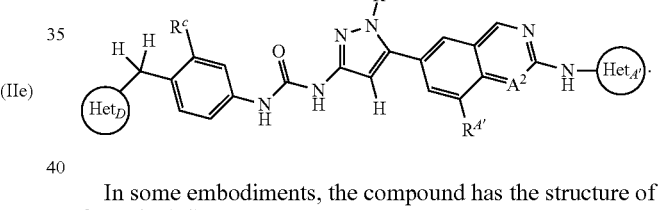
(IIi)

In some embodiments, the compound has the structure of formula (IIj)

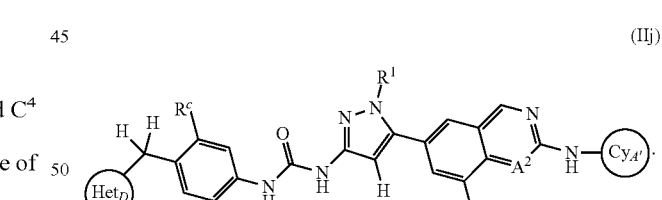
(IIj)

In some embodiments, the compound has the structure of formula (IIk)

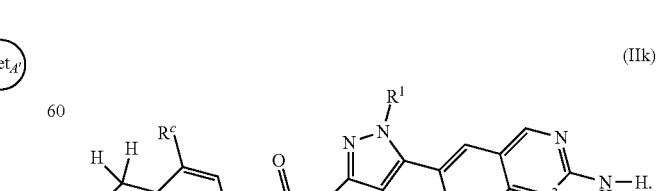
(IIk)

In some embodiments, the compound has the structure of formula (III)

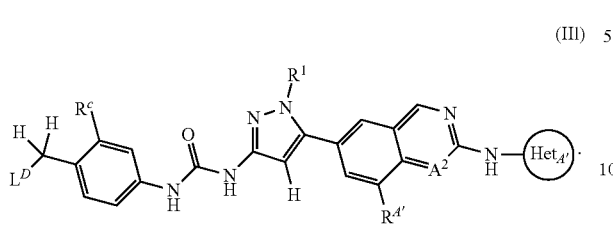
(III)

In some embodiments, the compound has the structure of formula (IIm)

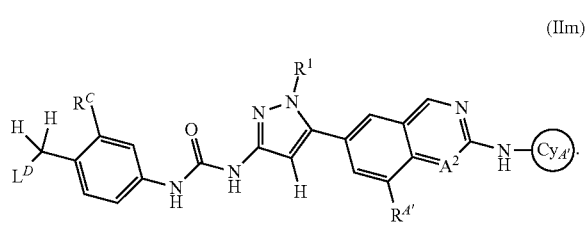
(IIm)

In another aspect, provided herein is a compound of Formula (III), or a pharmaceutically acceptable salt, or solvate thereof:

Formula (III)

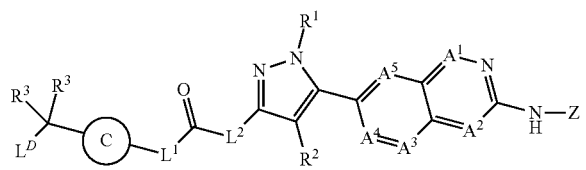

wherein,
Z is H

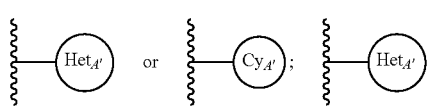

is an optionally substituted $C_3$-$C_{10}$ heterocyclyl containing at least one N, O, S, S(=O), or S(=O)$_2$; wherein if

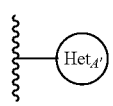

is substituted, then

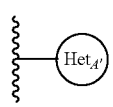

is substituted with 0-3 $R^5$;

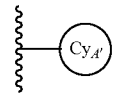

is a substituted $C_3$-$C_{10}$ cycloalkyl that is substituted with 1-3$R^4$ and 0-3$R^5$;
each $R^4$ is independently —OR$^6$, —SR$^6$, —S(=O)R$^7$, —S(=O)$_2$R$^7$, or —N(R$^6$)$_2$;
each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
$A^1$ is N or CR$^A$; $A^2$ is N or CR$^A$; $A^3$ is N or CR$^A$; $A^4$ is N or CR$^A$; $A^5$ is N or CR$^A$;
each $R^A$ is independently H or optionally substituted $C_1$-$C_6$alkyl;
$R^1$ and $R^2$ are each independently H or optionally substituted $C_1$-$C_6$alkyl;
$L^1$ and $L^2$ are each independently —CHY—, —CH$_2$— or —NH—;
Y is optionally substituted $C_1$-$C_6$alkyl;

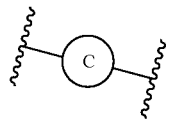

is optionally substituted aryl or optionally substituted heteroaryl, wherein if

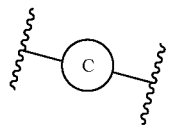

is substituted, then

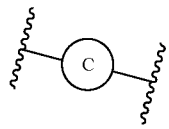

is substituted with 0-4 $R^c$;
each $R^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{10}$C(=O)R$^{11}$, —NR$^{10}$C(=O)OR$^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^3$ is independently H or optionally substituted $C_1$-$C_6$alkyl; $L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; wherein if $L^D$ is substituted, then $L^D$ is substituted with 0-4 $R^D$;

each $R^D$ is independently halogen, —CN, —OR$^{15}$, —SR$^{15}$, —S(=O)R$^{16}$, —S(=O)$_2$R$^{16}$, —S(=O)$_2$N(R$^{15}$)$_2$, —NR$^{15}$S(=O)$_2$R$^{16}$, —C(=O)R$^{16}$, —OC(=O)R$^{16}$, —CO$_2$R$^{15}$, —OCO$_2$R$^{15}$, —N(R$^{15}$)$_2$, —OC(=O)N(R$^{15}$)$_2$, —NR$^{15}$C(=O)R$^{16}$, —NR$^{15}$C(=O)OR$^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle, each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle, each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle, each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

$R^{12}$ is independently H or optionally substituted $C_3$-$C_6$alkyl;

$R^{13}$ is H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle, and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

In some embodiments, Z is H. In some embodiments, Z is

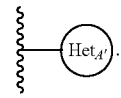

In some embodiments,

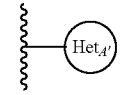

is optionally substituted $C_4$-$C_7$ heterocyclyl containing at least one N, O, S, S(=O), or S(=O)$_2$; wherein if

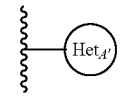

is substituted, then

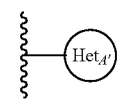

is substituted with 0-3 $R^5$.

In some embodiments,

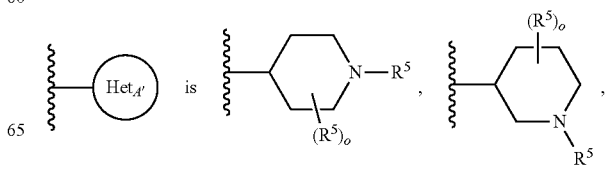

-continued

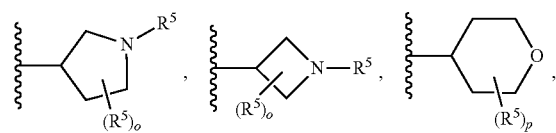

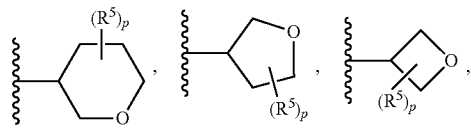

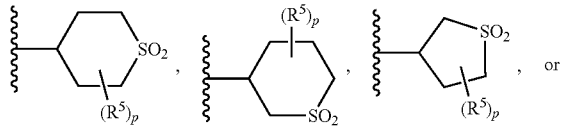

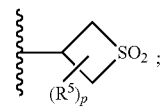

o is 0, 1, or 2; and p is 0, 1, 2, or 3.

In some embodiments,

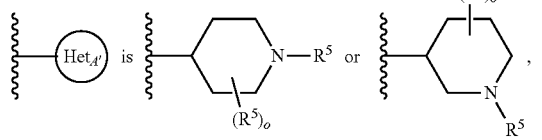

and o is 0, 1, or 2.

In some embodiments, Z is

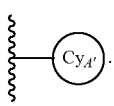

In some embodiments,

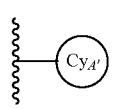

is substituted $C_4$-$C_7$ cycloalkyl that is substituted with 1-3$R^4$ and 0-3$R^5$.

In some embodiments,

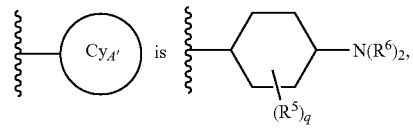

-continued

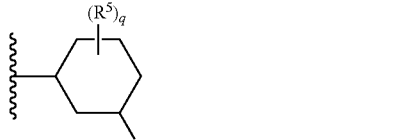

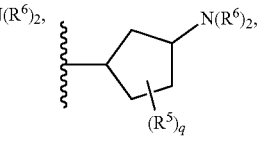

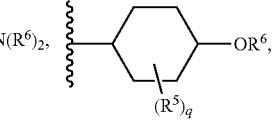

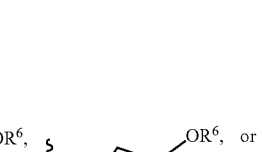

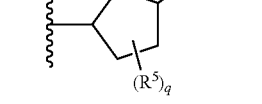

and q is 0, 1, 2, or 3.

In some embodiments,

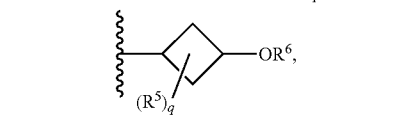

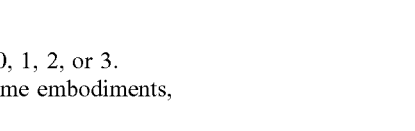

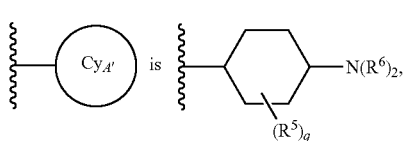

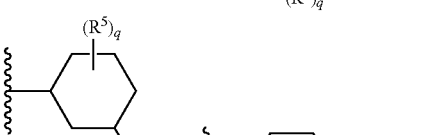

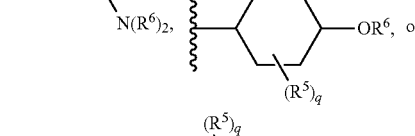

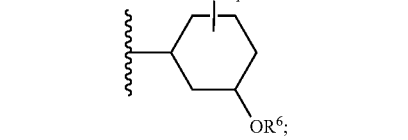

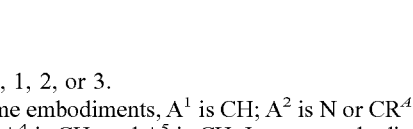

and q is 0, 1, 2, or 3.

In some embodiments, $A^1$ is CH; $A^2$ is N or $CR^A$; $A^3$ is N or $CR^A$; $A^4$ is CH; and $A^5$ is CH. In some embodiments, $A^2$ is N. In some embodiments, $A^2$ is $CR^A$. In some embodiments, $A^3$ is $CR^A$. In some embodiments, $R^A$ is optionally substituted $C_1$-$C_6$alkyl. In some embodiments, $R^A$ is methyl, ethyl, propyl or butyl. In some embodiments, $R^A$ is methyl, propyl or butyl. In some embodiments, $R^1$ is optionally substituted $C_1$-$C_6$alkyl. In some embodiments, $R^1$ is methyl. In some embodiments, $R^2$ is H. In some embodiments, $L^1$ and $L^2$ are each —NH—. In some embodiments, $L^1$ is —CH$_2$— and $L^2$ is —NH—. In some embodiments, $L^1$ is —NH— and $L^2$ is —CH$_2$—. In some embodiments, $L^1$ is —CHY—. In some embodiments, $L^2$ is —CHY—. In some embodiments, Y is optionally substituted $C_1$-$C_3$alkyl.

In some embodiments,

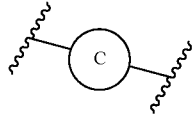

is optionally substituted aryl, wherein if

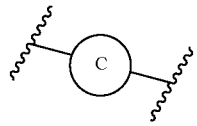

is substituted, then

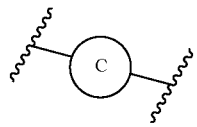

is substituted with 0-4 $R^c$.

In some embodiments,

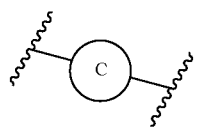

is optionally substituted heteroaryl wherein if

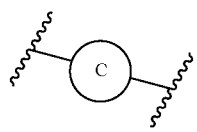

is substituted, then

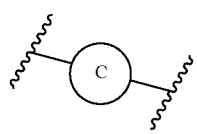

is substituted with 0-4 $R^c$.

In some embodiments,

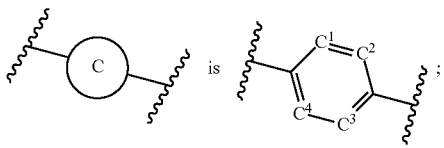

$C^1$ is N or $CR^C$; $C^2$ is N or $CR^C$; $C^3$ is N or $CR^C$; and $C^4$ is N or $CR^C$.

In some embodiments, $C^1$ is $CR^C$; $C^2$ is $CR^C$; $C^3$ is $CR^C$; and $C^4$ is $CR^C$. In some embodiments, $C^1$ is $CR^C$; $C^2$ is CH; $C^3$ is CH; and $C^4$ is CH. In some embodiments, $R^c$ is optionally substituted $C_1$-$C_6$fluoroalkyl. In some embodiments, $R^c$ is —$CF_3$. In some embodiments, each $R^3$ is independently H. In some embodiments, $L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; and if $L^D$ is substituted, then $L^D$ is substituted with 0-4 $R^D$. In some embodiments, $L^D$ is —N($R^{12}$)-(optionally substituted $C_1$-$C_6$ alkyl), and if $L^D$ is substituted, then $L^D$ is substituted with 0-4 $R^D$. In some embodiments, $L^D$ is —N($R^{12}$)—CH$_2$—CH$_2$—CH$_2$—CH$_3$, —N($R^{12}$)—CH$_2$—CH$_2$—CH$_3$, —N($R^{12}$)—CH$_2$—CH$_3$, or —N($R_{12}$)—CH$_3$. In some embodiments, $R^{12}$ is H or $C_3$-$C_4$alkyl. In some embodiments, $L^D$ is —N($R^{13}$)-(optionally substituted $C_1$-$C_6$ alkylene)-N($R^{14}$)$_2$, and if $L^D$ is substituted, then $L^D$ is substituted with 0-4 $R^D$. In some embodiments, $L^D$ is —N($R^{13}$CH)—CH$_2$—CH$_2$—CH$_2$—N($R^{14}$)$_2$, —N($R^{13}$)—CH$_2$—CH$_2$—CH$_2$—N($R^{14}$)$_2$, —N($R^{13}$)—CH$_2$—CH$_2$—N($R^{14}$)$_2$, or —N($R^{13}$)—CH$_2$—N($R^{14}$)$_2$. In some embodiments, each $R^{13}$ and $R^{14}$ is independently H or $C_1$-$C_4$alkyl. In some embodiments, $L^D$ is or -(optionally substituted $C_1$-$C_6$ alkylene)-N($R^{14}$)$_2$; and if $L^D$ is substituted, then $L^D$ is substituted with 0-4 $R^D$. In some embodiments, $L^D$ is —CH$_2$—CH$_2$—CH$_2$—CH$_2$—N($R^{14}$)$_2$, —CH$_2$—CH$_2$—CH$_2$—N($R^{14}$)$_2$, —CH$_2$—CH$_2$—N($R^{14}$)$_2$, or —CH$_2$—N($R^{14}$)$_2$. In some embodiments, each $R^{14}$ is independently H or $C_1$-$C_4$alkyl.

In some embodiments, the compound has the structure of formula (IIIa)

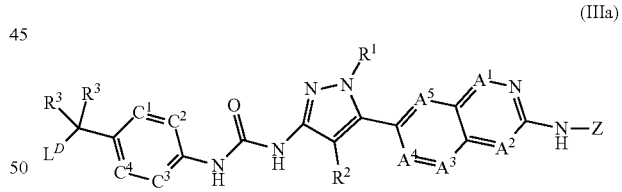

(IIIa)

wherein,
$C^1$ is N or $CR^C$; $C^2$ is N or $CR^C$; $C^3$ is N or $CR^C$; and $C^4$ is N or $CR^C$.

In some embodiments, the compound has the structure of formula (IIIb)

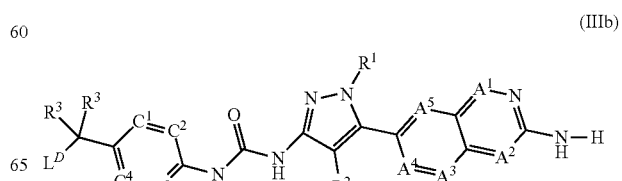

(IIIb)

wherein,
C¹ is N or CR^C; C² is N or CR^C; C³ is N or CR^C; and C⁴ is N or CR^C.

In some embodiments, the compound has the structure of formula (IIIc)

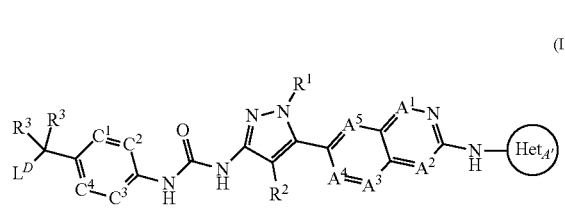

(IIIc)

wherein,
C¹ is N or CR^C; C² is N or CR^C; C³ is N or CR^C; and C⁴ is N or CR^C.

In some embodiments, the compound has the structure of formula (IIId)

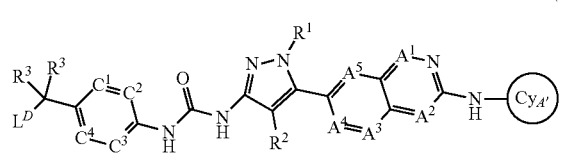

(IIId)

wherein,
C¹ is N or CR^C; C² is N or CR^C; C³ is N or CR^C; and C⁴ is N or CR^C.

In some embodiments, the compound has the structure of formula (IIIe)

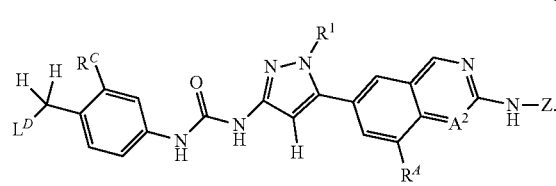

(IIIe)

In some embodiments, the compound has the structure of formula (IIIf)

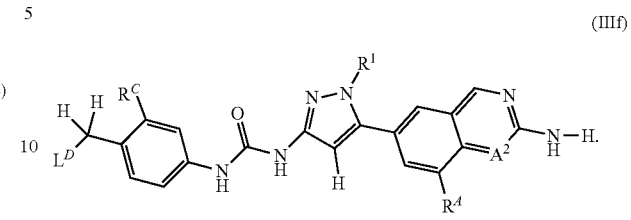

(IIIf)

In some embodiments, the compound has the structure of formula (IIIg)

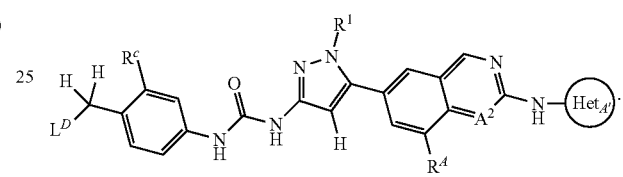

(IIIg)

In some embodiments, the compound has the structure of formula (IIIh)

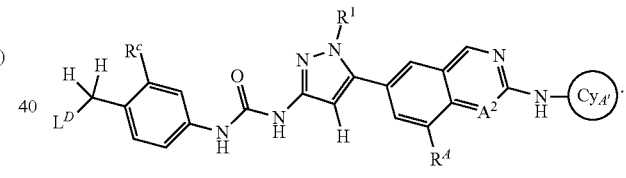

(IIIh)

In some embodiments, a compound described herein is selected from any one of the compounds from the following tables, Tables 1-3:

TABLE 1

| Compound. No | Structure | Name |
|---|---|---|
| 51 | ![structure] | 1-(1-methyl-5-(2-(piperidin-4-ylamino)quinazolin-6-yl)-1H-pyrazol-3-yl)-3-(5-((4-methylpiperazin-1-yl)methyl)-4-(trifluoromethyl)pyridin-2-yl)urea |

TABLE 1-continued

| Compound. No | Structure | Name |
|---|---|---|
| 50 | 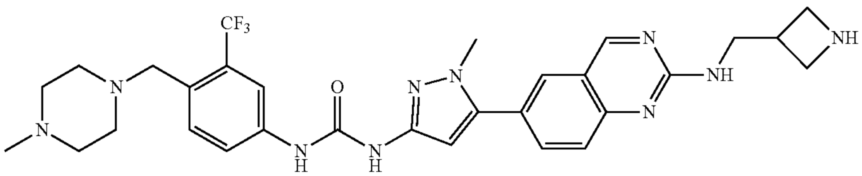 [SMILES: CN1CCN(Cc2ccc(NC(=O)Nc3cc(-c4ccc5nc(NCC6CNC6)ncc5c4)n(C)n3)cc2C(F)(F)F)CC1] | 1-(5-(2-((azetidin-3-ylmethyl)amino)quinazolin-6-yl)-1-methyl-1H-pyrazol-3-yl)-3-(4-((4-methylpiperazin-1-yl)methyl)-3-(trifluoromethyl)phenyl)urea |
| 49 | 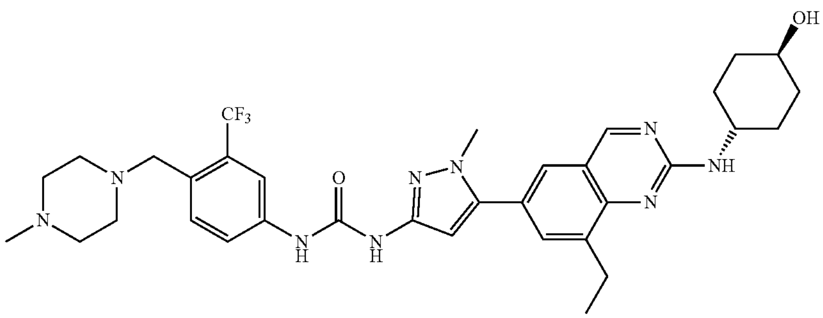 | 1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 46 | 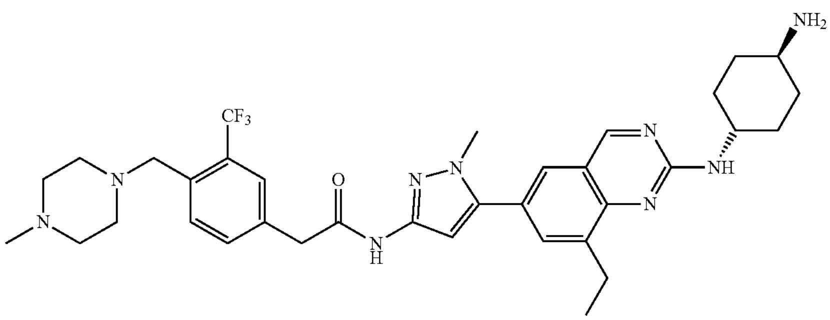 | N-(5-(2-(((1r,4r)-4-aminocyclohexyl)amino)-8-ethylquinazolin-6-yl)-1-methyl-1H-pyrazol-3-yl)-2-(4-((4-methylpiperazin-1-yl)methyl)-3-trifluoromethyl)phenyl)acetamide |
| 45 | 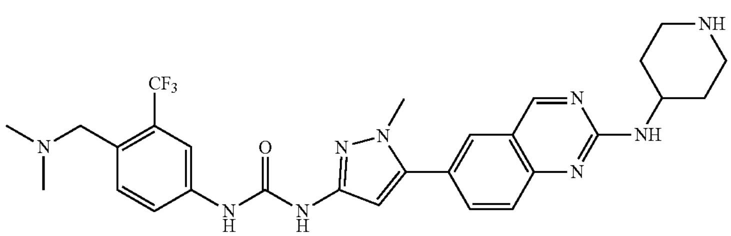 [SMILES: CN(C)Cc1ccc(NC(=O)Nc2cc(-c3ccc4nc(NC5CCNCC5)ncc4c3)n(C)n2)cc1C(F)(F)F] | 1-(4-((dimethylamino)methyl)-3-(trifluoromethyl)phenyl)-3-(1-methyl-5-(2-(piperidin-4-ylamino)quinazolin-6-yl)-1H-pyrazol-3-yl)urea |
| 44 | 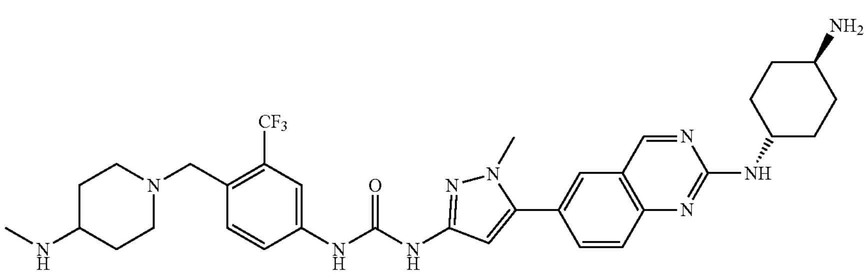 | 1-(5-(2-(((1r,4r)-4-aminocyclohexyl)amino)quinazolin-6-yl)-1-methyl-1H-pyrazol-3-yl)-3-(4-((4-(methylamino)piperidin-1-yl)methyl)-3-(trifluoromethyl)phenyl)urea |

TABLE 1-continued

| Compound. No | Structure | Name |
|---|---|---|
| 43 | 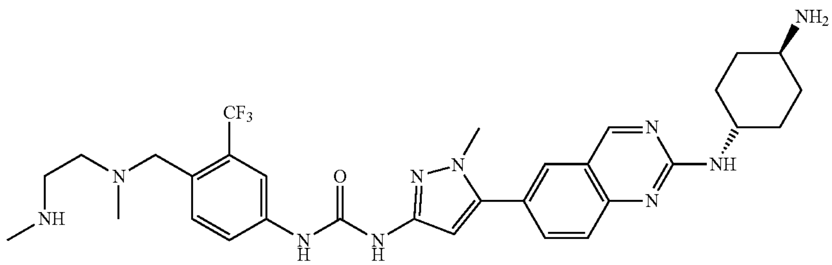 | 1-(5-(2-(((1r,4r)-4-aminocyclohexyl)amino)quinazolin-6-yl)-1-methyl-1H-pyrazol-3-yl)-3-(4-((methyl(2-(methylamino)ethyl)amino)methyl)-3-(trifluoromethyl)phenyl)urea |
| 42 | 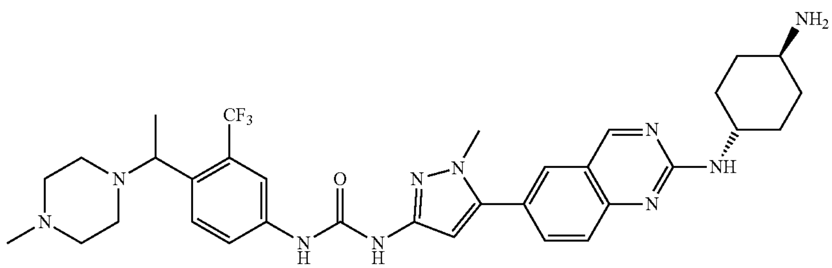 | 1-(5-(2-(((1r,4r)-4-aminocyclohexyl)amino)quinazolin-6-yl)-1-methyl-1H-pyrazol-3-yl)-3-(4-(1-(4-methylpiperazin-1-yl)ethyl)-3-(trifluoromethyl)phenyl)urea |
| 41 | 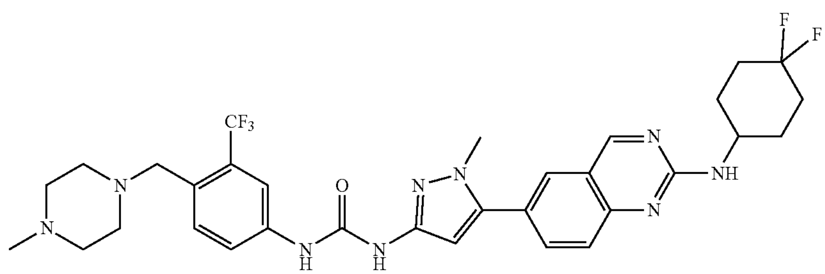 [SMILES: CN1CCN(Cc2ccc(NC(=O)Nc3cc(-c4ccc5nc(NC6CCC(F)(F)CC6)ncc5c4)n(C)n3)cc2C(F)(F)F)CC1] | 1-(5-(2-((4,4-difluorocyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 40 | 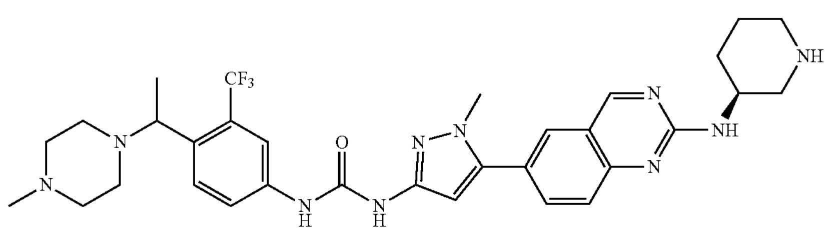 [SMILES: CC(c1ccc(NC(=O)Nc2cc(-c3ccc4nc(N[C@H]5CCCNC5)ncc4c3)n(C)n2)cc1C(F)(F)F)N1CCN(C)CC1] | 1-(1-methyl-5-(2-(((S)-piperidin-3-yl)amino)quinazolin-6-yl)-1H-pyrazol-3-yl)-3-(4-(1-(4-methylpiperazin-1-yl)ethyl)-3-(trifluoromethyl)phenyl)urea |
| 39 | 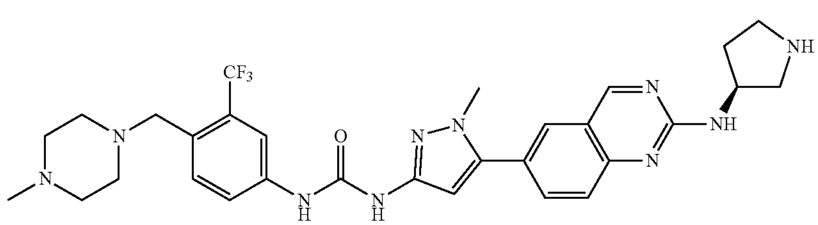 [SMILES: CN1CCN(Cc2ccc(NC(=O)Nc3cc(-c4ccc5nc(N[C@H]6CCNC6)ncc5c4)n(C)n3)cc2C(F)(F)F)CC1] | (S)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea |
| 38 | 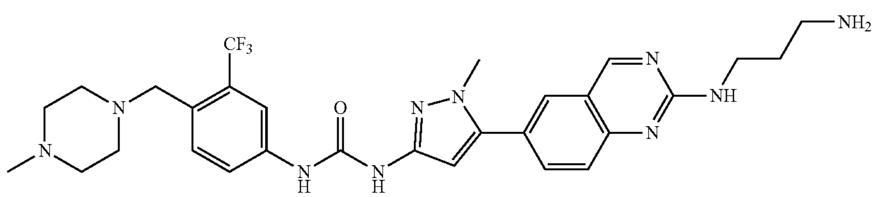 [SMILES: CN1CCN(Cc2ccc(NC(=O)Nc3cc(-c4ccc5nc(NCCCN)ncc5c4)n(C)n3)cc2C(F)(F)F)CC1] | 1-(5-(2-((3-aminopropyl)amino)quinazolin-6-yl)-1-methyl-1H-pyrazol-3-yl)-3-(4-((4-methylpiperazin-1-yl)methyl)-3-(trifluoromethyl)phenyl)urea |

TABLE 1-continued

| Compound. No | Structure | Name |
|---|---|---|
| 36 | 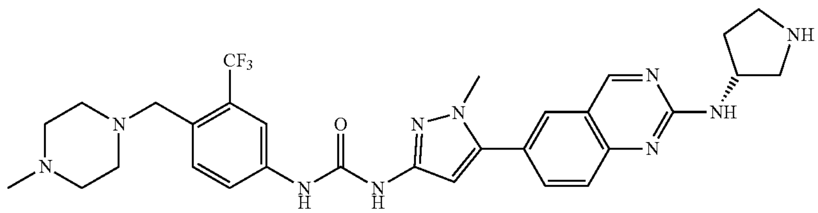 | (R)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea |
| 35 | 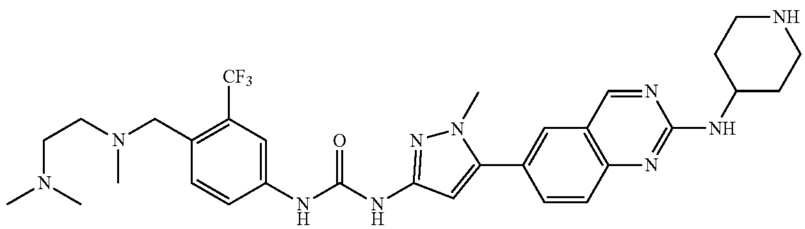 [SMILES: CN(C)CCN(C)Cc1ccc(NC(=O)Nc2cc(-c3ccc4nc(NC5CCNCC5)ncc4c3)n(C)n2)cc1C(F)(F)F] | 1-(4-(((2-(dimethylamino)ethyl)(methyl)amino)methyl)-3-(trifluoromethyl)phenyl)-3-(1-methyl-5-(2-(piperidin-4-ylamino)quinazolin-6-yl)-1H-pyrazol-3-yl)urea |
| 34 | 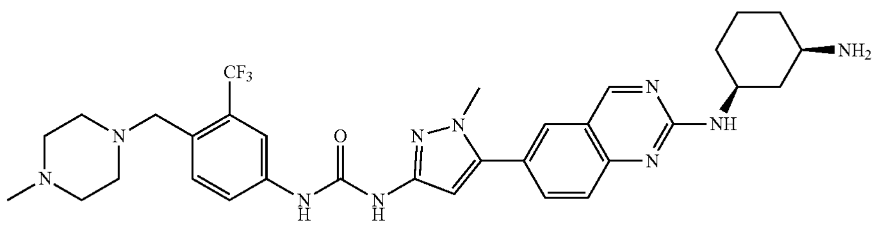 [SMILES: CN1CCN(Cc2ccc(NC(=O)Nc3cc(-c4ccc5nc(N[C@H]6CCC[C@@H](N)C6)ncc5c4)n(C)n3)cc2C(F)(F)F)CC1] | 1-(5-(2-(((1S,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 33 | 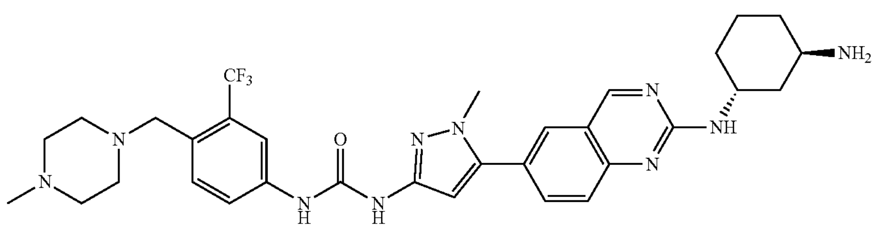 [SMILES: CN1CCN(Cc2ccc(NC(=O)Nc3cc(-c4ccc5nc(N[C@@H]6CCC[C@@H](N)C6)ncc5c4)n(C)n3)cc2C(F)(F)F)CC1] | 1-(5-(2-(((1R,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 32 | 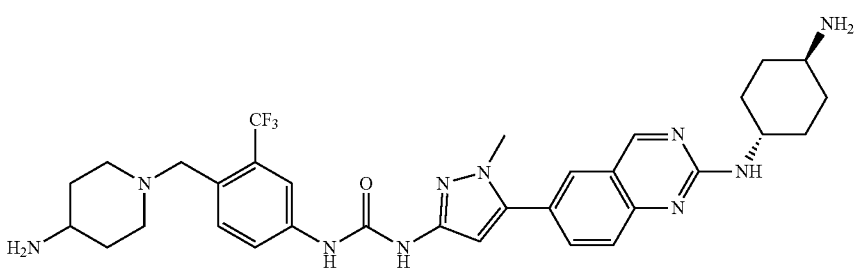 [SMILES: Cn1nc(NC(=O)Nc2ccc(CN3CCC(N)CC3)c(C(F)(F)F)c2)cc1-c1ccc2nc(N[C@H]3CC[C@H](N)CC3)ncc2c1] | 1-(5-(2-(((1r,4r)-4-aminocyclohexyl)amino)quinazolin-6-yl)-1-methyl-1H-pyrazol-3-yl)-3-(4-((4-aminopiperidin-1-yl)methyl)-3-(trifluoromethyl)phenyl)urea |
| 31 | 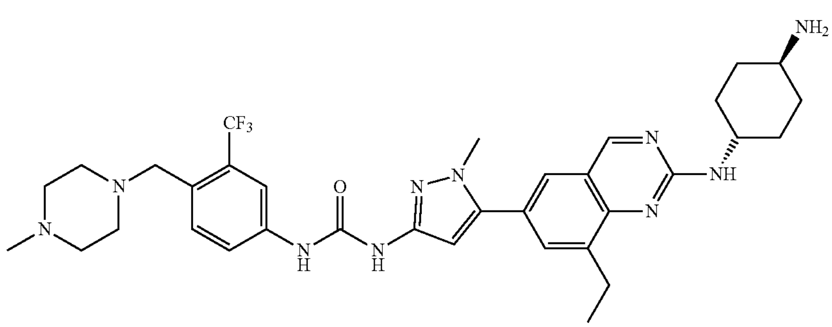 | 1-(5-(2-(((1r,4r)-4-aminocyclohexyl)amino)-8-ethylquinazolin-6-yl)-1-methyl-1H-pyrazol-3-yl)-3-(4-((4-methylpiperazin-1-yl)methyl)-3-(trifluoromethyl)phenyl)urea |

TABLE 1-continued

| Compound. No | Structure | Name |
|---|---|---|
| 29 | 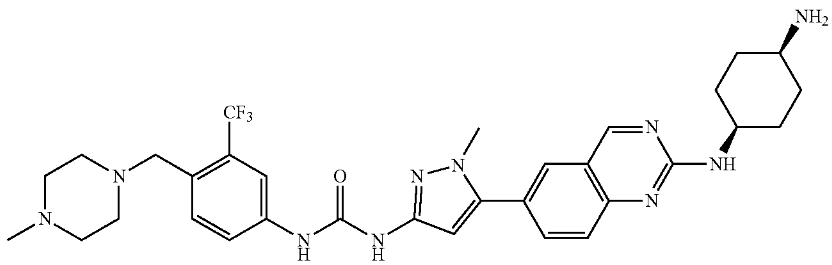 [SMILES: CN1CCN(Cc2ccc(NC(=O)Nc3cc(-c4ccc5nc(N[C@H]6CC[C@@H](N)CC6)ncc5c4)n(C)n3)cc2C(F)(F)F)CC1] | 1-(5-(2-(((1s,4s)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 26 | 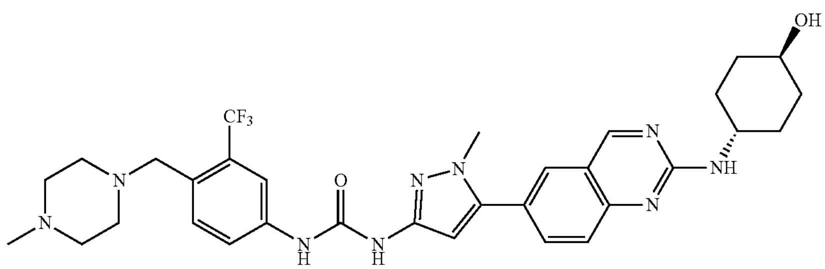 [SMILES: CN1CCN(Cc2ccc(NC(=O)Nc3cc(-c4ccc5nc(N[C@H]6CC[C@H](O)CC6)ncc5c4)n(C)n3)cc2C(F)(F)F)CC1] | 1-(5-(2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 23 | 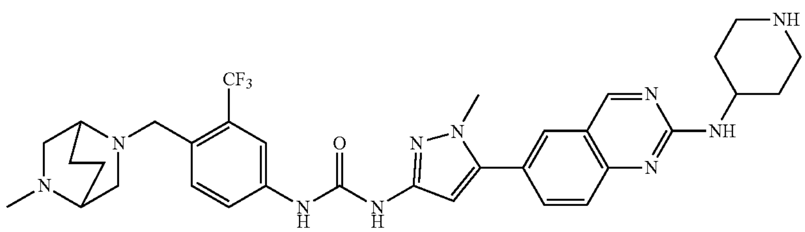 [SMILES: CN1CC2CCC1CN2Cc1ccc(NC(=O)Nc2cc(-c3ccc4nc(NC5CCNCC5)ncc4c3)n(C)n2)cc1C(F)(F)F] | 1-(4-((5-methyl-2,5-diazabicyclo[2.2.2]octan-2-yl)methyl)-3-(trifluoromethyl)phenyl)-3-(1-methyl-5-(2-(piperidin-4-ylamino)quinazolin-6-yl)-1H-pyrazol-3-yl)urea |
| 22 | 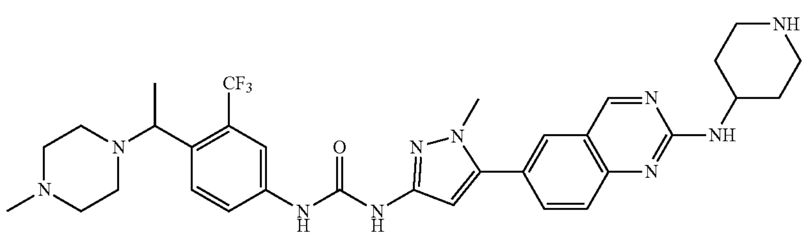 [SMILES: CC(c1ccc(NC(=O)Nc2cc(-c3ccc4nc(NC5CCNCC5)ncc4c3)n(C)n2)cc1C(F)(F)F)N1CCN(C)CC1] | 1-(1-methyl-5-(2-(piperidin-4-ylamino)quinazolin-6-yl)-1H-pyrazol-3-yl)-3-(4-(1-(4-methylpiperazin-1-yl)ethyl)-3-(trifluoromethyl)phenyl)urea |
| 21 | 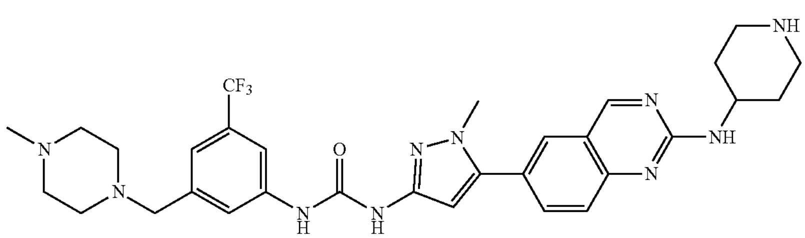 [SMILES: CN1CCN(Cc2cc(NC(=O)Nc3cc(-c4ccc5nc(NC6CCNCC6)ncc5c4)n(C)n3)cc(C(F)(F)F)c2)CC1] | 1-(1-methyl-5-(2-(piperidin-4-ylamino)quinazolin-6-yl)-1H-pyrazol-3-yl)-3-(3-((4-methylpiperazin-1-yl)methyl)-5-(trifluoromethyl)phenyl)urea |
| 20 | 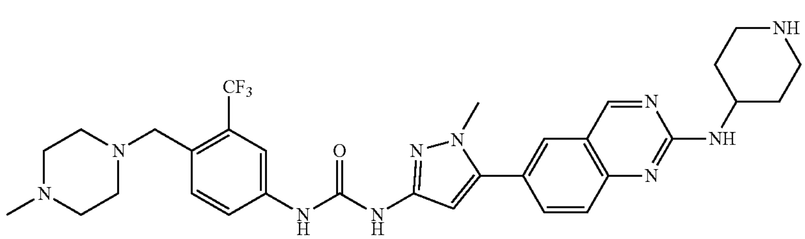 [SMILES: CN1CCN(Cc2ccc(NC(=O)Nc3cc(-c4ccc5nc(NC6CCNCC6)ncc5c4)n(C)n3)cc2C(F)(F)F)CC1] | 1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea |

TABLE 1-continued

| Compound. No | Structure | Name |
|---|---|---|
| 19 | 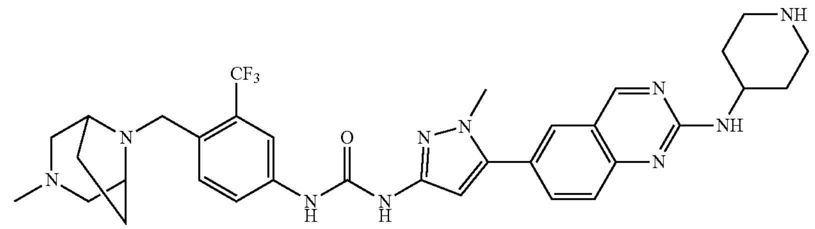 [SMILES: CN1CC2CCC(C1)N2Cc1ccc(NC(=O)Nc2cc(-c3ccc4nc(NC5CCNCC5)ncc4c3)n(C)n2)cc1C(F)(F)F] | 1-(4-((3-methyl-3,8-diazabicyclo[3.2.1]octan-8-yl)methyl)-3-(trifluoromethyl)phenyl)-3-(1-methyl-5-(2-(piperidin-4-ylamino)quinazolin-6-yl)-1H-pyrazol-3-yl)urea |
| 17 | 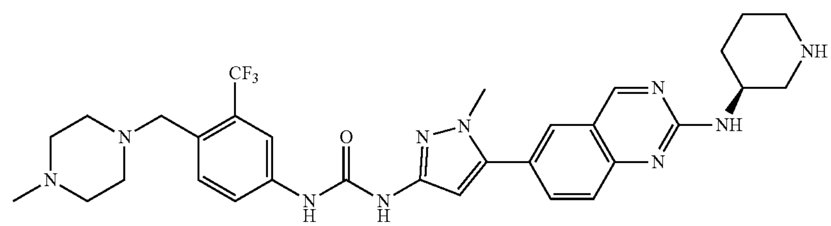 [SMILES: CN1CCN(Cc2ccc(NC(=O)Nc3cc(-c4ccc5nc(N[C@H]6CCCNC6)ncc5c4)n(C)n3)cc2C(F)(F)F)CC1] | (S)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea |
| 15 | 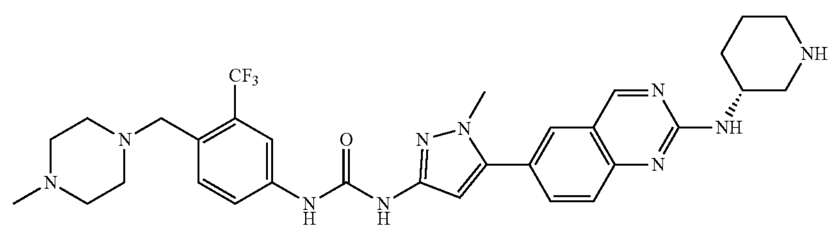 [SMILES: CN1CCN(Cc2ccc(NC(=O)Nc3cc(-c4ccc5nc(N[C@@H]6CCCNC6)ncc5c4)n(C)n3)cc2C(F)(F)F)CC1] | (R)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea |
| 14 | 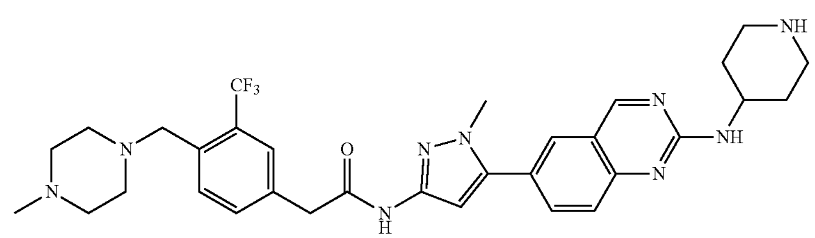 [SMILES: CN1CCN(Cc2ccc(CC(=O)Nc3cc(-c4ccc5nc(NC6CCNCC6)ncc5c4)n(C)n3)cc2C(F)(F)F)CC1] | N-(1-methyl-5-(2-(piperidin-4-ylamino)quinazolin-6-yl)-1H-pyrazol-3-yl)-2-(4-((4-methylpiperazin-1-yl)methyl)-3-(trifluoromethyl)phenyl)acetamide |
| 5 | 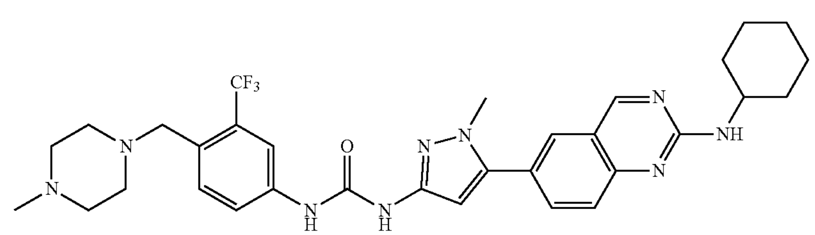 | 1-(5-(2-(cyclohexylamino)quinazolin-6-yl)-1-methyl-1H-pyrazol-3-yl)-3-(4-((4-methylpiperazin-1-yl)methyl)-3-(trifluoromethyl)phenyl)urea |
| 4 | 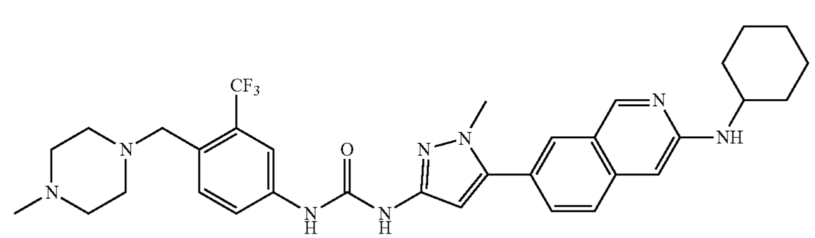 [SMILES: CN1CCN(Cc2ccc(NC(=O)Nc3cc(-c4ccc5nc(NC6CCCCC6)ncc5c4)n(C)n3)cc2C(F)(F)F)CC1] | 1-(5-(3-(cyclohexylamino)isoquinolin-7-yl)-1-methyl-1H-pyrazol-3-yl)-3-(4-((4-methylpiperazin-1-yl)methyl)-3-(trifluoromethyl)phenyl)urea |

TABLE 1-continued

| Compound. No | Structure | Name |
|---|---|---|
| 3 | 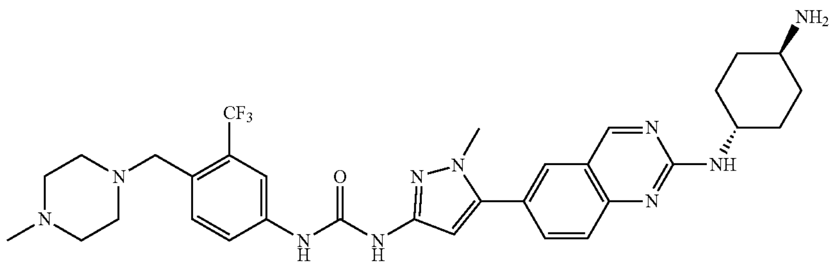 [SMILES: CN1CCN(Cc2ccc(NC(=O)Nc3cc(-c4ccc5nc(N[C@H]6CC[C@H](N)CC6)ncc5c4)n(C)n3)cc2C(F)(F)F)CC1] | 1-(5-(2-(((1r,4r)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea |
| 2 | 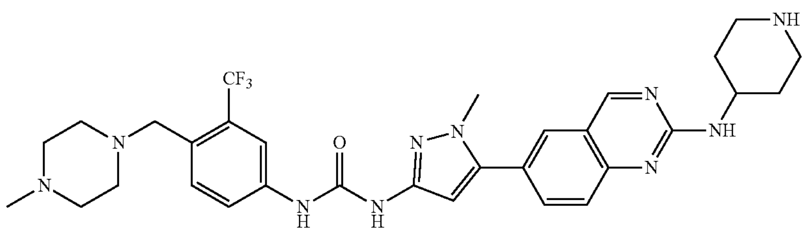 | 1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea |
| 1 | 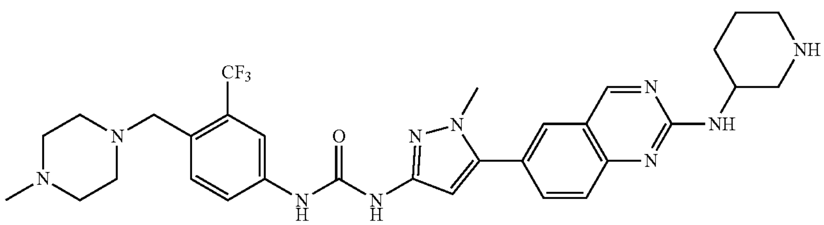 [SMILES: CN1CCN(Cc2ccc(NC(=O)Nc3cc(-c4ccc5nc(NC6CCCNC6)ncc5c4)n(C)n3)cc2C(F)(F)F)CC1] | 1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea |

TABLE 2

| Compound No. | Structure | Name |
|---|---|---|
| 12 | 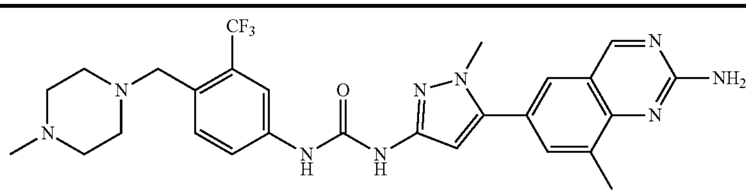 | 1-(5-(2-amino-8-methylquinazolin-6-yl)-1-methyl-1H-pyrazol-3-yl)-3-(4-((4-methylpiperazin-1-yl)methyl)-3-(trifluoromethyl)phenyl)urea |
| 11 | 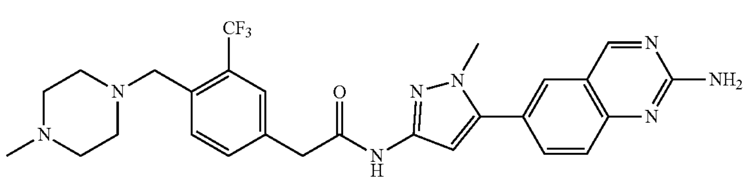 [SMILES: CN1CCN(Cc2ccc(CC(=O)Nc3cc(-c4ccc5nc(N)ncc5c4)n(C)n3)cc2C(F)(F)F)CC1] | N-(5-(2-aminoquinazolin-6-yl)-1-methyl-1H-pyrazol-3-yl)-2-(4-((4-methylpiperazin-1-yl)methyl)-3-(trifluoromethyl)phenyl)acetamide |
| 6 | 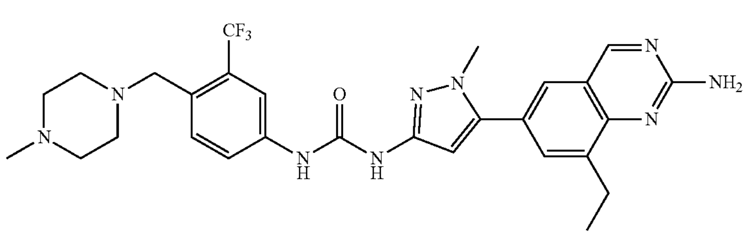 [SMILES: CCc1cc(-c2cc(NC(=O)Nc3ccc(CN4CCN(C)CC4)c(C(F)(F)F)c3)nn2C)cc2cnc(N)nc12] | 1-(5-(2-amino-8-ethylquinazolin-6-yl)-1-methyl-1H-pyrazol-3-yl)-3-(4-((4-methylpiperazin-1-yl)methyl)-3-(trifluoromethyl)phenyl)urea |

TABLE 3

| Compound No. | Structure | Name |
|---|---|---|
| 10 | 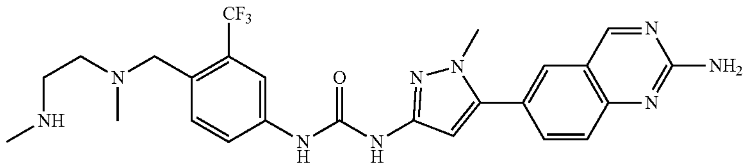 [SMILES: CNCCN(C)Cc1ccc(NC(=O)Nc2cc(-c3ccc4nc(N)ncc4c3)n(C)n2)cc1C(F)(F)F] | 1-(5-(2-aminoquinazolin-6-yl)-1-methyl-1H-pyrazol-3-yl)-3-(4-((methyl(2-(methylamino)ethyl)amino)methyl)-3-(trifluoromethyl)phenyl)urea |
| 9 | 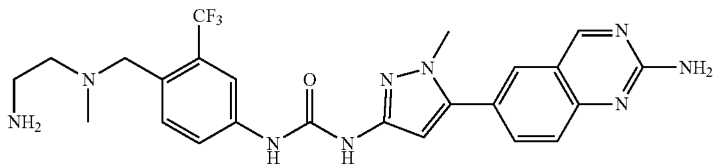 [SMILES: CN(CCN)Cc1ccc(NC(=O)Nc2cc(-c3ccc4nc(N)ncc4c3)n(C)n2)cc1C(F)(F)F] | 1-(4-(((2-aminoethyl)(methyl)amino)methyl)-3-(trifluoromethyl)phenyl)-3-(5-(2-aminoquinazolin-6-yl)-1-methyl-1H-pyrazol-3-yl)urea |

In some embodiments, the compound is:
1-(1-methyl-5-(2-(piperidin-4-ylamino)quinazolin-6-yl)-1H-pyrazol-3-yl)-3-(5-((4-methylpiperazin-1-yl)methyl)-4-(trifluoromethyl)pyridin-2-yl)urea;
1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
N-(5-(2-(((1r,4r)-4-aminocyclohexyl)amino)-8-ethyl quinazolin-6-yl)-1-methyl-1H-pyrazol-3-yl)-2-(4-((4-methylpiperazin-1-yl)methyl)-3-(trifluoromethyl)phenyl)acetamide;
1-(4-((dimethylamino)methyl)-3-(trifluoromethyl)phenyl)-3-(1-methyl-5-(2-(piperidin-4-yl amino)quinazolin-6-yl)-1H-pyrazol-3-yl)urea;
1-(5-(2-(((1r,4r)-4-aminocyclohexyl)amino)quinazolin-6-yl)-1-methyl-1H-pyrazol-3-yl)-3-(4-((4-(methylamino)piperidin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((methyl(2-(methylamino)ethyl)amino)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-(1-(4-methylpiperazin-1-yl)ethyl)-3-(trifluoromethyl)phenyl)urea;
1-(5-(2-((4,4-difluorocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(1-methyl-5-(2-(((S)-piperidin-3-yl)amino)quinazolin-6-yl)-1H-pyrazol-3-yl)-3-(4-(1-(4-methylpiperazin-1-yl)ethyl)-3-(trifluoromethyl)phenyl)urea;
(S)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea;
(R)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea;
1-(4-(((2-(dimethylamino)ethyl)(methyl)amino)methyl)-3-(trifluoromethyl)phenyl)-3-(1-methyl-5-(2-(piperidin-4-ylamino)quinazolin-6-yl)-1H-pyrazol-3-yl)urea;
1-(5-(2-(((1 S,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1R,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((4-aminopiperidin-1-yl)methyl)-3-(trifluoromethyl)phenyl)urea;
1-(5-(2-(((1r,4r)-4-aminocyclohexyl)amino)-8-ethyl quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1s,4s)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(4-((5-methyl-2,5-diazabicyclo[2.2.2]octan-2-yl)methyl)-3-(trifluoromethyl)phenyl)-3-(1-methyl-5-(2-(piperidin-4-ylamino)quinazolin-6-yl)-1H-pyrazol-3-yl)urea;
1-(1-methyl-5-(2-(piperidin-4-ylamino)quinazolin-6-yl)-1H-pyrazol-3-yl)-3-(4-(1-(4-methylpiperazin-1-yl)ethyl)-3-(trifluoromethyl)phenyl)urea;
1-(1-methyl-5-(2-(piperidin-4-ylamino)quinazolin-6-yl)-1H-pyrazol-3-yl)-3-(3-((4-methylpiperazin-1-yl)methyl)-5-(trifluoromethyl)phenyl)urea;
1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea;
1-(4-((3-methyl-3,8-diazabicyclo[3.2.1]octan-8-yl)methyl)-3-(trifluoromethyl)phenyl)-3-(1-methyl-5-(2-(piperidin-4-ylamino)quinazolin-6-yl)-1H-pyrazol-3-yl)urea;
(S)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea;
(R)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea;
N-(1-methyl-5-(2-(piperidin-4-ylamino)quinazolin-6-yl)-1H-pyrazol-3-yl)-2-(4-((4-methylpiperazin-1-yl)methyl)-3-(trifluoromethyl)phenyl)acetamide;
1-(5-(2-(cyclohexylamino)quinazolin-6-yl)-1-methyl-1H-pyrazol-3-yl)-3-(4-((4-methylpiperazin-1-yl)methyl)-3-(trifluoromethyl)phenyl)urea;
1-(5-(3-(cyclohexylamino)isoquinolin-7-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea; or
1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea.

In some embodiments, the compound is:
1-(5-(2-((azetidin-3-ylmethyl)amino)quinazolin-6-yl)-1-methyl-1H-pyrazol-3-yl)-3-(4-((4-methylpiperazin-1-yl)methyl)-3-(trifluoromethyl)phenyl)urea; or
1-(5-(2-((3-aminopropyl)amino)quinazolin-6-yl)-1-methyl-1H-pyrazol-3-yl)-3-(4-((4-methylpiperazin-1-yl)methyl)-3-(trifluoromethyl)phenyl)urea.

In some embodiments, the compound is:
1-(5-(2-amino-8-methylquinazolin-6-yl)-1-methyl-1H-pyrazol-3-yl)-3-(4-((4-methylpiperazin-1-yl)methyl)-3-(trifluoromethyl)phenyl)urea; or
1-(5-(2-amino-8-ethylquinazolin-6-yl)-1-methyl-1H-pyrazol-3-yl)-3-(4-((4-methylpiperazin-1-yl)methyl)-3-(trifluoromethyl)phenyl)urea.

In some embodiments, the compound is:
N-(5-(2-aminoquinazolin-6-yl)-1-methyl-1H-pyrazol-3-yl)-2-(4-((4-methylpiperazin-1-yl)methyl)-3-(trifluoromethyl)phenyl)acetamide.

In some embodiments, the compound is:
1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
N-(5-(2-(((1r,4r)-4-aminocyclohexyl)amino)-8-ethylquinazolin-6-yl)-1-methyl-1H-pyrazol-3-yl)-2-(4-((4-methylpiperazin-1-yl)methyl)-3-(trifluoromethyl)phenyl)acetamide;
1-(5-(2-amino-8-methylquinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)-8-ethyl quinazolin-6-yl)-1-methyl-1H-pyrazol-3-yl)-3-(4-((4-methylpiperazin-1-yl)methyl)-3-(trifluoromethyl)phenyl)urea; or
1-(5-(2-amino-8-ethylquinazolin-6-yl)-1-methyl-1H-pyrazol-3-yl)-3-(4-((4-methylpiperazin-1-yl)methyl)-3-(trifluoromethyl)phenyl)urea.

In some embodiments, the compound is:
1-(5-(2-aminoquinazolin-6-yl)-1-methyl-1H-pyrazol-3-yl)-3-(4-((methyl(2-(methylamino)ethyl)amino)methyl)-3-(trifluoromethyl)phenyl)urea; or
1-(4-(((2-aminoethyl)(methyl)amino)methyl)-3-(trifluoromethyl)phenyl)-3-(5-(2-aminoquinazolin-6-yl)-1-methyl-1H-pyrazol-3-yl)urea.

IRE1-Like Family of Proteins

In some embodiments, a compound disclosed herein selectively binds to a protein of the IRE1 family of proteins. Exemplary IRE1 family proteins include IRE1, IRE1α, or ERN1. Other exemplary IRE1 family proteins include IRE1 homologues or orthologues in other organisms. Exemplary organisms include human, non-human primate, mouse, rat, chicken, fruit fly, yeast, and others listed in Table 4. In some embodiments, the IRE1 protein is human IRE1α.

TABLE 4

| Organism | Accession # |
| --- | --- |
| Homo sapiens | NP_001424.3 |
| Mus musculus | NP_076402.1 |
| Rattus norvegicus | XP_006247696.1 |

In some embodiments, a compound disclosed herein selectively binds to an IRE1 family protein comprising a kinase domain and/or an RNase domain. In some embodiments, the kinase domain is a trans-autophosphorylation kinase domain. In some embodiments, the IRE1 family protein is IRE1α. An example arrangement of domains within an IRE1α protein is depicted in FIG. 1. An example alignment of IRE1 family protein orthologues is depicted in FIGS. 2A-2E.

In some embodiments, a compound disclosed herein selectively binds to a trans-autophosphorylation kinase domain region of IRE1α. In some embodiments, a compound disclosed herein selectively binds to a trans-autophosphorylation kinase domain region of IRE1α, for example within amino acid residues 568-833 of SEQ ID NO: 1, or equivalent amino acid residues thereof.

In some embodiments, a compound disclosed herein selectively binds to an ATP-binding pocket within a trans-autophosphorylation kinase domain region of IRE1α. In some embodiments, a compound disclosed herein selectively binds to an ATP-binding pocket within a trans-autophosphorylation kinase domain region of IRE1α, for example, one or more of amino acid resides 577-711, 577-586, 597, 599, 626, 642-643, 645, 648, 688, 692-693, 695, or 711 of SEQ ID NO: 1, or equivalent amino acid residues thereof.

In some embodiments, a compound disclosed herein selectively binds to an activation loop within a trans-autophosphorylation kinase domain region of IRE1α. In some embodiments, a compound disclosed herein selectively binds to an activation loop within a trans-autophosphorylation kinase domain region of IRE1α, for example, one or more of amino acid residues 710-736, 710-725, or 729-736 of SEQ ID NO: 1, or equivalent amino acid residues thereof.

In some embodiments, a compound disclosed herein selectively binds to an RNase domain region of IRE1α. In some embodiments, a compound disclosed herein selectively binds to an RNase domain region of IRE1α, for example within amino acid residues 835-963 of SEQ ID NO: 1, or equivalent amino acid residues thereof.

In some embodiments, a compound disclosed herein selectively binds to a kinase domain dimer interface amino acid residue. In some embodiments, a compound disclosed herein selectively binds to a kinase domain dimer interface amino acid residue, such as one or more of amino acid residues 569-701, 569, 591, 592, 594, 617, 620, 627, 628, 631, 674, 678, or 701 of SEQ ID NO: 1.

In some embodiments, a compound disclosed herein selectively binds to a first IRE1α and blocks dimerization between kinase domain dimer interface amino acid residues of the first IRE1α and a second IRE1α. In some embodiments, a compound disclosed herein selectively binds to a first IRE1α, and inhibit dimerization at one or more of amino acid residues 569-701, 569, 591, 592, 594, 617, 620, 627, 628, 631, 674, 678, or 701 of SEQ ID NO: 1.

In some embodiments, a compound disclosed herein selectively binds to a kinase-extension nuclease (KEN) domain dimer interface amino acid residue of an IRE1α. In some embodiments, a compound disclosed herein selectively binds to a KEN domain dimer interface amino acid residue, such as one or more of amino acid residues 840-925, 840, 844, 851, 908, 912, or 925 of SEQ ID NO: 1.

In some embodiments, a compound disclosed herein selectively binds to amino acid residues of a nuclease active site. In some embodiments, a compound disclosed herein selectively binds to amino acid residues of a nuclease active site, such as one or more of amino acid residues 847-910, 847, 850, 886, 888, 889, 890, 892, 902, 905, 906, or 910 of SEQ ID NO: 1.

In some embodiments, a compound disclosed herein selectively binds to an RNase domain and a trans-autophosphorylation kinase domain region of IRE1α. In some embodiments, a compound disclosed herein selectively binds to an RNase domain and an ATP-binding pocket within a trans-autophosphorylation kinase domain region of IRE1α. In some embodiments, a compound disclosed herein selectively binds to an RNase domain and an activation loop within a trans autophosphorylation kinase domain region of IRE1α.

In some embodiments, a compound disclosed herein selectively binds to IRE1α at two sites located in an RNase domain, trans-autophosphorylation kinase domain region, ATP-binding pocket, activation loop, or any combination thereof. In some embodiments, a compound disclosed herein selectively binds to IRE1α at two or more sites. In some embodiments, a compound disclosed herein selectively binds to IRE1α at two or more sites located in an RNase domain, trans-autophosphorylation kinase domain region, ATP-binding pocket, activation loop, or any combination thereof. In some embodiments, a compound disclosed herein selectively binds to IRE1α at three sites located in an RNase domain, trans-autophosphorylation kinase domain region, ATP-binding pocket, activation loop, or any combination thereof.

In some embodiments, a compound disclosed herein selectively binds to IRE1α at a first site located in an RNase domain, trans-autophosphorylation kinase domain region, ATP-binding pocket, or activation loop. In some embodiments, a first site comprises one or more of any amino acid residue within amino acid residues 465-977 of SEQ ID NO: 1. In some embodiments, a compound disclosed herein selectively binds to IRE1α at a second site located in an RNase domain, trans-autophosphorylation kinase domain region, ATP-binding pocket, or activation loop. In some examples, the first site is located within the same domain or region as the second site. In some examples, the first site is located within a different domain or region as the second site.

In some embodiments, a compound disclosed herein selectively binds to first IRE1α, thereby blocking dimerization of the first IRE1α to a second IRE1α. In some embodiments, a compound disclosed herein selectively binds to first IRE1α, thereby blocking auto-transphosphorylation of the first IRE1α or a second IRE1α to which the first IRE1α is dimerized.

In some embodiments, a compound disclosed herein selectively binds to a first IRE1α, thereby blocking activation of the first IRE1α or a second IRE1α to which the first IRE1α is dimerized.

In some embodiments, a compound disclosed herein selectively binds to a first IRE1α, thereby blocking kinase activity of the first IRE1α or a second IRE1α to which the first IRE1α is dimerized. In some embodiments, a compound disclosed herein selectively binds to a first IRE1α, thereby blocking RNase activity of the first IRE1α or a second IRE1α to which the first IRE1α is dimerized.

In some embodiments, a compound disclosed herein selectively binds to IRE1α when in a homo-dimerized conformation. In some embodiments, a compound disclosed herein selectively binds to IRE1α when in an oligomerized conformation. In some embodiments, a compound disclosed herein selectively binds to IRE1α when in a non-oligomerized or non-dimerized conformation. In some embodiments, a compound disclosed herein selectively binds to IRE1α when in an ATP-bound state. In some embodiments, a compound disclosed herein selectively binds to a IRE1 family protein when in a non-ATP-bound state. In some embodiments, the compound is a pharmaceutically acceptable salt, or solvate thereof.

IRE1 Signaling Pathway

In some embodiments, a compound disclosed herein selectively binds to an IRE1 family protein and alters a downstream signaling pathway. In some embodiments, a compound disclosed herein selectively binds to an IRE1 family protein and alters signaling of immunoglobulin heavy-chain binding protein (BIP), protein kinase R (PKR)-like endoplasmic reticulum kinase (PERK), glucose regulate protein 78 (Grp78), eukaryotic translation initiation factor 2α (eIF2α), X-box binding protein 1 (XBP1), activating transcription factor 6α (ATF6α), C/EBP homologous protein (CHOP), growth arrest and DNA damage-inducible protein 34 (GADD34), tumor necrosis factor receptor-associated factor 2 (TRAF2), JUN N-terminal kinase (JNK), regulated IRE1-dependent decay (RIDD), transcriptionally active XBP1 (XBP1s), or unspliced XBP1 (XBP1u). In some embodiments, a compound disclosed herein selectively binds to an IRE1 family protein and alters a downstream cellular process. In some embodiments, an IRE1 family protein is IRE1, IRE1α, or ERN1.

In some embodiments, a compound disclosed herein selectively binds to an IRE1 family protein and decreases or blocks a downstream signaling pathway. In some embodiments, a compound disclosed herein selectively binds to an IRE1 family protein and decreases or blocks activity or signaling of TXNIP, Caspase 1, Interleukin 1-beta, JNK, Bim, cytochrome C, Caspase 3, Caspase 8, mRNA degradation, miRNA degradation, apoptotosis-inducing proteins, or inflammation-inducing proteins. In some embodiments, a compound disclosed herein selectively binds to an IRE1 family protein and decreases XBP1 mRNA levels. In some embodiments, a compound disclosed herein selectively binds to an IRE1 family protein and decreases transcriptionally active XBP1 (XBP1s) mRNA levels. In some embodiments, a compound disclosed herein selectively binds to an IRE1 family protein and decreases spliced XBP1 mRNA levels. In some embodiments, an IRE1 family protein is IRE1, IRE1α, or ERN1.

In some embodiments, a compound disclosed herein selectively binds to an IRE1 family protein and increases, activates, or removes a block of a downstream signaling pathway. In some embodiments, a compound disclosed herein selectively binds to an IRE1 family protein and increases, activates, or removes a block of activity or signaling of Bcl2, Bcl-XL, Mcl-1, Bax, Bak, other anti-apoptotic proteins, or an mRNA translocon proteins. In some embodiments, an IRE1 family protein is IRE1, IRE1α, or ERN1.

In some embodiments, a compound disclosed herein selectively binds to an IRE1family protein and disrupts binding with an effector protein. In some cases, the effector protein binds to the IRE1 family protein when in a dimerized or oligomerized state. In some cases, the effector protein binds to the IRE1 family protein when in a non-dimerized or non-oligomerized state. In some cases, the effector protein is immunoglobulin heavy-chain binding protein (BIP), protein kinase R (PKR)-like endoplasmic reticulum kinase (PERK), glucose regulate protein 78 (Grp78), tumor necrosis factor receptor-associated factor 2 (TRAF2), JUN N-terminal kinase (JNK), transcriptionally active XBP1 (XBP1s), unspliced XBP1 (XBP1u), regulated IRE1-dependent decay (RIDD), Heat shock protein 90 kDa alpha (HSP 90-alpha), or misfolded protein. In some embodiments, an IRE1 family protein is IRE1, IRE1α, or ERN1.

In some embodiments, a compound disclosed herein selectively binds to an IRE1 family protein and alters activity of a cellular process or cellular function, such as regulated IRE1-dependent decay (RIDD), RNA decay, translation, autophagy, cell survival, ER protein folding, ERAD, reactive oxygen species generation, transport, ER-associated protein degradation (ERAD), protein synthesis, or apoptosis. In some embodiments, where an altered or lack of a cellular process or cellular function is associate with a disease state, selective binding of a compound disclosed herein results in inhibiting or alleviating the disease state, or inhibiting a deleterious activity associated with the disease state. In some embodiments, an IRE1 family protein is IRE1, IRE1α, or ERN1.

Diseases Associated with Altered IRE1 Pathway Signaling

In some cases, a compound disclosed herein is used to treat or ameliorate a disease associated with altered IRE1α pathway signaling when administered to a subject in need thereof. In some cases, a compound disclosed herein is used to treat or ameliorate the effects of a disease associated with altered IRE1α pathway signaling when administered to a subject in need thereof. Exemplary disease associated with altered IRE1α signaling include cancer. In some cases, a compound disclosed herein is used to treat or ameliorate a cancer when administered to a subject in need thereof. Exemplary cancers include tumors, solid and hematologic cancers. In some cases, a compound disclosed herein is used to treat or ameliorate a cell proliferative disorder when administered to a subject in need thereof. In some cases, the cell proliferative disorder is a cancer. In some cases, the cancer is ovarian cancer, breast cancer, triple negative breast cancer (TNBC).

An IRE1α pathway can be involved in a variety of pathological conditions, including neurodegenerative diseases, inflammation, metabolic disorders, liver dysfunction, brain ischemia, heart ischemia, autoimmune diseases, and cancer. In some cases, modulation of this pathway provides therapeutic methods useful for treatment of such diseases.

In some instances, a compound disclosed herein is used to reinforce anti-tumor mechanisms. In some cases, an anti-tumor mechanism comprises direct inhibition of tumor growth. In some cases, an anti-tumor mechanism comprises induction of anti-tumor immunity. In some cases, anti-tumor mechanisms comprise direct inhibition of tumor growth and simultaneous induction of anti-tumor immunity. In some cases, a compound disclosed herein can prevent lipid accumulation in myeloid cells exposed to ovarian cancer-derived ascites supernatants. In some cases, a compound disclosed herein can block myeloid cell immunosuppression mediated by tumor-associated factors. In some cases, a compound disclosed herein can be employed as therapeutic compound that enhances dendritic cell and T cell anti-tumor activity in mammals. For example, the compounds disclosed herein can be used to treat murine and human ovarian cancers.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use will depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%), 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In one embodiment, the therapeutic effectiveness of one of the compounds described herein is enhanced by administration of an adjuvant {i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

EXAMPLES

Example A1: Synthesis of tert-butyl ((1r,4r)-4-((6-(4,4,5,5-tetramethyl-1,3,2-dioxaborolan-2-yl)quinazolin-2-yl)amino)cyclohexyl)carbamate (1A)

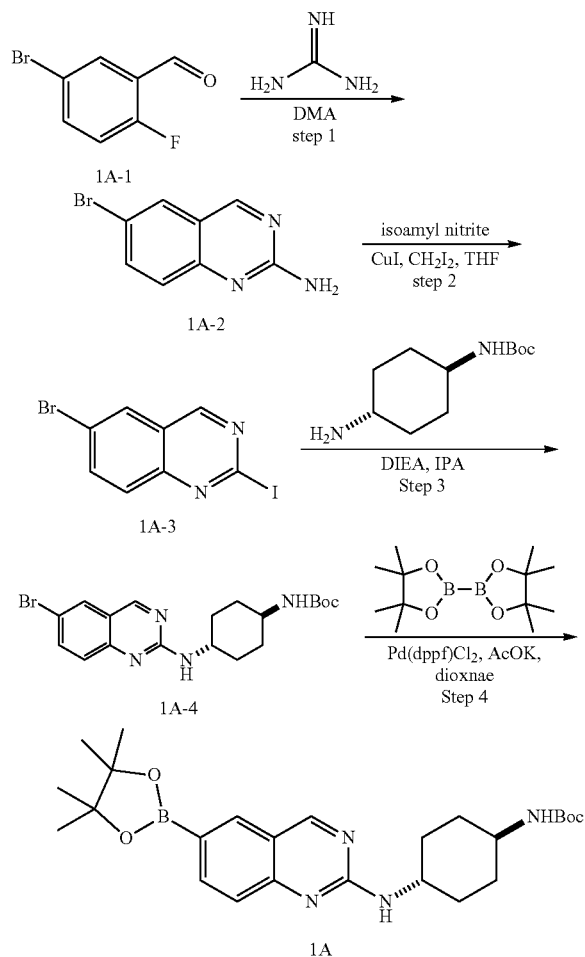

Step 1: 6-bromoquinazolin-2-amine (1A-2)

To a solution of 5-bromo-2-fluoro-benzaldehyde (20.0 g, 98.5 mmol) in DMA (700 mL) was added guanidine-carbonic acid (26.6 g, 147.7 mmol). The mixture was stirred at 160° C. for 0.5 h, cooled to rt and concentrated. The residue was diluted with $H_2O$ (300 mL) and extracted with ethyl acetate (200 mL×3). The combined organic layers were washed with brine (100 mL×3), dried over $Na_2SO_4$, filtered and concentrated under reduced pressure to give a residue. The residue was washed with DCM (300 mL) to get compound 1A-2 (4.0 g).

Step 2: 6-bromo-2-iodoquinazoline (1A-3)

To a solution of compound 1A-2 (2.0 g, 8.9 mmol) in THF (20.0 mL) under $N_2$ were added of isoamylnitrite (3.1 g, 26.8 mmol, 3.6 mL), diiodomethane (11.9 g, 44.7 mmol, 3.6 mL) and CuI (1.7 g, 8.9 mmol). The mixture was stirred at 80° C. for 2 h, cooled to rt, quenched by addition of ice water (100 mL), and extracted with ethyl acetate (100 mL×3). The combined organic layers were washed with brine (100 mL×3), dried over anhydrous $Na_2SO_4$, filtered and concentrated. The residue was purified by column chromatography ($SiO_2$) to afford compound 1A-3 (2.1 g).

Step 3: 1-tert-butyl ((1r,4r)-4-((6-bromoquinazolin-2-yl)amino)cyclohexyl)carbamate (1A-4)

To a solution of compound 1A-3 (4.0 g, 11.9 mmol) in IPA (120.0 mL) was added DIEA (4.6 g, 35.8 mmol, 6.2 mL) and tert-butyl ((1r,4r)-4-aminocyclohexyl)carbamate (7.6 g, 35.8 mmol). The mixture was stirred at 80° C. for 12 h, cooled to rt and filtered. The collected solid was washed with Dichloromethane/Methanol (10/1, 60 mL). The combined filtrate was concentrated to give a residue which was purified by column chromatography ($SiO_2$) to afford compound 1A-4 (3.6 g, 6.8 mmol, 57.2% yield). M+H+=421.1 (LCMS); $^1$H NMR (CHLOROFORM-d, 400 MHz) δ 8.87 (s, 1H), 7.78 (d, J=1.8 Hz, 1H), 7.71 (dd, J=2.0, 9.0 Hz, 1H), 7.44 (d, J=9.2 Hz, 1H), 5.19 (br d, J=7.9 Hz, 1H), 4.43 (br s, 1H), 3.93 (br d, J=7.5 Hz, 1H), 3.49 (br s, 1H), 2.27-2.00 (m, 4H), 1.46 (s, 9H), 1.40-1.29 (m, 4H).

Step 4: tert-butyl ((1r,4r)-4-((6-(4,4,5,5-tetramethyl-1,3,2-dioxaborolan-2-yl)quinazolin-2-yl)amino)cyclohexyl)carbamate (1A)

A mixture of compound 1A-4 (2.0 g, 4.7 mmol), 4,4,5,5-tetramethyl-2-(4,4,5,5-tetramethyl-1,3,2-dioxaborolan-2-yl)-1,3,2-dioxaborolane (1.3 g, 5.2 mmol), AcOK (1.4 g, 14.2 mmol) and Pd(dppf)Cl$_2$ (347 mg, 474.6 umol) in dioxane (50 mL) was degassed and purged with $N_2$ for 3 times, and heated at 90° C. for 12 h under $N_2$. The reaction was cooled to rt and concentrated to give a residue. The residue was purified by column chromatography ($SiO_2$) to afford compound 1A (2.7 g, crude). M+H$^+$=469.2 (LCMS).

Example A2: Synthesis of tert-butyl 4-((6-(3-amino-1-methyl-1H-pyrazol-5-yl)quinazolin-2-yl)(tert-butoxycarbonyl)amino)piperidine-1-carboxylate (2A)

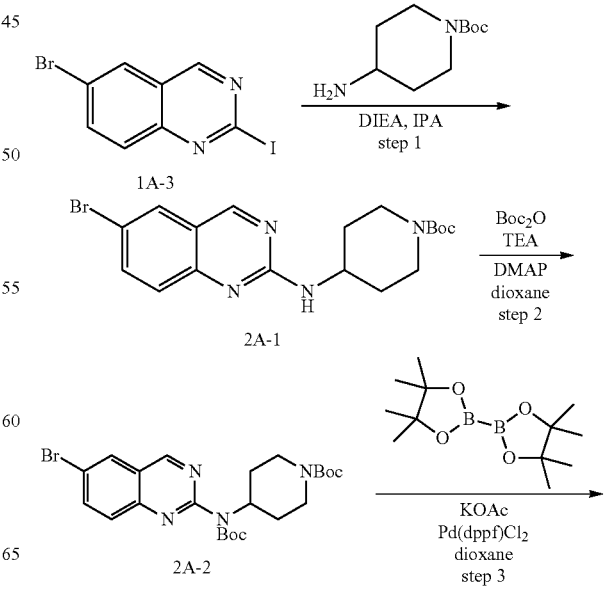

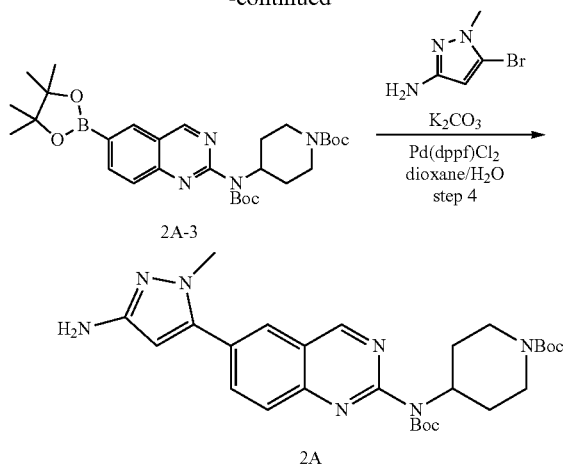

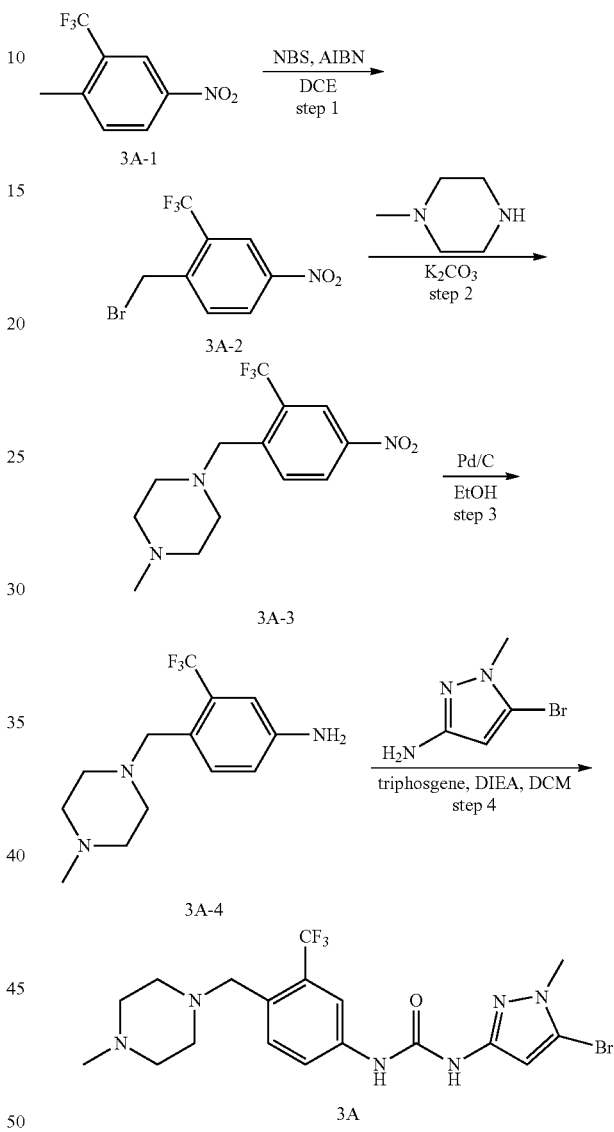

Step 1: tert-butyl 4-((6-bromoquinazolin-2-yl)amino)piperidine-1-carboxylate (2-1)

To a solution of compound 1A-3 (200 mg, 597.1 umol) in isopropanol (3.0 mL) was added tert-butyl 4-aminopiperidine-1-carboxylate (598 mg, 3.0 mmol) and DIEA (232 mg, 1.8 mmol, 312.9 uL). The mixture was stirred at 80° C. for 2 h, cooled to rt and concentrated. The residue was purified by prep-TLC ($SiO_2$) to afford compound 2A-1 (131 mg).

Step 2: tert-butyl 4-((6-bromoquinazolin-2-yl)(tert-butoxycarbonyl)amino)piperidine-1-carboxylate (2A-2)

To a mixture of compound 2A-1 (200 mg, 916.3 umol) and triethylamine (278 mg, 2.7 mmol, 381.0 uL) in dichloromethane (4 mL) were added tert-butoxycarbonyl tert-butyl carbonate (600 mg, 2.8 mmol) and DMAP (111 mg, 916.3 umol). The mixture was stirred at 25° C. for 12 h, concentrated to get crude residue to which dioxane (2 mL) was added. The mixture was stirred at 90° C. for 12 h, cooled to rt and concentrated. The residue was purified by column chromatography ($SiO_2$) to afford 2A-2 (400 mg).

Step 3: tert-butyl 4-((tert-butoxycarbonyl)(6-(4,4,5,5-tetramethyl-1,3,2-dioxaborolan-2-yl)quinazolin-2-yl)amino)piperidine-1-carboxylate (2A-3)

To a solution of compound 2A-2 (400 mg, 394.1 umol) and KOAc (58 mg, 591.2 umol) in dioxane (10 mL) were added 4,4,5,5-tetramethyl-2-(4,4,5,5-tetramethyl-1,3,2-dioxaborolan-2-yl)-1,3,2-dioxaborolane (120 mg, 472.9 umol) and Pd(dppf)$Cl_2$ (28 mg, 39.4 umol). The mixture was stirred at 90° C. for 12 h under $N_2$, cooled to rt and concentrated to give a crude residue, which was purified by prep-TLC ($SiO_2$) to afford compound 2A-3 (150 mg).

Step 4: tert-butyl 4-((6-(3-amino-1-methyl-1H-pyrazol-5-yl)quinazolin-2-yl)(tert-butoxy carbonyl)amino)piperidine-1-carboxylate (2A)

To a solution of compound 2A-3 (150 mg, 270.5 umol) and $K_2CO_3$ (112 mg, 811.5 umol) in dioxane (4 mL) and $H_2O$ (400 uL) were added 5-Bromo-1-methyl-1H-pyrazol-3-amine (47 mg, 270.5 umol) and Pd(dppf)$Cl_2$ (19 mg, 27.0 umol). The mixture was stirred at 90° C. for 12 h under $N_2$. The mixture was cooled to rt and concentrated to give a residue, which was purified by prep-TLC ($SiO_2$) to afford compound 2A (100 mg).

Example A3: Synthesis of 1-(5-bromo-1-methyl-1H-pyrazol-3-yl)-3-(4-((4-methylpiperazin-1-yl)methyl)-3-(trifluoromethyl)phenyl)urea (3A)

Step 1: 1-(bromomethyl)-4-nitro-2-(trifluoromethyl)benzene (3A-2)

To a solution of 1-methyl-4-nitro-2-(trifluoromethyl)benzene (8.0 g, 39.0 mmol) in DCE (240 mL) was added AIBN (640 mg, 3.9 mmol) and NBS (6.9 g, 39.0 mmol). The mixture was stirred at 80° C. for 12 h, cooled to rt and concentrated. The residue was purified by column chromatography ($SiO_2$) to afford compound 3A-2 (11.0 g).

Step 2: 1-methyl-4-(4-nitro-2-(trifluoromethyl)benzyl)piperazine (3A-3)

To a solution of 3A-2 (11.0 g, 38.7 mmol) in DCM (120 mL) was added 1-methylpiperazine (7.7 g, 77.4 mmol, 8.6 mL) and $K_2CO_3$ (5.3 g, 38.7 mmol). The mixture was stirred at 25° C. for 1 h, washed with water (80 mL×2), dried over anhydrous Na$_2$SO$_4$, filtered and concentrated to give a residue. The residue was purified by column chromatography (SiO$_2$) to give compound 3A-3 (3.5 g).

Step 3: 4-((4-methylpiperazin-1-yl)methyl)-3-(trifluoromethyl)aniline (3A-4)

To a solution of compound 3A-3 (3.5 g, 11.5 mmol) in EtOH (40 mL) was added Pd/C (350 mg, 10%). The mixture was stirred under H$_2$ (1 atm) for 1 h, filtered and concentrated to give compound 3A-4 (3.2 g), which was used into the next step without further purification.

Step 4: 1-(5-bromo-1-methyl-1H-pyrazol-3-yl)-3-(4-((4-methylpiperazin-1-yl)methyl)-3-(trifluoromethyl)phenyl)urea (3A)

To a solution of compound 3A-4 (400 mg, 1.4 mmol) in DCM (12 mL) was added DIEA (283 mg, 2.1 mmol, 382.4 uL) and triphosgene (143 mg, 481.8 umol) at −20° C. The mixture was stirred at −20° C. for 0.5 h. A solution of 5-Bromo-1-methyl-1H-pyrazol-3-amine (257 mg, 1.4 mmol) in DCM (4.0 mL) was added and the resulting mixture was stirred at 25° C. for 12 h. The reaction was quenched with MeOH (3.0 mL) and concentrated. The residue was purified by prep-TLC (SiO$_2$) to give compound 3A (500 mg, 799.3 umol, 54.7% yield). M+H$^+$=475.1 (LCMS)

Example A4: Synthesis of 1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea (2)

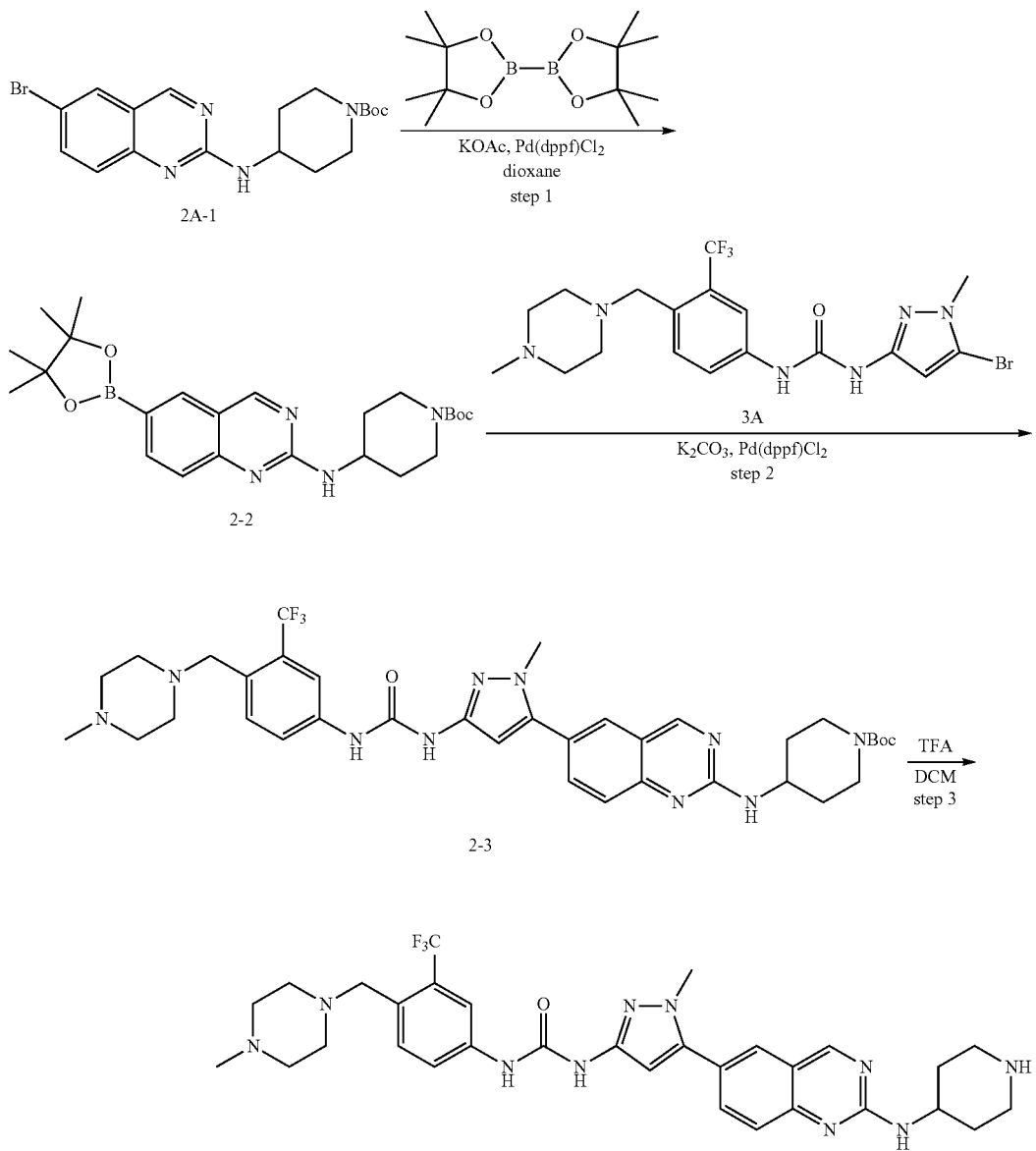

Step 1: tert-butyl 4-((6-(4,4,5,5-tetramethyl-1,3,2-dioxaborolan-2-yl)quinazolin-2-yl)amino) piperidine-1-carboxylate (2-2)

A mixture of compound 2A-1 (131 mg, 321.6 umol), KOAc (95 mg, 964.9 umol), 4,4,5,5-tetramethyl-2-(4,4,5,5-tetramethyl-1,3,2-dioxaborolan-2-yl)-1,3,2-dioxaborolane (98 mg, 386.0 umol), Pd(dppf)Cl$_2$ (24 mg, 32.2 umol) in dioxane (4.0 mL) was degassed and purged with N$_2$ for 3 times, and then the mixture was stirred at 90° C. for 12 h under N$_2$. The reaction mixture was concentrated and the residue was purified by prep-TLC (SiO$_2$) to afford compound 2-2 (100 mg).

Step 2: tert-butyl 4-((6-(1-methyl-3-(3-(4-((4-methylpiperazin-1-yl)methyl)-3-(trifluoromethyl)phenyl) ureido)-1H-pyrazol-5-yl)quinazolin-2-yl)amino) piperidine-1-carboxylate (2-3)

To a solution of compound 2-2 (50 mg, 110.0 umol) in dioxane (1.8 mL) and H$_2$O (180 uL) was added K$_2$CO$_3$ (46 mg, 330.1 umol), compound 3A (52 mg, 110.0 umol) and Pd(dppf)Cl$_2$ (8 mg, 11.0 umol). The mixture was degassed and purged with N$_2$ for 3 times and then stirred at 90° C. for 12 h under N$_2$. The reaction mixture was concentrated and the residue was purified by prep-TLC (SiO$_2$) to afford compound 2-3 (34 mg).

Step 3: 1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea (2)

To a solution of compound 2-3 (34 mg, 69.2 umol) in DCM (2.0 mL) was added trifluoroacetic acid (1.0 mL). The mixture was stirred at 25° C. for 0.5 h. The reaction mixture was concentrated under reduced pressure. The residue was purified by prep-HPLC to give 2 (4.6 mg, 5.7 umol, 8.2% yield, TFA). M+H$^+$=623.4 (LCMS); $^1$H NMR (METHANOL-d$_4$, 400 MHz): δ 9.27 (br s, 1H), 8.03 (br s, 1H), 7.93 (br s, 2H), 7.79-7.68 (m, 1H), 7.66 (br s, 3H), 7.37 (br d, J=8.6 Hz, 1H), 6.48-6.32 (m, 1H), 5.87 (s, 1H), 3.82 (br d, J=19.0 Hz, 3H), 3.72 (s, 2H), 3.58-3.34 (m, 4H), 3.25-3.08 (m, 4H), 3.00 (br s, 1H), 2.88 (s, 3H), 2.47 (br s, 1H), 2.32 (br d, J=15.4 Hz, 2H), 1.89 (br d, J=11.9 Hz, 2H), 1.38-1.19 (m, 2H).

The following compounds were synthesized according to procedures described in example A$^4$ above for the preparation of compound 2.

| Comp ID | Structure | Chemical Name | Mass (M + H$^+$) | $^1$H NMR (MeOD, 400 MHz) |
|---|---|---|---|---|
| 1 | 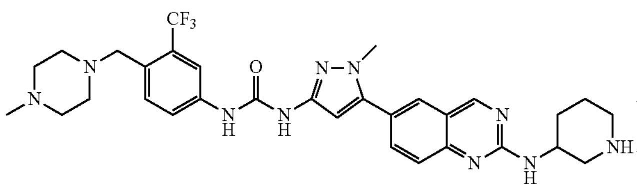 | 1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea, trifluoroacetate salt | Calc'd for C$_{31}$H$_{38}$F$_3$N$_{10}$O: 623.3; Found: 623.4 | $^1$H NMR (DMSO-d$_6$, 400 MHz) δ 9.49 (s, 1H), 9.33-9.18 (m, 2H), 8.80 (br s, 2H), 8.03 (s, 2H), 7.87 (br d, J = 9.2 Hz, 1H), 7.76 (br s, 1H), 7.63-7.51 (m, 3H), 6.54 (s, 1H), 3.79 (s, 3H), 3.64 (s, 2H), 3.40 (br d, J = 19.7 Hz, 3H), 3.25-3.12 (m, 2H), 3.09-2.72 (m, 9H), 2.45-2.26 (m, 2H), 2.06-1.86 (m, 2H), 179-1.55 (m, 2H) |
| 3 | 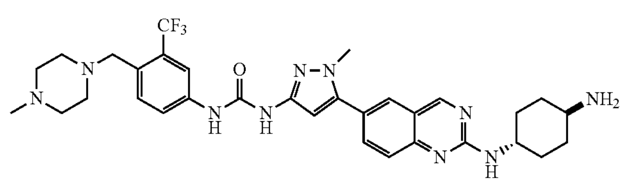 [SMILES: CN1CCN(Cc2ccc(NC(=O)Nc3cc(-c4ccc5nc(N[C@H]6CC[C@H](N)CC6)ncc5c4)n(C)n3)cc2C(F)(F)F)CC1] | 1-(5-(2-(((1r,4r)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea, trifluoroacetate salt | Calc'd for C$_{32}$H$_{40}$F$_3$N$_{10}$O: 637.3; Found: 637.4 | $^1$H NMR (DMSO-d$_6$, 400 MHz) δ 9.44 (br s, 1 H), 9.27 (s, 1 H), 9.19 (br s, 1 H), 8.01 (s, 1 H), 7.88 (br s, 3 H), 7.53-7.61 (m, 3 H), 6.52 (s, 1 H), 3.78 (s, 3 H), 3.62 (br s, 2H), 3.32-3.44 (m, 2 H), 2.82-3.04 (m, 4 H), 2.77 (s, 3 H), 2.26-2.45 (m, 4 H), 1.92-2.08 (m, 4 H), 1.31-1.52 (m, 4 H) |
| 5 | 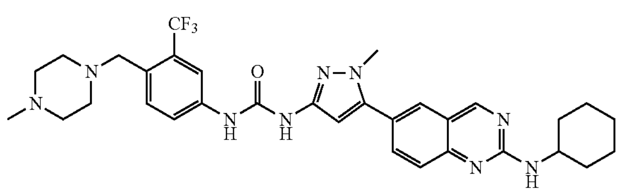 [SMILES: CN1CCN(Cc2ccc(NC(=O)Nc3cc(-c4ccc5nc(NC6CCCCC6)ncc5c4)n(C)n3)cc2C(F)(F)F)CC1] | 1-(5-(2-(cyclohexylamino)quinazolin-6-yl)-1-methyl-1H-pyrazol-3-yl)-3-(4-((4-methylpiperazin-1-yl)methyl)-3-(trifluoromethyl)phenyl)urea | Calc'd for C$_{32}$H$_{39}$F$_3$N$_9$O: 622.3; Found: 622.4 | δ 9.32 (br s, 1H), 9.13 (s, 2H), 7.98 (dd, J = 2.0, 19.6 Hz, 2H), 7.80 (dd, J = 2.0, 8.8 Hz, 1H), 7.65-7.38 (m, 4H), 6.50 (s, 1H), 3.94-3.82 (m, 4H), 3.57-3.48 (m, 2H), 2.43-2.29 (m, 7H), 2.19 (s, 3H), 1.94 (br s, 2H), 1.79-1.70 (m, 2H), 1.61 (br d, J = 12.6 Hz, 1H), 1.45-1.07 (m, 6H) |

| Comp ID | Structure | Chemical Name | Mass (M + H⁺) | ¹H NMR (MeOD, 400 MHz) |
|---|---|---|---|---|
| 15 | 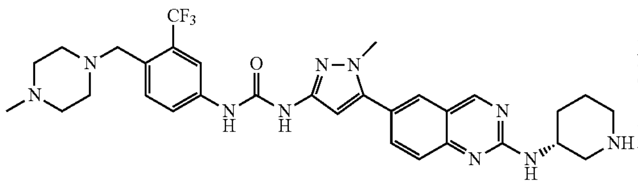 | (R)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea, formate salt | Calc'd for $C_{31}H_{38}F_3N_{10}O$: 623.3; Found: 623.4 | δ 9.13 (s, 1H), 8.54 (br s, 1H), 7.98-7.87 (m, 2H), 7.82 (dd, J = 2.0, 8.8 Hz, 1H), 7.69-7.57 (m, 3H), 6.41 (s, 1H), 4.41-4.29 (m, 1H), 3.83 (s, 3H), 3.73-3.56 (m, 3H), 3.39-3.25 (m, 1H), 3.13 (br s, 4H), 3.06-2.94 (m, 2H), 2.94-2.68 (m, 7H), 2.22-2.01 (m, 2H), 1.98-1.64 (m, 2H) |
| 17 | 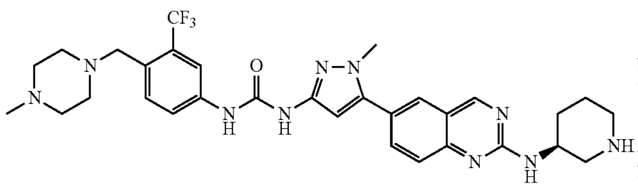 | (S)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea, formate salt | Calc'd for $C_{31}H_{38}F_3N_{10}O$: 623.3; Found: 623.4 | δ 9.17 (s, 1 H), 7.95 (s, 2 H), 7 81-7.93 (m, 1 H), 7.61-7.71 (m, 3 H), 6.43 (s, 1 H), 4.34-4.43 (m, 1 H), 3.85 (s, 3 H), 3.58-3.81 (m, 3 H), 3.37 (br s, 1 H), 3.15-3.24 (m, 4 H), 2.98-3.10 (m, 2 H), 2.56-2.85 (m, 7H), 2.06-2.23 (m, 2 H), 1.73-1.98 (m, 2 H) |
| 26 | 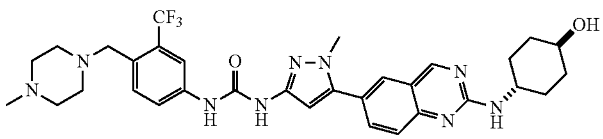 | 1-(5-(2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{32}H_{39}F_3N_9O_2$: 638.3; Found: 638.4 | δ 9.07 (br s, 1H), 8.43 (br s, 1H), 7.90 (br d, J = 16.8 Hz, 2H), 7.80 (br, d, J = 8.8 Hz, 1H), 7.70-7.58 (m, 3H) 6.38 (br s, 1H), 3.83 (s, 3H), 3.69 (s, 2H), 3.59 (br d, J = 3.5 Hz, 1H), 3.14 (br s, 4H), 2.76 (s, 6H), 2.16-1.95 (m, 4H), 1.52-1.33 (m, 4H) |
| 29 | 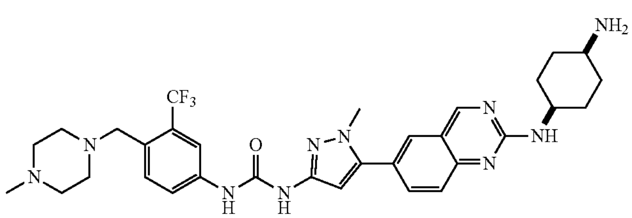 | 1-(5-(2-(((1s,4s)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{32}H_{40}F_3N_{10}O$: 637.3; Found: 637.4 | δ 9.13 (s, 1 H), 8.38-8.50 (m, 2 H), 7.93 (br d, J = 6.62 Hz, 2 H), 7.83 (br d, J = 8.60 Hz, 1 H), 7.61-7.69 (m, 3 H), 6.41 (s, 1 H), 4.20 (br s, 1 H), 3.84 (s, 3 H), 3.69 (s, 2 H), 3.24-3.28 (m, 1 H), 3.16 (br s, 4 H), 2.55-2.80 (m, 7 H), 2.00-2.10 (m, 2 H), 1.73-1.95 (m, 6 H) |
| 33 | 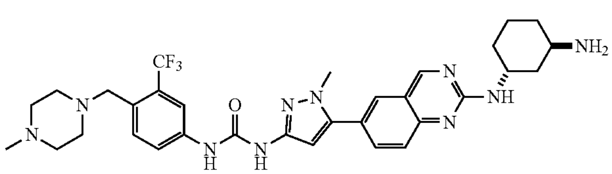 | 1-(5-(2-(((1R,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{32}H_{40}F_3N_{10}O$: 637.3; Found: 637.0 | δ 9.11 (s, 1H), 8.49 (br s, 2H), 7.92 (br d, J = 12.8 Hz, 2H), 7.81 (br d, J = 8.6 Hz, 1H), 7.71-7.49 (m, 3H), 6.41 (br s, 1H), 4.44 (br s, 1H), 3.83 (s, 3H), 3.67 (br s, 2H), 3.49 (br s, 1H), 3.11 (br s, 3H), 2.81-2.52 (m, 7H), 2.33 (br d, J = 12.3 Hz, 1H), 2.00 (br d, J = 11.0 Hz, 1H), 1.81 (br s, 5H), 1.56 (br s, 1H) |

| Comp ID | Structure | Chemical Name | Mass (M + H+) | ¹H NMR (MeOD, 400 MHz) |
|---|---|---|---|---|
| 34 | 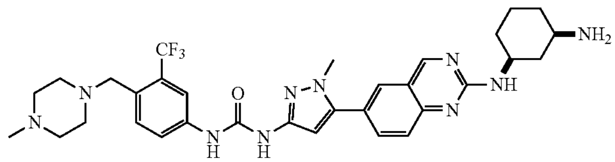 | 1-(5-(2-(((1S,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{32}H_{40}F_3N_{10}O$: 637.3; Found: 637.3 | δ 9.09 (s, 1H), 8.58 (br s, 1H), 7.97-7.84 (m, 2H), 7.80 (br d, J = 9.0 Hz, 1H), 7.69-7.55 (m, 3H), 6.40 (br s, 1H), 4.06 (br t, J = 11.2 Hz, 1H), 3.83 (s, 3H), 3.68 (br s, 2H), 3.28-3.03 (m, 5H), 2.86-2.56 (m, 7H), 2.50 (br d, J = 10.6 Hz, 1H), 2.14-1.90 (m, 3H), 1.55 (q, J = 13.0 Hz, 1H), 1.46-1.26 (m, 3H) |
| 36 | 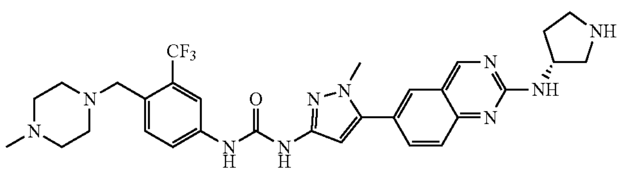 [SMILES: CN1CCN(Cc2ccc(NC(=O)Nc3cc(-c4ccc5nc(N[C@@H]6CCNC6)ncc5c4)n(C)n3)cc2C(F)(F)F)CC1] | (R)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea, formate salt | Calc'd for $C_{30}H_{36}F_3N_{10}O$: 609.3; Found: 609.0 | δ 9.20 (s, 1H), 8.53 (br s, 2H), 7.98 (dd, J = 1.8, 6.1 Hz, 2H), 7.89 (dd, J = 2.0, 8.8 Hz, 1H), 7.75-7.65 (m, 3H), 6.46 (s, 1H), 4.79-4.71 (m, 1H), 3.88 (s, 3H), 3.74-3.56 (m, 4H), 3.53-3.41 (m, 2H), 3.22-3.01 (m, 4H), 2.83-2.58 (m, 7H), 2.53-2.41 (m, 1H), 2.30-2.19 (m, 1H) |
| 38 | 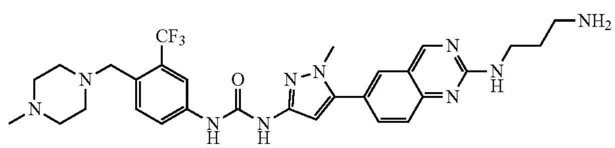 [SMILES: CN1CCN(Cc2ccc(NC(=O)Nc3cc(-c4ccc5nc(NCCCN)ncc5c4)n(C)n3)cc2C(F)(F)F)CC1] | 1-(5-(2-((3-aminopropyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{29}H_{36}F_3N_{10}O$: 597.3; Found: 597.2 | δ 9.15 (s, 1 H), 8.52 (br s, 2 H), 7.95 (s, 2 H), 7.86 (dd, J = 8.80, 1.96 Hz, 1 H), 7.62-7.72 (m, 3 H), 6.43 (s, 1 H), 3.85 (s, 3 H), 3.62-3.74 (m, 4 H), 3.03-3.17 (m, 6 H), 2.63-2.78 (m, 7 H), 2.05 (m, J = 6.72 Hz, 2 H) |
| 39 | 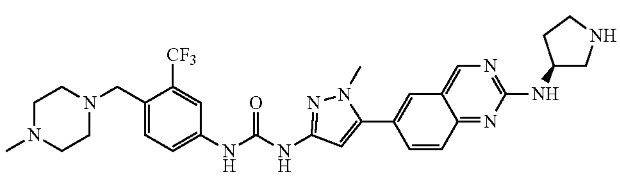 [SMILES: CN1CCN(Cc2ccc(NC(=O)Nc3cc(-c4ccc5nc(N[C@H]6CCNC6)ncc5c4)n(C)n3)cc2C(F)(F)F)CC1] | (S)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea, formate salt | Calc'd for $C_{30}H_{36}F_3N_{10}O$: 609.3; Found: 609.2 | δ 9.17 (s, 1H), 7.96 (br d, J = 9.5 Hz, 2H), 7.86 (br d, J = 8.8 Hz, 1H), 7.76-7.59 (m, 3H), 6.45 (br s, 1H), 4.74 (br s, 1H), 3.86 (s, 3H), 3.76-3.67 (m, 2H), 3.64-3.53 (m, 2H), 3.52-3.45 (m, 2H), 3.16 (br s, 4H), 2.78 (s, 3H), 2.71 (br s, 4H), 2.46 (qd, J = 7.1, 13.9 Hz, 1H), 2.34-2.14 (m, 1H) |
| 41 | 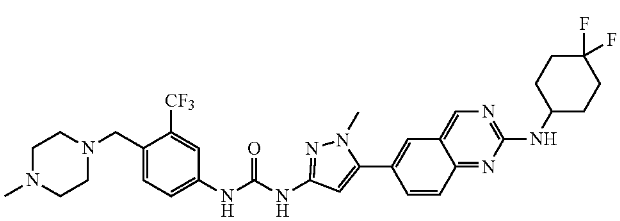 [SMILES: CN1CCN(Cc2ccc(NC(=O)Nc3cc(-c4ccc5nc(NC6CCC(F)(F)CC6)ncc5c4)n(C)n3)cc2C(F)(F)F)CC1] | 1-(5-(2-((4,4-difluorocyclohexyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{32}H_{37}F_3N_9O$: 658.3; Found: 658.2 | δ 9.10 (s, 1H), 7.91 (br d, J = 11.8 Hz, 2H), 7.82 (br d, J = 8.8 Hz, 1H), 7.72-7.57 (m, 3H), 6.40 (s, 1H), 4.12 (br s, 1H), 3.84 (s, 3H), 3.67 (s, 2H), 2.92 (br s, 4H), 2.60 (s, 7H), 2.12 (br d, J = 9.2 Hz, 4H), 2.03-1.87 (m, 2H), 1.81-1.61 (m, 2H) |

-continued

| Comp ID | Structure | Chemical Name | Mass (M + H⁺) | ¹H NMR (MeOD, 400 MHz) |
|---|---|---|---|---|
| 50 | 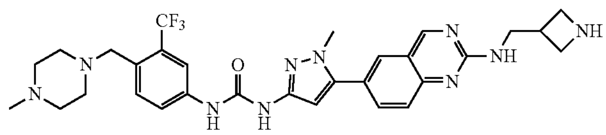 [SMILES: CN1CCN(Cc2ccc(NC(=O)Nc3cc(-c4ccc5nc(NCC6CNC6)ncc5c4)n(C)n3)cc2C(F)(F)F)CC1] | 1-(5-(2-((azetidin-3-ylmethyl)amino)quinazolin-6-yl)-1-methyl-1H-pyrazol-3-yl)-3-(4-((4-methylpiperazin-1-yl)methyl)-3-(trifluoromethyl)phenyl)urea, formate salt | Calc'd for $C_{30}H_{36}F_3N_{10}O$: 609.3; Found: 609.3 | δ 9.14 (s, 1H), 8.55 (br s, 1H), 7.94 (br d, J = 4.4 Hz, 2H), 7.84 (br d, J= 9.2 Hz, 1H), 7.71-7.59 (m, 3H), 6.42 (br s, 1H), 4.19-4.01 (m, 3H), 3.92-3.62 (m, 7H), 3.33 (br s, 2H), 3.13 (br s, 4H), 2.90-2.47 (m, 7H) |

Example A5: Synthesis of 1-(5-(3-(cyclohexylamino)isoquinolin-7-yl)-1-methyl-1H-pyrazol-3-yl)-3-(4-((4-methylpiperazin-1-yl)methyl)-3-(trifluoromethyl)phenyl)urea (4)

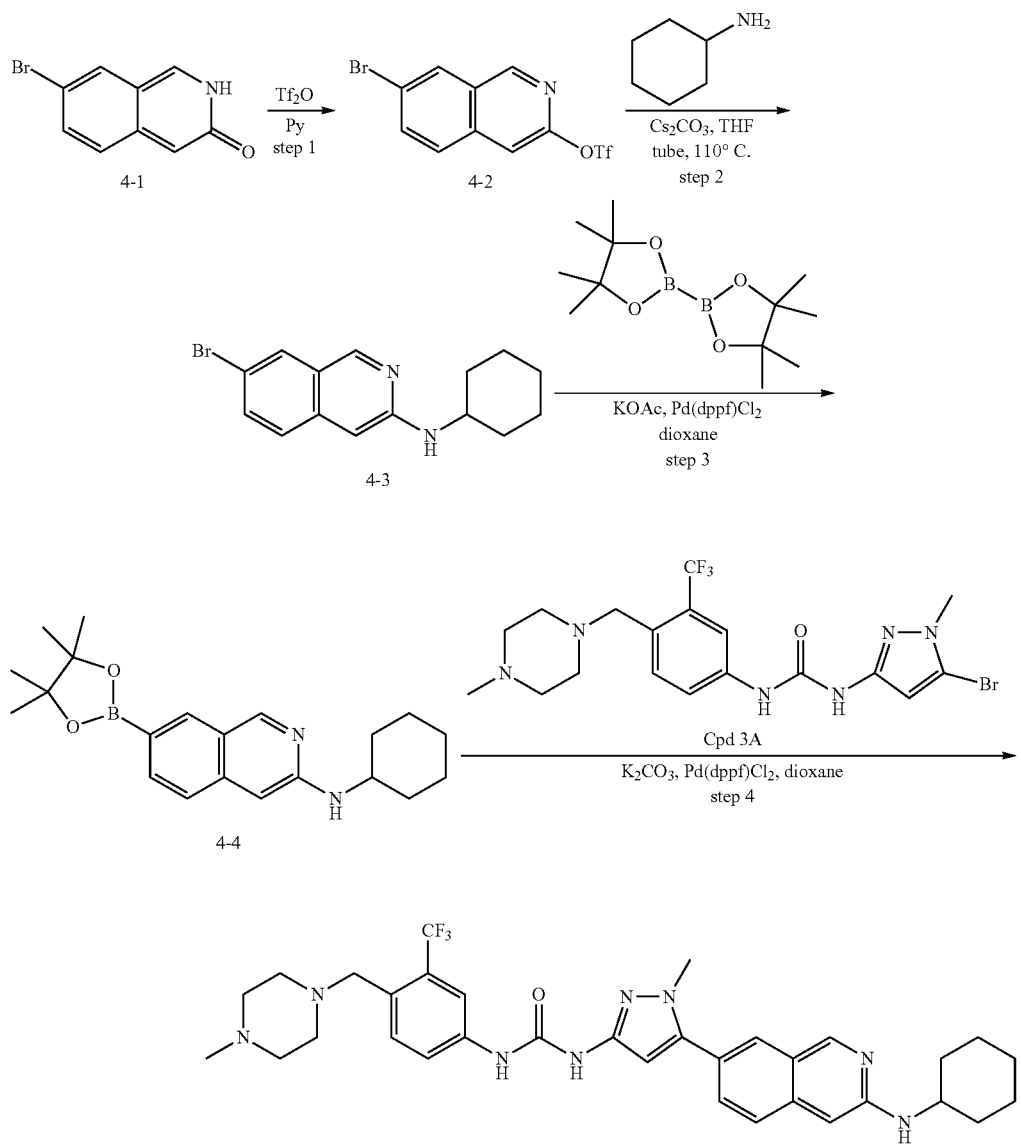

Step 1: 7-bromoisoquinolin-3-yl trifluoromethanesulfonate (4-2)

A solution of compound 7-bromoisoquinolin-3(2H)-one (45.0 g, 200 mmol) in pyridine (500 mL) was cooled to 0° C. and Tf$_2$O (170.0 g, 602 mmol, 99.4 mL) was added dropwise. The mixture was stirred at 25° C. for 2 h, concentrated, diluted with H$_2$O (200 mL) and extracted with ethyl acetate (300 mL×3). The combined organic layers were washed with brine (200 mL×3), dried over Na$_2$SO$_4$, filtered and concentrated. The residue was purified by column chromatography (SiO$_2$) to afford compound 4-2 (21.0 g, 58.9 mmol, 29.3% yield). $^1$H NMR (DMSO-d$_6$, 400 MHz): δ 9.25 (s, 1H), 8.57 (s, 1H), 8.17 (s, 1H), 8.13-8.08 (m, 1H), 8.07-8.02 (m, 1H)

Step 2: 7-bromo-N-cyclohexylisoquinolin-3-amine (4-3)

To a solution of compound 4-2 (200 mg, 561 umol) in THF (10 mL) were added Cs$_2$CO$_3$ (548 mg, 1.6 mmol) and cyclohexanamine (835 mg, 8.4 mmol, 960.2 uL). The mixture was stirred at 110° C. for 12 h. The mixture was diluted with H$_2$O (10 mL) and extracted with ethyl acetate (20 mL×3). The combined organic layers were washed with brine (10 mL×3), dried over Na$_2$SO$_4$, filtered and concentrated under reduced pressure to give a residue. The residue was purified by column chromatography (SiO$_2$) to afford compound 4-3 (60 mg).

Step 2: N-cyclohexyl-7-(4,4,5,5-tetramethyl-1,3,2-dioxaborolan-2-yl)isoquinolin-3-amine (4-4)

To a solution of compound 4-3 (60 mg, 196.5 umol) in dioxane (2 mL) was added 4,4,5,5-tetramethyl-2-(4,4,5,5-tetramethyl-1,3,2-dioxaborolan-2-yl)-1,3,2-dioxaborolane (59 mg, 235.9 umol), KOAc (28 mg, 294.8 umol), Pd(dppf)Cl$_2$ (14 mg, 19.6 umol). The mixture was stirred at 90° C. for 12 h under N$_2$. The mixture was concentrated. The residue was purified by prep-TLC (SiO$_2$) to afford compound 4-4 (50 mg).

Step 3: 1-(5-(3-(cyclohexylamino)isoquinolin-7-yl)-1-methyl-1H-pyrazol-3-yl)-3-(4-((4-methylpiperazin-1-yl)methyl)-3-(trifluoromethyl)phenyl)urea (4)

To a solution of compound 4-4 (50 mg, 141.9 umol) and K$_2$CO$_3$ (39 mg, 283.8 umol) in dioxane (2 mL) and H$_2$O (200 uL) were added compound 3A (80 mg, 170.3 umol) and Pd(dppf)Cl$_2$ (10 mg, 14.1 umol). The mixture was stirred at 90° C. for 12 h under N$_2$. The mixture was cooled to rt and concentrated. The residue was purified by prep-TLC (SiO$_2$) followed by prep-HPLC to afford compound 4 (7.0 mg, 8.19 umol, 5.7% yield, TFA). M+H$^+$=621.3 (LCMS); $^1$H NMR (METHANOL-d$_4$, 400 MHz): δ 8.99 (s, 1H), 8.08 (s, 1H), 7.93 (s, 1H), 7.85-7.79 (m, 2H), 7.66 (br d, J=4.2 Hz, 2H), 7.32-7.26 (m, 1H), 6.50 (s, 1H), 3.86 (s, 3H), 3.73 (s, 2H), 3.66-3.57 (m, 1H), 2.95-2.37 (m, 7H), 2.08 (br d, J=13.0 Hz, 2H), 1.93-1.64 (m, 4H), 1.57-1.22 (m, 7H), 0.92 (dd, J=6.5, 13.3 Hz, 1H).

Example A6: Synthesis of 5-((4-methylpiperazin-1-yl)methyl)-4-(trifluoromethyl)pyridin-2-amine (51-4)

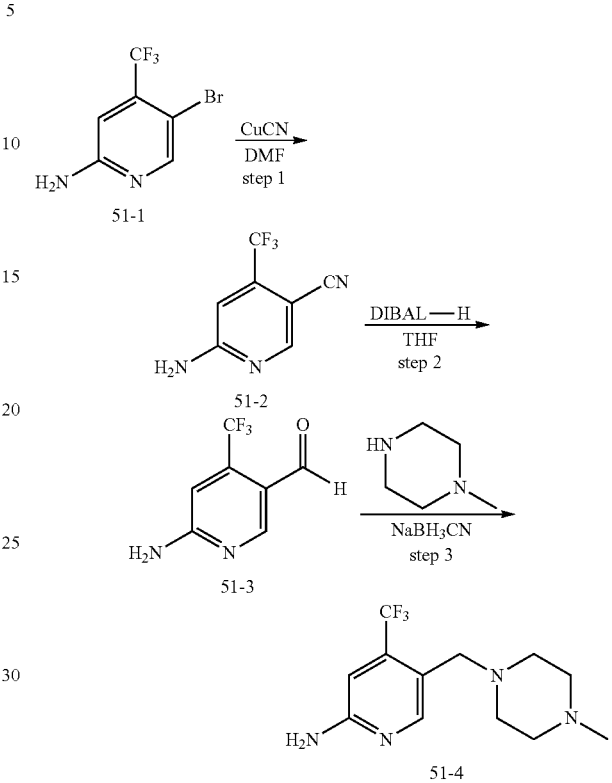

Step 1: 6-amino-4-(trifluoromethyl)nicotinonitrile (51-2)

A mixture of 5-bromo-4-(trifluoromethyl)pyridin-2-amine (500 mg, 2.1 mmol) and CuCN (556 mg, 6.2 mmol) in DMF (10.0 mL) was stirred at 170° C. for 4 h. The mixture was cooled to rt and concentrated. The residue was purified by column chromatography (SiO$_2$) to afford compound 51-2 (350 mg, 90%). $^1$H NMR (CDCl$_3$, 400 MHz): δ 8.49 (s, 1H), 6.78 (s, 1H).

Step 2: 6-amino-4-(trifluoromethyl)nicotinaldehyde (51-3)

To a solution of compound 51-2 (240 mg, 1.2 mmol) in THF (10.0 mL) was added DIBAL-H (1 M, 5.9 mL) at 0° C. The mixture was warmed to 25° C. for 12 h, quenched with MeOH (191 mg, 5.9 mmol, 242.4 uL) at 25° C., filtered and concentrated to give a residue. The residue was purified by column chromatography (SiO$_2$) to afford compound 51-3 (100 mg, 41%). $^1$H NMR (CDCl$_3$, 400 MHz): δ10.04 (d, J=1.7 Hz, 1H), 8.75 (s, 1H), 6.66 (s, 1H).

Step 3: 5-((4-methylpiperazin-1-yl)methyl)-4-(trifluoromethyl)pyridin-2-amine (51-4)

To a solution of compound 51-3 (110 mg, 289.2 umol) and 1-methylpiperazine (34 mg, 347.1 umol, 38.6 uL) in MeOH (2.0 mL) was added AcOH (868 ug, 14.4 umol, 0.8 uL). After 2 h at 30° C., NaBH$_3$CN (90 mg, 1.4 mmol) was added. The resulting mixture was stirred at 30° C. for 12 h and concentrated. The residue was purified by prep-TLC (SiO$_2$) to afford compound 51-4 (60 mg).

Example A7: Synthesis of 1-(4-((3-methyl-3,8-diazabicyclo[3.2.1]octan-8-yl)methyl)-3-(trifluoromethyl)phenyl)-3-(1-methyl-5-(2-(piperidin-4-ylamino)quinazolin-6-yl)-1H-pyrazol-3-yl)urea (19)

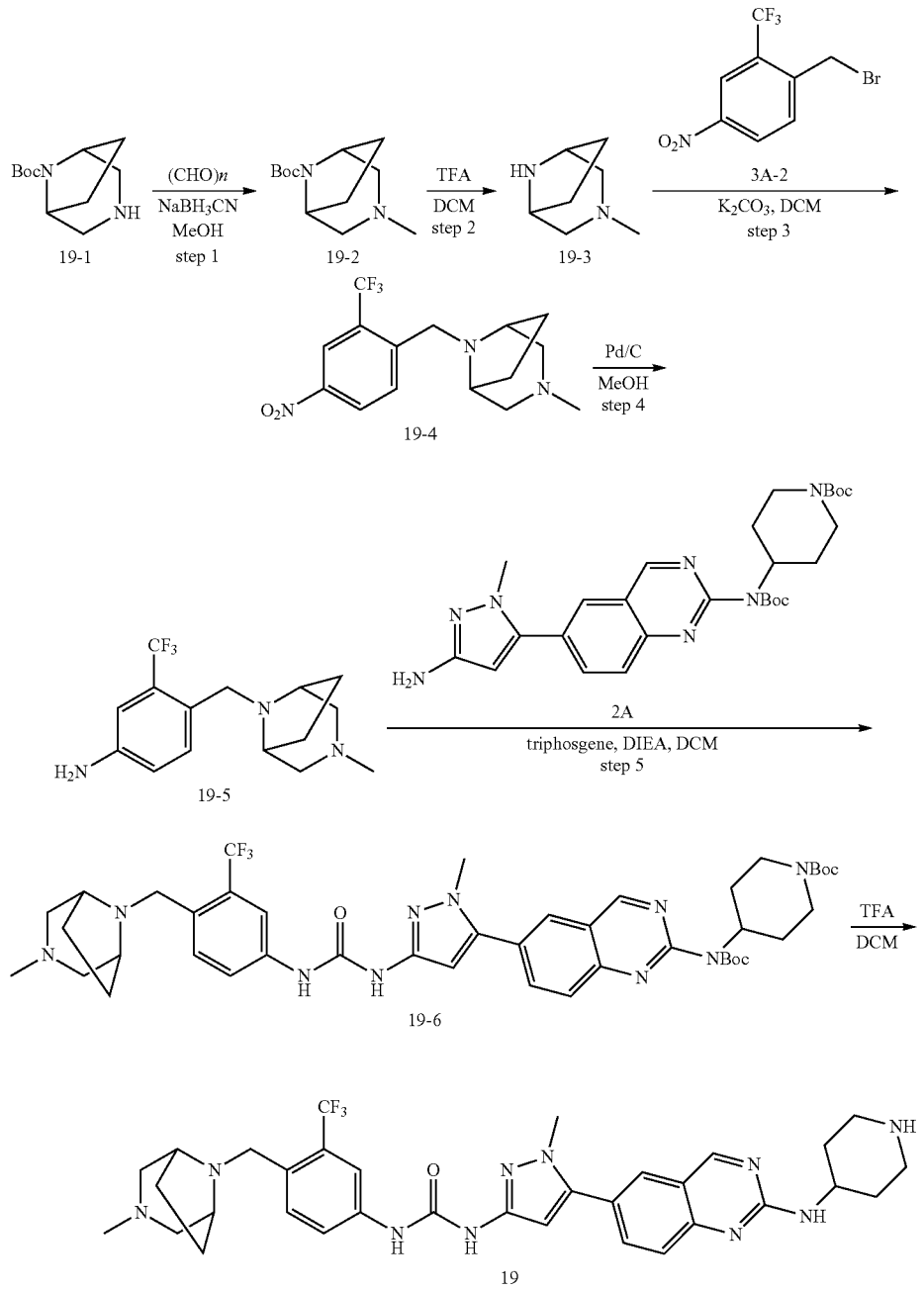

Step 1: tert-Butyl 3-methyl-3,8-diazabicyclo[3.2.1]octane-8-carboxylate (19-2)

To a solution of tert-butyl 3,8-diazabicyclo[3.2.1]octane-8-carboxylate (200 mg, 942.1 umol) and paraformaldehyde (254 mg, 2.8 mmol) in methanol (2 mL) was added AcOH (2 mg, 47.1 umol, 2.7 uL) (pH=5). The mixture was stirred at 45° C. for 2 h. Then NaBH$_3$CN (296 mg, 4.7 mmol) was added and stirred at 45° C. for 12 h. The mixture was concentrated, diluted with NaHCO$_3$ (5 mL) and extracted with dichloromethane (5 mL×3). The combined organic layers were washed with brine (5 mL×2), dried over Na$_2$SO$_4$, filtered and concentrated. The residue was purified by prep-TLC (SiO$_2$) to afford compound 19-2 (200 mg). $^1$H NMR (CDCl$_3$, 400 MHz): δ 4.28-4.00 (m, 2H), 2.63 (dd, J=2.2, 10.5 Hz, 2H), 2.23 (s, 5H), 1.94-1.76 (m, 4H), 1.47 (s, 9H).

Step 2: 3-methyl-3,8-diazabicyclo[3.2.1]octane (19-3)

A solution of compound 19-2 (200 mg, 883.7 umol) in dichloromethane (2 mL) and trifluoroacetic acid (1 mL) was stirred at 25° C. for 10 min. The mixture was concentrated to get compound 19-3 (212 mg, TFA).

Step 3: 3-methyl-8-(4-nitro-2-(trifluoromethyl)benzyl)-3,8-diazabicyclo[3.2.1]octane (19-4)

To a solution of compound 3A-2 (551 mg, 970.7 umol) and K$_2$CO$_3$ (365 mg, 2.6 mmol) in DCM (2 mL) was added compound 19-3 (212 mg, 882.5 umol, TFA). The mixture was stirred at 25° C. for 12 h. The mixture was concentrated to get crude residue. The residue was purified by prep-TLC (SiO$_2$) to afford compound 19-4 (140 mg). $^1$H NMR (CDCl$_3$, 400 MHz): δ 8.50 (d, J=2.2 Hz, 1H), 8.43-8.38 (m, 1H), 8.37-8.33 (m, 1H), 3.76 (s, 2H), 3.07 (br s, 2H), 2.79-2.53 (m, 2H), 2.35 (br d, J=9.9 Hz, 2H), 2.28 (s, 3H), 2.07-1.85 (m, 4H).

Step 4: 4-((3-methyl-3,8-diazabicyclo[3.2.1]octan-8-yl)methyl)-3-(trifluoromethyl)aniline (19-5)

To a solution of compound 19-4 (140 mg, 425.1 umol) in methanol (10 mL) was added Pd/C (10%, 0.1 g) under N$_2$. The suspension was degassed and purged with H$_2$ 3 times. The mixture was stirred under H$_2$ (15 Psi) at 25° C. for 0.5 h, filtered and concentrated under reduced pressure to give a residue. The residue was purified by prep-TLC (SiO$_2$) to afford compound 19-5 (80 mg).

Step 5: tert-butyl 4-((tert-butoxycarbonyl)(6-(1-methyl-3-(3-(4-((3-methyl-3,8-diazabicyclo[3.2.1]octan-8-yl)methyl)-3-(trifluoromethyl)phenyl)ureido)-1H-pyrazol-5-yl)quinazolin-2-yl)amino)piperidine-1-carboxylate (19-6)

To a solution of compound 19-5 (50 mg, 167 umol) and DIEA (32 mg, 250 umol, 43.8 uL) in dichloromethane (2 mL) was cooled to −30° C. and triphosgene (16 mg, 55.1 umol) was added. The mixture was stirred at −30° C. for 1 h. Then a solution of compound 2A (69 mg, 133.6 umol) in dichloromethane (1 mL) was added. After 12 h at 25° C., MeOH (1 mL) was added and the resulting mixture was concentrated. The residue was purified by prep-TLC (SiO$_2$) to afford compound 19-6 (50 mg).

Step 6: 1-(4-((3-methyl-3,8-diazabicyclo[3.2.1]octan-8-yl)methyl)-3-(trifluoromethyl)phenyl)-3-(1-methyl-5-(2-(piperidin-4-ylamino)quinazolin-6-yl)-1H-pyrazol-3-yl)urea (19)

A solution of compound 19-6 (50 mg, 58.9 umol) in trifluoroacetic acid (1 mL) and dichloromethane (2 mL) was stirred at 25° C. for 10 min. The mixture was concentrated to get crude residue. The residue was dissolved in MeOH (2.0 mL) and basified pH to 8 with NH$_3$.H$_2$O (25% purity). The residue was purified by prep-HPLC to get 19 (14.7 mg, 21.1 umol, 35.8% yield, FA). M+H+=649.4 (LCMS); $^1$H NMR (METHANOL-d$_4$, 400 MHz): δ 9.13 (s, 1H), 8.51 (br s, 1H), 7.92 (t, J=2.0 Hz, 2H), 7.85-7.80 (m, 2H), 7.64 (t, J=9.4 Hz, 2H), 6.41 (s, 1H), 4.30-4.22 (m, 1H), 3.84 (s, 3H), 3.69 (s, 2H), 3.47 (td, J=3.7, 13.1 Hz, 2H), 3.37-3.31 (m, 2H), 3.24-3.13 (m, 4H), 2.97 (br d, J=11.5 Hz, 2H), 2.67 (s, 3H), 2.31 (br dd, J=3.3, 14.3 Hz, 2H), 2.25-2.12 (m, 2H), 1.98-1.79 (m, 4H).

The following compounds were synthesized according to procedures described in example above for the preparation of compound 19.

| Comp ID | Structure | Chemical Name | Mass (M + H$^+$) | $^1$H NMR (MeOD, 400 MHz) |
|---|---|---|---|---|
| 23 | 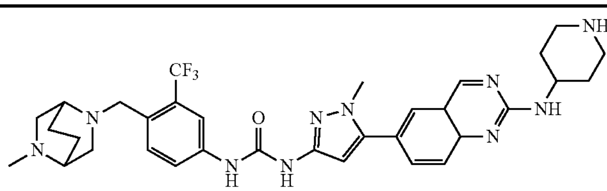 | 1-(4-((5-methyl-2,5-diazabicyclo[2.2.2]octan-2-yl)methyl)-3-(trifluoromethyl)phenyl)-3-(1-methyl-5-(2-(piperidin-4-ylamino)quinazolin-6-yl)-1H-pyrazol-3-yl)urea, formate salt | Calc'd for C$_{33}$H$_{40}$F$_3$N$_{10}$O: 649.3; Found: 649.3 | δ 9.12 (s, 1H), 8.51 (br s, 2H), 7.92 (br d, J = 9.7 Hz, 2H), 7.82 (br d, J = 8.8 Hz, 1H), 7.71-7.58 (m, 3H), 6.41 (s, 1H), 4.31-4.18 (m, 1H), 3.89-3.79 (m, 5H), 3.53-3.39 (m, 4H), 3.37-3.23 (m, 2H), 3.17 (br t, J = 11.1 Hz, 2H), 2.95-2.84 (m, 4H), 2.78 (br d, J = 11.5 Hz, 1H), 2.30 (br d, J = 11.9 Hz, 2H), 2.23-2.06 (m, 2H), 2.03-1.77 (m, 3H), 1.77-1.58 (m, 1H) |
| 51 | 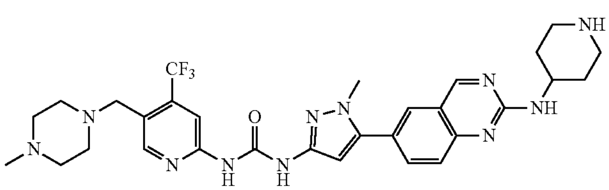 [SMILES: CN1CCN(Cc2cnc(NC(=O)Nc3cc(-c4ccc5nc(NC6CCNCC6)ncc5c4)n(C)n3)cc2C(F)(F)F)CC1] | 1-(1-methyl-5-(2-(piperidin-4-ylamino)quinazolin-6-yl)-1H-pyrazol-3-yl)-3-(5-((4-methylpiperazin-1-yl)methyl)-4-(trifluoromethyl)pyridin-2-yl)urea, formate salt | Calc'd for C$_{30}$H$_{37}$F$_3$N$_{11}$O: 624.3; Found: 624.3 | δ 9.06 (s, 1H), 8.50 (s, 1H), 8.38 (br s, 2H), 7.87 (d, J = 1.7 Hz, 1H), 7.77 (dd, J = 1.9, 8.7 Hz, 1H), 7.56 (d, J = 8.7 Hz, 1H), 7.36-7.19 (m, 3H), 6.50 (br s, 1H), 4.26-4.12 (m, 1H), 3.77 (s, 3H), 3.68-3.61 (m, 2H), 3.45-3.30 (m, 3H), 3.17-3.03 (m, 5H), 3.00-2.87 (m, 2H), 2.66 (s, 4H), 2.25 (br dd, J = 3.1, 14.2 Hz, 3H), 1.88-1.67 (m, 5H) |

Example A8: Synthesis of N-(5-(3-aminoisoquinolin-7-yl)-1-methyl-1H-pyrazol-3-yl)-2-(4-((4-methylpiperazin-1-yl)methyl)-3-(trifluoromethyl)phenyl)acetamide (11)

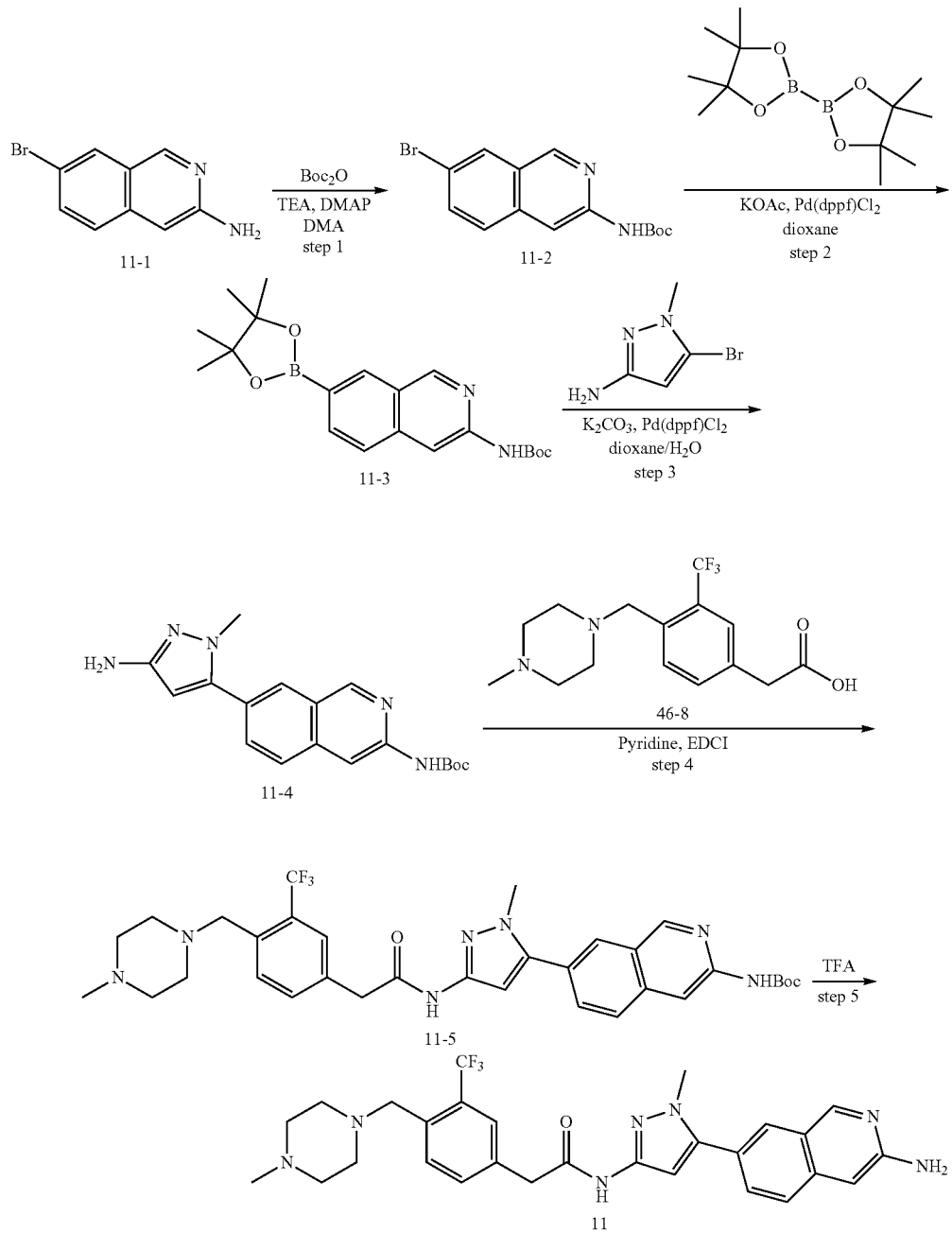

Step 1: tert-butyl (7-bromoisoquinolin-3-yl)carbamate (11-2)

To a solution of 7-bromoisoquinolin-3-amine 11-1 (34.0 g, 53 mmol) and TEA (16.0 g, 160 mmol, 22 mL) in DMA (300 mL) was added tert-butoxycarbonyl tert-butyl carbonate (34.9 g, 160 mmol, 36.7 mL) and DMAP (1.3 g, 10.6 mmol). The mixture was stirred at 20° C. for 12 h, and concentrated to give a crude residue which was purified by column chromatography (SiO$_2$) to afford compound 11-2 (7.0 g, crude).

Step 2: tert-butyl (7-(4,4,5,5-tetramethyl-1,3,2-dioxaborolan-2-yl)isoquinolin-3-yl)carbamate (11-3)

To a solution of 11-2 (7.0 g, 21.6 mmol) and KOAc (4.2 g, 43.3 mmol) in dioxane (160 mL) were added 4,4,5,5- tetramethyl-2-(4,4,5,5-tetramethyl-1,3,2-dioxaborolan-2-yl)-1,3,2-dioxaborolane (6.6 g, 25.9 mmol) and Pd(dppf)Cl₂ (792 mg, 1 mmol). The mixture was stirred at 90° C. for 12 h under N₂, cooled to rt and concentrated. The residue was purified by column chromatography (SiO₂) to afford compound 11-3 (3.6 g).

Step 3: tert-butyl (7-(3-amino-1-methyl-1H-pyrazol-5-yl)isoquinolin-3-yl)carbamate (11-4)

To a solution of compound 11-3 (2.0 g, 5.4 mmol) and K₂CO₃ (2.2 g, 16.2 mmol) in dioxane (40 mL) and H₂O (4 mL) were added 5-bromo-1-methyl-1H-pyrazol-3-amine (1.0 g, 5.9 mmol) and Pd(dppf)Cl₂ (395 mg, 540 umol). The mixture was stirred at 90° C. for 12 h under N₂, cooled to rt and concentrated. The residue was purified by prep-TLC (SiO₂) followed by prep-HPLC. The eluent was adjusted to pH=8 with sat. NaHCO₃ and extracted with ethyl acetate (20 mL×3). The combined organic layers were dried over Na₂SO₄, filtered and concentrated under reduced pressure to afford 11-4 (114.9 mg, 337.0 umol, 6.2% yield). M+H⁺=340.2 (LCMS); ¹H NMR (DMSO-d₆, 400 MHz): δ 9.89 (s, 1H), 9.12 (s, 1H), 8.17 (s, 1H), 8.09 (s, 1H), 7.92 (d, J=8.6 Hz, 1H), 7.73 (dd, J=1.5, 8.6 Hz, 1H), 5.67 (s, 1H), 4.63 (br s, 1H), 3.66 (s, 3H), 1.50 (s, 9H).

Step 4: tert-butyl (7-(1-methyl-3-(2-(4-((4-methylpiperazin-1-yl)methyl)-3-(trifluoromethyl) phenyl)acetamido)-1H-pyrazol-5-yl)isoquinolin-3-yl)carbamate (11-5)

To a solution of compound 46-8 (30 mg, 88.4 umol) in pyridine (2.0 mL) was added compound 11-4 (30 mg, 88.4 umol) and EDCI (51 mg, 265.2 umol). The mixture was stirred at 45° C. for 12 h, cooled to rt and concentrated to give a residue, which was purified by prep-TLC (SiO₂) to give compound 11-5 (40 mg).

Step 5: N-(5-(3-aminoisoquinolin-7-yl)-1-methyl-1H-pyrazol-3-yl)-2-(4-((4-methylpiperazin-1-yl)methyl)-3-(trifluoromethyl)phenyl)acetamide (11)

To a solution of compound 11-5 (40 mg, 62.7 umol) in DCM (2.0 mL) was added TFA (1.0 mL). The mixture was stirred at 25° C. for 15 min and concentrated. The residue was dissolved in MeOH (2.0 mL), basified to pH~8 with NH₃.H₂O (25% purity) and concentrated. The residue was purified by prep-HPLC to afford 11 (16.9 mg, 28.6 umol, 45.7% yield, FA). M+H⁺=538.0 (LCMS); ¹H NMR (METHANOL-d₄, 400 MHz): δ δ 8.82 (s, 1H), 7.89 (s, 1H), 7.78-7.66 (m, 2H), 7.63-7.47 (m, 3H), 6.80 (s, 1H), 6.64 (s, 1H), 3.89-3.69 (m, 7H), 3.18 (br s, 4H), 2.87-2.58 (m, 7H).

Example A9: Synthesis of 1-(1-methyl-5-(2-(piperidin-4-ylamino)quinazolin-6-yl)-1H-pyrazol-3-yl)-3-(3-((4-methylpiperazin-1-yl)methyl)-5-(trifluoromethyl)phenyl)urea (21)

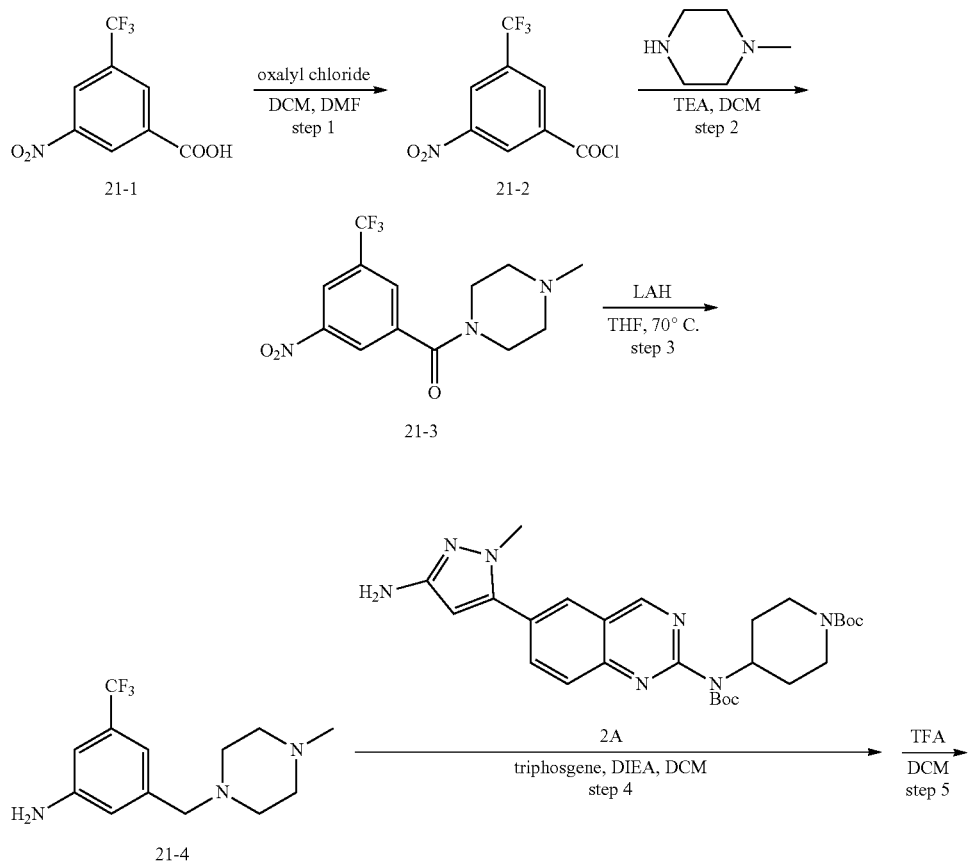

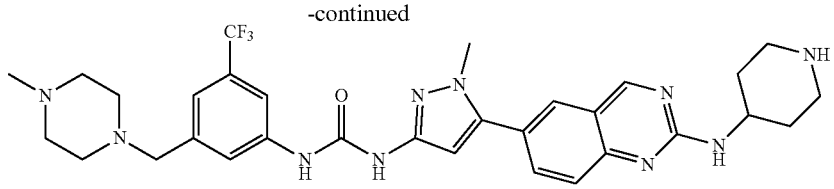

21

Step 1: 3-nitro-5-(trifluoromethyl)benzoyl chloride (21-2)

To a solution of 3-nitro-5-(trifluoromethyl)benzoic acid (2.0 g, 8.5 mmol) in DCM (20 mL) was added oxalyl chloride (1.6 g, 12.8 mmol, 1.1 mL) and DMF (6 mg, 85.1 umol, 6.6 uL) at 25° C. The mixture was stirred at 25° C. for 0.5 h. The reaction was concentrated to give compound 21-2 (2.0 g, crude).

Step 2: (4-methylpiperazin-1-yl)(3-nitro-5-(trifluoromethyl)phenyl)methanone (21-3)

To a solution of compound 21-2 (948 mg, 9.5 mmol, 1.0 mL) in DCM (20.0 mL) was added TEA (2.4 g, 23.6 mmol, 3.2 mL) and 3-nitro-5-(trifluoromethyl)benzoyl chloride (2.0 g, 7.8 mmol) at 0° C. The mixture was stirred at 25° C. for 10 min and concentrated to give a residue. The residue was purified by column chromatography (SiO$_2$) to afford compound 21-3 (2.0 g, 6.1 mmol, 77.5% yield). $^1$H NMR (METHANOL-d$_4$, 400 MHz): δ 8.55 (s, 1H) 8.46 (t, J=1.65 Hz, 1H) 8.02 (s, 1H) 3.84 (br s, 2H) 3.43 (br s, 2H) 2.29-2.67 (m, 7H).

Step 3: 3-((4-methylpiperazin-1-yl)methyl)-5-(trifluoromethyl)aniline (21-4)

To a solution of LAH (1.2 g, 31.5 mmol) in THF (20.0 mL) was added compound 21-3 (1.0 g, 3.1 mmol) in THF (15.0 mL) via syringe at 25° C. The mixture was stirred at 70° C. for 3 h, quenched with H$_2$O (2 mL), aqueous NaOH (2 mL 10%) and H$_2$O (6 mL). The mixture was filtered and washed with methyl alcohol (20 mL×3), and concentrated to give a residue. The residue was purified by prep-TLC (SiO$_2$) to afford compound 21-4 (250 mg).

Step 4 and 5: 1-(1-methyl-5-(2-(piperidin-4-ylamino)quinazolin-6-yl)-1H-pyrazol-3-yl)-3-(3-((4-methylpiperazin-1-yl)methyl)-5-(trifluoromethyl)phenyl)urea (21)

Compound 21 (21.3 mg, 30.6 umol, 25.1% yield, FA) was prepared from 21-4 (50 mg, 182.9 umol) according to similar procedures as described in the synthesis of compound 19. M+H$^+$=623.0 (LCMS); $^1$H NMR (METHANOL-d$_4$, 400 MHz): δ 9.10 (s, 1H), 8.55 (br s, 2H), 7.88 (s, 1H), 7.84-7.77 (m, 2H), 7.68 (br s, 1H), 7.60 (br d, J=8.8 Hz, 1H), 7.29 (s, 1H), 6.41 (br s, 1H), 4.23 (br s, 1H), 3.83 (s, 3H), 3.63 (s, 2H), 3.47 (br d, J=12.6 Hz, 2H), 3.24-3.06 (m, 6H), 2.82-2.59 (m, 7H), 2.29 (br d, J=13.0 Hz, 2H), 1.93-1.78 (m, 2H).

Example A10: Synthesis of 1-(1-methyl-5-(2-(piperidin-4-ylamino)quinazolin-6-yl)-1H-pyrazol-3-yl)-3-(4-(1-(4-methylpiperazin-1 1-yl)ethyl)-3-(trifluoromethyl)phenyl)urea (22)

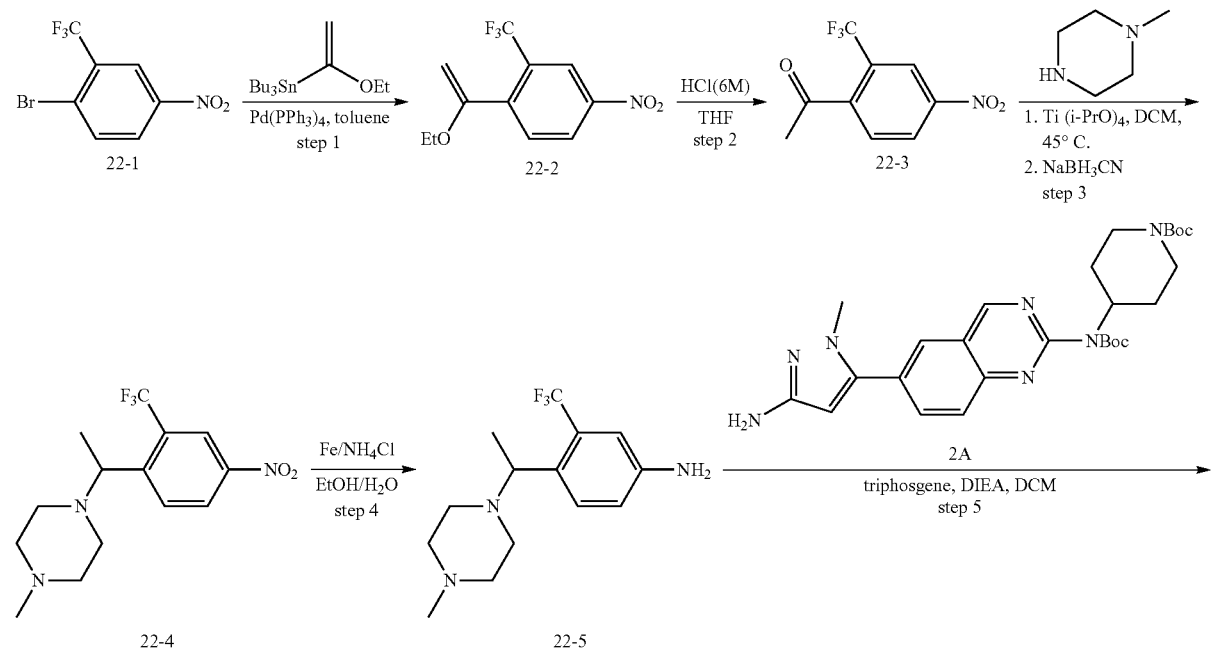

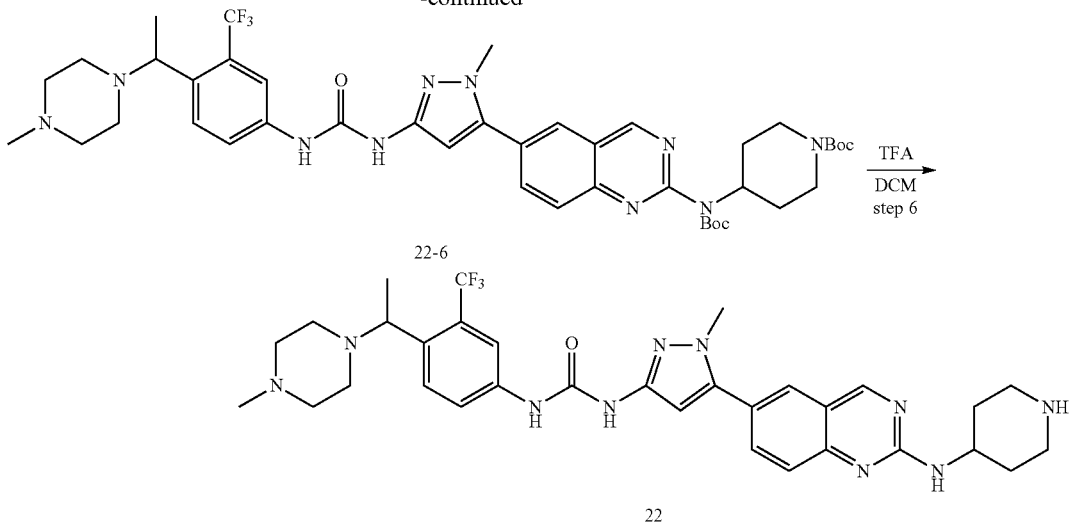

Step 1: 1-(1-ethoxyvinyl)-4-nitro-2-(trifluoromethyl) benzene (22-2)

A mixture of tributyl(1-ethoxyvinyl)stannane (5.4 g, 14.8 mmol, 5.0 mL) and 1-bromo-4-nitro-2-(trifluoromethyl)benzene (4.0 g, 14.8 mmol), Pd(PPh$_3$)$_4$ (1.7 g, 1.4 mmol) in toluene (100 mL) was stirred at 100° C. for 5 h under N$_2$. The mixture was cooled to rt and concentrated. The residue was purified by column chromatography (SiO$_2$) to give compound 22-2 (7.0 g).

Step 2: 1-(4-nitro-2-(trifluoromethyl)phenyl)ethan-1-one (22-3)

A solution of compound 22-2 (7.0 g, 13.4 mmol) in HCl (20 mL) (6M) and THF (20 mL) was stirred at 25° C. for 10 min, diluted with H$_2$O (20 mL) and extracted with ethyl acetate (20 mL×3). The combined organic layers were washed with brine (20 mL×3), dried over Na$_2$SO$_4$, filtered and concentrated. The residue was purified by column chromatography (SiO$_2$) to give compound 22-3 (3.0 g, 86%). $^1$H NMR (CDCl$_3$, 400 MHz): δ 8.59 (d, J=1.8 Hz, 1H), 8.48 (dd, J=1.8, 8.3 Hz, 1H), 7.65 (d, J=8.3 Hz, 1H), 2.63 (s, 3H).

Step 3: 1-methyl-4-(1-(4-nitro-2-(trifluoromethyl) phenyl)ethyl)piperazine (22-4)

To a solution of compound 22-3 (500 mg, 2.14 mmol) and 1-methylpiperazine (322 mg, 3.2 mmol, 357.2 uL) in DCM (20 mL) was added Ti(i-PrO)$_4$ (1.2 g, 4.2 mmol, 1.2 mL). After the mixture was stirred at 45° C. for 12 h, NaBH$_3$CN (1.1 g, 17.1 mmol) was added and the mixture was stirred at 45° C. for 12 h. The reaction was filtered and concentrated to give a residue, which was purified by column chromatography (SiO$_2$) to afford compound 22-4 (300 mg).

Step 4: 4-(1-(4-methylpiperazin-1-yl)ethyl)-3-(trifluoromethyl)aniline (22-5)

To a solution of compound 22-4 (200 mg, 630.3 umol) in EtOH (3.0 mL) and H$_2$O (600 uL) was added Fe (176 mg, 3.1 mmol) and NH$_4$Cl (101 mg, 1.8 mmol). The mixture was stirred at 80° C. for 12 h, cooled to rt, filtered and concentrated. The residue was purified by prep-TLC (SiO$_2$) to afford compound 22-5 (80 mg).

Step 5: tert-butyl 4-((tert-butoxycarbonyl)(6-(1-methyl-3-(3-(4-(1-(4-methylpiperazin-1-yl)ethyl)-3-(trifluoromethyl)phenyl)ureido)-1H-pyrazol-5-yl) quinazolin-2-yl)amino) piperidine-1-carboxylate (22-6)

To a solution of compound 22-5 (50 mg, 174.0 umol) and DIEA (34 mg, 261.0 umol, 45.6 uL) in DCM (3.0 mL) was added triphosgene (17 mg, 57.4 umol) at −20° C. After 1 h at −20° C., compound 2A (91 mg, 174.0 umol) in DCM (2.0 mL) was added and the resulting mixture was slowly warmed to 25° C. and stirred at 25° C. for 12 h. The reaction was quenched with MeOH (1.0 mL) and concentrated to give a residue. The residue was purified by prep-TLC (SiO$_2$) to afford compound 22-6 (50 mg).

Step 6: 1-(1-methyl-5-(2-(piperidin-4-ylamino)quinazolin-6-yl)-1H-pyrazol-3-yl)-3-(4-(1-(4-methylpiperazin-1-yl)ethyl)-3-(trifluoromethyl)phenyl) urea (22)

To a solution of compound 22-6 (50 mg, 59.7 umol) in DCM (2.0 mL) was added TFA (1.0 mL). The mixture was stirred at 25° C. for 15 min. The reaction was concentrated. The residue was dissolved in MeOH (2.0 mL), basified to pH~8 with NH$_3$·H$_2$O (25% purity), and concentrated to give a residue. The residue was purified by prep-HPLC to afford 22 (10.1 mg, 14.7 umol, 24.7% yield, FA). M+H$^+$=637.3 (LCMS); $^1$H NMR (METHANOL-d$_4$, 400 MHz): δ 6 9.12 (s, 1H), 8.50 (br s, 2H), 7.91 (br s, 2H), 7.82 (br d, J=8.6 Hz, 1H), 7.76 (d, J=8.6 Hz, 1H), 7.69-7.60 (m, 2H), 6.41 (s, 1H), 4.25 (br t, J=10.1 Hz, 1H), 3.83 (s, 3H), 3.69 (br d, J=6.0 Hz, 1H), 3.47 (br d, J=12.8 Hz, 2H), 3.31-3.29 (m, 2H), 3.24-3.00 (m, 6H), 2.71 (s, 3H), 2.53 (br s, 2H), 2.31 (br d, J=12.8 Hz, 2H), 1.94-1.75 (m, 2H), 1.32 (d, J=6.4 Hz, 3H).

The following compounds were synthesized according to procedures described in example above for the preparation of compound 22.

| Comp ID | Structure | Chemical Name | Mass (M + H+) | 1H NMR (MeOD, 400 MHz) |
|---|---|---|---|---|
| 40 | 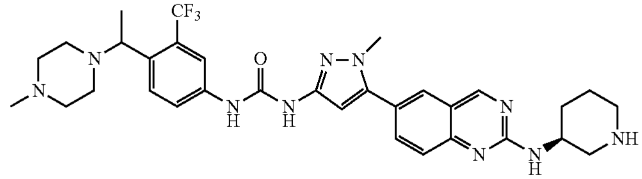 [SMILES: CC(c1ccc(NC(=O)Nc2cc(-c3ccc4nc(N[C@H]5CCCNC5)ncc4c3)n(C)n2)cc1C(F)(F)F)N1CCN(C)CC1] | 1-(1-methyl-5-(2-(((S)-piperidin-3-yl)amino)quinazolin-6-yl)-1H-pyrazol-3-yl)-3-(4-(1-(4-methylpiperazin-1-yl)ethyl)-3-(trifluoromethyl)phenyl)urea, formate salt | Calc'd for $C_{32}H_{40}F_3N_{10}O$: 637.3; Found: 637.2 | δ 9.16 (s, 1H), 8.52 (br s, 2H), 7.99-7.88 (m, 2H), 7.85 (br d, J = 8.8 Hz, 1H), 7.81-7.74 (m, 1H), 7.66 (br t, J = 8.6 Hz, 2H), 6.43 (s, 1H), 4.38 (br s, 1H), 3.84 (s, 3H), 3.75-3.59 (m, 2H), 3.35 (br s, 1H), 3.21-2.96 (m, 7H), 2.74 (s, 3H), 2.54 (br s, 3H), 2.23-2.03 (m, 2H), 1.98-1.70 (m, 2H), 1.33 (br d, J = 6.1 Hz, 3H) |
| 42 | 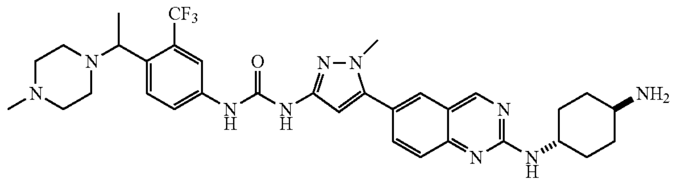 | 1-5-(2-(((1r,4r)-4-aminocyclohexyl)amino)quinazolin-6-yl)-1-methyl-1H-pyrazol-3-yl)-3-(4-(1-(4-methylpiperazin-1-yl)ethyl)-3-(trifluoromethyl)phenyl)urea, formate salt | Calc'd for $C_{33}H_{42}F_3N_{10}O$: 651.3; Found: 651.3 | δ 9.13 (s, 1H), 8.51 (br s, 2H), 7.97-7.90 (m, 2H), 7.88-7.77 (m, 2H), 7.67 (br dd, J = 8.7, 18.6 Hz, 2H), 6.44 (s, 1H), 4.01 (br t, J = 11.3 Hz, 1H), 3.87 (s, 3H), 3.79-3.69 (m, 1H), 3.18 (br s, 5H), 2.95-2.47 (m, 7H), 2.30-2.12 (m, 4H), 1.71-1.44 (m, 4H), 1.36 (br d, J = 6.4 Hz, 3H) |

Example A11: Synthesis of 1-(4-(((2-aminoethyl)(methyl)amino)methyl)-3-(trifluoromethyl) phenyl)-3-(5-(2-aminoquinazolin-6-yl)-1-methyl-1H-pyrazol-3-yl)urea (9)

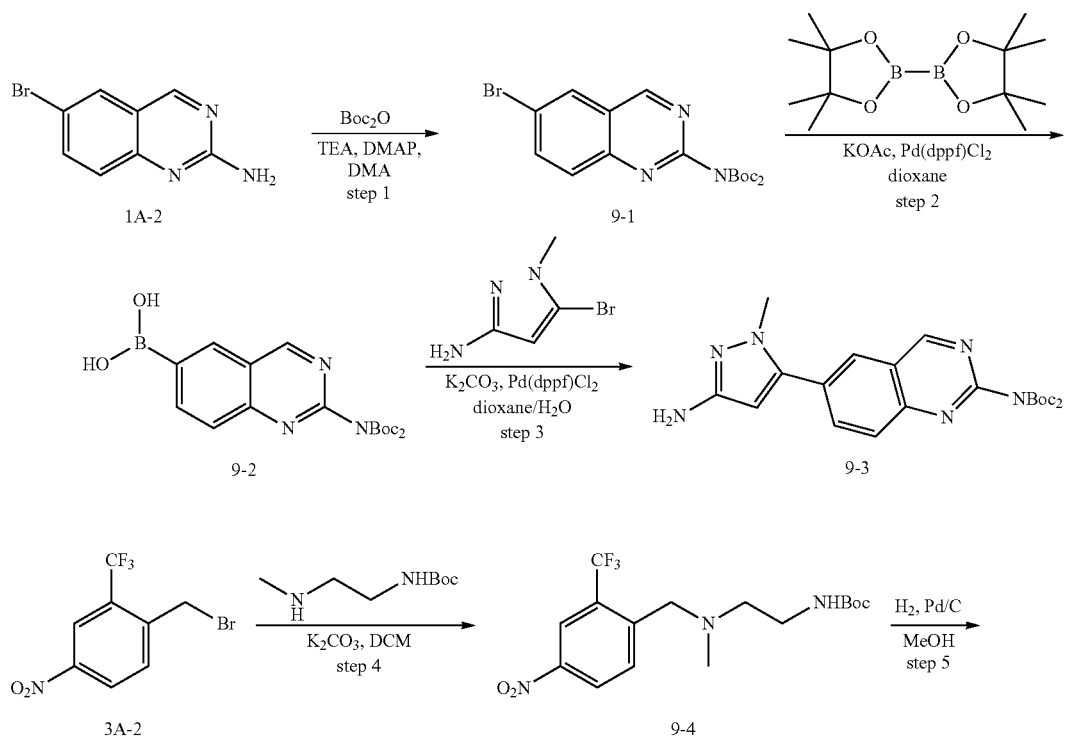

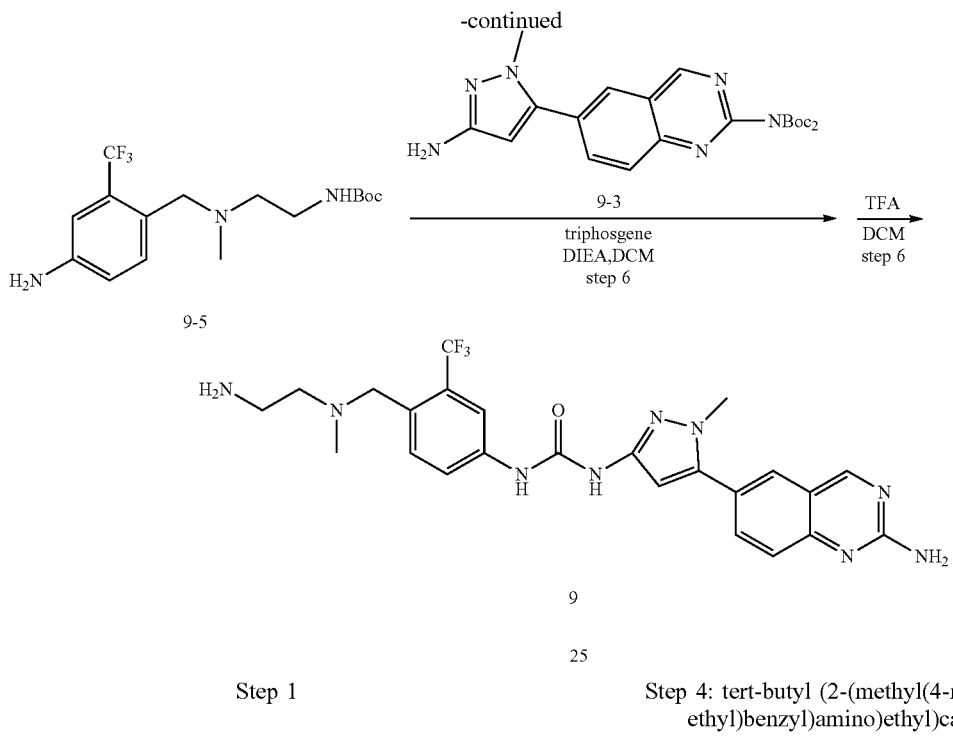

Step 1

To a solution of compound 1A-2 (4.0 g, 17.8 mmol) and TEA (5.4 g, 53.5 mmol, 7.42 mL) in DMA (100.0 mL) were added Boc$_2$O (3.9 g, 17.8 mmol, 4.1 mL) and DMAP (1.0 g, 8.9 mmol). The mixture was stirred at 25° C. for 12 h, diluted with H$_2$O (100 mL) and extracted with ethyl acetate (100 mL×3). The combined organic layers were washed with brine (50 mL×3), dried over Na$_2$SO$_4$, filtered and concentrated. The residue was purified by column chromatography (SiO$_2$) to afford compound 9-1 (1.4 g, 3.3 mmol, 18.4% yield).

Step 2

A mixture of compound 9-1 (400 mg, 942.7 umol), 4,4,5,5-tetramethyl-2-(4,4,5,5-tetramethyl-1,3,2-dioxaborolan-2-yl)-1,3,2-dioxaborolane (287 mg, 1.1 mmol), KOAc (277 mg, 2.8 mmol), and Pd(dppf)Cl$_2$ (68 mg, 94.2 umol) in dioxane (20 mL) was degassed and purged with N$_2$ three times, and heated at 90° C. for 12 h under N$_2$. The mixture was cooled to rt and concentrated to give a residue. The residue was purified by column chromatography (SiO$_2$) and prep-HPLC (TFA condition). The product was basified with NaHCO$_3$ to PH=8 to afford compound 9-2 (150 mg, 385.4 umol, 40.8% yield).

Step 3

A mixture of compound 9-2 (1.5 g, 3.1 mmol), compound 5-bromo-1-methyl-1H-pyrazol-3-amine (672 mg, 3.8 mmol), K$_2$CO$_3$ (1.3 g, 9.5 mmol) and Pd(dppf)Cl$_2$ (232 mg, 318.2 umol) in dioxane (30 mL) and H$_2$O (3.0 mL) was stirred at 90° C. for 12 h under N$_2$. The reaction was cooled to rt and concentrated to give a residue. The residue was purified by column chromatography (SiO$_2$) to afford 9-3 (821.2 mg, 1.7 mmol, 56.2% yield). M+H$^+$=441.3 (LCMS); $^1$H NMR (METHANOL-d$_4$, 400 MHz): δ 9.63 (s, 1H), 8.28 (d, J=1.1 Hz, 1H), 8.18-8.11 (m, 1H), 8.10-8.03 (m, 1H), 5.91 (s, 1H), 3.75 (s, 3H), 1.40 (s, 18H)

Step 4: tert-butyl (2-(methyl(4-nitro-2-(trifluoromethyl)benzyl)amino)ethyl)carbamate (9-4)

A mixture of tert-butyl N-[2-(methylamino)ethyl]carbamate (1.0 g, 5.7 mmol), compound 3A-2 (1.6 g, 5.7 mmol), K$_2$CO$_3$ (1.1 g, 8.6 mmol) in DCM (20 mL) was stirred at 25° C. for 12 h under N$_2$. The reaction mixture was concentrated and the residue was purified by column chromatography (SiO$_2$) to afford compound 9-4 (1.3 g, 2.2 mmol, 39.6% yield).

Step 5: tert-butyl (2-((4-amino-2-(trifluoromethyl)benzyl)(methyl)amino)ethyl)carbamate (9-5)

A mixture of compound 9-4 (1.1 g, 2.9 mmol), Pd/C (300 mg, 2.9 mmol, 10.0% purity) in MeOH (20 mL) was degassed and purged with H$_2$ for 3 times, and then the mixture was stirred at 20° C. for 0.5 h under H$_2$ (15 psi). The reaction mixture was filtered and concentrated to afford compound 9-5 (1.0 g, 2.5 mmol, 87.9% yield).

Step 6 and Step 7: 1-(4-(((2-aminoethyl)(methyl)amino)methyl)-3-(trifluoromethyl) phenyl)-3-(5-(2-aminoquinazolin-6-yl)-1-methyl-1H-pyrazol-3-yl) urea (9)

Compound 9 (2.4 mg, 3.8 umol, 15.5% yield, FA) was prepared from 9-3 (101 mg, 230.3 umol) and 9-5 (100 mg, 287.8 umol) according to similar procedures as described in the synthesis of compound 22. M+H$^+$=514.3 (LCMS); $^1$H NMR (METHANOL-d$_4$, 400 MHz): 9.18 (s, 1H), 7.97 (d, J=1.76 Hz, 1H), 7.82-7.94 (m, 2H), 7.75-7.79 (m, 1H), 7.68-7.74 (m, 1H), 7.61 (d, J=8.60 Hz, 1H), 6.42 (s, 1H), 3.78-3.88 (m, 3H), 3.71 (s, 2H), 3.07 (t, J=5.84 Hz, 2H), 2.66-2.72 (m, 2H), 2.23-2.29 (m, 3H).

The following compounds were synthesized according to procedures described in example above for the preparation of compound 9.

| Comp ID | Structure | Chemical Name | Mass (M + H+) | 1H NMR (MeOD, 400 MHz) |
|---|---|---|---|---|
| 10 | 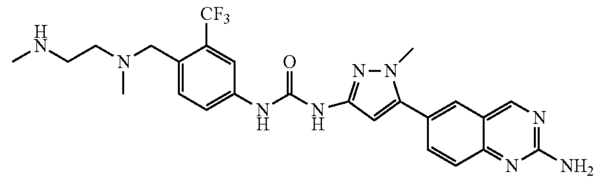 [SMILES: CNCCN(C)Cc1ccc(NC(=O)Nc2cc(-c3ccc4nc(N)ncc4c3)n(C)n2)cc1C(F)(F)F] | 1-(5-(2-aminoquinazolin-6-yl)-1-methyl-1H-pyrazol-3-yl)-3-(4-((methyl(2-(methylamino)ethyl)amino)methyl)-3-(trifluoromethyl)phenyl) urea, formate salt | Calc'd for C25H29F3N9O: 528.2; Found: 528.3 | δ 9.18 (s, 1 H), 7.97 (d, J = 1.76 Hz, 1 H), 7.84-7.92 (m, 2 H), 7.70-7.80 (m, 2 H), 7.61 (d, J = 8.82 Hz, 1 H), 6.42 (s, 1 H), 3.86 (s, 3 H), 3.71 (s, 2H), 3.15 (t, J = 5.84 Hz, 2 H), 2.66-2.72 (m, 5 H), 2.28 (s, 3 H) |

Example A12: Synthesis of 1-(5-(2-(((1r,4r)-4-aminocyclohexyl)amino)-8-ethylquinazolin-6-yl)-1-methyl-1H-pyrazol-3-yl)-3-(4-((4-methylpiperazin-1-yl)methyl)-3-(trifluoromethyl) phenyl)urea (31)

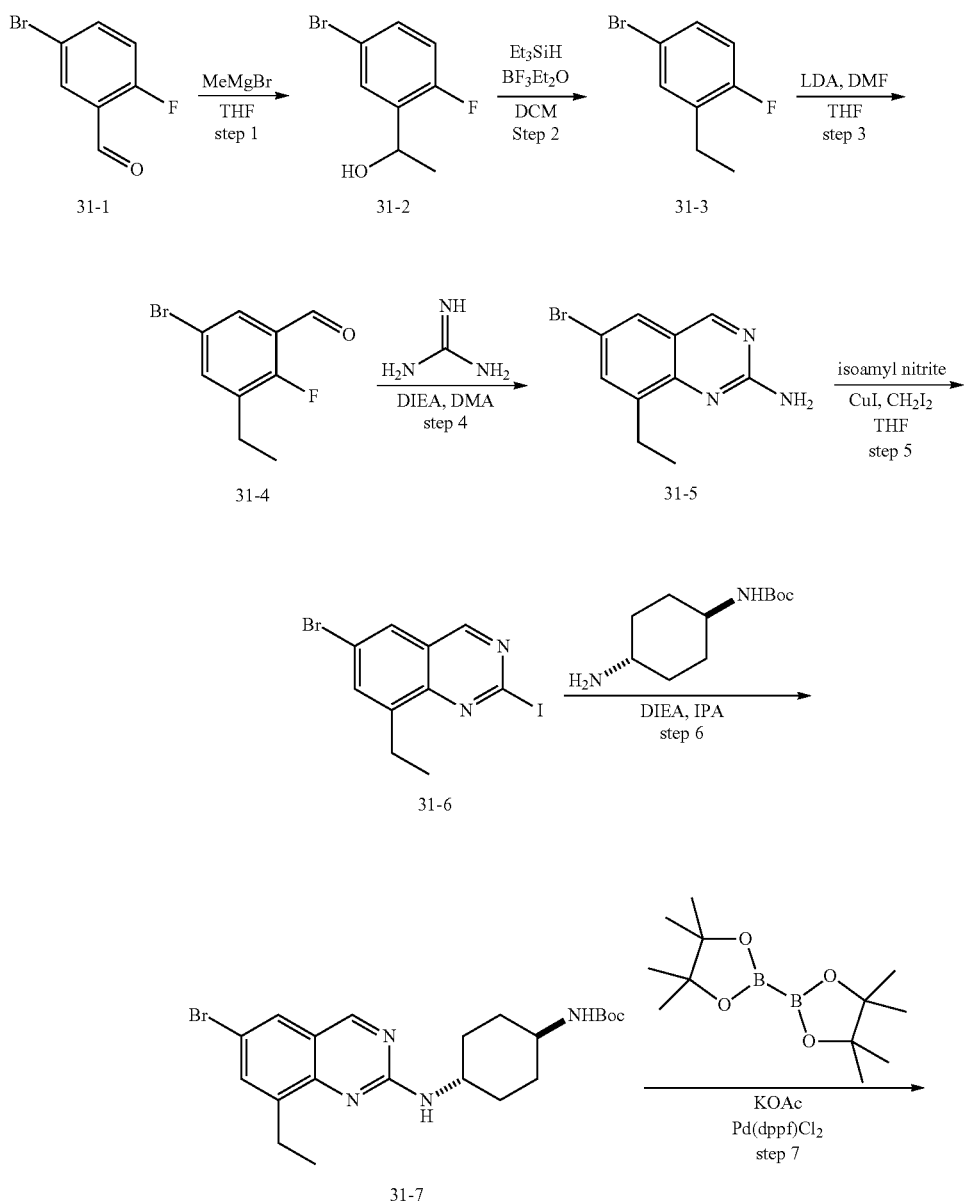

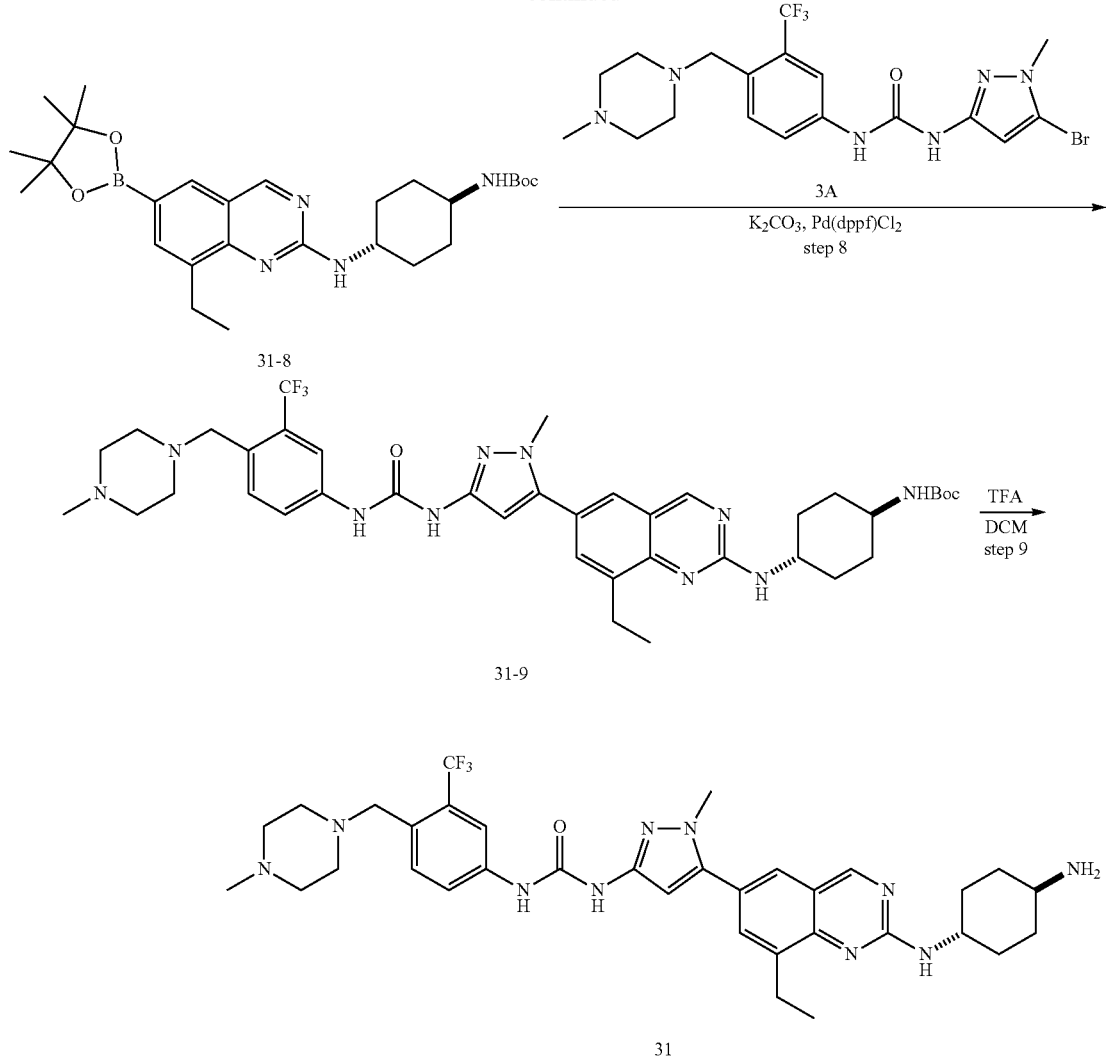

Step 1: 1-(5-bromo-2-fluorophenyl)ethan-1-ol (31-2)

A solution of 5-bromo-2-fluoro-benzaldehyde (55.0 g, 270.9 mmol) in THF (500.0 mL) was cooled to 0° C. Then MeMgBr (3 M, 94.8 mL) was added. The mixture was stirred at 0° C. for 0.5 h, quenched with NH$_4$Cl (500 mL) and extracted with ethyl acetate (500 mL×3). The combined organic layers were washed with brine (500 mL×3), dried over Na$_2$SO$_4$, filtered and concentrated under reduced pressure to give a residue. The residue was purified by column chromatography (SiO$_2$) to afford compound 31-2 (46.0 g).

Step 2: 4-bromo-2-ethyl-1-fluorobenzene (31-3)

To a solution of compound 31-2 (46.0 g, 210.0 mmol) and triethylsilane (48.8 g, 420.0 mmol, 66.9 mL) in DCM (500.0 mL) was added BF$_3$.Et$_2$O (59.6 g, 420.0 mmol, 51.8 mL) at 0° C. The mixture was stirred at 25° C. for 2 h, concentrated, quenched by addition of Sat. NaHCO$_3$ (200 mL) at 0° C., and extracted with ethyl acetate (200 mL×3). The combined organic layers were washed with brine (200 mL×3), dried over Na$_2$SO$_4$, filtered and concentrated. The residue was purified by column chromatography (SiO$_2$) to afford compound 31-3 (24.0 g). $^1$H NMR (CHLOROFORM-d, 400 MHz) δ 7.31 (dd, J=2.2, 6.6 Hz, 1H), 7.27-7.21 (m, 1H), 6.87 (t, J=9.2 Hz, 1H), 2.62 (q, J=7.5 Hz, 2H), 1.20 (t, J=7.6 Hz, 3H).

Step 3: 5-bromo-3-ethyl-2-fluorobenzaldehyde (31-4)

To a solution of compound 31-3 (24.0 g, 82.7 mmol) in THF (500 mL) was added LDA (2 M, 49.6 mL) at −78° C. The mixture was stirred at −78° C. for 1 h. Then dimethyl formamide (7.8 g, 107.5 mmol, 8.3 mL) was added and stirred for 1 h at −78° C. The reaction mixture was quenched by addition of NH$_4$Cl (100 mL) and the resulting mixture was extracted with ethyl acetate (200 mL×3). The combined organic layers were washed with brine (100 mL×3), dried over Na$_2$SO$_4$, filtered and concentrated under reduced pressure to give a residue. The residue was purified by column chromatography (SiO$_2$) to afford compound 31-4 (13.0 g). $^1$H NMR (CDCl$_3$, 400 MHz) δ 10.30 (s, 1H), 7.81 (dd, J=2.6, 5.7 Hz, 1H), 7.58 (dd, J=2.6, 6.4 Hz, 1H), 2.73 (q, J=7.6 Hz, 2H), 1.30-1.25 (m, 3H)

Step 4: 6-bromo-8-ethylquinazolin-2-amine (31-5)

To a solution of carbonic acid-guanidine (3.5 g, 19.4 mmol) and DIEA (5.0 g, 38.9 mmol, 6.8 mL) in DMA (20 mL) was added a solution of compound 31-4 (3.0 g, 12.98 mmol) in DMA (5 mL). The mixture was stirred at 160° C. for 1 h, poured into ice water (30 mL) and extracted with ethyl acetate (40 mL×3). The combined organic layers were washed with brine (30 mL×3), dried over $Na_2SO_4$, filtered and concentrated under reduced pressure to give a residue. The residue was purified by column chromatography ($SiO_2$) to afford compound 31-5 (1.2 g). $^1$H NMR (DMSO-$d_6$, 400 MHz) δ 9.03 (s, 1H), 7.85 (d, J=2.4 Hz, 1H), 7.60 (d, J=2.4 Hz, 1H), 6.94 (s, 2H), 2.98-2.88 (m, 2H), 1.22-1.17 (m, 3H)

Step 5: 6-bromo-8-ethyl-2-iodoquinazoline (31-6)

To a mixture of compound 31-5 (1.2 g, 4.76 mmol) and $CH_2I_2$ (6.3 g, 23.8 mmol, 1.92 mL) in tetrahydrofuran (24.0 mL) were added CuI (906 mg, 4.7 mmol) and isoamyl nitrite (1.6 g, 14.3 mmol, 2.0 mL). After the mixture was stirred at 80° C. for 2 h under $N_2$, $NH_3 \cdot H_2O$ (30 mL) was added. The resulting mixture was extracted with ethyl acetate (50 mL×3) and the combined organic layers were washed with brine (50 mL×3), dried over $Na_2SO_4$, filtered and concentrated. The residue was purified by column chromatography ($SiO_2$) to afford compound 31-6 (400 mg).

Step 6: tert-butyl ((1r,4r)-4-((6-bromo-8-ethylquinazolin-2-yl)amino)cyclohexyl)carbamate (31-7)

To a mixture of compound 31-6 (350 mg, 964.2 umol) and DIEA (373 mg, 2.8 mmol, 505.2 uL) in isopropanol (10 mL) was added tert-butyl ((1r,4r)-4-aminocyclohexyl)carbamate (413 mg, 1.9 mmol). The mixture was stirred at 80° C. for 12 h, cooled to rt and concentrated. The residue was purified by prep-TLC ($SiO_2$) to afford compound 31-7 (350 mg).

Step 7: tert-butyl ((1r,4r)-4-((8-ethyl-6-(4,4,5,5-tetramethyl-1,3,2-dioxaborolan-2-yl)quinazolin-2-yl)amino)cyclohexyl)carbamate (31-8)

To a mixture of compound 31-7 (150 mg, 333.7 umol) and KOAc (98 mg, 1.0 mmol) in dioxane (2 mL) were added 4,4,5,5-tetramethyl-2-(4,4,5,5-tetramethyl-1,3,2-dioxaborolan-2-yl)-1,3,2-dioxaborolane (101 mg, 400.5 umol) and $Pd(dppf)Cl_2$ (24 mg, 33.3 umol). The mixture was stirred at 90° C. for 12 h under $N_2$, cooled to rt and concentrated. The residue was purified by prep-TLC ($SiO_2$) to afford compound 31-8 (100 mg).

Step 8: tert-butyl ((1r,4r)-4-((8-ethyl-6-(4,4,5,5-tetramethyl-1,3,2-dioxaborolan-2-yl)quinazolin-2-yl)amino)cyclohexyl)carbamate (31-9)

To a mixture of compound 31-8 (100 mg, 201.4 umol) and $K_2CO_3$ (83 mg, 604.2 umol) in dioxane (2 mL) and $H_2O$ (200 uL) were added compound 3A (76 mg, 161.1 umol) and $Pd(dppf)Cl_2$ (14 mg, 20.1 umol). The mixture was stirred at 90° C. for 12 h under $N_2$, cooled to rt and concentrated. The residue was purified by prep-TLC ($SiO_2$) to afford compound 31-9 (40 mg).

Step 9: 1-(5-(2-(((1r,4r)-4-aminocyclohexyl)amino)-8-ethylquinazolin-6-yl)-1-methyl-1H-pyrazol-3-yl)-3-(4-((4-methylpiperazin-1-yl)methyl)-3-(trifluoromethyl) phenyl)urea (31)

A solution of compound 31-9 (40 mg, 52.3 umol) in TFA (1 mL) and dichloromethane (2 mL) was stirred at 20° C. for 10 min. The mixture was concentrated to get crude residue, adjusted to pH=7 with $NH_3 \cdot H_2O$ (25%), and purified by prep-HPLC to give 31 (16.1 mg, 22.1 umol, 42.3% yield). M+H$^+$=665.5 (LCMS); $^1$H NMR (METHANOL-$d_4$, 400 MHz) δ 9.02 (s, 1H), 7.92 (s, 1H), 7.68 (br d, J=11.9 Hz, 2H), 7.64-7.56 (m, 2H), 6.36 (br s, 1H), 3.93 (br s, 1H), 3.83 (s, 3H), 3.60 (s, 2H), 3.07 (q, J=7.3 Hz, 2H), 2.80 (br s, 1H), 2.49 (br s, 8H), 2.29-2.14 (m, 5H), 2.00 (br s, 2H), 1.45-1.29 (m, 7H)

Example A13: Synthesis of 1-(5-(2-amino-8-ethylquinazolin-6-yl)-1-methyl-1H-pyrazol-3-yl)-3-(4-((4-methylpiperazin-1-yl)methyl)-3-(trifluoromethyl) phenyl)urea (6)

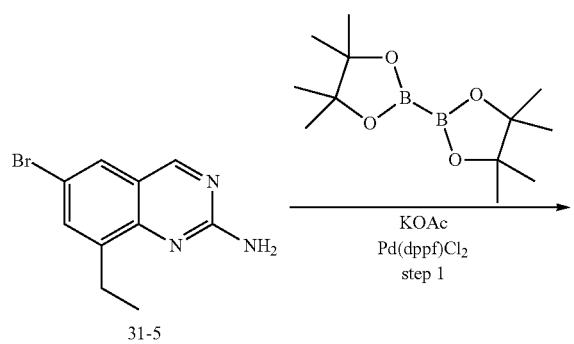

-continued

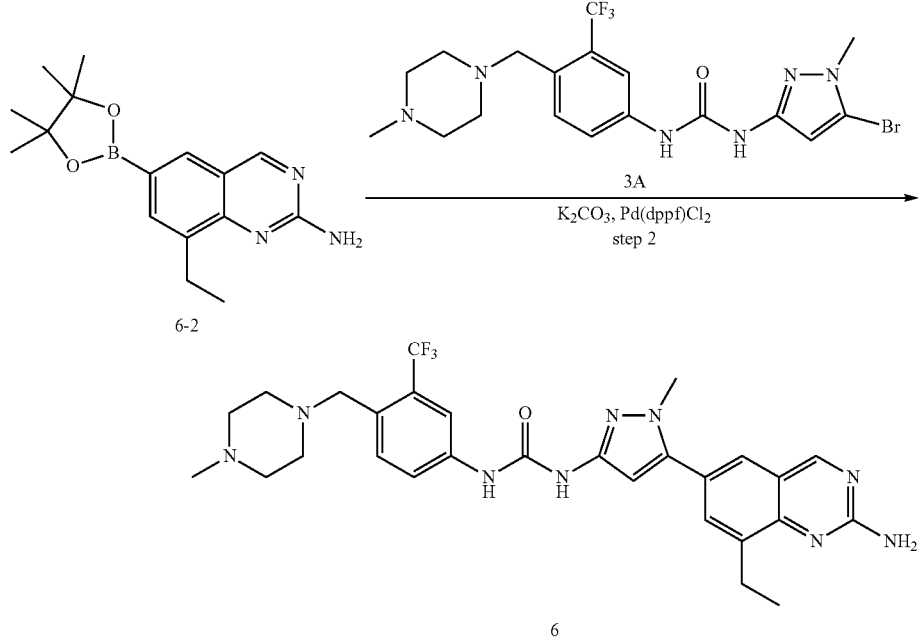

Step 1: 8-ethyl-6-(4,4,5,5-tetramethyl-1,3,2-dioxaborolan-2-yl)quinazolin-2-amine (6-2)

To a mixture of compound 31-5 (150 mg, 594 umol) and KOAc (87 mg, 892 umol) in dioxane (4 mL) were added 4,4,5,5-tetramethyl-2-(4,4,5,5-tetramethyl-1,3,2-dioxaborolan-2-yl)-1,3,2-dioxaborolane (181 mg, 713 umol) and Pd(dppf)Cl$_2$ (43 mg, 59.5 umol). The mixture was stirred at 90° C. for 12 h under N$_2$. The mixture was concentrated and the crude residue was purified by prep-TLC (SiO$_2$) to afford compound 6-2 (100 mg).

Step 2: 1-(5-(2-amino-8-ethylquinazolin-6-yl)-1-methyl-1H-pyrazol-3-yl)-3-(4-((4-methylpiperazin-1-yl)methyl)-3-(trifluoromethyl)phenyl)urea (6)

To a mixture of compound 6-2 (50 mg, 167 umol) and K$_2$CO$_3$ (69 mg, 501.3 umol) in dioxane (2 mL) and H$_2$O (200 uL) were added compound 3A (79 mg, 167.1 umol) and Pd(dppf)Cl$_2$ (6 mg, 8.3 umol). The mixture was stirred at 90° C. for 12 h under N$_2$, cooled to rt 1H), 3.85 (s, 3H), 3.70 (s, 2H), 3.18-3.01 (m, 6H), 2.82-2.55 (m, 7H), 1.33 (t, J=7.5 Hz, 3H).

Example A14: Synthesis of 1-(5-(2-amino-8-methylquinazolin-6-yl)-1-methyl-1H-pyrazol-3-yl)-3-(4-((4-methylpiperazin-1-yl)methyl)-3-(trifluoromethyl)phenyl)urea (12)

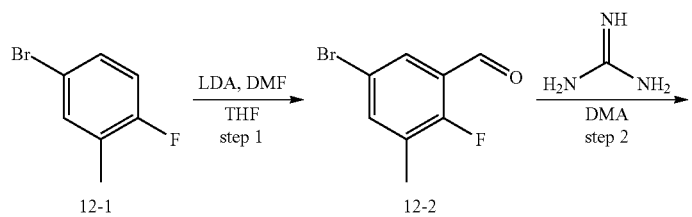

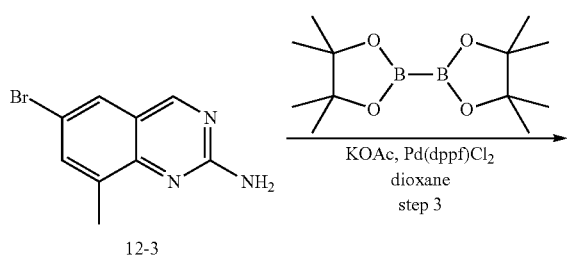

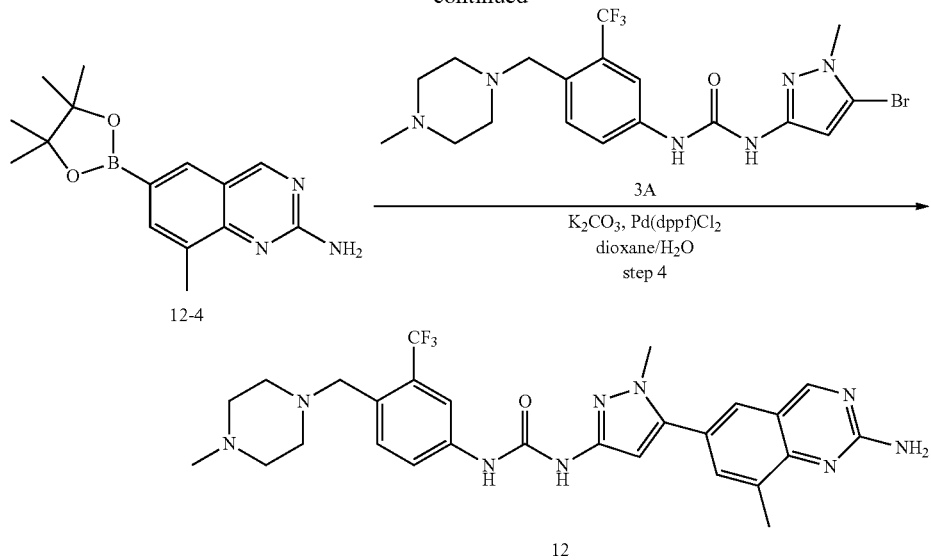

Step 1: 5-bromo-2-fluoro-3-methylbenzaldehyde (12-2)

To a solution of 4-bromo-1-fluoro-2-methyl-benzene (2.0 g, 10.5 mmol) in THF (20.0 mL) was added dropwise LDA (2 M, 6.3 mL) at −78° C. over 5 min. After addition, the mixture was stirred at −78° C. for 1 h, and DMF (1.1 g, 15.8 mmol, 1.2 mL) was added dropwise. The resulting mixture was stirred for 25 min, quenched by addition of $NH_4Cl$ (30 mL) at 15° C., and the resulting mixture was extracted with ethyl acetate (50 mL×3). The combined organic layers were washed with brine (50 mL), dried over $Na_2SO_4$, filtered and concentrated. The residue was purified by column chromatography ($SiO_2$) to afford compound 12-2 (1.3 g, 5.2 mmol). $^1H$ NMR ($CDCl_3$, 400 MHz) δ 10.25 (s, 1H), 7.75 (dd, J=5.62, 2.54 Hz, 1H), 7.54 (dd, J=6.50, 2.09 Hz, 1H), 2.30 (d, J=2.21 Hz, 3H).

Step 2: 6-bromo-8-methylquinazolin-2-amine (12-3)

To a solution of compound 12-2 (1.2 g, 5.8 mmol) in DMA (10.0 mL) was added carbonic acid-guanidine (1.5 g, 8.7 mmol). The mixture was stirred at 160° C. for 0.5 h, cooled to rt, diluted with water (10 mL) and extracted with ethyl acetate (50 mL×3). The combined organic layers were washed with brine (50 mL), dried over $Na_2SO_4$, filtered and concentrated. The residue was washed with dichloromethane (50 mL×3) to give a product compound 12-3 (120 mg).

Step 3 and step 4 are carried out according to similar procedures as described in the synthesis of compound 6.

Compound 12 (4.8 mg, 8.3 umol, 1.8% yield) was obtained. M+H+=554.3 (LCMS); $^1H$ NMR (METHANOL-$d_4$, 400 MHz) δ 9.11 (s, 1H), 7.94 (d, J=2.21 Hz, 1H), 7.78 (d, J=1.54 Hz, 1H), 7.69-7.72 (m, 2H), 7.61-7.64 (m, 1H), 6.39 (s, 1H), 3.86 (s, 3H), 3.63 (s, 2H), 2.39-2.66 (m, 11H), 2.29 (s, 3H)

Example A15: Synthesis of 1-(5-(2-(((1r,4r)-4-aminocyclohexyl)amino)quinazolin-6-yl)-1-methyl-1H-pyrazol-3-yl)-3-(4-((4-aminopiperidin-1-yl)methyl)-3-(trifluoromethyl)phenyl) urea (32)

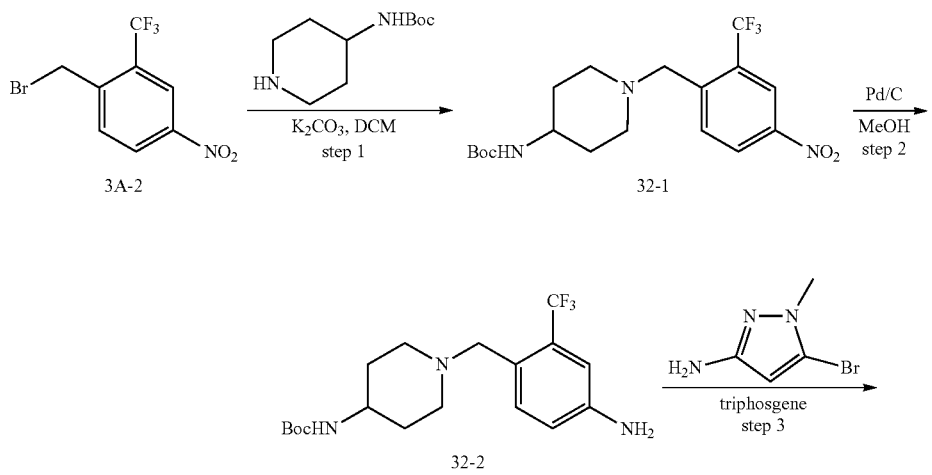

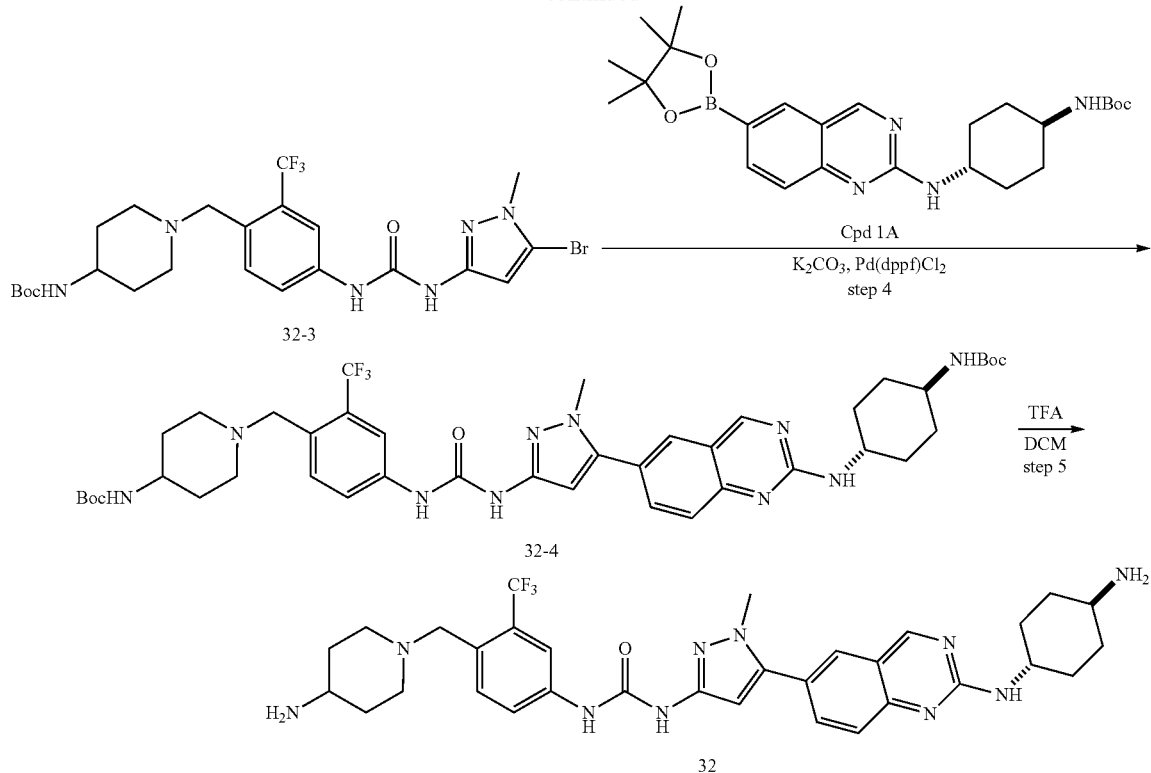

Step 1: tert-butyl (1-(4-nitro-2-(trifluoromethyl)benzyl)piperidin-4-yl)carbamate (32-1)

To a solution of compound 3A-2 (1.0 g, 3.5 mmol) and K$_2$CO$_3$ (1.4 g, 10.5 mmol) in DCM (30.0 mL) was added tert-butyl N-(4-piperidyl)carbamate (2.1 g, 10.5 mmol). The mixture was stirred at 25° C. for 12 h. The mixture was diluted with H$_2$O (10 mL) and extracted with ethyl acetate (10 mL×3). The combined organic layers were washed with brine (10 mL×3), dried over Na$_2$SO$_4$, filtered and concentrated. The residue was purified by column chromatography (SiO$_2$) to afford compound 32-1 (1.0 g).

Step 2: tert-butyl (1-(4-amino-2-(trifluoromethyl)benzyl)piperidin-4-yl)carbamate (32-2)

A solution of compound 32-1 (100 mg, 247.8 umol) in MeOH (10.0 mL) was added Pd/C (10 mg, 247.8 umol, purity 10%). The mixture was stirred at 25° C. for 10 min under H$_2$ (15 psi). The reaction mixture was filtered and concentrated under reduced pressure to give compound 32-2 (70 mg). $^1$H NMR (CDCl$_3$, 400 MHz): δ 7.39 (d, J=8.3 Hz, 1H), 6.87-6.82 (m, 1H), 6.72 (dd, J=2.3, 8.2 Hz, 1H), 4.36 (br s, 1H), 3.68 (br s, 1H), 3.42 (br d, J=2.2 Hz, 2H), 2.67 (br d, J=11.5 Hz, 2H), 2.06 (br t, J=10.6 Hz, 1H), 1.82 (br d, J=11.0 Hz, 2H), 1.54 (br s, 2H), 1.41-1.33 (m, 9H)

Step 3: tert-butyl (1-(4-(3-(5-bromo-1-methyl-1H-pyrazol-3-yl)ureido)-2-(trifluoromethyl) benzyl)piperidin-4-yl)carbamate (32-3)

To a solution of compound 32-2 (70 mg, 187.4 umol) and DIEA (36 mg, 281.1 umol, 49.1 uL) in DCM (3.0 mL) at −20° C. was added triphosgene (18 mg, 61.8 umol). The mixture was stirred at −20° C. for 1 h. Then a solution of 5-bromo-1-methyl-1H-pyrazol-3-amine (33 mg, 187.4 umol) in DCM (1.0 mL) was added. The resulting mixture was stirred at 25° C. for 12 h and concentrated to get a crude residue which was purified by prep-TLC (SiO$_2$) to afford compound 32-3 (90 mg).

Step 4: tert-butyl (1-(4-(3-(5-(2-(((1r,4r)-4-((tert-butoxycarbonyl)amino)cyclohexyl) amino)quinazolin-6-yl)-1-methyl-1H-pyrazol-3-yl)ureido)-2-(trifluoromethyl)benzyl) piperidin-4-yl)carbamate (32-4)

To a solution of compound 1A (100 mg, 213.4 umol) and K$_2$CO$_3$ (88 mg, 640.4 umol) in dioxane (2.0 mL) and H$_2$O (200 uL) were added compound 32-3 (85 mg, 149.4 umol) and Pd(dppf)Cl$_2$ (15 mg, 21.3 umol). The mixture was stirred at 90° C. for 12 h under N$_2$, cooled to rt and concentrated. The residue was purified by prep-TLC (SiO$_2$) to afford compound 32-4 (80 mg).

Step 5: 1-(5-(2-(((1r,4r)-4-aminocyclohexyl)amino)quinazolin-6-yl)-1-methyl-1H-pyrazol-3-yl)-3-(4-((4-aminopiperidin-1-yl)methyl)-3-(trifluoromethyl)phenyl) urea (32)

A solution of compound 32-4 (80 mg, 95.59 umol) in TFA (1.0 mL) and DCM (2.0 mL) was stirred at 25° C. for 5 min. The mixture was concentrated and the residue was dissolved in MeOH (2.0 mL), basified to pH-8 with NH$_3$·H$_2$O (25% purity) and concentrated to give a residue. The residue was purified by prep-HPLC to afford 32 (16.9 mg, 23.9 umol, 25.0% yield, FA). M+H$^+$=637.1 (LCMS); $^1$H NMR (METHANOL-d$_4$, 400 MHz) δ 9.09 (br s, 1H), 8.49 (br s, 1H), 7.90 (br d, J=5.7 Hz, 2H), 7.81 (br d, J=8.6 Hz, 1H), 7.70-7.56 (m, 3H), 6.40 (br s, 1H), 3.96 (br s, 1H), 3.83 (s, 3H), 3.61 (br s, 2H), 3.12 (br d, J=18.7 Hz, 2H), 2.91 (br d, J=11.9 Hz, 2H), 2.29-2.05 (m, 6H), 1.95 (br d, J=12.1 Hz, 2H), 1.72-1.38 (m, 6H).

The following compounds were synthesized according to procedures described in example above for the preparation of compound 32.

| Comp ID | Structure | Chemical Name | Mass (M + H$^+$) | $^1$H NMR (MeOD, 400 MHz) |
|---|---|---|---|---|
| 43 | 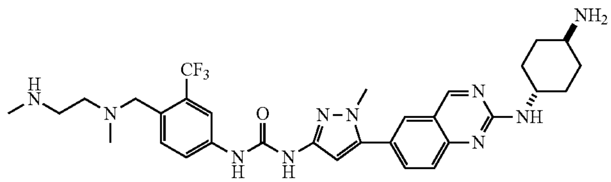 | 1-5-(2-(((1r,4r)-4-aminocyclohexyl)amino)quinazolin-6-yl)-1-methyl-1H-pyrazol-3-yl)-3-(4-((methyl(2-(methylamino)ethyl)amino)methyl)-3-(trifluoromethyl)phenyl)urea, formate salt | Calc'd for C$_{31}$H$_{40}$F$_3$N$_{10}$O: 625.3; Found: 625.2 | δ 9.13 (s, 1H), 8.51 (br s, 2H), 7.94 (br d, J = 16.1 Hz, 2H), 7.88-7.75 (m, 2H), 7.74-7.60 (m, 2H), 6.44 (br s, 1H), 4.00 (br t, J = 11.0 Hz, 1H), 3.87 (s, 3H), 3.72 (s, 2H), 3.24-3.10 (m, 3H), 2.78-2.66 (m, 5H), 2.34-2.23 (m, 5H), 2.16 (br d, J = 10.8 Hz, 2H), 1.70-1.44 (m, 4H) |
| 44 | 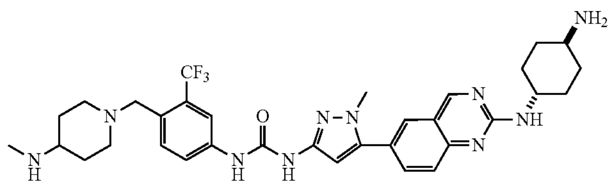 | 1-(5-(2-(((1r,4r)-4-aminocyclohexyl)amino)quinazolin-6-yl)-1-methyl-1H-pyrazol-3-yl)-3-(4-((4-(methylamino)piperidin-1-yl)methyl)-3-(trifluoromethyl)phenyl)urea, forrnate salt | Calc'd for C$_{33}$H$_{42}$F$_3$N$_{10}$O: 651.3; Found: 651.3 | δ 9.10 (br s, 1H), 8.42 (br s, 3H), 7.91 (br s, 2H), 7.82(br d, J = 8.8 Hz, 1H), 7.71-7.54 (m, 3H), 6.40 (br s, 1H), 3.97 (br s, 1H), 3.84 (s, 3H), 3.62 (br s, 2H), 3.22-2.88 (m, 4H), 2.67 (s, 3H), 2.28-1.98 (m, 8H), 1.72-1.39 (m, 6H) |

Example A16: Synthesis of 1-(4-((2-(dimethylamino)ethyl-methyl-amino)methyl]-3-(trifluoromethyl)phenyl)-3-(1-methyl-5-(2-(4-piperidylamino)quinazolin-6-yl)pyrazol-3-yl)urea (35)

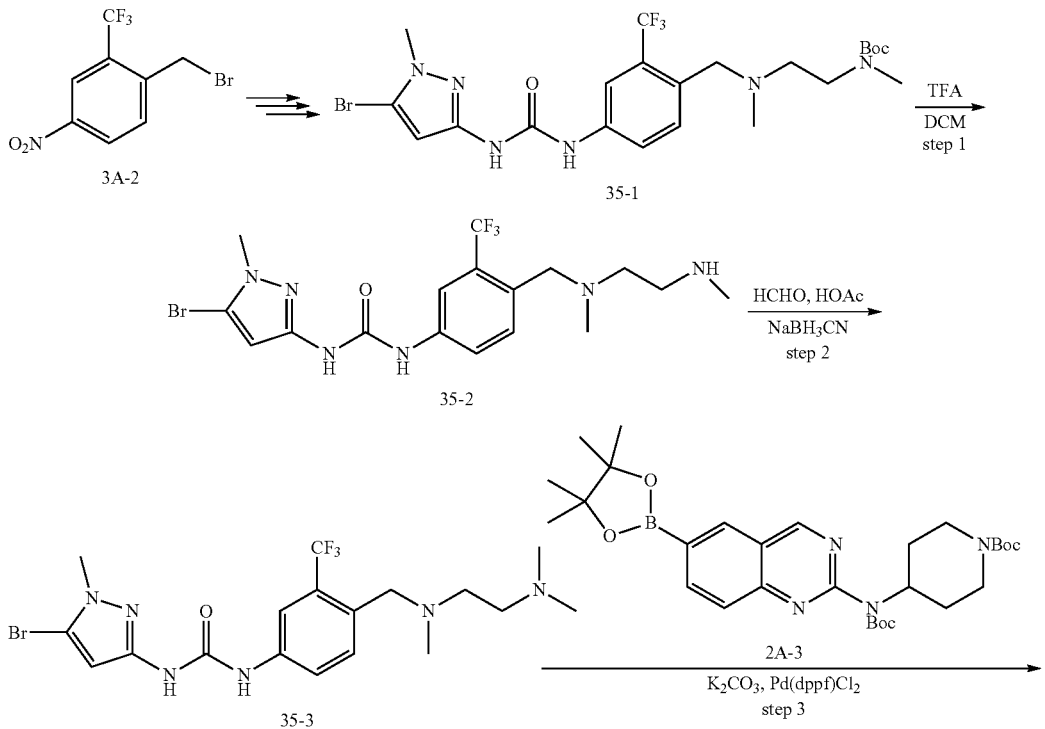

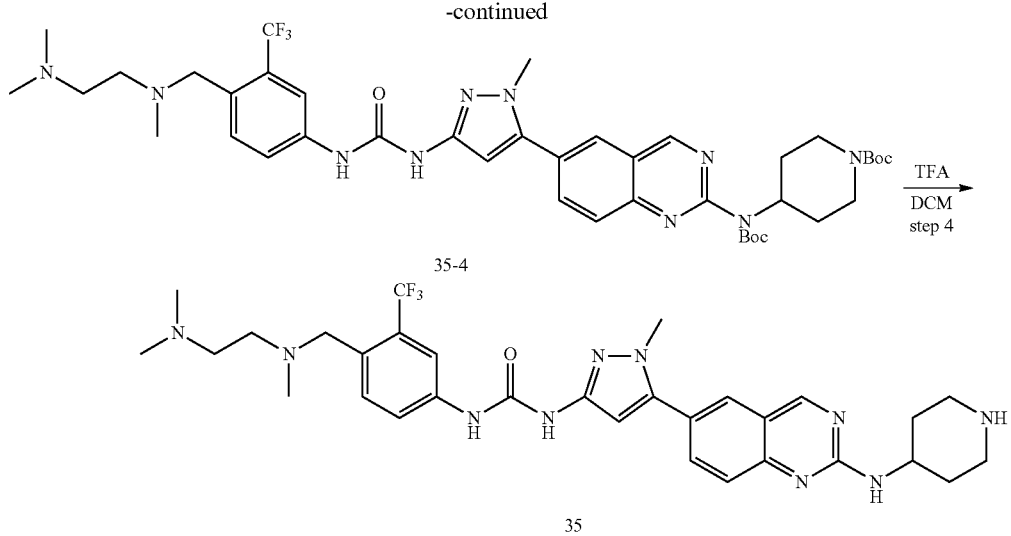

Step 1: 1-(5-bromo-1-methyl-1H-pyrazol-3-yl)-3-(4-((methyl(2-(methylamino)ethyl)amino) methyl)-3-(trifluoromethyl)phenyl)urea (35-2)

A solution of compound 35-1 (110 mg, 195.2 umol, prepared from 3A-2 according to similar procedures as described in the synthesis of 3A in example 2) in dichloromethane (2.0 mL) was added trifluoroacetic acid (1.0 mL). The mixture was stirred at 25° C. for 3 h and concentrated under reduced pressure to afford compound 35-2 (100 mg, TFA).

Step 2: 1-(5-bromo-1-methyl-1H-pyrazol-3-yl)-3-(4-(((2-(dimethylamino)ethyl)(methyl) amino)methyl)-3-(trifluoromethyl)phenyl)urea (35-3)

To a solution of compound 35-2 (100 mg, TFA) in methanol (2.0 mL) was added triethylamine (50.0 uL) to pH~7, then paraformaldehyde (58 mg, 647.5 umol) and HOAc (100.0 uL) were added to pH~5. The resulting mixture was stirred at 25° C. for 2 h, and NaBH$_3$CN (67 mg, 1.1 mmol) was added. The mixture was stirred at 25° C. for 12 h and concentrated under reduced pressure. The residue was diluted with H$_2$O (5 mL) and extracted with dichloromethane (5 mL×3). The combined organic layers were washed with brine (5 mL×3), dried over anhydrous Na$_2$SO$_4$, filtered and concentrated to give a residue which was purified by prep-TLC (SiO$_2$) to afford compound 35-3 (30 mg).

Step 3: tert-butyl 4-((tert-butoxycarbonyl)(6-(3-(3-(4-(((2-(dimethylamino)ethyl)(methyl) amino) methyl)-3-(trifluoromethyl)phenyl)ureido)-1-methyl-1H-pyrazol-5-yl)quinazolin-2-yl)amino)piperidine-1-carboxylate (35-4)

A mixture of compound 35-3 (30 mg, 62.9 umol), compound 2A-3 (34 mg, 62.9 umol), K$_2$CO$_3$ (26 mg, 188.6 umol), Pd(dppf)Cl$_2$ (5 mg, 6.3 umol) and in dioxane (2.0 mL) and H$_2$O (200 uL) was degassed and purged with N$_2$ for 3 times, and heated at 90° C. for 12 h under N$_2$. The reaction mixture was cooled to rt and filtered. The filtrate was concentrated and the residue was purified by prep-TLC (SiO$_2$) to afford compound 35-4 (13 mg).

Step 4: 1-(4-((2-(dimethylamino)ethyl-methyl-amino)methyl]-3-(trifluoromethyl)phenyl)-3-(1-methyl-5-(2-(4-piperidylamino)quinazolin-6-yl)pyrazol-3-yl)urea (35)

To a solution of compound 35-4 (13 mg, 15.8 umol) in dichloromethane (2.0 mL) was added trifluoroacetic acid (1.0 mL). The mixture was stirred at 25° C. for 30 min and concentrated. The residue was purified by prep-HPLC to give 35 (3.6 mg, 4.9 umol, 30.8% yield, FA). M+H$^+$=625.3 (LCMS); $^1$H NMR (METHANOL-d$_4$, 400 MHz) δ 9.18 (s, 1H), 8.54 (br s, 2H), 7.97 (br s, 2H), 7.88 (d, J=8.7 Hz, 1H), 7.80-7.70 (m, 2H), 7.68 (d, J=8.8 Hz, 1H), 6.45 (s, 1H), 4.30 (br t, J=10.3 Hz, 1H), 3.88 (s, 3H), 3.75 (s, 2H), 3.51 (br d, J=13.0 Hz, 2H), 3.28 (br t, J=5.9 Hz, 2H), 3.24-3.13 (m, 2H), 2.83 (s, 6H), 2.78 (br t, J=5.8 Hz, 2H), 2.43-2.27 (m, 5H), 1.98-1.81 (m, 2H).

Example A17: Synthesis of 1-(4-((dimethylamino) methyl)-3-(trifluoromethyl)phenyl)-3-(1-methyl-5-(2-(piperidin-4-ylamino)quinazolin-6-yl)-1H-pyrazol-3-yl)urea (45)

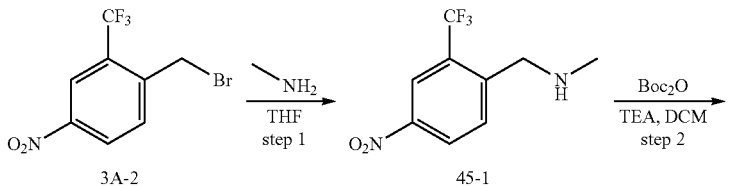

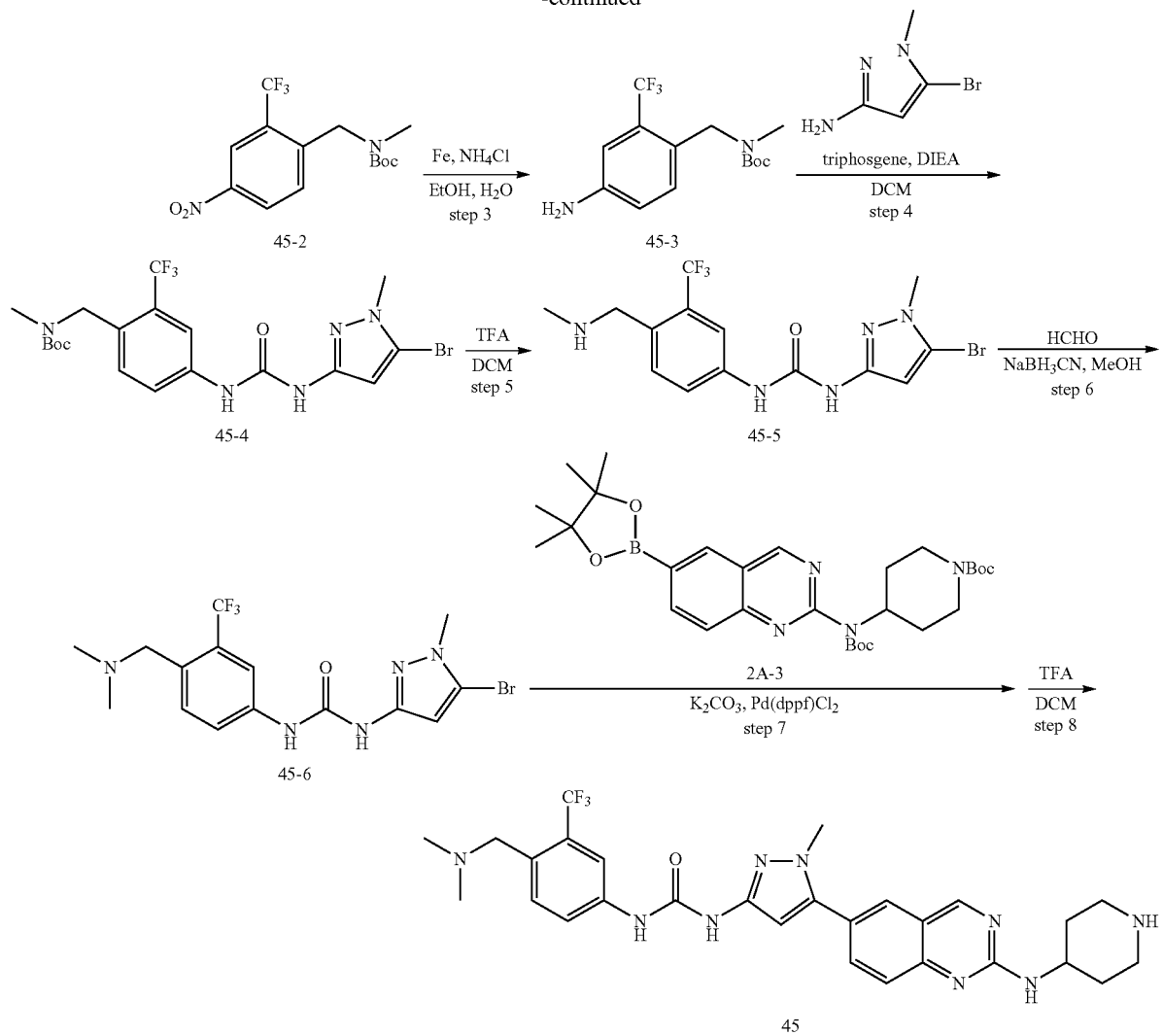

Step 1: N-methyl-1-(4-nitro-2-(trifluoromethyl)phenyl)methanamine (45-1)

To a solution of compound 3A-2 (1.0 g, 3.5 mmol) was added methanamine (2 M, 8.80 mL) in THF. The mixture was stirred at 25° C. for 12 h and concentrated under reduced pressure to give compound 45-1 (1.2 g).

Step 2: tert-butyl methyl(4-nitro-2-(trifluoromethyl)benzyl)carbamate (45-2)

To a solution of compound 45-1 (1.2 g, 5.1 mmol) in DCM (30 mL) was added TEA (1.6 g, 15.4 mmol, 2.1 mL) and tert-butoxycarbonyl tert-butyl carbonate (3.4 g, 15.4 mmol, 3.5 mL). The mixture was stirred at 30° C. for 12 h and concentrated to give a crude residue which was purified by column chromatography ($SiO_2$) to afford compound 45-2 (1.3 g).

Step 3: tert-butyl (4-amino-2-(trifluoromethyl)benzyl)(methyl)carbamate (45-3)

To a solution of compound 45-2 (500 mg, 1.5 mmol) in EtOH (10 mL) and $H_2O$ (2.0 mL) were added Fe (419 mg, 7.5 mmol) and $NH_4C_1$ (240 mg, 4.5 mmol, 157.3 uL). The mixture was stirred at 80° C. for 2 h, cooled to rt, filtered and concentrated. The residue was purified by column chromatography ($SiO_2$) to afford compound 45-3 (190 mg).

Step 4: tert-butyl (4-(3-(5-bromo-1-methyl-1H-pyrazol-3-yl)ureido)-2-(trifluoromethyl) benzyl)(methyl)carbamate (45-4)

To a solution of compound 45-3 (190 mg, 624.3 umol) in DCM (6.0 mL) was added DIEA (121 mg, 936.5 umol, 163.6 uL). The mixture was cooled to −20° C. for 0.5 h and then added bis(trichloromethyl) carbonate (61 mg, 206.0 umol) quickly avoiding water. The mixture was stirred at −20° C. for 0.5 h, and 5-bromo-1-methyl-1H-pyrazol-3-amine (109 mg, 624.3 umol) in DCM (4.0 mL) was added dropwise. The resulting mixture was stirred at 25° C. for 12 h and concentrated. The residue was purified by column chromatography ($SiO_2$) to afford compound 45-4 (62 mg).

Step 5: 1-(5-bromo-1-methyl-1H-pyrazol-3-yl)-3-(4-((methylamino)methyl)-3-(trifluoromethyl)phenyl) urea (45-5)

To a solution of compound 45-4 (62 mg, 122.4 umol) in DCM (2.0 mL) was added TFA (1.0 mL). The mixture was stirred at 25° C. for 0.5 h and concentrated under reduced pressure to afford compound 45-5 (120 mg, TFA).

Step 6: 1-(5-bromo-1-methyl-1H-pyrazol-3-yl)-3-(4-((dimethylamino)methyl)-3-(trifluoro methyl)phenyl)urea (45-6)

To a solution of compound 45-5 (120 mg, 230.7 umol TFA) in MeOH (2.0 mL) was added TEA (50.0 uL) to pH~7, then paraformaldehyde (62 mg, 692.0 umol) and $CH_3COOH$ (100 uL) were added to pH~5. The resulting mixture was stirred at 25° C. for 2 h, $NaBH_3CN$ (72 mg, 1.1 mmol) was added and the mixture was stirred at 25° C. for 12 h. The reaction mixture was concentrated, diluted with $H_2O$ (5 mL), and extracted with DCM (5 mL×3). The combined organic layers were washed with brine (5 mL), dried over $Na_2SO_4$, filtered and concentrated to give a residue, which was purified by prep-TLC ($SiO_2$) to afford compound 45-6 (15 mg).

Step 7 and step 8: 1-(4-((dimethylamino)methyl)-3-(trifluoromethyl)phenyl)-3-(1-methyl-5-(2-(piperidin-4-ylamino)quinazolin-6-yl)-1H-pyrazol-3-yl) urea (45)

Compound 45 (4.5 mg, 7.1 umol, 20.2% yield, FA) was prepared from 45-6 (15 mg, 35.7 umol) according to similar procedures as described in the synthesis of compound 31. M+H=568.2 (LCMS); $^1$H NMR (METHANOL-$d_4$, 400 MHz): δ 9.06 (s, 1H), 8.38 (br s, 2H), 7.98 (s, 1H), 7.85 (s, 1H), 7.76 (dd, J=1.7, 8.8 Hz, 1H), 7.69-7.61 (m, 1H), 7.61-7.51 (m, 2H), 6.35 (s, 1H), 4.25-4.10 (m, 1H), 3.96 (s, 2H), 3.76 (s, 3H), 3.40 (br d, J=13.0 Hz, 2H), 3.17-3.02 (m, 2H), 2.53 (s, 6H), 2.24 (br d, J=11.6 Hz, 2H), 1.90-1.66 (m, 2H).

Example A18: Synthesis of N-(5-(2-(((1r,4r)-4-aminocyclohexyl)amino)-8-ethylquinazolin-6-yl)-1-methyl-1H-pyrazol-3-yl)-2-(4-((4-methylpiperazin-1-yl)methyl)-3-(trifluoromethyl) phenyl)acetamide (46)

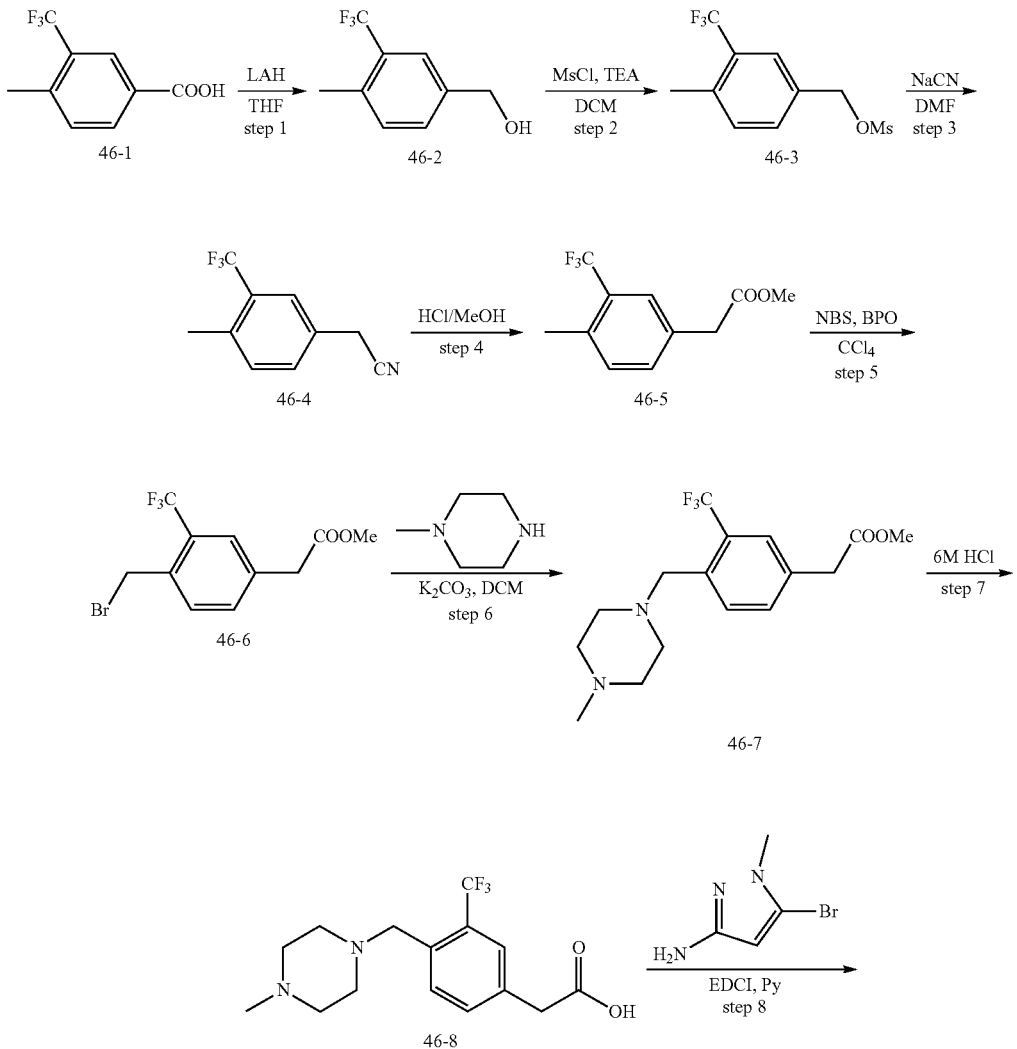

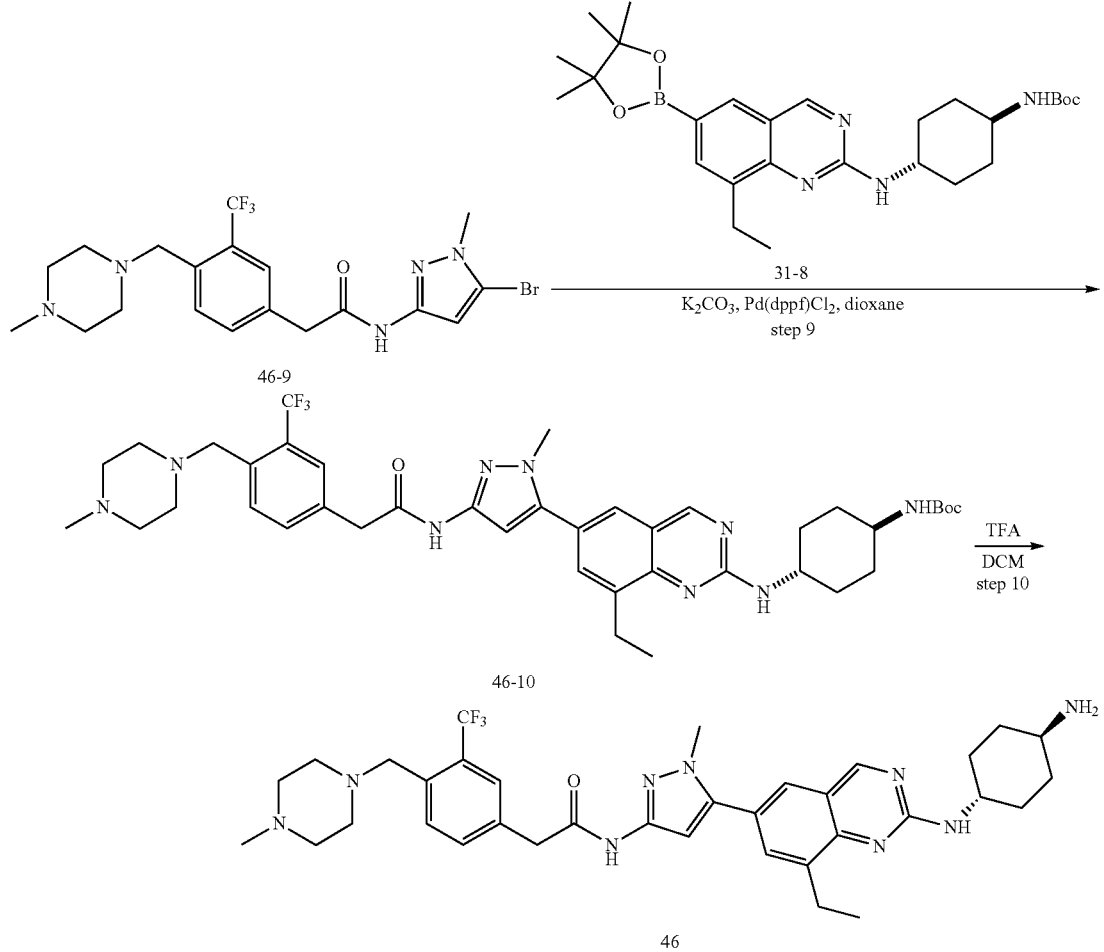

Step 1: (4-methyl-3-(trifluoromethyl)phenyl)methanol (46-2)

To a solution of LAH (223 mg, 5.9 mmol) in THF (5.0 mL) was added 4-methyl-3-(trifluoromethyl)benzoic acid (1.0 g, 4.9 mmol) in THF (10.0 mL) dropwise at 0° C. The mixture was stirred at 25° C. for 12 h, and quenched with H$_2$O (1.0 ml) and NaOH (10%, 1.0 ml).

The mixture was filtered and concentrated. The residue was purified by column chromatography (SiO$_2$) to give compound 46-2 (900 mg, 3.7 mmol, 77.2% yield). $^1$H NMR (CDCl$_3$, 400 MHz): δ 7.59 (s, 1H), 7.40 (br d, J=7.9 Hz, 1H), 7.24 (s, 1H), 4.69 (d, J=5.1 Hz, 2H), 2.46 (s, 3H)

Step 2: 4-methyl-3-(trifluoromethyl)benzyl methanesulfonate (46-3)

To a solution of compound 46-2 (800 mg, 4.2 mmol) in DCM (20 mL) was added TEA (1.3 g, 12.6 mmol, 1.8 mL) and MsCl (723 mg, 6.3 mmol, 488.4 uL) at 0° C. The mixture was stirred at 25° C. for 1 h, added water (20 mL) and extracted with DCM (20 mL×3). The combined organic phase was washed with brine (30 mL×3), dried over anhydrous Na$_2$SO$_4$, filtered and concentrated to give compound 46-3 (900 mg, crude).

Step 3: 2-(4-methyl-3-(trifluoromethyl)phenyl)acetonitrile (46-4)

To a solution of compound 46-3 (900 mg, 3.3 mmol) in DMF (15.0 mL) was added NaCN (198 mg, 4.0 mmol). The mixture was stirred at 25° C. for 1 h, diluted with water (15 mL) and extracted with ethyl acetate (15 mL×3). The combined organic layers were washed with brine (15 mL×3), dried over anhydrous Na$_2$SO$_4$, filtered and concentrated. The residue was purified by column chromatography (SiO$_2$) to afford compound 46-4 (600 mg). $^1$H NMR (CDCl$_3$, 400 MHz): δ 7.53 (s, 1H), 7.40 (br d, J=7.9 Hz, 1H), 7.30 (d, J=7.9 Hz, 1H), 3.75 (s, 2H), 2.47 (s, 3H)

Step 4: methyl 2-(4-methyl-3-(trifluoromethyl)phenyl)acetate (46-5)

The mixture of compound 46-4 (500 mg, 2.5 mmol) in HCl/MeOH (5.0 mL) (12 M) was stirred at 25° C. for 0.5 h and concentrated to give a residue. The residue was purified by prep-TLC (SiO$_2$) to give compound 46-5 (460 mg).

Step 5: methyl 2-(4-(bromomethyl)-3-(trifluoromethyl)phenyl)acetate (46-6)

To a solution of compound 46-5 (460 mg, 1.9 mmol) in CCl$_4$ (15.0 mL) was added BPO (48 mg, 198.0 umol) and NBS (388 mg, 2.2 mmol). The mixture was stirred at 80° C. for 12 h, cooled to rt and concentrated to give a residue which was purified by column chromatography (SiO$_2$) to give compound 46-6 (450 mg).

Step 6: methyl 2-(4-((4-methylpiperazin-1-yl)methyl)-3-(trifluoromethyl)phenyl)acetate (46-7)

To a solution of compound 46-6 (450 mg, 578.6 umol) in DCM (5.0 mL) was added $K_2CO_3$ (120 mg, 868.0 umol) and 1-methylpiperazine (116 mg, 1.2 mmol, 128.8 uL). The mixture was stirred at 25° C. for 1 h and concentrated to give a residue. The residue was purified by column chromatography (SiO$_2$) followed by prep-HPLC (TFA condition). The product was basified to pH~8 with saturated NaHCO$_3$ and extracted with Ethyl acetate (40 mL×3), dried over anhydrous Na$_2$SO$_4$, filtered and concentrated to give compound 46-7 (110 mg, 299.6 umol, 51.7% yield). $^1$H NMR (CDCl$_3$, 400 MHz): δ 7.73 (d, J=8.3 Hz, 1H), 7.51 (s, 1H), 7.42 (d, J=7.9 Hz, 1H), 3.70 (s, 3H), 3.67-3.60 (m, 4H), 2.51 (br s, 8H), 2.30 (s, 3H)

Step 7: 2-(4-((4-methylpiperazin-1-yl)methyl)-3-(trifluoromethyl)phenyl)acetic acid (46-8)

The mixture of compound 46-7 (200 mg, 605.4 umol) in HCl (4.0 mL) (6 M) was stirred at 100° C. for 12 h. The reaction was cooled to rt and concentrated to give compound 46-8 (100 mg).

Step 8: N-(5-bromo-1-methyl-1H-pyrazol-3-yl)-2-(4-((4-methylpiperazin-1-yl)methyl)-3-(trifluoromethyl)phenyl)acetamide (46-9)

To a solution of compound 46-8 (140 mg, 442.5 umol) in pyridine (2.0 mL) were added 5-bromo-1-methyl-1H-pyrazol-3-amine (77 mg, 442.5 umol) and EDCI (254 mg, 1.3 mmol). The mixture was stirred at 45° C. for 12 h, cooled to rt and concentrated to give a residue. The residue was purified by prep-TLC (SiO$_2$) to afford compound 46-9 (77 mg, 30% yield). M+H+=472.0 (LCMS).

Step 9: tert-butyl ((1r,4r)-4-((8-ethyl-6-(1-methyl-3-(2-(4-((4-methylpiperazin-1-yl)methyl)-3-(trifluoromethyl)phenyl)acetamido)-1H-pyrazol-5-yl)quinazolin-2-yl)amino)cyclohexyl carbamate (46-10)

A mixture of compound 31-8 (67 mg, 162.3 umo), compound 46-9 (77 mg, 162 umol), K$_2$CO$_3$ (67 mg, 487.0 umol) and Pd(dppf)Cl$_2$ (11 mg, 16.2 umol) in H$_2$O (300.0 uL) and dioxane (3.0 mL) was degassed and purged with N$_2$ for 3 times, and then heated at 90° C. for 12 h under N$_2$. The reaction was cooled to rt and concentrated. The residue was purified by prep-TLC (SiO$_2$) to afford compound 46-10 (100 mg). M+H$^+$=764.4 (LCMS).

Step 10: N-(5-(2-(((1r,4r)-4-aminocyclohexyl)amino)-8-ethylquinazolin-6-yl)-1-methyl-1H-pyrazol-3-yl)-2-(4-((4-methylpiperazin-1-yl)methyl)-3-(trifluoromethyl) phenyl)acetamide (46)

To a solution of compound 46-10 (100 mg, 130.9 umol) in DCM (2.0 mL) was added TFA (1.0 mL). The mixture was stirred at 20° C. for 15 min and concentrated to give a residue. The residue was dissolved in MeOH (1 mL), basified pH to 8 with NH$_3$.H$_2$O (25%), concentrated and purified by prep-HPLC to afford compound 46 (27.1 mg, 34.6 umol, 26.5% yield, FA). M+H$^+$=664.3 (LCMS); $^1$H NMR (METHANOL-d$_4$, 400 MHz): δ 9.03 (s, 1H), 8.54 (br s, 2H), 7.80-7.66 (m, 3H), 7.65-7.59 (m, 2H), 6.66 (s, 1H), 4.05-3.93 (m, 1H), 3.85-3.74 (m, 7H), 3.25-3.03 (m, 7H), 2.81-2.66 (m, 7H), 2.31 (br d, J=11.2 Hz, 2H), 2.17 (br d, J=11.1 Hz, 2H), 1.70-1.43 (m, 4H), 1.34 (t, J=7.5 Hz, 3H).

The following compounds were synthesized according to procedures described in example above for the preparation of compound 46.

| Comp ID | Structure | Chemical Name | Mass (M + H$^+$) | $^1$H NMR (MeOD, 400 MHz) |
|---|---|---|---|---|
| 14 | (CF$_3$ piperazinylmethyl-phenyl-acetamide-pyrazolyl-quinazolinyl-piperidinylamino structure) | N-(1-methyl-5-(2-(piperidin-4-ylamino)quinazolin-6-yl)-1H-pyrazol-3-yl)-2-(4-((4-methylpiperazin-1-yl)methyl)-3-(trifluoromethyl)phenyl)acetamide, formate salt | Calc'd for C$_{32}$H$_{39}$F$_3$N$_9$O: 622.3; Found: 622.0 | δ 9.08 (s, 1H), 8.50 (br s, 1H), 7.85 (d, J = 1.1 Hz, 1H), 7.80-7.68 (m, 3H), 7.63-7.56 (m, 2H), 6.66 (s, 1H), 4.29-4.19 (m, 1H), 3.85-3.70 (m, 7H), 3.48 (br d, J = 12.8 Hz, 2H), 3.26-3.12 (m, 6H), 2.86-2.61 (m, 7H), 2.35-2.25 (m, 2H), 1.93-1.80 (m, 2H) |

Example A19: Synthesis of 1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl) phenyl)urea (49)

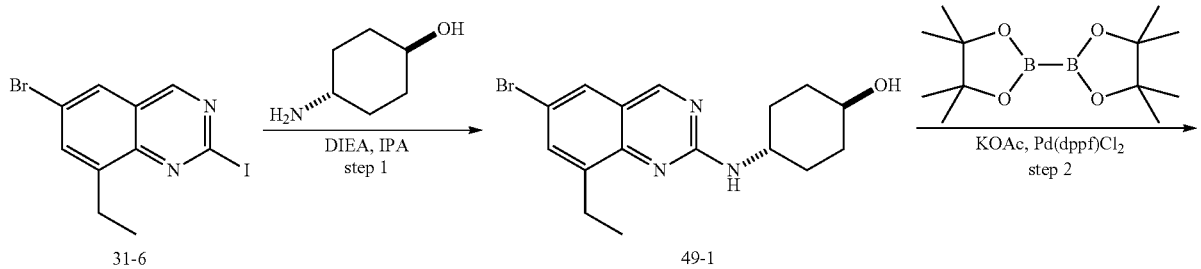

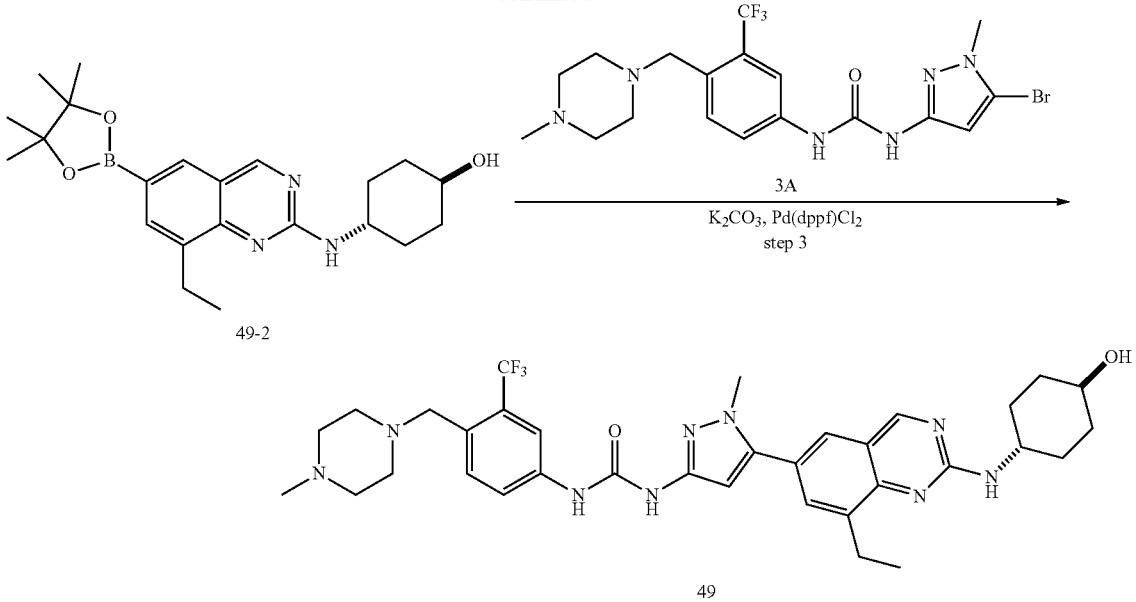

Step 1: (1r,4r)-4-((6-bromo-8-ethylquinazolin-2-yl)amino)cyclohexan-1-ol (49-1)

To a solution of compound 31-6 (240 mg, 661.1 umol) in IPA (12.0 mL) were added DIEA (256 mg, 1.9 mmol, 346.4 uL) and 4-aminocyclohexanol (152 mg, 1.3 mmol). The mixture was stirred at 80° C. for 12 h, cooled to rt and concentrated. The residue was purified by column chromatography (SiO$_2$) to afford compound 49-1 (150 mg).

Step 2: (1r,4r)-4-((8-ethyl-6-(4,4,5,5-tetramethyl-1,3,2-dioxaborolan-2-yl)quinazolin-2-yl) amino)cyclohexan-1-ol (49-2)

A mixture of compound 49-1 (150 mg, 428.2 umol), AcOK (126 mg, 1.3 mmol), 4,4,5,5-tetramethyl-2-(4,4,5,5-tetramethyl-1,3,2-dioxaborolan-2-yl)-1,3,2-dioxaborolane (120 mg, 471.1 umol) and Pd(dppf)Cl$_2$ (31 mg, 42.8 umol) in dioxane (8.0 mL) was degassed and purged with N$_2$ three times, and stirred at 90° C. for 12 h. The reaction mixture was cooled to rt and concentrated to give a residue which was purified by prep-TLC (SiO$_2$) to give compound 49-2 (200 mg).

Step 3: 1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl) phenyl)urea (49)

A mixture of compound 49-2 (100 mg, 251.6 umol), compound 3A (120 mg, 251.7 umol), K$_2$CO$_3$ (104 mg, 755.0 umol) and Pd(dppf)Cl$_2$ (18 mg, 25.1 umol) in dioxane (3.0 mL) and H$_2$O (300 uL) was degassed and purged with N$_2$ three times before it was stirred at 90° C. for 12 h under N$_2$. The reaction mixture was concentrated and the crude residue was purified by prep-TLC (SiO$_2$) followed by prep-HPLC to afford 49 (27.6 mg, 37.6 umol, 14.9% yield, FA). M+H$^+$ =666.3 (LCMS); $^1$H NMR (METHANOL-d$_4$, 400 MHz) δ 9.03 (s, 1H), 8.53 (br dd, J=1.9, 3.7 Hz, 1H), 7.96 (s, 1H), 7.76-7.61 (m, 4H), 6.39 (s, 1H), 4.00-3.91 (m, 1H), 3.86 (s, 3H), 3.72 (s, 2H), 3.68-3.59 (m, 1H), 3.29-3.03 (m, 6H), 2.94-2.56 (m, 7H), 2.21 (br s, 2H), 2.09-1.98 (m, 2H), 1.53-1.41 (m, 4H), 1.37 (t, J=7.5 Hz, 3H).

Example B1: In Vitro FRET Assay

In vitro FRET assay was performed to evaluate the ability of select compounds to inhibit IRE1, the results of which are summarized in Table 5. To perform the in vitro FRET assay, 1× complete assay buffer (CAB; 1M DTT, 50 mM sodium citrate pH 7.15, 1 mM magnesium acetate, 0.02% tween 20) was used to dilute SignalChem IRE1α protein to a final concentration of 2 nM. Selected compounds were serially diluted with DMSO in a non-binding black 384-well plate for a total of 15 ul in each well. 2 ul of the serially diluted compound or DMSO control were then added to new wells containing 98 ul of 1×CAB, for a total volume of 100 ul, 10 ul of which were then transferred to wells of a new plate. 5 ul of the diluted IRE1α was then added to each well. 5 ul of a 400 mM XBP1 RNA probe was then added to each well. Fluorescence was then read over 30 minutes in kinetic mode (485/515 nm).

Two RNA probes were used, XBP1 wildtype (SEQ ID NO: 2) which is able to be spliced by active IRE1α or XBP1 mutant (SEQ ID NO: 3) which is unable to be spliced. Each probe contained a 5' 6-FAM modification and a 3' IOWA Black FQ modification.

A second FRET assay was performed to assess ATP-mediated inhibition. In this case, compounds and IRE1α were prepared and combined as discussed above, with the addition of ATP up to 1 mM final concentration. This mixture was incubated at room temperature for 60 minutes and then 5 ul of 400 nM XBP1 wildtype or mutant RNA probe was added. Plates were then read over 30 minutes in kinetic mode (485/515 nm).

TABLE 5

| Compound Ref. No. | Mean EC$_{50}$ |
|---|---|
| 1; TFA | A |
| 2; TFA | A |
| 3; TFA | A |

TABLE 5-continued

| Compound Ref. No. | Mean EC$_{50}$ |
|---|---|
| 4; TFA | D |
| 5 | D |
| 6; Formic Acid | B |
| 9; Formic Acid | D |
| 10; Formic Acid | B |
| 11; Formic Acid | D |
| 12 | B |
| 14; Formic Acid | D |
| 15; Formic Acid | A |
| 17; Formic Acid | A |
| 19; Formic Acid | B |
| 20; Formic Acid | D |
| 21; Formic Acid | D |
| 22; Formic Acid | A |
| 23; Formic Acid | D |
| 26; Formic Acid | A |
| 29; Formic Acid | A |
| 31 | A |
| 32; Formic Acid | A |
| 33; Formic Acid | A |
| 34; Formic Acid | A |
| 35; Formic Acid | C |
| 36; Formic Acid | A |
| 38; Formic Acid | A |
| 39; Formic Acid | A |
| 40; Formic Acid | A |
| 41; Formic Acid | D |
| 42; Formic Acid | A |
| 43; Formic Acid | A |
| 44; Formic Acid | A |
| 45; Formic Acid | D |
| 46; Formic Acid | D |
| 49; Formic Acid | A |
| 50; Formic Acid | B |
| 51; Formic Acid | C |

Note:
Biochemical assay Mean EC$_{50}$ data are designated within the following ranges: A: ≤5 nM; B: >5 nM to ≤50 nM; C: >50 nM to ≤100 nM; and D: >100 nM.

Example B2: In Vitro Luciferase Assay

Compounds disclosed herein were assessed for disruption of IRE-1 signaling using a IRE1α Endoribonuclease Nano-luciferase Assay. Briefly, 2.5×10$^6$ 293T cells were seeded in in a 10 cm$^2$ tissue culture plate. About 24 hours later, the cells were transfected with Effectene. In a 15 mL Tube, the following was added: 2 μg XBP1 luciferase reporter plasmid (PGK-Luc2-P2A-XBP1u-Nanoluciferase-PEST); 300 μl EC buffer; and 16 μl Enhancer, followed by incubation at room temp for 5 minutes. Next, 60 μl Effectene (Qiagen 301427) was added, followed by incubation at room temperature for 10 minutes. 2.6 mL cDMEM media was added. Old media was aspirated from the cells, followed by addition of 7 mL fresh media. Full transfection mixture was added dropwise to cells. Cells were incubated for 6 hours, followed by tripsinization, centrifugation and resuspension in 11 mL media. 100 uL of cells were plated per a well in a 96 well plate. A day later, stressors of choice +/- inhibitors were added. To harvest, media was aspirated from cells completely, then 50 uL 1× passive lysis buffer (Promega: E1941) was added per well and put on shaker (300 rpm) for 30 minutes at room temperature. Cells were centrifuged, and 15 uL sample per well was added to a new, opaque white 384 well plate (Corning 3570). 15 uL OneGlo (nanoluciferase kit, Promega N1630) was added. Plates were spun down, placed on shaker (300 rpm) for 10 minutes. Plates were read on luminometer, 1000 ms integration time per well. 15 uL Stop and Glo (nanoluciferase kit) was added. Plates were spun down, placed on shaker (300 rpm) for 10 minutes. Plates were read on luminometer, 1000 ms second integration time per well. Recordings are provided below in Table 6.

TABLE 6

| Compound Ref. No. | Mean EC$_{50}$ |
|---|---|
| 1; TFA | B |
| 2; TFA | D |
| 3; TFA | B |
| 5 | D |
| 6; Formic Acid | C |
| 9; Formic Acid | D |
| 10; Formic Acid | D |
| 12 | D |
| 15; Formic Acid | D |
| 17; Formic Acid | B |
| 19; Formic Acid | D |
| 21; Formic Acid | D |
| 22; Formic Acid | D |
| 23; Formic Acid | D |
| 26; Formic Acid | A |
| 29; Formic Acid | B |
| 31 | A |
| 32; Formic Acid | C |
| 33; Formic Acid | D |
| 34; Formic Acid | D |
| 35; Formic Acid | D |
| 36; Formic Acid | D |
| 38; Formic Acid | D |
| 39; Formic Acid | D |
| 40; Formic Acid | A |
| 41; Formic Acid | D |
| 42; Formic Acid | A |
| 43; Formic Acid | B |

Note:
Biochemical assay Mean EC$_{50}$ data are designated within the following ranges: A: ≤5 nM; B: >5 nM to ≤50 nM; C: >50 nM to ≤100 nM; and D: >100 nM.

Example B3: ELISA Assay

Total human of mouse CD4 T cells are isolated with Miltenyl MACS beads. Mouse CD4 T cells are isolated from mouse spleen while human CD4 T cells were isolated from human PBMCs. CD4 T cells are washed and then mixed with CD3/CD28 activator Dynabeads at 8 pm. After a 36 hour incubation, select IRE1α inhibitor compounds or IRE1α inhibitor controls are added and incubated for 2 hours.

After the two hour incubation, mouse or human ascites supernatants or cRPMI control are added. After a 10 hour incubation, supernatants are isolated and used in an IFN-g ELISA assay. Trizol is added to each ELISA well containing T Cells for isolating RNA. ELISA assay is performed according to eBioscience Ready-Set-Go IFN-g ELISA kit protocol.

Example B4: DC Lipid Accumulation Assay

Approximately 3×10$^6$ bone marrow cells (after RBC lysis) are seeded in 10 mL cRPMI with 20 ng/mL GM-CSF in a petri dish. On culture day 3, 10 mL of cRPMI+20 ng/mL GM-CSF is added. On culture day 6, non-adherent cells from each plate are collected and resuspended in 20 mL of fresh cRPMI+20 ng/mL GM-CSF. On culture day 7, suspension cells are harvested, counted, and the resuspended at 500,000 cells per 180 microliters in fresh cRPMI+20 ng/mL GM-CSF+110% final concentration of IRE1α inhibitor compounds or DMSO as a control. 180 microliters of cell suspension are added to each well of a 96 well flat bottom TC-treated plate and incubated for 2 hours. 20 ul of 10×LPS (1 ug/mL) prepared in cRPMI+20 ng/mL GM-CSF is added to indicated wells and incubated for another 6 hours. Cells are spun down and supernatant was stored in a new 96-well V-bottom plate. 200 microliters of trizol is added to pelleted cells to subsequent RNA analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

SEQ ID NO: 1
MPARRLLLLLTLLLPGLGIFGSTSTVTLPETLLFVSTLDGSLHAVSKRTG
SIKWTLKEDPVLQVPTHVEEPAFLPDPNDGSLYTLGSKNNEGLTKLPFTI
PELVQASPCRSSDGILYMGKKQDIWYVIDLLTGEKQQTLSSAFADSLCPS
TSLLYLGRTEYTITMYDTKTRELRWNATYFDYAASLPEDDVDYKMSHFVS
NGDGLVVTVDSESGDVLWIQNYASPVVAFYVWQREGLRKVMHINVAVETL
RYLTFMSGEVGRITKWKYPFPKETEAKSKLTPTLYVGKYSTSLYASPSMV
HEGVAVVPRGSTLPLLEGPQTDGVTIGDKGECVITPSTDVKFDPGLKSKN
KLNYLRNYWLLIGHHETPLSASTKMLERFPNNLPKHRENVIPADSEKKSF
EEVINLVDQTSENAPTTVSRDVEEKPAHAPARPEAPVDSMLKDMATIILS
TFLLIGWVAFIITYPLSMHQQQQLQHQQFQKELEKIQLLQQQQQQLPFHP
PGDTAQDGELLDTSGPYSESSGTSSPSTSPRASNHSLCSGSSASKAGSSP
SLEQDDGDEETSVVIVGKISFCPKDVLGHGAEGTIVYRGMFDNRDVAVKR
ILPECFSFADREVQLLRESDEHPNVIRYFCTEKDRQFQYIAIELCAATLQ
EYVEQKDFAHLGLEPITLLQQTTSGLAHLHSLNIVHRDLKPHNILISMPN
AHGKIKAMISDFGLCKKLAVGRHSFSRRSGVPGTEGWIAPEMLSEDCKEN
PTYTVDIFSAGCVFYYVISEGSHPFGKSLQRQANILLGACSLDCLHPEKH
EDVIARELIEKMIAMDPQKRPSAKHVLKHPFFWSLEKQLQFFQDVSDRIE
KESLDGPIVKQLERGGRAVVKMDWRENITVPLQTDLRKFRTYKGGSVRDL
LRAMRNKKHHYRELPAEVRETLGSLPDDFVCYFTSRFPHLLAHTYRAMEL
CSHERLFQPYYFHEPPEPQPPVTPDAL

SEQ ID NO: 2
CAUGUCCGCAGCACAUG

SEQ ID NO: 3
CAUGUCCCCAGCACAUG

What is claimed is:

1. A compound of Formula (I), or a pharmaceutically acceptable salt thereof:

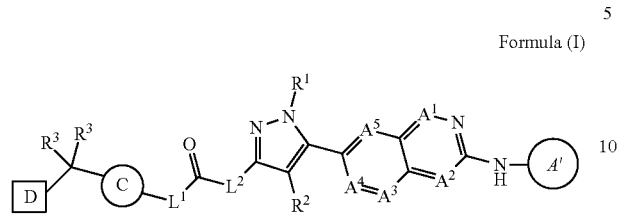

Formula (I)

wherein,

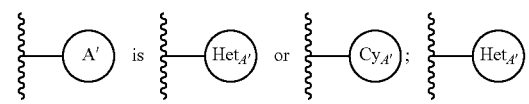

is an optionally substituted $C_3$-$C_{10}$ heterocyclyl containing at least one N, O, S, S(=O), or S(=)2; wherein if

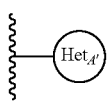

is substituted, then

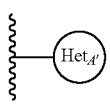

is substituted with 0-3 $R^5$;

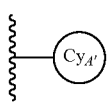

is a substituted $C_3$-$C_{10}$ cycloalkyl that is substituted with 1-3 W and 0-3$R^5$;

each $R^4$ is independently —$OR^6$, —$SR^6$, —S(=O)$R^7$, —S(=O)$_2R^7$, or —N($R^6$)$_2$;

each $R^5$ is independently halogen, —CN, —$OR^8$, —S(=O)$R^9$, —S(=O)$_2R^9$, —S(=O)$_2N(R^8)_2$, —$NR^8$S(=O)$_2R^9$, —C(=O)$R^9$, -OC(=O)$R^9$, —$CO_2R^8$, —$OCO_2R^9$, —N($R^8)_2$, —OC(=O)N($R^8)_2$, —$NR^8$C(=O)$R^9$, -$NR^8$C(=O)O$R^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

$A^1$ is N or $CR^A$; $A^2$ is N or $CR^A$; $A^3$ is N or $CR^A$; $A^4$ is N or $CR^A$; $A^5$ is N or $CR^A$;

each $R^A$ is independently 11 or optionally substituted $C_1$-$C_6$alkyl;

$R^1$ and $R^2$ are each independently H or optionally substituted $C_1$-$C_6$alkyl;

$L^1$ and $L^2$ are each independently —CHY—, —$CH_2$— or —NH—;

Y is optionally substituted $C_1$-$C_6$alkyl;

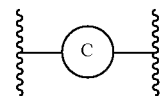

is optionally substituted aryl or optionally substituted heteroaryl, wherein if

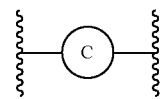

is substituted, then

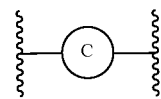

is substituted with 0-4 $R^c$;

each $R^c$ is independently H, halogen, —CN, —$OR^{10}$, —$SR^{10}$, —S(=O)$R^{11}$, —S(=O)$_2R^{11}$, —S(=O)$_2N$($R^{10}$2, —$NR^{10}$S(=O)$_2R^{11}$, —C(=O)$R^{11}$, —OC(=O)$R^{11}$, —$CO_2R^{10}$, —$OCO_2R^{11}$, —N($R^{10})_2$, —OC(=O)N($R^{10})_2$, —$NR^{10}$C(=O)$R^{11}$, —$NR^{10}$C(=O)O$R^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^3$ is independently H or optionally substituted $C_1$-$C_6$alkyl;

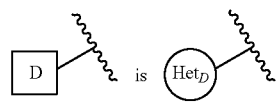

or $L^D$;

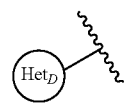

is optionally substituted heterocyclyl containing at least one N atom; wherein if

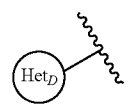

is substituted, then

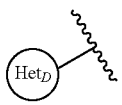

is substituted with 0-4 $R^D$;

$L^D$ is —N($R^{12}$)-(optionally substituted $C_1$-$C_6$ alkyl), —N($R^{13}$)-(optionally substituted $C_1$-$C_6$ alkylene)-N($R^{14}$)$_2$ or -(optionally substituted $C_1$-$C_6$ alkylene)-N($R^{14}$)$_2$; wherein if $L^D$ is substituted, then $L^D$ is substituted with 0-4 $R^D$;

each $R^D$ is independently halogen, —CN, —O$R^{15}$, —S$R^{15}$, —S(=O)$R^{16}$, —S(=O)$_2R^{16}$, —S(=O)$_2$N($R^{15}$)$_2$, —N$R^{15}$S(=O)$_2R^{16}$, —C(=O)$R^{16}$, —OC(=O)$R^{16}$, —CO$_2R^{15}$, —OCO$_2R^{16}$, —N($R^{15}$)$_2$, —OC(=O)N($R^{15}$)$_2$, —N$R^{15}$C(=O)$R^{16}$, —N$R^{13}$C(=O)O$R^{16}$ optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_7$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl; optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$ are taken together with the N atom to which they are attached to form an optionally substituted heterocycle;

each $R^{11}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{12}$ and $R^{13}$ is independently H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl.

2. The compound of claim 1, or a pharmaceutically acceptable salt thereof,

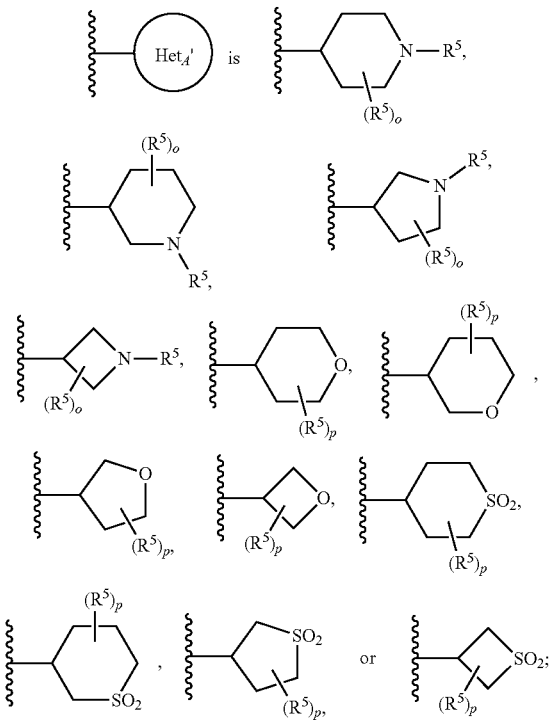

wherein o is 0, 1, or 2; and p is 0, 1, 2, or 3.

3. The compound of claim 1, or a pharmaceutically acceptable salt thereof, wherein

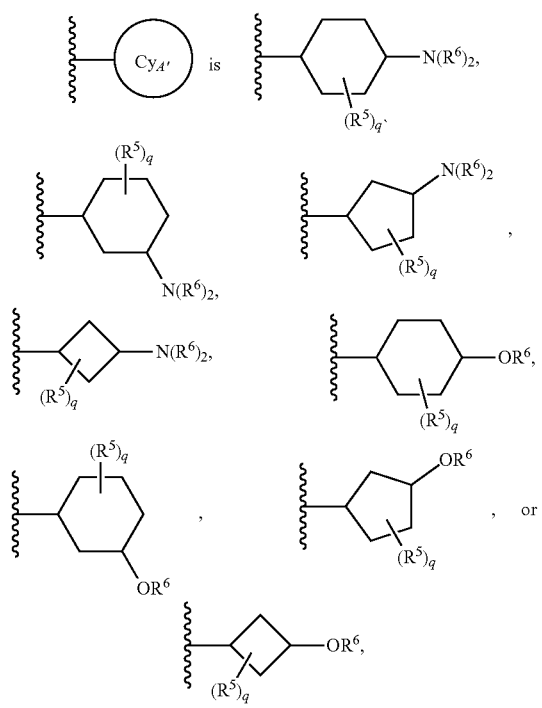

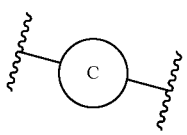

and q is 0, 1, 2, or 3.

4. The compound of any claim 1, or a pharmaceutically acceptable salt thereof, wherein $A^1$ is CH; $A^2$ is N or $CR^A$; $A^3$ is N or $CR^A$; $A^4$ is CH; and $A^5$ is CH.

5. The compound of claim 1, or a pharmaceutically acceptable salt thereof, wherein $R^A$ is optionally substituted $C_1$-$C_6$alkyl.

6. The compound of claim 1, or a pharmaceutically acceptable salt thereof, wherein $R^1$ is optionally substituted $C_1$-$C_6$alkyl.

7. The compound of claim 1, or a pharmaceutically acceptable salt thereof, wherein $R^2$ is H.

8. The compound of claim 1, or a pharmaceutically acceptable salt thereof, wherein $L^1$ and $L^2$ are each —NH—.

9. The compound of claim 1, or a pharmaceutically, acceptable salt thereof, wherein

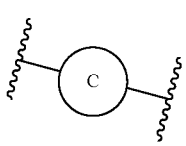

is optionally substituted aryl, wherein if

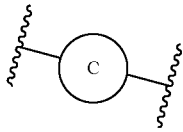

is substituted, then

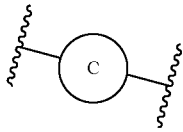

is substituted with 0-4 $R^c$.

10. The compound of claim 1, or pharmaceutically acceptable salt thereof, wherein

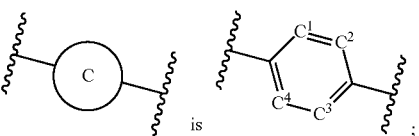

$C^1$ is N or $CR^c$; $C^2$ is N or $CR^c$; $C^3$ is N or $CR^c$; and $C^4$ is N or $CR^c$.

11. The compound of claim 10, or a pharmaceutically acceptable salt thereof, wherein $R^c$; is optionally substituted $C_1$-$C_6$fluoroalkyl.

12. The compound of claim 1, or a pharmaceutically acceptable salt thereof, wherein each $R^3$ is independently H.

13. The compound of claim 1, or a pharmaceutically acceptable salt thereof, wherein

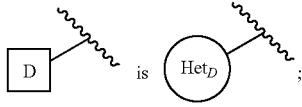

wherein

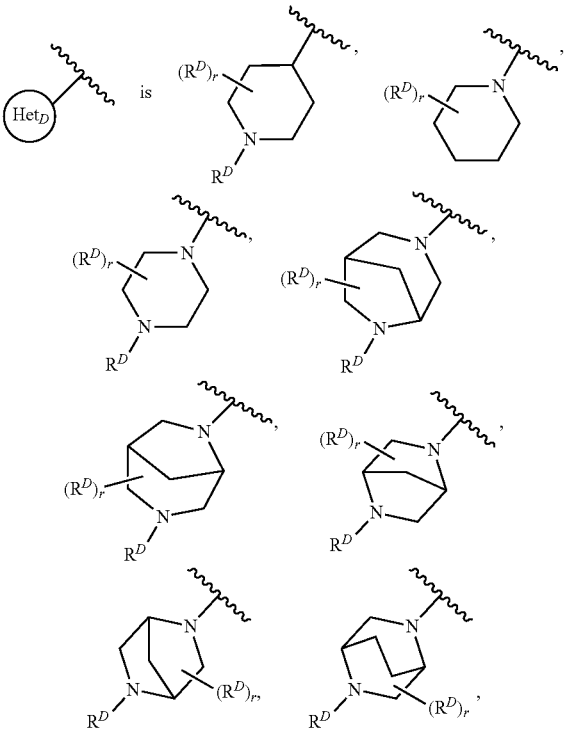

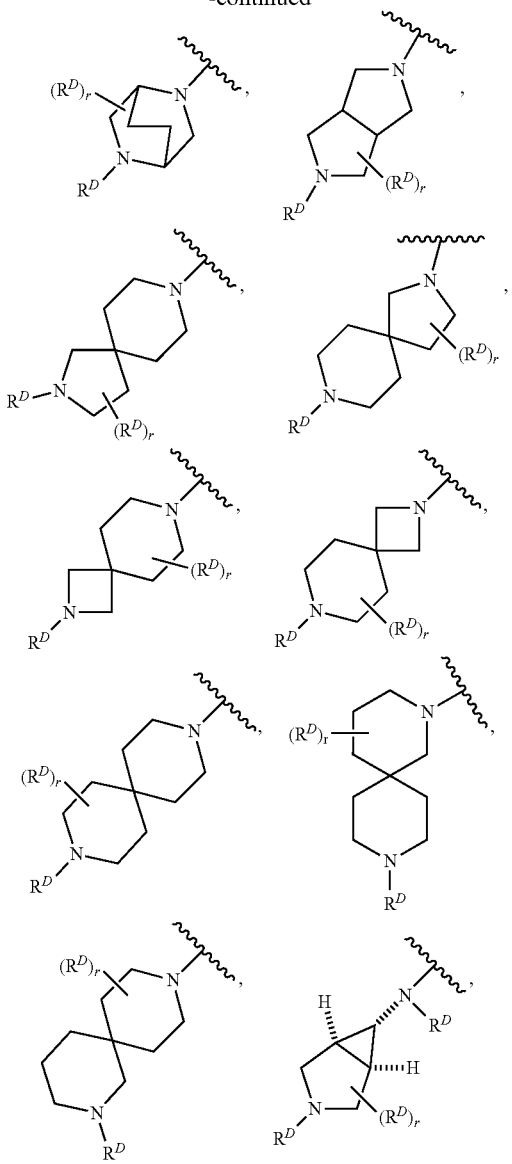
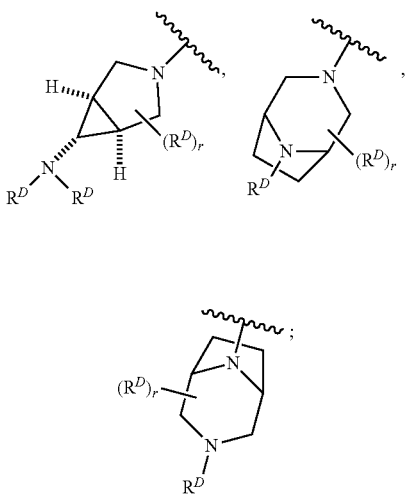

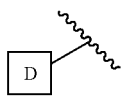

wherein r is 0, 1, or 2.

14. The compound of claim 1, or a pharmaceutically acceptable salt thereof, wherein

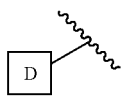

is $L^D$, wherein $L^D$ is —N($R^{13}$)-(optionally substituted $C_1$-$C_6$alkylene)-N($R^{14}$)$_2$, and if $L^D$ is substituted, then $L^D$ is substituted with 0-4 $R^D$.

15. The compound of claim 1, or a pharmaceutically acceptable salt thereof, wherein the compound has the structure of formula (Ia), (Ib), (Ic), (Id), (Ie), (If), (Ig), (Ih), or (Ii):

(Ia)

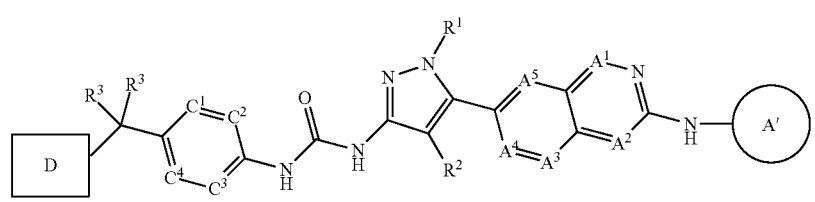

(Ib)

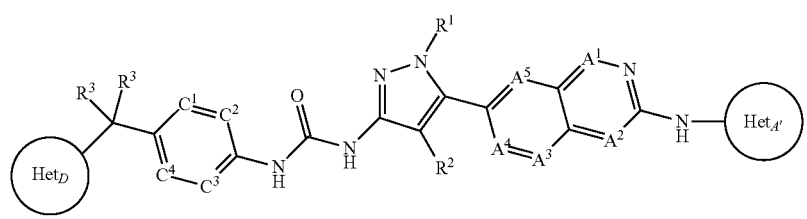

-continued
(Ic)
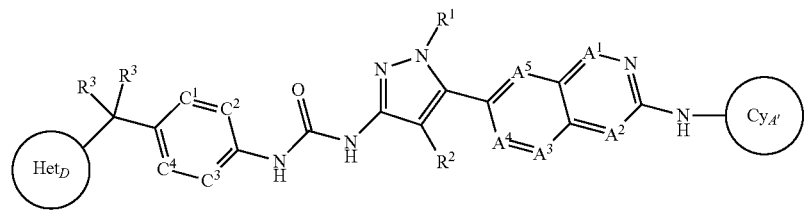
(Id)
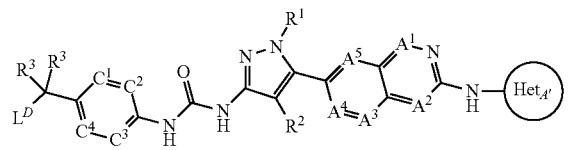
(Ie)
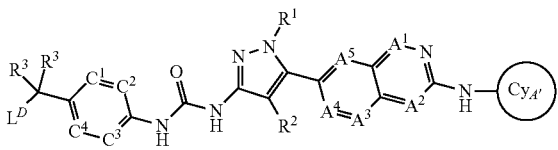
(If)
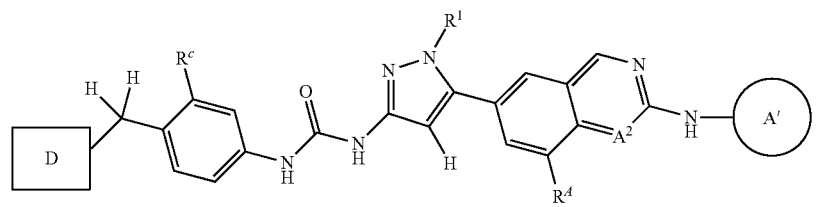
(Ig)
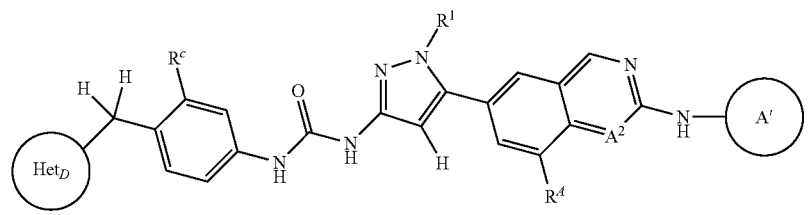
(Ih)
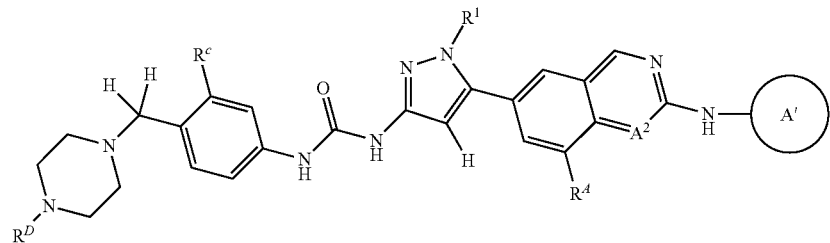
(Ii)
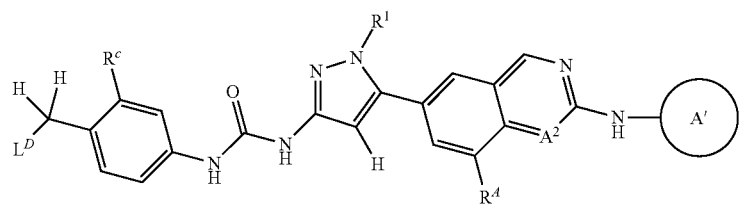

wherein,
$C^1$ is N or $CR^c$; $C^2$ is N or $CR^c$; $C^3$ is N or $CR^c$; and $C^4$ is N or $CR^c$.

16. A compound of Formula (II), or a pharmaceutically acceptable salt thereof:

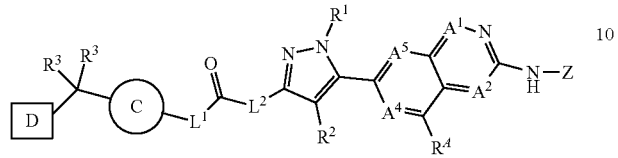

Formula (II)

wherein,
Z is H,

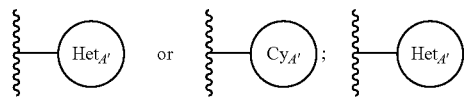

is an optionally substituted $C_3$-$C_{10}$heterocyclyl containing at least one N, O, S, S(=O), or S(=O)$_2$; wherein if

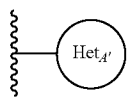

is substituted, then

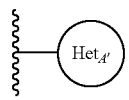

is substituted with 0-3 $R^5$;

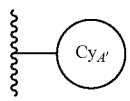

is a substituted $C_3$-$C_{10}$cycloalkyl that is substituted with 1-3$R^4$ and 0-3$R^5$;
each $R^4$ is independently —OR$^6$, —SR$^6$, —S(=O)R$^7$, —S(=O)$_2$R$^7$, or —N(R$^6$)$_2$;
each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, OC(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
$A^1$ is N or $CR^A$; $A^2$ is N or $CR^A$; $A^4$ is N or $CR^A$; $A^5$ is N or $CR^A$;
each $R^A$ is independently H or optionally substituted $C_1$-$C_6$alkyl;

$R^A$ is optionally substituted $C_1$-$C_6$alkyl;
$R^1$ and $R^2$ are each independently H or optionally substituted $C_1$-$C_6$alkyl;
$L^1$ and $L^2$ are each independently —CHY—, —CH$_2$— or —NH—;
Y is optionally substituted $C_1$-$C_6$alkyl;

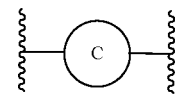

is optionally substituted aryl or optionally substituted heteroaryl, wherein if

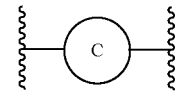

is substituted, then

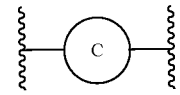

is substituted with 0-4 $R^c$;
each $R_c$ is independently H, halogen, —CN, —OR$^{10}$, —SR$^{10}$, —S(=O)R$^{11}$, —S(=O)$_2$R$^{11}$), —S(=O)$_2$N(R$^{10}$)$_2$, —NR$^{10}$S(=O)$_2$R$^{11}$, —OC(=O)R$^{11}$, —OC(=O)R$^{11}$, —CO$_2$R$^{10}$, —OCO$_2$R$^{11}$, —N(R$^{10}$)$_2$, —OC(=O)N(R$^{10}$)$_2$, —NR$^{10}$C(=O)R$^{11}$, —NR$^{10}$C(=O)OR$^{11}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;
each $R^3$ is independently H or optionally substituted $C_1$-$C_6$alkyl;

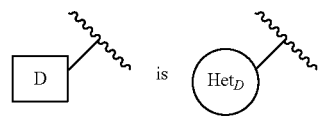

or $L^D$;

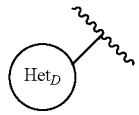

is optionally substituted heterocyclyl containing at least one N atom; wherein if

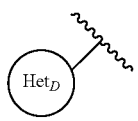

is substituted, then

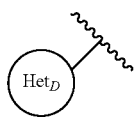

is substituted with 0-4 $R^D$;

$L^D$ is —N($R^{12}$)-(optionally substituted $C_1$-$C_6$alkyl), —N($R^{13}$)-(optionally substituted $C_1$-$C_6$alkylene)-N($R^{14}$)$_2$ or -(optionally substituted $C_1$-$C_6$alkylene)-N($R^{14}$)$_2$; wherein if $L^D$ is substituted, then $L^D$ is substituted with 0-4 $R^D$;

each $R^D$ is independently halogen, —CN, —S$R^{15}$, —S(=O)$R^{16}$, —S(=O)$_2$$R^{16}$, —S(=O)$_2$N($R^{15}$)$_2$, —N$R^{15}$S(=O)$_2$$R^{16}$, —C(=O)$R^{16}$, —OC(=O)$R^{16}$— CO$_2$$R^{15}$, —OcO$_2$$R^{16}$, —N($R^{15}$)$_2$, —OC(=O)N($R^{15}$)$_2$, —N$R^{15}$C(=O)$R^{16}$, —N$R^{15}$C(=O)O$R^{16}$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

each $R^6$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^6$ are taken together with the N atom to which they are attached to form an optionally substituted heterocycle;

each $R^7$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^8$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^8$ are taken together with the N atom to which they are attached to form an optionally substituted heterocycle;

each $R^9$ is independently optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl;

each $R^{10}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{10}$) are taken together with the N atop to which they are attached to form an optionally substituted heterocycle;

each $R^{11}$ is independently optionally substituted $C_1$-$C_6$alkyl optionally substituted $C_1$-$C_6$fluoroalkyl, optionally substituted $C_1$-$C_6$heteroalkyl, optionally substituted $C_1$-$C_{10}$cycloalkyl, optionally substituted $C_2$-$C_{10}$heterocycloalkyl, optionally substituted aryl, or optionally substituted heteroaryl;

each $R^{12}$ and $R^{13}$ is independently H or optionally substituted $C_1$-$C_6$alkyl;

each $R^{14}$ is independently H or optionally substituted $C_1$-$C_6$alkyl; or two $R^{14}$ are taken together with the N atom to which they are attached to form an optionally, substituted heterocycle;

each $R^{15}$ is independently hydrogen, optionally substituted $C_1$-$C_6$alkyl, optionally substituted $C_1$-$C_6$fluoroalkyl, optionally substituted $C_1$-$C_6$heteroalkyl, optionally substituted $C_3$-$C_{10}$cycloalkyl, optionally substituted $C_2$-$C_{10}$heterocycloalkyl, optionally substituted aryl, or optionally substituted heteroaryl; or two $R^{15}$ are taken together with the N atom to which they are attached to form an optionally substituted heterocycle; and each $R^{16}$ is independently optionally substituted $C_1$-$C_6$alkyl, optionally substituted $C_1$-$C_6$fluoroalkyl, optionally substituted $C_1$-$C_6$heteroalkyl, optionally substituted $C_1$-$C_{10}$cycloalkyl, optionally substituted $C_2$-$C_{10}$heterocycloalkyl, optionally substituted aryl, or optionally substituted heteroaryl.

17. The compound of claim 16, or a pharmaceutically acceptable salt thereof, wherein Z is H.

18. The compound of claim 16, or a pharmaceutically acceptable salt thereof, wherein the compound has the structure of formula (IIa), (IIb), (IIc), (IId), (IIe), (If), (IIg), (IIh), (IIi), (IIj), (IIk), (III), or (IIm):

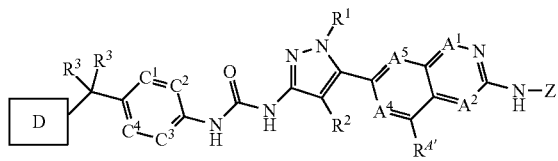

(IIa)

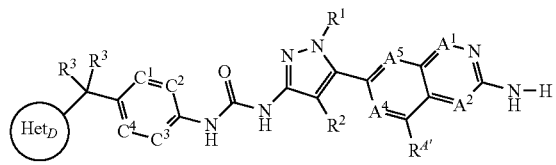

(IIb)

-continued
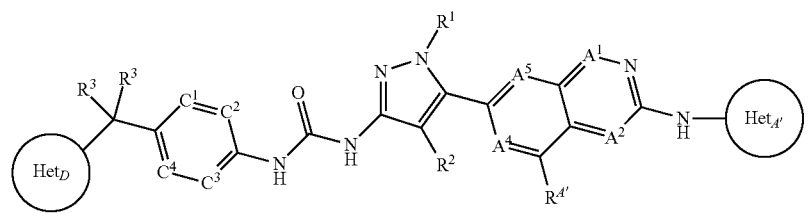
(IIc)
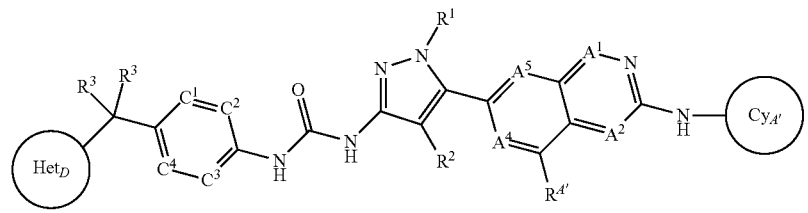
(IId)
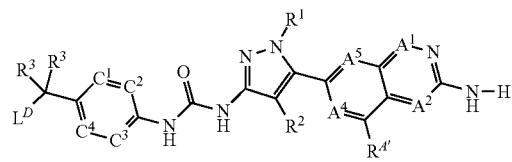
(IIe)
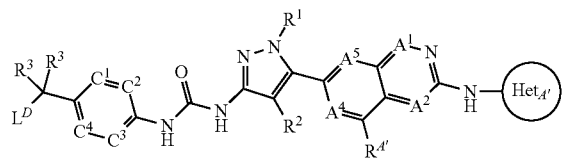
(IIf)
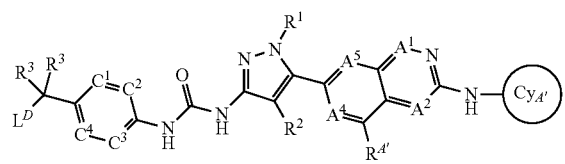
(IIg)
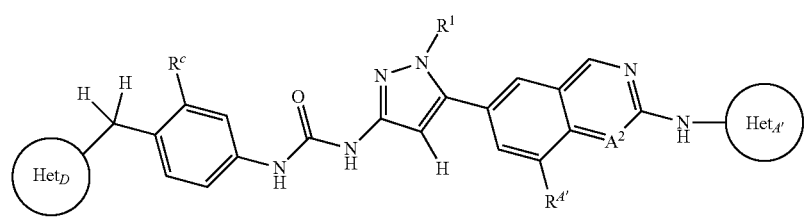
(IIh)
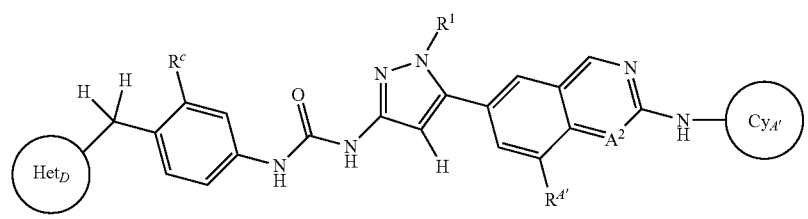
(IIi)
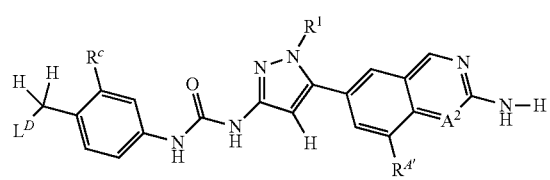
(IIj)
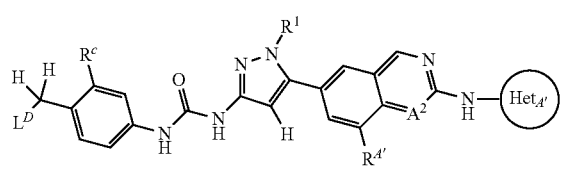
(IIk)
(III)

-continued (IIm)

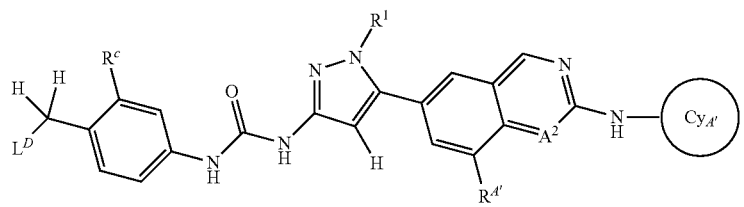

wherein, $C^1$ is N or $CR^c$; $C^2$ is N or $CR^c$; $C^3$ is N or $CR^c$; and $C^4$ is N or $CR^c$.

19. A pharmaceutical composition comprising a compound of claim 16 or a pharmaceutically acceptable salt thereof.

20. A compound of Formula (III), or a pharmaceutically acceptable salt thereof:

Formula (III)

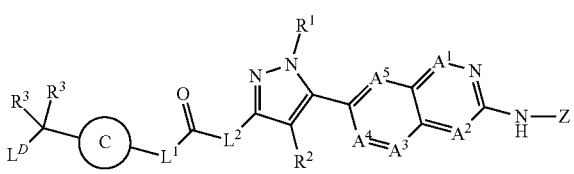

wherein,

Z is H,

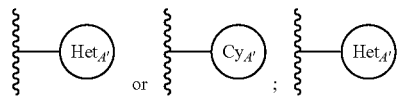

is an optionally substituted $C_3$-$C_{10}$ heterocyclyl containing at least one N, O, S, S(=O), or S(=O)$_2$; wherein if

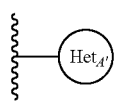

is substituted, then

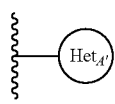

is substituted with 0-3 $R^5$;

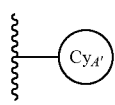

is a substituted $C_3$-$C_{10}$cycloalkyl that is substituted with 1-3$R^4$ and 0-3$R^5$;

each $R^4$ is independently —OR$^6$, —SR$^6$, —S(=O)R$^7$, —S(=O)$_2$R$^7$, or —N(R$^6$)$_2$;

each $R^5$ is independently halogen, —CN, —OR$^8$, —SR$^8$, —S(=O)R$^9$, —S(=O)$_2$R$^9$, —S(=O)$_2$N(R$^8$)$_2$, —NR$^8$S(=O)$_2$R$^9$, —C(=O)R$^9$, —OC(=O)R$^9$, —CO$_2$R$^8$, —OCO$_2$R$^9$, —N(R$^8$)$_2$, —CO(=O)N(R$^8$)$_2$, —NR$^8$C(=O)R$^9$, —NR$^8$C(=O)OR$^9$, optionally substituted $C_1$-$C_6$alkyl, optionally substituted $C_1$-$C_6$fluoroalkyl, optionally substituted $C_1$-$C_6$heteroalkyl, optionally substituted $C_3$-$C_6$cycloalkyl, optionally substituted aryl, or optionally substituted heteroaryl;

$A^1$ is N car $CR^4$; A is N car $CR^4$; $A^3$ is N car $CR^4$; $A^4$ is N or $CR^4$; $A^5$ is N or $CR^4$;

each $R^4$ is independently H or optionally substituted $C_1$-$C_6$alkyl;

$R^1$ and $R^2$ are each independently H or optionally substituted $C_1$-$C_6$alkyl;

$L^1$ and $L^2$ are each independently —CHY—, —CH$_2$— or —NH—;

Y is optionally substituted $C_1$-$C_6$alkyl;

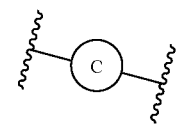

is optionally substituted aryl or optionally substituted heteroaryl, wherein if

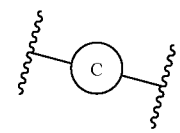

is substituted, then

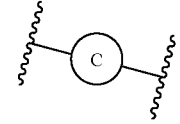

is substituted with 0-4 $R^c$;

each $R^c$ is independently H, halogen, —CN, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^1$, —N(R$^1$)$_2$) OC(=O)N(R$^{10}$)$_2$, —NR$^{10}$C(=O)R$^{11}$, —NR$^{11}$C(=O)

OR$^{11}$, optionally substituted C$_1$-C$_6$alkyl, optionally substituted C$_1$-C$_6$fluoroalkyl, optionally substituted C$_1$-C$_6$heteroalkyl, optionally substituted C$_3$-C$_6$cycloalkyl, optionally substituted aryl, or optionally substituted heteroaryl;

each R$^3$ is independently or optionally substituted C$_1$-C$_6$alkyl;

L$^1$ is —N(R$^{12}$)-(optionally substituted C$_1$-C$_6$ alkyl), —N(R$^{13}$)-(optionally substituted C$_1$-C$_6$ alkylene)-N(R$^{14}$)$_2$ or -(optionally substituted C$_1$-C$_6$ alkylene)-N(R$^{14}$)$_2$; wherein if L$^D$ is substituted, then L$^D$ is substituted with 0-4 R$^D$;

each R$^D$ is independently halogen, —CN, —OR$^{15}$, —SR$^{15}$, —S(=O)R$^{16}$, —S(=O)$_2$R$^{16}$, —S(=O)$_2$N(R$^{15}$)$_2$, —NR$^{15}$S(=O)$_2$R$^{16}$, —C(=O)R$^{16}$, —OC(=O)R$^{16}$, —CO$_2$R$^{15}$, —OCO$_2$R$^{16}$, —N(R$^{15}$)$_2$, OC(=O)N(R$^{15}$)$_2$, —NR$^{15}$C(=O)R$^{16}$, —NR$^{15}$C(=O)OR$^{16}$, optionally substituted C$_1$-C$_6$alkyl, optionally substituted C$_1$-C$_6$fluoroalkyl, optionally substituted C$_1$-C$_6$heteroalkyl, optionally substituted C$_3$-C$_6$cycloalkyl, optionally substituted aryl, or optionally substituted heteroaryl;

each R$^6$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two R$^6$ are taken together with the N atom to which they are attached to form an optionally substituted heterocycle;

each R$^7$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_7$-C$_{10}$heterocycloalkyl, optionally substituted aryl, or optionally substituted heteroaryl;

each R$^8$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_7$-C$_{10}$heterocycloalkyl, optionally substituted aryl, or optionally substituted heteroaryl; or two R$^8$ are taken together with the N atom to which they are attached to form an optionally substituted heterocycle;

each R$^9$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;

each R$^{10}$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two R$^{10}$ are taken together with the N atom to which they are attached to form an optionally substituted heterocycle;

each R$^{11}$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl;

R$^{12}$ is independently H or optionally substituted C$_3$-C$_6$alkyl;

R$^{13}$ is H or optionally substituted C$_1$-C$_6$alkyl;

each R$^{14}$ is independently H or optionally substituted C$_1$-C$_6$alkyl; or two R$^{14}$ are taken together with the N atom to which they are attached to form an optionally substituted heterocycle;

each R$^{15}$ is independently hydrogen, optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycloalkyl, optionally substituted C$_2$-C$_{10}$heterocycloalkyl, optionally substituted aryl, or optionally substituted heteroaryl; or two R$^{15}$ are taken together with the N atom to which they are attached to form an optionally, substituted heterocycle; and each R$^{16}$ is independently optionally substituted C$_1$-C$_6$alkyl, optionally substituted C$_1$-C$_6$fluoroalkyl, optionally substituted C$_1$-C$_6$heteroalkyl, optionally substituted C$_3$-C$_{10}$cycioalkyl, optionally substituted C$_2$-C$_{10}$heterocycloalkyl, optionally substituted aryl, or optionally substituted heteroaryl.

21. The compound of claim 20, or a pharmaceutically acceptable salt thereof, wherein Z is H.

22. The compound of claim 20, or a pharmaceutically acceptable salt thereof, wherein the compound has the structure of formula (IIIa), (IIIb), (IIIc), (IIId), (IIIe), (IIIf), (IIIg), or (IIIh):

-continued (IIIe)

(IIIf)

(IIIg)

(IIIh)

wherein,
C¹ is N or CR$^c$; C² is N or CR$^c$; C³ is N or CR$^c$; and C⁴ is N or CR$^c$.

23. A pharmaceutical composition comprising a compound according o claim 1 or a pharmaceutically acceptable salt thereof.

24. A compound selected from:
(R)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea;
(R)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea;
(S)-1-(1-methyl-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea;
(S)-1-(1-methyl-5-(2-(pyrrolidin-3-ylamino)quinazolin-6-yl)-1H-pyrazol-3-yl)-3-(4-((4-methylpiperazin-1-yl)methyl)-3-(trifluoromethyl)phenyl)urea;
1-(1-methyl-5-(2-4-(S)-piperidin-3-yl)amino)quinazolin-6-yl)-1H-pyrazol-3-yl)-3-(4-(1-(4-methylpiperazin-1-yl)ethyl)-3-(trifluoromethyl)phenyl)urea;
1-(1-meth-5-(2-(piperidin-3-ylamino)quinazolin-6-yl)-1H-pyrazol-3-yl)-3-(4-((4-methylpiperazin-1-yl)methyl)-3-(trifluoromethyl)phenyl)urea;
1-(1-methyl-5-(2-(piperidin-4-ylamino)quinazolin-6-yl)-1H-pyrazol-3-yl)-3-(3-((4-methylpiperazin-1-yl)methyl)-5-(trifluoromethyl)phenyl)urea;
1-(1-methyl-5-(2-(piperidin-4-ylamino)quinazolin-6-yl)-1H-pyrazol-3-yl)-3-(4-((4-methylpiperazin-1-yl)methyl)-3-(trifluoromethyl)phenyl)urea;
1-(1-methyl-5-(2-(piperidin-4-ylamino)quinazolin-6-yl)-1H-pyrazol-3-yl)-3-(4-(1-(4-methylpiperazin-1-yl)ethyl)-3-(trifluoromethyl)phenyl)urea;
1-(1-methyl-5-(2-(piperidin-4-ylamino)quinazolin-6-yl)-1H-pyrazol-yl)-3-(5-methylpiperazin-1-yl)methyl)-4-(trifluoromethyl)pyridin-2-yl)urea;
1-(4-(((2-(dimethylamino)ethyl)(methyl)amino)methyl)-3-(trifluoromethyl)phenyl)-3-(1-methyl-5-(2-(piperidin-4-ylamino)quinazolin-6-yl)-1H-pyrazol-3-yl)area;
1-(4-(((2-aminoethyl)(methyl)amino)methyl)-3-(trifluoromethyl)phenyl)-3-(5-(2-aminoquinazolin-6-yl)-1-methyl-1H-pyrazol-3-yl)urea;
1-(4-((3-methyl-3,8-diazabicyclo[3.2.1]octan-8-yl)methy)-3-(trifluoromethyl)phenyl)-3-(1-methyl-5-(2-(piperidin-4-ylamino)quinazolin-6-yl)-1H-pyrazol-3-yl)urea;
1-(4-((5-methyl-2,5-diazabicyclo[2.2.2]octan-2-yl)methyl)-3-(trifluoromethyl)phenyl)-3-(1-methyl-5-(2-(piperidin-4-ylamino)quinazolin-6-yl)-1H-pyrazol-3-yl)urea;
1-(4-((dimethylamino)methyl)-3-(trifluoromethyl)phenyl)-3-(1-methyl-5-(2-(piperidin-4-ylamino)quinazolin-6-yl)-1H-pyrazol-3-yl)urea;
1-(5-(2-(((1R,3R)-3-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)-8-ethylquinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((4-(methylamino)piperidin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((4-aminopiperidin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-((methyl(2-(methylamino)ethyl)amino)methyl)-3-(trifluoromethyl)phenyl)urea;
1-(5-(2-(((1r,4r)-4-aminocyclohexyl)amino)quinazolin-6-yl)-1-methyl-1H-pyrazol-3-yl)-3-(4-(1-(4-methylpiperazin-1-yl)ethyl)-3-(trifluoromethyl)phenyl)urea;
1-(5-(2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(((1s,4s)-4-aminocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-((3-aminopropyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-((4,4-difluorocyclohexyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-((azetidin-3-ylmethyl)amino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-(cyclohexylamino)quinazolin-6-yl)-1-methyl-1H-pyrazol-3-yl)-3-(4-((4-methylpiperazin-1-yl)methyl)-3-(trifluoromethyl)phenyl)urea;
1-(5-(2-amino-8-ethylquinazolin-6-yl)-1-methyl-1H-pyrazol-3-yl)-3-(4-((4-methylpiperazin-1-yl)methyl)-3-(trifluoromethyl)phenyl)urea;
1-(5-(2-amino-8-methylquinazolin-6-yl)-1-methyl-1H-pyrazol-3-yl)-3-(4-((4-methylpiperazin-1-yl)methyl)-3-(trifluoromethyl)phenyl)urea;

1-(5-(2-aminoquinazolin-6-yl)-1-methyl-1H-pyrazol-3-yl)-3-(4-((methyl(2-(methylamino)ethyl)amino)methyl)-3-(trifluoromethyl)phenyl)urea;

1-(5-(3-(cyclohexylamino)isoquinolin-7-yl)-1-methyl-1H-pyrazol-3-yl)-3-(4-((4-methylpiperazin-1-yl)methyl)-3-(trifluoromethyl)phenyl)urea;

1-(5-(8-ethyl-2-(((1r,4r)-4-hydroxycyclohexyl)amino)quinazolin-6-yl)-1-methyl-1H-pyrazol-3-yl)-3-(4-((4-methylpiperazin-1-yl)methyl)-3-(trifluoromethyl)phenyl)urea;

N-(1-methyl-5-(2-(piperidin-4-ylamino)quinazolin-6-yl)-1H-pyrazol-3-yl)-2-(4-((4-methylpiperazin-1-yl)methyl)-3-(trifluoromethyl)phenyl)acetamide;

N-(5-(2-(((1r,4r)-4-aminocyclohexyl)amino)-8-ethylquinazolin-6-yl)-1-methyl-1H-pyrazol-3-yl)-2-(4-((4-methylpiperazin-1-yl)methyl)-3-(trifluoromethyl)phenyl)acetamide; and N-(5-(2-aminoquinazolin-6-yl)-1-methyl-1H-pyrazol-3-yl)-2-(4-((4-methylpiperazin-1-yl)methyl)-3-(trifluoromethyl)phenyl)acetamide; and pharmaceutically acceptable salts thereof.

25. A pharmaceutical composition comprising a compound of claim 20 or a pharmaceutically acceptable salt thereof.

* * * * *

UNITED STATES PATENT AND TRADEMARK OFFICE
CERTIFICATE OF CORRECTION

PATENT NO. : 10,934,275 B2  
APPLICATION NO. : 16/463056  
DATED : March 2, 2021  
INVENTOR(S) : Vacca et al.

Page 1 of 3

It is certified that error appears in the above-identified patent and that said Letters Patent is hereby corrected as shown below:

On the Title Page

In Column 2, item (56) under "Other Publications", Line 9, delete "Seriai" and insert --Serial-- therefor In the Claims In Column 157, Line 24, in Claim 1, delete "S(=)2;" and insert --S(=O)$_2$;-- therefor In Column 157, Line 49, in Claim 1, delete "1-3W" and insert --1-3R$^4$-- therefor In Column 157, Line 64, in Claim 1, delete "11" and insert --H-- therefor In Column 158, Lines 31-32, in Claim 1, delete "-S(=O)$_2$N(R$^{10}$$_2$," and insert -- -S(=O)$_2$N(R$^{10}$)$_2$,-- therefor In Column 159, Lines 20-21, in Claim 1, delete "-NR$^{13}$C(=O)OR$^{16}$" and insert -- -NR$^{15}$C(=O)OR$^{16}$,-- therefor In Column 159, Line 30, in Claim 1, delete "C$_7$-C$_{10}$heterocycloalkyl," and insert --C$_2$-C$_{10}$heterocycloalkyl,-- therefor In Column 168, Line 1, in Claim 16, delete "R$^A$" and insert --R$^{A'}$-- therefor In Column 168, Line 37, in Claim 16, delete "-S(=O)$_2$R$^{11}$)," and insert -- -S(=O)$_2$R$^{11}$,-- therefor In Column 168, Line 38, in Claim 16, delete "-OC(=O)R$^{11}$," and insert -- -C(=O)R$^{11}$,-- therefor In Column 169, Line 24, in Claim 16, after "-CN,", insert -- -OR$^{15}$,--

Signed and Sealed this  
Twenty-fifth Day of May, 2021

Drew Hirshfeld  
*Performing the Functions and Duties of the*  
*Under Secretary of Commerce for Intellectual Property and*  
*Director of the United States Patent and Trademark Office*

In Column 169, Lines 25-26, in Claim 16, delete "-OC(=O)R$^{16}$-CO$_2$R$^{15}$, -OcO$_2$R$^{16}$," and insert -- -OC(=O)R$^{16}$, -CO$_2$R$^{15}$, -OCO$_2$R$^{16}$,-- therefor In Column 170, Line 16, in Claim 16, delete "R$^{10}$)" and insert --R$^{10}$-- therefor In Column 170, Line 16, in Claim 16, delete "atop" and insert --atom-- therefor In Column 170, Line 22, in Claim 16, delete "C$_1$-C$_{10}$cycloalkyl," and insert --C$_3$-C$_{10}$cycloalkyl,-- therefor In Column 170, Line 45, in Claim 16, delete "C$_1$-C$_{10}$cycloalkyl," and insert --C$_3$-C$_{10}$cycloalkyl,-- therefor In Column 170, Line 52, in Claim 18, delete "(If)," and insert --(IIf),-- therefor In Column 174, Line 25, in Claim 20, delete "car" and insert --or-- therefor In Column 174, Line 25, in Claim 20, delete "A" and insert --A$^2$-- therefor In Column 174, Line 25, in Claim 20, delete "car" and insert --or-- therefor In Column 174, Line 25, in Claim 20, delete "car" and insert --or-- therefor In Column 174, Line 66, in Claim 20, delete "-OCO$_2$R$^1$, -N(R$^1$)$_2$)" and insert -- -OCO$_2$R$^{11}$, -N(R$^{10}$)$_2$,-- therefor In Column 175, Line 3, in Claim 20, delete "C$_1$-C$_0$heteroalkyl," and insert --C$_1$-C$_6$heteroalkyl,-- therefor In Column 175, Line 6, in Claim 20, after "independently", insert --H--

In Column 175, Line 8, in Claim 20, delete "L$^1$" and insert --L$^D$-- therefor In Column 175, Line 37, in Claim 20, delete "C$_7$-C$_{10}$heterocycloalkyl," and insert --C$_2$-C$_{10}$heterocycloalkyl,-- therefor In Column 175, Line 43, in Claim 20, delete "C$_7$-C$_{10}$heterocycloalkyl," and insert --C$_2$-C$_{10}$heterocycloalkyl,-- therefor In Column 177, Line 38, in Claim 23, delete "o" and insert --to-- therefor In Column 177, Line 56, in Claim 24, delete "1-(1-meth-5-" and insert --1-(1-methyl-5- -- therefor In Column 177, Line 60, in Claim 24, delete "1H-pyrazol-3-yl-" and insert --1H-pyrazol-3-yl)-3- -- therefor

CERTIFICATE OF CORRECTION (continued)
U.S. Pat. No. 10,934,275 B2

In Column 177, Line 66, in Claim 24, delete "1l1" and insert --1H-- therefor

In Column 178, Line 2, in Claim 24, delete "1H-pyrazol-yl)-3-(5-methylpiperazin-1-yl)methyl)-4-" and insert --1H-pyrazol-3-yl)-3-(5-((4-methylpiperazin-1-yl)methyl)-4- -- therefor In Column 178, Line 6, in Claim 24, delete "area;" and insert --urea;-- therefor

SEQUENCE LISTING

<160> NUMBER OF SEQ ID NOS: 7

<210> SEQ ID NO 1
<211> LENGTH: 977
<212> TYPE: PRT
<213> ORGANISM: Homo sapiens

<400> SEQUENCE: 1

| Met | Pro | Ala | Arg | Arg | Leu | Leu | Leu | Leu | Leu | Thr | Leu | Leu | Leu | Pro | Gly |
|---|---|---|---|---|---|---|---|---|---|---|---|---|---|---|---|
| 1 | | | | 5 | | | | | 10 | | | | | 15 | |

| Leu | Gly | Ile | Phe | Gly | Ser | Thr | Ser | Thr | Val | Thr | Leu | Pro | Glu | Thr | Leu |
| | | | 20 | | | | | 25 | | | | | 30 | | |

| Leu | Phe | Val | Ser | Thr | Leu | Asp | Gly | Ser | Leu | His | Ala | Val | Ser | Lys | Arg |
| | | 35 | | | | | 40 | | | | | 45 | | | |

| Thr | Gly | Ser | Ile | Lys | Trp | Thr | Leu | Lys | Glu | Asp | Pro | Val | Leu | Gln | Val |
| | 50 | | | | | 55 | | | | | 60 | | | | |

| Pro | Thr | His | Val | Glu | Glu | Pro | Ala | Phe | Leu | Pro | Asp | Pro | Asn | Asp | Gly |
| 65 | | | | | 70 | | | | | 75 | | | | | 80 |

| Ser | Leu | Tyr | Thr | Leu | Gly | Ser | Lys | Asn | Asn | Glu | Gly | Leu | Thr | Lys | Leu |
| | | | | 85 | | | | | 90 | | | | | 95 | |

| Pro | Phe | Thr | Ile | Pro | Glu | Leu | Val | Gln | Ala | Ser | Pro | Cys | Arg | Ser | Ser |
| | | | 100 | | | | | 105 | | | | | 110 | | |

| Asp | Gly | Ile | Leu | Tyr | Met | Gly | Lys | Lys | Gln | Asp | Ile | Trp | Tyr | Val | Ile |
| | | 115 | | | | | 120 | | | | | 125 | | | |

| Asp | Leu | Leu | Thr | Gly | Glu | Lys | Gln | Gln | Thr | Leu | Ser | Ser | Ala | Phe | Ala |
| | 130 | | | | | 135 | | | | | 140 | | | | |

| Asp | Ser | Leu | Cys | Pro | Ser | Thr | Ser | Leu | Leu | Tyr | Leu | Gly | Arg | Thr | Glu |
| 145 | | | | | 150 | | | | | 155 | | | | | 160 |

| Tyr | Thr | Ile | Thr | Met | Tyr | Asp | Thr | Lys | Thr | Arg | Glu | Leu | Arg | Trp | Asn |
| | | | | 165 | | | | | 170 | | | | | 175 | |

| Ala | Thr | Tyr | Phe | Asp | Tyr | Ala | Ala | Ser | Leu | Pro | Glu | Asp | Asp | Val | Asp |
| | | | 180 | | | | | 185 | | | | | 190 | | |

| Tyr | Lys | Met | Ser | His | Phe | Val | Ser | Asn | Gly | Asp | Gly | Leu | Val | Val | Thr |
| | | 195 | | | | | 200 | | | | | 205 | | | |

-continued

```
Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
                245                 250                 255

Ser Gly Glu Val Gly Arg Ile Thr Lys Trp Lys Tyr Pro Phe Pro Lys
                260                 265                 270

Glu Thr Glu Ala Lys Ser Lys Leu Thr Pro Thr Leu Tyr Val Gly Lys
            275                 280                 285

Tyr Ser Thr Ser Leu Tyr Ala Ser Pro Ser Met Val His Glu Gly Val
    290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
                340                 345                 350

Asn Tyr Leu Arg Asn Tyr Trp Leu Leu Ile Gly His His Glu Thr Pro
            355                 360                 365

Leu Ser Ala Ser Thr Lys Met Leu Glu Arg Phe Pro Asn Asn Leu Pro
370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
                405                 410                 415

Thr Val Ser Arg Asp Val Glu Glu Lys Pro Ala His Ala Pro Ala Arg
            420                 425                 430

Pro Glu Ala Pro Val Asp Ser Met Leu Lys Asp Met Ala Thr Ile Ile
            435                 440                 445

Leu Ser Thr Phe Leu Leu Ile Gly Trp Val Ala Phe Ile Ile Thr Tyr
450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Leu
                485                 490                 495

Pro Phe His Pro Pro Gly Asp Thr Ala Gln Asp Gly Glu Leu Leu Asp
            500                 505                 510

Thr Ser Gly Pro Tyr Ser Glu Ser Gly Thr Ser Ser Pro Ser Thr
            515                 520                 525

Ser Pro Arg Ala Ser Asn His Ser Leu Cys Ser Gly Ser Ser Ala Ser
530                 535                 540

Lys Ala Gly Ser Ser Pro Ser Leu Glu Gln Asp Asp Gly Asp Glu Glu
545                 550                 555                 560

Thr Ser Val Val Ile Val Gly Lys Ile Ser Phe Cys Pro Lys Asp Val
                565                 570                 575

Leu Gly His Gly Ala Glu Gly Thr Ile Val Tyr Arg Gly Met Phe Asp
            580                 585                 590

Asn Arg Asp Val Ala Val Lys Arg Ile Leu Pro Glu Cys Phe Ser Phe
            595                 600                 605

Ala Asp Arg Glu Val Gln Leu Leu Arg Glu Ser Asp Glu His Pro Asn
610                 615                 620
```

-continued

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
            645                 650                 655

Asp Phe Ala His Leu Gly Leu Glu Pro Ile Thr Leu Leu Gln Gln Thr
        660                 665                 670

Thr Ser Gly Leu Ala His Leu His Ser Leu Asn Ile Val His Arg Asp
    675                 680                 685

Leu Lys Pro His Asn Ile Leu Ile Ser Met Pro Asn Ala His Gly Lys
690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
            725                 730                 735

Trp Ile Ala Pro Glu Met Leu Ser Glu Asp Cys Lys Glu Asn Pro Thr
        740                 745                 750

Tyr Thr Val Asp Ile Phe Ser Ala Gly Cys Val Phe Tyr Tyr Val Ile
    755                 760                 765

Ser Glu Gly Ser His Pro Phe Gly Lys Ser Leu Gln Arg Gln Ala Asn
770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
            805                 810                 815

Pro Gln Lys Arg Pro Ser Ala Lys His Val Leu Lys His Pro Phe Phe
        820                 825                 830

Trp Ser Leu Glu Lys Gln Leu Gln Phe Phe Gln Asp Val Ser Asp Arg
    835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
            885                 890                 895

Val Arg Asp Leu Leu Arg Ala Met Arg Asn Lys Lys His His Tyr Arg
        900                 905                 910

Glu Leu Pro Ala Glu Val Arg Glu Thr Leu Gly Ser Leu Pro Asp Asp
    915                 920                 925

Phe Val Cys Tyr Phe Thr Ser Arg Phe Pro His Leu Leu Ala His Thr
930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
            965                 970                 975

Leu

<210> SEQ ID NO 2
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 2

```
cauguccgca gcacaug                                                    17
```

<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 3

```
caugucccca gcacaug                                                    17
```

<210> SEQ ID NO 4
<211> LENGTH: 434
<212> TYPE: PRT
<213> ORGANISM: Saccharomyces cerevisiae

<400> SEQUENCE: 4

```
Ser Arg Ile Ala Asn Ile Pro Asn Phe Glu Gln Ser Leu Lys Asn Leu
1               5                   10                  15

Val Val Ser Glu Lys Ile Leu Gly Tyr Gly Ser Ser Gly Thr Val Val
            20                  25                  30

Phe Gln Gly Ser Phe Gln Gly Arg Pro Val Ala Val Lys Arg Met Leu
        35                  40                  45

Ile Asp Phe Cys Asp Ile Ala Leu Met Glu Ile Lys Leu Leu Thr Glu
    50                  55                  60

Ser Asp His Pro Asn Val Ile Arg Tyr Tyr Cys Ser Glu Thr Thr
65                  70                  75                  80

Asp Arg Phe Leu Tyr Ile Ala Leu Glu Leu Cys Asn Leu Asn Leu Gln
                85                  90                  95

Asp Leu Val Glu Ser Lys Asn Val Ser Asp Glu Asn Leu Lys Leu Gln
            100                 105                 110

Lys Glu Tyr Asn Pro Ile Ser Leu Leu Arg Gln Ile Ala Ser Gly Val
        115                 120                 125

Ala His Leu His Ser Leu Lys Ile Ile His Arg Asp Leu Lys Pro Gln
    130                 135                 140

Asn Ile Leu Val Ser Thr Ser Ser Arg Phe Thr Ala Asp Gln Gln Thr
145                 150                 155                 160

Gly Ala Glu Asn Leu Arg Ile Leu Ile Ser Asp Phe Gly Leu Cys Lys
                165                 170                 175

Lys Leu Asp Ser Gly Gln Ser Ser Phe Arg Thr Asn Leu Asn Asn Pro
            180                 185                 190

Ser Gly Thr Ser Gly Trp Arg Ala Pro Glu Leu Leu Glu Glu Ser Asn
        195                 200                 205

Asn Leu Gln Thr Lys Arg Arg Leu Thr Arg Ser Ile Asp Ile Phe Ser
    210                 215                 220

Met Gly Cys Val Phe Tyr Tyr Ile Leu Ser Lys Gly Lys His Pro Phe
225                 230                 235                 240

Gly Asp Lys Tyr Ser Arg Glu Ser Asn Ile Ile Arg Gly Ile Phe Ser
                245                 250                 255

Leu Asp Glu Met Lys Cys Leu His Asp Arg Ser Leu Ile Ala Glu Ala
            260                 265                 270

Thr Asp Leu Ile Ser Gln Met Ile Asp His Asp Pro Leu Lys Arg Pro
        275                 280                 285

Thr Ala Met Lys Val Leu Arg His Pro Leu Phe Trp Pro Lys Ser Lys
    290                 295                 300
```

```
Lys Leu Glu Phe Leu Leu Lys Val Ser Asp Arg Leu Glu Ile Glu Asn
305                 310                 315                 320

Arg Asp Pro Pro Ser Ala Leu Leu Met Lys Phe Asp Ala Gly Ser Asp
            325                 330                 335

Phe Val Ile Pro Ser Gly Asp Trp Thr Val Lys Phe Asp Lys Ile Phe
            340                 345                 350

Met Asp Asn Leu Glu Arg Tyr Arg Lys Tyr His Ser Ser Lys Leu Met
            355                 360                 365

Asp Leu Leu Arg Ala Leu Arg Asn Lys Tyr His His Phe Met Asp Leu
            370                 375                 380

Pro Glu Asp Ile Ala Glu Leu Met Gly Pro Val Pro Asp Gly Phe Tyr
385                 390                 395                 400

Asp Tyr Phe Ile Lys Arg Phe Pro Asn Leu Leu Ile Gly Val Tyr Met
                405                 410                 415

Ile Val Lys Glu Asn Leu Ser Asp Asp Gln Ile Leu Arg Glu Phe Leu
            420                 425                 430

Tyr Ser

<210> SEQ ID NO 5
<211> LENGTH: 424
<212> TYPE: PRT
<213> ORGANISM: Homo sapiens

<400> SEQUENCE: 5

Asp Asp Gly Asp Glu Glu Thr Ser Val Val Ile Val Gly Lys Ile Ser
1               5                   10                  15

Phe Cys Pro Lys Asp Val Leu Gly His Gly Ala Glu Gly Thr Ile Val
                20                  25                  30

Tyr Arg Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
        50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Cys Phe Ala His Leu Gly Leu Glu Pro
            100                 105                 110

Ile Thr Leu Leu Gln Gln Thr Thr Ser Gly Leu Ala His Leu His Ser
        115                 120                 125

Leu Asn Ile Val His Arg Asp Leu Lys Pro His Asn Ile Leu Ile Ser
130                 135                 140

Met Pro Asn Ala His Gly Lys Ile Lys Ala Met Ile Ser Asp Phe Gly
145                 150                 155                 160

Leu Cys Lys Lys Leu Ala Val Gly Arg His Ser Phe Ser Arg Arg Ser
                165                 170                 175

Gly Val Pro Gly Thr Glu Gly Trp Ile Ala Pro Glu Met Leu Ser Glu
            180                 185                 190

Asp Cys Lys Glu Asn Pro Thr Tyr Thr Val Asp Ile Phe Ser Ala Gly
        195                 200                 205

Cys Val Phe Tyr Tyr Val Val Ser Glu Gly Ser His Pro Phe Gly Lys
    210                 215                 220

Ser Leu Gln Arg Gln Ala Asn Ile Leu Leu Gly Ala Cys Ser Leu Asp
225                 230                 235                 240
```

```
Cys Leu His Pro Glu Lys His Glu Asp Val Ile Ala Arg Glu Leu Ile
                245                 250                 255

Glu Lys Met Ile Ala Met Asp Pro Gln Lys Arg Pro Ser Ala Asn Asp
            260                 265                 270

Val Leu Lys His Pro Phe Phe Trp Ser Leu Glu Lys Gln Leu Gln Phe
        275                 280                 285

Phe Gln Asp Val Ser Asp Arg Ile Glu Lys Glu Ser Leu Asp Gly Pro
    290                 295                 300

Ile Val Lys Gln Leu Glu Arg Gly Gly Arg Ala Val Val Lys Met Asp
305                 310                 315                 320

Trp Arg Glu Asn Ile Thr Asp Pro Leu Gln Thr Asp Leu Arg Lys Phe
                325                 330                 335

Arg Thr Tyr Lys Gly Gly Ser Val Arg Asp Leu Leu Arg Ala Met Arg
            340                 345                 350

Asn Lys Lys His His Tyr Arg Asp Leu Pro Glu Glu Val Arg Glu Thr
        355                 360                 365

Leu Gly Thr Leu Pro Asp Asp Phe Val Cys Tyr Phe Thr Ser Arg Phe
    370                 375                 380

Pro His Leu Leu Ala His Thr Tyr Arg Ala Met Glu Leu Cys Ser His
385                 390                 395                 400

Glu Arg Leu Phe Gln Pro Tyr Tyr Phe His Glu Pro Glu Pro Gln
                405                 410                 415

Pro Pro Val Thr Pro Asp Ala Leu
            420

<210> SEQ ID NO 6
<211> LENGTH: 423
<212> TYPE: PRT
<213> ORGANISM: Mus musculus

<400> SEQUENCE: 6

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
            20                  25                  30

Tyr Lys Gly Met Phe Asp Asn Arg Asp Val Ala Val Lys Arg Ile Leu
        35                  40                  45

Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
        115                 120                 125

Asn Ile Val His Arg Asp Leu Lys Pro His Asn Ile Leu Leu Ser Met
    130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
```

```
                180                 185                 190
Cys Lys Asp Asn Pro Thr Tyr Thr Val Asp Ile Phe Ser Ala Gly Cys
            195                 200                 205

Val Phe Tyr Tyr Val Ile Ser Glu Gly Asn His Pro Phe Gly Lys Ser
    210                 215                 220

Leu Gln Arg Gln Ala Asn Ile Leu Leu Gly Ala Cys Asn Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Arg Pro Ser Ala Lys His Val
            260                 265                 270

Leu Lys His Pro Phe Phe Trp Ser Leu Glu Lys Gln Leu Gln Phe Phe
        275                 280                 285

Gln Asp Val Ser Asp Arg Ile Glu Lys Glu Ala Leu Asp Gly Pro Ile
    290                 295                 300

Val Arg Gln Leu Glu Arg Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Lys His His Tyr Arg Glu Leu Pro Ala Glu Val Gln Glu Thr Leu
        355                 360                 365

Gly Ser Ile Pro Asp Asp Phe Val Arg Tyr Phe Thr Ser Arg Phe Pro
    370                 375                 380

His Leu Leu Ser His Thr Tyr Gln Ala Met Glu Leu Cys Arg His Glu
385                 390                 395                 400

Arg Leu Phe Gln Thr Tyr Tyr Trp His Glu Pro Thr Glu Pro Gln Pro
                405                 410                 415

Pro Val Ile Pro Tyr Ala Leu
            420

<210> SEQ ID NO 7
<211> LENGTH: 423
<212> TYPE: PRT
<213> ORGANISM: Rattus norvegicus

<400> SEQUENCE: 7

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
                20                  25                  30

Tyr Lys Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
        50                  55                  60

Ser Asp Glu His Pro Asn Val Ile Arg Tyr Phe Cys Thr Glu Lys Asp
65                  70                  75                  80
```

-continued

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
            115                 120                 125

Asn Ile Val His Arg Asp Leu Lys Pro His Asn Ile Leu Leu Ser Met
        130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
            180                 185                 190

Cys Lys Glu Asn Pro Thr Tyr Thr Val Asp Ile Phe Ser Ala Gly Cys
            195                 200                 205

Val Phe Tyr Tyr Val Ile Ser Glu Gly Asn His Pro Phe Gly Lys Ser
        210                 215                 220

Leu Gln Arg Gln Ala Asn Ile Leu Leu Gly Ala Cys Ser Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
            260                 265                 270

Leu Lys His Pro Phe Phe Trp Ser Leu Glu Lys Gln Leu Gln Phe Phe
        275                 280                 285

Gln Asp Val Ser Asp Arg Ile Glu Lys Glu Ser Leu Asp Gly Pro Ile
    290                 295                 300

Val Arg Gln Leu Glu Arg Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Arg His His Tyr Arg Glu Leu Pro Leu Glu Val Gln Glu Thr Leu
        355                 360                 365

Gly Ser Ile Pro Asp Asp Phe Val Arg Tyr Phe Thr Ser Arg Phe Pro
370                 375                 380

His Leu Leu Ser His Thr Tyr Arg Ala Met Glu Leu Cys Arg His Glu
385                 390                 395                 400

Arg Leu Phe Gln Thr Tyr Tyr Trp His Glu Pro Thr Glu Ala Gln Pro
                405                 410                 415

Pro Gly Ile Pro Asp Ala Leu
            420